(12) United States Patent
Velculescu et al.

(10) Patent No.: US 10,982,279 B2
(45) Date of Patent: *Apr. 20, 2021

(54) CELL-FREE DNA FOR ASSESSING AND/OR TREATING CANCER

(71) Applicant: The Johns Hopkins University, Baltimore, MD (US)

(72) Inventors: Victor E. Velculescu, Dayton, MD (US); Stephen Cristiano, Baltimore, MD (US); Alessandro Leal, Baltimore, MD (US); Jillian A. Phallen, Baltimore, MD (US); Jacob Fiksel, Baltimore, MD (US); Vilmos Adleff, Baltimore, MD (US); Robert B. Scharpf, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/730,938

(22) Filed: Dec. 30, 2019

(65) Prior Publication Data

US 2020/0131571 A1  Apr. 30, 2020

Related U.S. Application Data

(63) Continuation of application No. PCT/US2019/032914, filed on May 17, 2019.

(60) Provisional application No. 62/795,900, filed on Jan. 23, 2019, provisional application No. 62/673,516, filed on May 18, 2018.

(51) Int. Cl.
| | | |
|---|---|---|
| *C12Q 1/68* | (2018.01) | |
| *C12P 19/34* | (2006.01) | |
| *C12Q 1/6874* | (2018.01) | |
| *G16B 40/00* | (2019.01) | |
| *G16B 30/00* | (2019.01) | |
| *C12Q 1/6886* | (2018.01) | |

(52) U.S. Cl.
CPC ......... *C12Q 1/6874* (2013.01); *C12Q 1/6886* (2013.01); *G16B 30/00* (2019.02); *G16B 40/00* (2019.02); *C12Q 2600/156* (2013.01)

(58) Field of Classification Search
CPC . C12Q 1/6869; C12Q 2535/122; G16B 20/00
See application file for complete search history.

(56) References Cited

U.S. PATENT DOCUMENTS

| | | | |
|---|---|---|---|
| 9,233,125 | B2 | 1/2016 | Davila |
| 9,499,870 | B2 | 11/2016 | Babiarz et al. |
| 2009/0280479 | A1 | 11/2009 | Hoon |
| 2014/0050788 | A1 | 2/2014 | Daniel et al. |
| 2014/0227705 | A1 | 8/2014 | Vogelstein |
| 2014/0271635 | A1 | 9/2014 | Brogdon |
| 2016/0138112 | A1 | 5/2016 | Janne et al. |
| 2016/0194404 | A1 | 7/2016 | June et al. |
| 2017/0024513 | A1 | 1/2017 | Lo et al. |
| 2017/0211143 | A1 | 7/2017 | Shendure et al. |

FOREIGN PATENT DOCUMENTS

| | | |
|---|---|---|
| WO | 2017/190067 A1 | 11/2017 |
| WO | 2018/027176 A1 | 2/2018 |
| WO | 2019/222657 A1 | 11/2019 |

OTHER PUBLICATIONS

Gusnanto, A. et al. "Estimating optimal window size for analysis of low-coverage next-generation sequence data" Bioinformatics, vol. 30, No. 13, 2014, pp. 1823-1829. (Year: 2014).*
Snyder, M.W. et al. "Cell-free DNA Comprises an In Vivo Nucleosome Footprint that Informs Its Tissues-Of-Origin" with Supplemental Information, Cell 164, 57-68, (Year: 2016).*
Friedman. Greedy function approximation: A gradient boosting machine. Ann Stat., (2001), 29 (5), pp. 1189-1232.
Friedman. Stochastic gradient boosting. Comput Stat Data An., (2002), 38, pp. 367-378.
Efron et al. Improvements on cross-validation: The .632+ bootstrap method. J Am Stat Assoc., (1997), 92 (438), pp. 548-560.
Burnham et al. Single-stranded DNA library preparation uncovers the origin and diversity of ultrashort cell-free DNA in plasm. Scientific Reports., (2016), 6, 27859.
Sanchez et al. New insights into structural features and optimal detection of circulating tumor DNA determined by single-strand DNA analysis. NPJ Genomic Medicine., (2018), 3, 31.
Newman et al. Integrated digital error suppression for improved detection of circulating tumor DNA. Nat Biotechnol., (2016), 34 (5), pp. 547-555.
Fisher et al., A scalable, fully automated process for construction of sequence-ready human exome targeted capture libraries. Genome Biol., (2011), 12 (1), R1.
Jones et al., Personalized genomic analyses for cancer mutation discovery and interpretation. Sci Transl. Med., (2015), 7 (283), 283ra53.
Xie et al., Age-related mutations associated with clonal hematopoietic expansion and malignancies. Nat Med., (2014), 20 (12), pp. 1472-1478.
McKerrell et al., Leukemia-associated somatic mutations drive distinct patterns of age-related clonal hemopoiesis. Cell Rep., (2015), 10 (8), pp. 1239-1245.
Genovese et al., Clonal hematopoiesis and blood-cancer risk inferred from blood DNA sequence. N Engl J Med., (2014), 371 (26), pp. 2477-2487.

(Continued)

*Primary Examiner* — Stephen T Kapushoc
(74) *Attorney, Agent, or Firm* — Mintz Levin Cohn Ferris Glovsky and Popeo, P.C.; Peter F. Corless

(57) ABSTRACT

This document relates to methods and materials for assessed, monitored, and/or treated mammals (e.g., humans) having cancer. For example, methods and materials for identifying a mammal as having cancer (e.g., a localized cancer) are provided. For example, methods and materials for assessing, monitoring, and/or treating a mammal having cancer are provided.

16 Claims, 33 Drawing Sheets

(56) References Cited

OTHER PUBLICATIONS

Langmead et al. Fast gapped-read alignment with Bowtie 2. Nat Methods., (2012), 9 (4), pp. 357-359.
Pardoll. The blockade of immune checkpoints in cancer immunotherapy. Nat. Rev Cancer., (2012), 12 (4), pp. 252-264.
Sun et al. Nivolumab effectively inhibit platinum-resistant ovarian cancer cells via induction of cell apoptosis and inhibition of ADAM17 expression. Eur Rev Med Phaimacol Sci., (2017), 21 (6), pp. 1198-1205.
Hamanishi et al. Safety and Antitumor Activity of Anti-PD-1 Antibody, Nivolumab, in Patients With Platinum-Resistant Ovarian Cancer. J. Clin. Oncol., (2015), 33 (34), pp. 4015-4022.
Brahmer et al. Safety and activity of anti-PD-L1 antibody in patients with advanced cancer. N Engl J Med., (2012), 366 (26), pp. 2455-2465.
Ricciuti et al. Long-Lasting Response to Nivolumab and Immune-Related Adverse Events in a Nonsquamous Metastatic Non-Small Cell Lung Cancer Patient. J. Thorac Oncol., (2017), 12 (5), e51-e55.
Ellis et al. Immune Checkpoint Inhibitors for Patients With Advanced Non-Small-Cell Lung Cancer: A Systematic Review. Clin Lung Cancer., (2017), 18 (5), pp. 444-459.e1.
Zou et al. More valuable than platinum: first-line pembrolizumab in advanced stage non-small-cell lung cancer. Ann Oncol., (2017), 28 (4), pp. 685-687.
Sorscher. Pembrolizumab in Non-Small-Cell Lung Cancer. N Engl J Med., (2017), 376 (10), pp. 996-997.
Hui et al. Pembrolizumab as first-line therapy for patients with PD-L1-positive advanced non-small cell lung cancer: a phase 1 trial. Ann Oncol., (2017), 28 (4), pp. 874-881.
Vansteenkiste et al. Prospects and progress of atezolizumab in non-small cell lung cancer. Expert Opin Biol Ther., (2017), 17 (6), pp. 781-789.
Hellmann et al. Nivolumab plus ipilimumab as first-line treatment for advanced non-small-cell lung cancer (CheckMate 012): results of an open-label, phase 1, multicohort study. Lancet Oncol., (2017), 18 (1), pp. 31-41.
Chen. Immune checkpoint inhibitors for nonsmall cell lung cancer treatment. J. Chin Med Assoc., (2017), 80 (1), pp. 7-14.
Rosenberg et al. Adoptive cell transfer as personalized immunotherapy for human cancer. Science., (2015), 348 (6230), pp. 62-68.
Benjamini et al. Summarizing and correcting the GC content bias in high-throughput sequencing. Nucleic Acids Res. (2012), 40 (10), e72.
Yee et al. Personalized Therapy: Tumor Antigen Discovery for Adoptive Cellular Therapy. Cancer J., (2016), 23 (2), pp. 144-148.
Chen et al. CAR T-cell intrinsic PD-1 checkpoint blockade: A two-in-one approach for solid tumor immunotherapy. Oncoimmunology., (2016), 6 (2), e1273302.
Jahr et al. DNA Fragments in the Blood Plasma of Cancer Patients: Quantitations and Evidence for Their Origin from Apoptotic and Necrotic Cells. Cancer Res., (2001), 61 (4), pp. 1659-1665.
Taylor et al. Unbiased Detection of Somatic Copy Number Aberrations in cfDNA of Lung Cancer Cases and High-Risk Controls with Low Coverage Whole Genome Sequencing. Adv Exp Med Biol., (2016), 924, pp. 29-32., abstract, p. 30.
Cohen et al. Detection and localization of surgically resectable cancers with a multi-analyte blood test. Science., (2018), 359 (6378), pp. 926-930.
Aravanis et al. Next-Generation Sequencing of Circulating Tumor DNA for Early Cancer Detection. Cell., (2017), 168 (4), pp. 571-574.
Ma et al. Cell-Free DNA Provides a Good Representation of the Tumor Genome Despite Its Biased Fragmentation Patterns. Plos One., (2017), 12 (1), e0169231.
Diehl et al. Circulating mutant DNA to assess tumor dynamics. Nat Med., (2008), 14 (9), pp. 985-990.
Han et al. Circulating Tumor DNA as Biomarkers for Cancer Detection. Genomics, Proteomics, & Biomarkers., (2017), 15 (2), pp. 59-72.
Rossi et al. Cell-Free DNA and Circulating Tumor Cells: Comprehensive Liquid Biopsy Analysis in Advanced Breast Cancer. Clin Cancer Res., (2018), 24 (3), pp. 560-568.
De Mattos-Arrudo et al. Cell-free circulating tumour DNA as a liquid biopsy in breast cancer. Molecular Oncology., (2016), 10 (3), pp. 464-474.
Leon et al. Free DNA in the Serum of Cancer Patients and the Effect of Therapy. Cancer Research., (1977), 37 (3), pp. 646-650.
Torre et al. Global cancer statistics, 2012. CA Cancer J Clin., (2015), 65 (2), pp. 87-108.
Who. Guide to Cancer Early Diagnosis. Guide to Cancer Early Diagnosis. World Health Organization., Geneva, Switzerland., (2017).
Robin et al. pROC: an open-source package for R and S+ to analyze and compare ROC curves. BMC Bioinformatics, (2011), 12, 77.
Morell. CEA serum levels in non-neoplastic disease. Int J Biol Markers., (1992), 7 (3), pp. 160-166.
Galli et al. CA 19-9: handle with care. Clin Chem Lab Med., (2013), 51 (7), pp. 1369-1383.
Sikaris. CA125—a test with a change of heart. Heart, lung & circulation., (2011), 20, pp. 634-640.
Lin et al. Screening for Colorectal Cancer: A Systematic Review for the U.S. Preventive Services Task Force. Rockville (MD): Agency for Healthcare Research and Quality (US)., (2016), Report No. 14-05203-EF-1.
Wanebo et al. Preoperative carcinoembryonic antigen level as a prognostic indicator in colorectal cancer. N Engl J Med., (1978), 299 (9), pp. 448-451.
Zauber. The impact of screening on colorectal cancer mortality and incidence: has it really made a difference? Dig Dis Sci., (2015), 60, pp. 681-691.
Phallen et al. Direct detection of early-stage cancers using circulating tumor DNA. Sci Transl Med., (2017), 9 (403), pii. eaan2415.
Alix-Panabieres et al. Clinical Applications of Circulating Tumor Cells and Circulating Tumor DNA as Liquid Biopsy. Cancer Discovery., (2016), 6, pp. 479-491.
Siravegna et al. Integrating liquid biopsies into the management of cancer. Nature Reviews Clinical Oncology., (2017), 14 (9), pp. 531-548.
Haber et al. Blood-based analyses of cancer: circulating tumor cells and circulating tumor DNA. Cancer Discovery., (2014), 4 (6), pp. 650-661.
Husain et al. Cancer DNA in the Circulation: The Liquid Biopsy. JAMA., (2017), 318 (13), pp. 1272-1274.
Wan et al. Liquid biopsies come of age: towards implementation of circulating tumour DNA. Nat Rev Cancer., (2017), 17 (4), pp. 223-238.
Newman et al. An ultrasensitive method for quantitating circulating tumor DNA with broad patient coverage. Nat Med., (2014), 20 (5), pp. 548-554.
Fortin et al. Reconstructing A/B compartments as revealed by Hi-C using long-range correlations in epigenetic data. Genome Biol., (2015) 16 (1), 180.
Leary et al. Development of personalized tumor biomarkers using massively parallel sequencing. Sci Transl Med., (2010), 2 (20), 20ra14.
Leary et al. Detection of chromosomal alterations in the circulation of cancer patients with whole-genome sequencing. Sci Transl Med., (2012), 4 (162), 162ra154.
Chan et al. Noninvasive detection of cancer-associated genome-wide hypomethylation and copy number aberrations by plasma DNA bisulfite sequencing. Proc Natl Acad Sci U S A., (2013), 110 (47), pp. 18761-18768.
Sausen et al. Integrated genomic analyses identify ARID1A and ARID1B alterations in the childhood cancer neuroblastoma. Nat Genet., (2013), 45 (1), pp. 12-17.
Jiang et al. Lengthening and shortening of plasma DNA in hepatocellular carcinoma patients. Proc Natl Acad Sci USA., (2015), 112 (11), E1317-1325.
Wang et al. Increased plasma DNA integrity in cancer patients. Cancer Res., (2003), 63 (14), pp. 3966-3968.
Jiang et al. Increased plasma DNA integrity index in head and neck cancer patients. Int J Cancer., (2006), 119 (11), pp. 2673-2676.

(56) References Cited

OTHER PUBLICATIONS

Umetani et al. Prediction of breast tumor progression by integrity of free circulating DNA in serum. J Clin Oncol., (2006), 24 (26), pp. 4270-4276.
Chan et al. Persistent aberrations in circulating DNA integrity after radiotherapy are associated with poor prognosis in nasopharyngeal carcinoma patients. Clin Cancer Res., (2008), 14 (13), pp. 4141-4145.
Mouliere et al. High fragmentation characterizes tumour-derived circulating DNA. PLoS One., (2011), 6 (9), e23418.
Mouliere et al. Multi-marker analysis of circulating cell-free DNA toward personalized medicine for colorectal cancer. Mol Oncol., (2014), 8 (5), pp. 927-941.
Mouliere et al. Enhanced detection of circulating tumor DNA by fragment size analysis. Sci Transl Med., (2018), 10 (466), eaat4921.
Snyder et al. Cell-free DNA Comprises an In Vivo Nucleosome Footprint that Informs Its Tissues-Of-Origin. Cell., (2016), 164 (1-2), pp. 57-68.
Underhill et al. Fragment Length of Circulating Tumor DNA. PLoS Genet., (2016), 12 (7), e1006162.
Ulz et al. Inferring expressed genes by whole-genome sequencing of plasma DNA. Nat Genet., (2016), 48 (10), pp. 1273-1278.
Ivanov et al. Non-random fragmentation patterns in circulating cell-free DNA reflect epigenetic regulation. BMC Genomics., (2015), 16 (Suppl 13), S1.
Jiang et al. Preferred end coordinates and somatic variants as signatures of circulating tumor DNA associated with hepatocellular carcinoma. Proc Natl Acad Sci USA., (2018), 115 (46), E10925-E10933.
Shen et al. Sensitive tumour detection and classification using plasma cell-free DNA methylomes. Nature., (2018), 563 (7732), pp. 579-583.
Corces et al. The chromatin accessibility landscape of primary human cancers. Science., (2018), 362 (6413), eaav1898.
Polak et al. Cell-of-origin chromatin organization shapes the mutational landscape of cancer. Nature., (2015), 518 (7539), pp. 360-364.
Lieberman-Aiden et al. Comprehensive mapping of long-range interactions reveals folding principles of the human genome. Science., (2009), 326 (5950), pp. 289-293.
Alix-Panabieres et al. (May 2016) "Clinical Applications of Circulating Tumor Cells and Circulating Tumor DNA as Liquid Biopsy", Cancer Discovery, 6(5):479-491.
Aravanis et al. (Feb. 9, 2017) "Next-Generation Sequencing of Circulating Tumor DNA for Early Cancer Detection", Cell, 168:571-574.
Benjamini et al. (Feb. 9, 2012) "Summarizing and Correcting the GC Content Bias in High-Throughput Sequencing", Nucleic Acids Research, e72, 40(10):14 pages.
Bettegowda et al. (Feb. 19, 2014) "Detection of Circulating Tumor DNA in Early- and Late-Stage Human Malignancies", Science Translational Medicine, 224ra24, 6(224):13 pages.
Brahmer et al. (Jun. 2012) "Safety and Activity of Anti-PD-L1 Antibody in Patients with Advanced Cancer", The New England Journal of Medicine, 366(26):2455-2465.
Burnham et al. (Jun. 14, 2016) "Single-Stranded DNA Library Preparation Uncovers the Origin and Diversity of Ultrashort Cell-Free DNA in Plasma", Scientific Reports, 6:9 pages.
Chan et al. (Nov. 19, 2013) "Noninvasive Detection of Cancer-Associated Genomewide Hypomethylation and Copy Number Aberrations by Plasma DNA Bisulfite Sequencing", PNAS, 110(47):18761-18768.
Chan et al. (2008) "Persistent Aberrations in Circulating DNA Integrity after RadiotherapyAreAssociated with Poor Prognosis in Nasopharyngeal Carcinoma Patients", Clinical Cancer Research, 14(13):4141-4145.
Chang et al. (May 2017) "CARs: Synthetic Immunoreceptors for Cancer Therapy and Beyond", Trends in Molecular Medicine, 23(5):430-450.

Chen et al. (2016) "CAR T-Cell Intrinsic PD-1 Checkpoint Blockade: A Two-in-One Approach for Solid Tumor Immunotherapy", OncoImmunology, e1273302, 6(2):4 pages.
Chen (2017) "Immune Checkpoint Inhibitors for Nonsmall Cell Lung Cancer Treatment", Journal of the Chinese Medical Association, 80:7-14.
Chu et al. (May 2, 2017) "Liquid Biopsy: Unlocking the Potentials of Cell-Free DNA", Virchows Archly, 471:147-154.
Cohen et al. (Feb. 2018) "Detection and localization of surgically resectable cancers with a multi-analyte blood test", Science, 359(6378):926-930.
Corces et al. (Oct. 26, 2018) "The Chromatin Accessibility Landscape of Primary Human Cancers", Science, aaav1898, 362:15 pages.
De Mattos-Arrudo et al. (2016) "Cell-Free Circulating Tumour DNA as a Liquid Biopsy in Breast Cancer5", Molecular Oncology, 10: 464-474.
Diehl et al. (Sep. 2008) "Circulating Mutant DNA to Assess Tumor Dynamics", Nature Medicine, 14(9):985-990.
Efron et al. (Jun. 1997) "Improvements on Cross-Validation: The .632 + Bootstrap Method", Journal of the American Statistical Association, 92(438):548-560.
Ellis et al. (Sep. 2017) "Immune Checkpoint Inhibitors for Patients With Advanced NoneSmall-Cell Lung Dancer: A Systematic Review", Clinical Lung Cancer, 18(5):444-459.
Fisher (2011) "A Scalable, Fully Automated Process for Construction of Sequence-Ready Human Exome Targeted Capture Libraries", Genome Biology, R1, 12:15 pages.
Fortin et al. (2015) "Reconstructing A/B Compartments as Revealed by Hi-C Using Long-Range Correlations in Epigenetic Data", Fortin and Hansen Genome Biology, 16(180):23 pages.
Friedman (2001) "Greedy Function Approximation: A Gradient Boosting Machine", The Annals of Statistics, 29 (5):1189-1232.
Friedman (2002) "Stochastic Gradient Boosting", Computational Statistics & Data Analysis, 38:367-378.
Galli et al. (2013) "CA 19-9: handle with care", Clinical Chemistry and Laboratory Medicine, 51(7):1369-1383.
Genovese et al. (Nov. 26, 2014) "Clonal Hematopoiesis and Blood-Cancer Risk Inferred from Blood DNA Sequence", The New England Journal of Medicine, 371:2477-2487.
Haber et al. (2014) "Blood-based Analyses of Cancer: Circulating Tumor Cells and Circulating Tumor DNA", Cancer Discovery, 4(6):650-661.
Hamanishi et al. (Dec. 1, 2015) "Safety and Antitumor Activity of Anti—PD-1 Antibody, Nivolumab, in Patients With Platinum-Resistant Ovarian Cancer", Journal of Clinical Oncology, 33(34):4015-4022.
Han et al. (2017) "Circulating Tumor DNA as Biomarkers for Cancer Detection", Genomics Proteomics Bioinformatics, 15: 59-72.
Hellmann et al. (Dec. 5, 2016) "Nivolumab plus Ipilimumab as Fi Rst-Line Treatment for Advanced Non-Small-Cell Lung Cancer (CheckMate 012): Results of an Open-Label, Phase 1, Multicohort Study", The Lancet Oncology, 18:31-41.
Hui et al. (Feb. 7, 2017) "Pembrolizumab as First-Line Therapy for Patients with PD-L1-Positive Advanced Non-Small Cell Lung Cancer: A Phase 1 Trial", Annals of Oncology, 28:874-881.
Husain et al. (2017) "Cancer DNA in the Circulation: The Liquid Biopsy", JAMA, 318(13):1272-1274.
Ivanov et al. (2015) "Non-Random Fragmentation Patterns in Circulating Cell-Free DNA Reflect Epigenetic Regulation", BMC Genomics, 16(Suppl 13):12 pages.
Jahr et al. (Feb. 15, 2001) "DNA Fragments in the Blood Plasma of Cancer Patients: Quantitations and Evidence for Their Origin from Apoptotic and Necrotic Cells1", Cancer Research, 61:1659-1665.
Jiang et al. (Sep. 21, 2006) "Increased Plasma DNA Integrity Index in Head and Neck Cancer Patients", International Journal of Cancer, 119:2673-2676.
Jiang et al. (Feb. 2, 2015) "Lengthening and Shortening of Plasma DNA in Hepatocellular Carcinoma Patients", PNAS, 112(11):E1317-E1325.
Jones et al. (Apr. 15, 2015) "Personalized Genomic Analyses for Cancer Mutation Discovery and Interpretation", Science Translational Medicine, 283ra53, 7(283):11 pages.

(56) References Cited

OTHER PUBLICATIONS

Langmead et al. (Apr. 2012) "Fast Gapped-Read Alignment with Bowtie 2", Nature Methods, 9(4):357-359.
Leary et al. (Nov. 28, 2012) "Detection of Chromosomal Alterations in the Circulation of Cancer Patients with Whole-Genome Sequencing", Science Translational Medicine, 162ra154, 4(162):14 pages.
Leary et al. (Feb. 24, 2010) "Development of Personalized Tumor Biomarkers Using Massively Parallel Sequencing", Science Translational Medicine, 20ra14, 2(20):8 pages.
Leon et al. (Mar. 1977) "Free DNA in the Serum of Cancer Patients and the Effect of Therapy", Cancer Research, 37:646-650.
Leberman-Aiden et al. (Oct. 9, 2009) "Comprehensive Mapping of Long-Range Interactions Reveals Folding Principles of the Human Genome", Science, 286(5950):289-293.
Lin et al. (2016) "Screening for Colorectal Cancer: A Systematic Review for the U.S. Preventive Services Task Force", Rockville (MD): Agency for Healthcare Research and Quality (US), Report No. 14-05203-EF-1, 239 pages.
Ma et al. (Jan. 3, 2017) "Cell-Free DNA Provides a Good Representation of the Tumor Genome Despite Its Biased Fragmentation Patterns", Plos One, e0169231, 12(1):18 pages.
McKerrell et al. (Mar. 3, 2015) "Leukemia-Associated Somatic Mutations Drive Distinct Patterns of Age-Related Clonal Hemopoiesis", Cell Reports, 10:1239-1245.
Morell (1992) "CEA Serum Levels in Non-neoplastic Disease", The International Journal of Biological Markers, 7 (3):160-166.
Mouliere et al. (Nov. 7, 2018) "Enhanced Detection of Circulating Tumor DNA by Fragment Size Analysis", Science Translational Medicine, eaat4921, 10:13 pages.
Mouliere et al. (Sep. 2011) "High Fragmentation Characterizes Tumour-Derived Circulating Dna", Plos One, e23418, 6(9):10 pages.
Mouliere et al. (2014) "Multi-Marker Analysis of Circulating Cell-Free DNA Toward Personalized Medicine for Colorectal Cancer", Molecular Oncology, 8:927-941.
Newman, et al. (May 2014) "An Ultrasensitive Method for Quantitating Circulating Tumor DNA with Broad Patient Coverage", Nature Medicine, 20(5):548-554.
Newman et al. (May 2016) "Integrated Digital Error Suppression for Improved Detection of Circulating Tumor DNA", Nature Biotechnology, 34(5):547-555.
Pardoll (Mar. 22, 2012) "The Blockade of Immune Checkpoints in Cancer Immunotherapy", Nature Reviews Cancer, 12(4)252-264.
Phallen et al. (2017) "Direct detection of early-stage cancers using circulating tumor DNA", Science Translational Medicine, 9(403), eaan2415, 14 pages.
Phallen et al. (Dec. 20, 2018) "Early Noninvasive Detection of Response to Targeted Therapy inNon-Small Cell Lung Cancer", Cancer Research, 79(6):1204-1213.
Polak et al. (Feb. 19, 2015) "Cell-of-Origin Chromatin Organization Shapes the Mutational Landscape of Cancer", Nature, 518:360-364.
Ricciuti et al. (May 2017) "Long-Lasting Response to Nivolumab and Immune-Related Adverse Events in a Nonsquamous Metastatic Non-Small Cell Lung Cancer Patient", Journal of Thoracic Oncology, 12(5):E51-E55.
Robin et al. (2011) "pROC: An Open-Source Package for R and S+ to Analyze and Compare ROC Curves", BMC Bioinformatics, 12(77):8 pages.
Rosenberg et al. (2015) "Adoptive Cell Transfer as Personalized Immunotherapy for Human Cancer", Science, 348 (6230):62-68.
Rossi et al. (Nov. 27, 2017) "Cell-Free DNA and Circulating Tumor Cells: Comprehensive Liquid Biopsy Analysis in Advanced Breast Cancer", Clinical Cancer Research, 24(3):560-568.
Sanchez et al. (Nov. 23, 2018) "New Insights into Structural Features and Optimal Detection of Circulating Tumor DNA Determined by Single-Strand DNA Analysis", NPJ Genomic Medicine, 3:12 pages.
Sausen et al. (Jan. 2013) "Integrated Genomic Analyses Identify ARID1A and ARID1B Alterations in the Childhood Cancer Neuroblastoma", Nature Genetics, 45(1):12-17.
Shen et al. (Nov. 22, 2018) "Sensitive Tumour Detection and Classification Using Plasma Cell-Free DNA Methylomes", Nature, 563:21 pages.
Sikaris et al. (2011) "CA125—A Test with a Change of Heart", Heart, Lung and Circulation, 20(10):634-640.
Siravegna et al. (2017) "Integrating Liquid Biopsies into the Management of Cancer", Nature Reviews Clinical Dncology, 14(9):531-548.
Snyder et al. (Jan. 14, 2016) "Cell-free DNA Comprises an In Vivo Nucleosome Footprint that Informs Its Tissues-Of-Origin", Cell, 164:57-68.
Sorscher (Mar. 9, 2017) "Pembrolizumab in Non-Small-Cell Lung Cancer", The New England Journal of Medicine, 376(10):996-997.
Sun et al. (2017) "Nivolumab Effectively Inhibit Platinum-Resistant Ovarian Cancer Cells via Induction of Cell Apoptosis and Inhibition of ADAM17 Expression", European Review for Medical and Pharmacological Sciences, 21:1198-1205.
Torre et al. (2015) "Global Cancer Statistics, 2012", CA: A Cancer Journal for Clinicians, 65(2):87-108.
Ulz et al. (Oct. 2016) "Inferring Expressed Genes by Whole-Genome Sequencing of Plasma DNA", Nature Genetics, 48(10):1273-1278.
Umetani et al. (Sep. 10, 2006) "Prediction of Breast Tumor Progression by Integrity of Free Circulating DNA in Serum", Journal of Clinical Oncology, 24(26):4270-4276.
Underhill et al. (Jul. 18, 2016) "Fragment Length of Circulating Tumor DNA", Plos Genetics, e1006162, 12(7): 24 pages.
Vansteenkiste et al. (Mar. 28, 2017) "Prospects and Progress of Atezolizumab in Nonsmall Cell Lung Cancer", Expert Opinion on Biological Therapy, 17(6):781-789.
Wan et al. (2017) "Liquid Biopsies Come of Age: Towards Implementation of Circulating Tumour DNA", Nature Reviews Cancer, 17(4):223-238.
Wanebo et al. (1978) "Preoperative Carcinoembryonic Antigen Level as a Prognostic Indicator in Colorectal Cancer", The New England Journal of Medicine, 299(9):448-451.
Wang et al. (Jul. 15, 2003) "Increased Plasma DNA Integrity in Cancer Patients", Cancer Research, 63:3966-3968.
Who (2017) "Guide to Cancer Early Diagnosis. Guide to Cancer Early Diagnosis", World Health Organization., Geneva, Switzerland, 42 pages.
Xie et al. (Dec. 2014) "Age-Related Mutations Associated with Clonal Hematopoietic Expansion and Malignancies", Nature Medicine, 20(12):1472-1478.
Yee et al. (Mar./Apr. 2017) "Personalized Therapy Tumor Antigen Discovery for Adoptive Cellular Therapy", The Cancer Journal, 23(2):144-148.
Zauber et al. (2015) "The Impact of Screening on Colorectal Cancer Mortality and Incidence: Has it Really Made a Difference?", Digestive Diseases and Sciences, 60(3):681-691.
Zou et al. (Feb. 28, 2017) "More Valuable than Platinum: First-Line Pembrolizumab in Advanced Stage Non-Small-Cell Lung Cancer", Annals of Oncology, 28(4):685-687.
International Search Report dated Sep. 5, 2019 in corresponding International Application No. PCT/US2019/032914 (3 pages).
F. Taylor et al., "Unbiased Detection of Somatic Copy Number Aberrations in cfDNA of Lung Cancer Cases and High-Risk Controls with Low Coverage Whole Genome Sequencing", Adv. Exp. Med. Biol. 2016;924:29-32, abstract, p. 30.
Written Opinion of the International Searching Authority dated Sep. 5, 2019 in corresponding PCT Application No. PCT/US2019/032914 (5 pages).

* cited by examiner

Chromosome 1

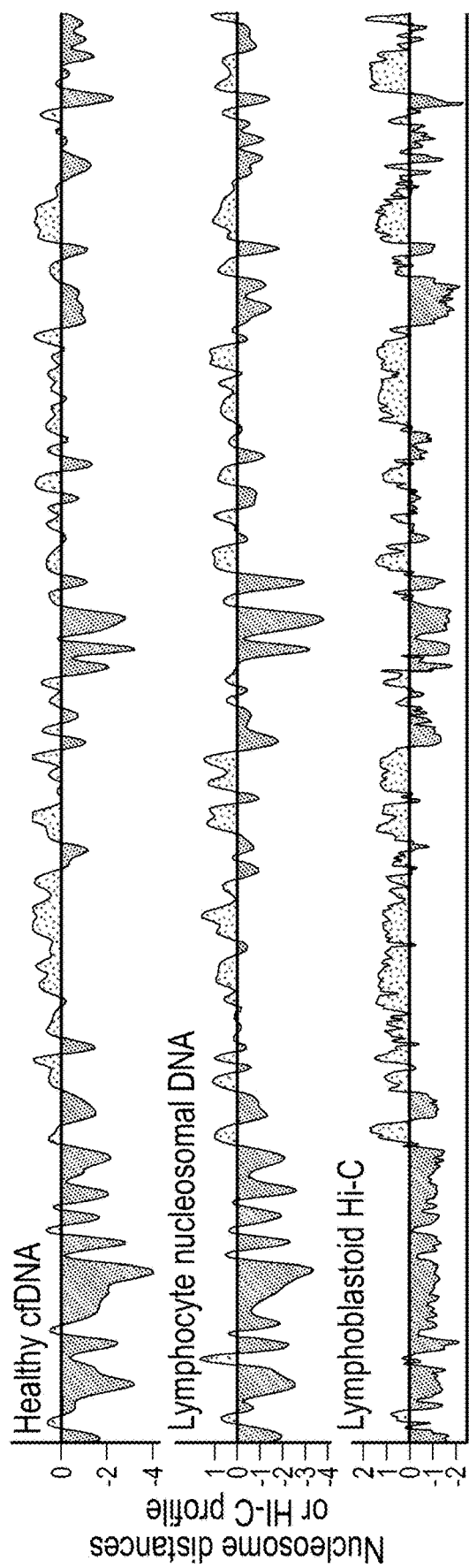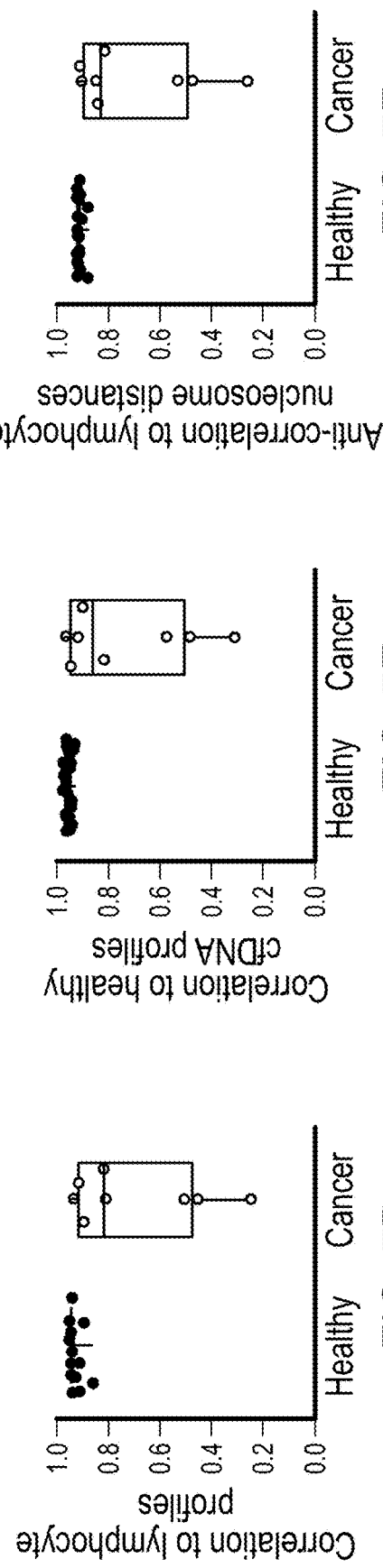

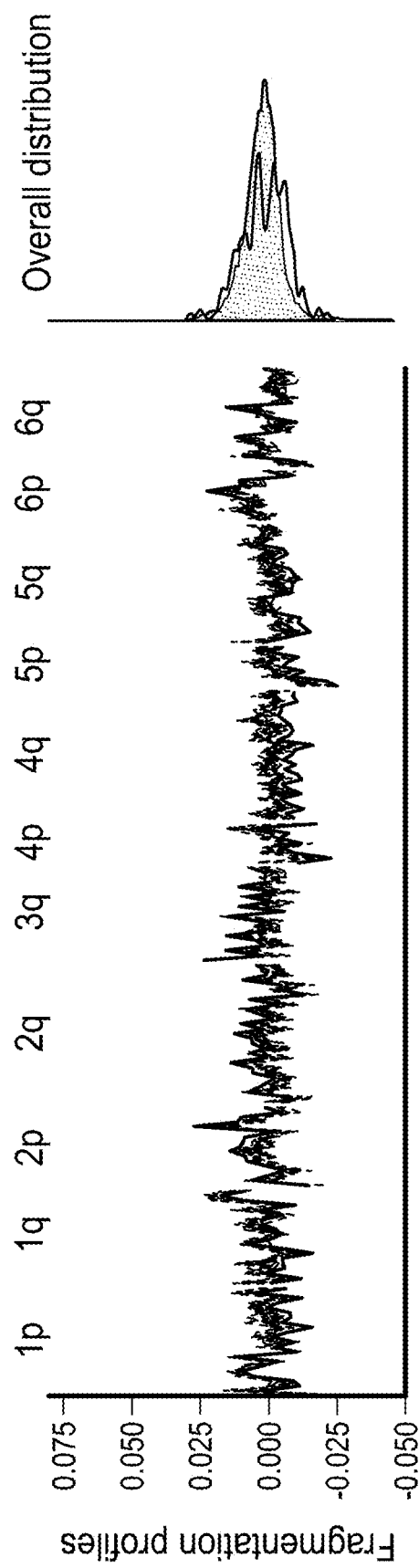
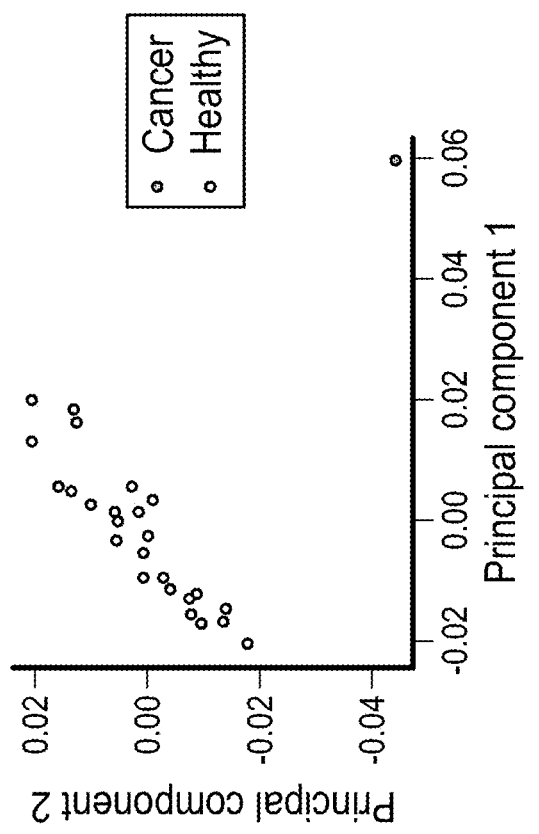
FIG. 12A
FIG. 12B

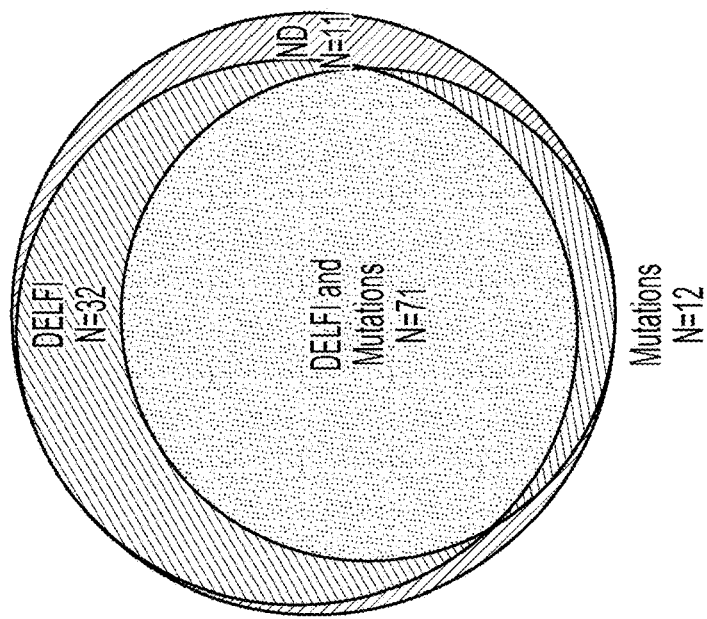

| Detection Approach* | Patients Analyzed | Patients Detected | Fraction of Patients Detected | 95% CI |
|---|---|---|---|---|
| DELFI | 126 | 103 | 82% | 74%-88% |
| Mutations | 126 | 83 | 66% | 57%-74% |
| DELFI and Mutations | 126 | 115 | 91% | 85%-96% |
| Stage I | 32 | 27 | 84% | 67%-95% |
| Stage II | 52 | 48 | 92% | 81%-98% |
| Stage III | 25 | 23 | 92% | 74%-99% |
| Stage IV | 16 | 16 | 100% | 79%-100% |

*Cancer Detection Using DELFI, Sequence Mutations, and the Combination of DELFI and Mutations was performed at Specificities of 98%, >99%, and 98%, respectively. Per Stage Sensitivities are included for all Cases Except for one Patient with Stage X.

FIG. 20

CELL-FREE DNA FOR ASSESSING AND/OR TREATING CANCER

CROSS-REFERENCE TO RELATED APPLICATIONS

This application is a continuation application of International Application No. PCT/US2019/032914, filed May 17, 2019, which claims the benefit of U.S. Patent Application Ser. No. 62/673,516, filed on May 18, 2018, and claims the benefit of U.S. Patent Application Ser. No. 62/795,900, filed on Jan. 23, 2019. The disclosure of the prior applications are considered part of (and are incorporated by reference in) the disclosure of this application.

STATEMENT REGARDING FEDERAL FUNDING

This invention was made with U.S. government support under grant No. CA121113 from the National Institutes of Health. The U.S. government has certain rights in the invention.

BACKGROUND

1. Technical Field

This document relates to methods and materials for assessing and/or treating mammals (e.g., humans) having cancer. For example, this document provides methods and materials for identifying a mammal as having cancer (e.g., a localized cancer). For example, this document provides methods and materials for monitoring and/or treating a mammal having cancer.

2. Background Information

Much of the morbidity and mortality of human cancers world-wide is a result of the late diagnosis of these diseases, where treatments are less effective (Torre et al., 2015 *CA Cancer J Clin* 65:87; and World Health Organization, 2017 *Guide to Cancer Early Diagnosis*). Unfortunately, clinically proven biomarkers that can be used to broadly diagnose and treat patients are not widely available (Mazzucchelli, 2000 *Advances in clinical pathology* 4:111; Ruibal Morell, 1992 *The International journal of biological markers* 7:160; Galli et al., 2013 *Clinical chemistry and laboratory medicine* 51:1369; Sikaris, 2011 *Heart, lung & circulation* 20:634; Lin et al., 2016 in *Screening for Colorectal Cancer: A Systematic Review for the U.S. Preventive Services Task Force*. (Rockville, Md.); Wanebo et al., 1978 N Engl J Med 299A48; and Zauber, 2015 *Dig Dis Sci* 60:681).

SUMMARY

Recent analyses of cell-free DNA suggests that such approaches may provide new avenues for early diagnosis (Phallen et al., 2017 *Sci Transl Med* 9; Cohen et al., 2018 *Science* 359:926; Alix-Panabieres et al., 2016 *Cancer discovery* 6:479; Siravegna et al., 2017 *Nature reviews. Clinical oncology* 14:531; Haber et al., 2014 *Cancer discovery* 4:650; Husain et al., 2017 *JAMA* 318:1272; and Wan et al., 2017 *Nat Rev Cancer* 17:223).

This document provides methods and materials for determining a cell free DNA (cfDNA) fragmentation profile in a mammal (e.g., in a sample obtained from a mammal). In some cases, determining a cfDNA fragmentation profile in a mammal can be used for identifying a mammal as having cancer. For example, cfDNA fragments obtained from a mammal (e.g., from a sample obtained from a mammal) can be subjected to low coverage whole-genome sequencing, and the sequenced fragments can be mapped to the genome (e.g., in non-overlapping windows) and assessed to determine a cfDNA fragmentation profile. This document also provides methods and materials for assessing and/or treating mammals (e.g., humans) having, or suspected of having, cancer. In some cases, this document provides methods and materials for identifying a mammal as having cancer. For example, a sample (e.g., a blood sample) obtained from a mammal can be assessed to determine if the mammal has cancer based, at least in part, on the cfDNA fragmentation profile. In some cases, this document provides methods and materials for monitoring and/or treating a mammal having cancer. For example, one or more cancer treatments can be administered to a mammal identified as having cancer (e.g., based, at least in part, on a cfDNA fragmentation profile) to treat the mammal.

Described herein is a non-invasive method for the early detection and localization of cancer. cfDNA in the blood can provide a non-invasive diagnostic avenue for patients with cancer. As demonstrated herein, DNA Evaluation of Fragments for early Interception (DELFI) was developed and used to evaluate genome-wide fragmentation patterns of cfDNA of 236 patients with breast, colorectal, lung, ovarian, pancreatic, gastric, or bile duct cancers as well as 245 healthy individuals. These analyses revealed that cfDNA profiles of healthy individuals reflected nucleosomal fragmentation patterns of white blood cells, while patients with cancer had altered fragmentation profiles. DELFI had sensitivities of detection ranging from 57% to >99% among the seven cancer types at 98% specificity and identified the tissue of origin of the cancers to a limited number of sites in 75% of cases. Assessing cfDNA (e.g., using DELFI) can provide a screening approach for early detection of cancer, which can increase the chance for successful treatment of a patient having cancer. Assessing cfDNA (e.g., using DELFI) can also provide an approach for monitoring cancer, which can increase the chance for successful treatment and improved outcome of a patient having cancer. In addition, a cfDNA fragmentation profile can be obtained from limited amounts of cfDNA and using inexpensive reagents and/or instruments.

In general, one aspect of this document features methods for determining a cfDNA fragmentation profile of a mammal. The methods can include, or consist essentially of, processing cfDNA fragments obtained from a sample obtained from the mammal into sequencing libraries, subjecting the sequencing libraries to whole genome sequencing (e.g., low-coverage whole genome sequencing) to obtain sequenced fragments, mapping the sequenced fragments to a genome to obtain windows of mapped sequences, and analyzing the windows of mapped sequences to determine cfDNA fragment lengths. The mapped sequences can include tens to thousands of windows. The windows of mapped sequences can be non-overlapping windows. The windows of mapped sequences can each include about 5 million base pairs. The cfDNA fragmentation profile can be determined within each window. The cfDNA fragmentation profile can include a median fragment size. The cfDNA fragmentation profile can include a fragment size distribution. The cfDNA fragmentation profile can include a ratio of small cfDNA fragments to large cfDNA fragments in the windows of mapped sequences. The cfDNA fragmentation profile can be over the whole genome. The cfDNA fragmentation profile can be over a subgenomic interval (e.g., an interval in a portion of a chromosome).

In another aspect, this document features methods for identifying a mammal as having cancer. The methods can include, or consist essentially of, determining a cfDNA fragmentation profile in a sample obtained from a mammal, comparing the cfDNA fragmentation profile to a reference cfDNA fragmentation profile, and identifying the mammal as having cancer when the cfDNA fragmentation profile in the sample obtained from the mammal is different from the reference cfDNA fragmentation profile. The reference cfDNA fragmentation profile can be a cfDNA fragmentation profile of a healthy mammal. The reference cfDNA fragmentation profile can be generated by determining a cfDNA fragmentation profile in a sample obtained from the healthy mammal. The reference DNA fragmentation pattern can be a reference nucleosome cfDNA fragmentation profile. The cfDNA fragmentation profiles can include a median fragment size, and a median fragment size of the cfDNA fragmentation profile can be shorter than a median fragment size of the reference cfDNA fragmentation profile. The cfDNA fragmentation profiles can include a fragment size distribution, and a fragment size distribution of the cfDNA fragmentation profile can differ by at least 10 nucleotides as compared to a fragment size distribution of the reference cfDNA fragmentation profile. The cfDNA fragmentation profiles can include position dependent differences in fragmentation patterns, including a ratio of small cfDNA fragments to large cfDNA fragments, where a small cfDNA fragment can be 100 base pairs (bp) to 150 bp in length and a large cfDNA fragments can be 151 bp to 220 bp in length, and where a correlation of fragment ratios in the cfDNA fragmentation profile can be lower than a correlation of fragment ratios of the reference cfDNA fragmentation profile. The cfDNA fragmentation profiles can include sequence coverage of small cfDNA fragments, large cfDNA fragments, or of both small and large cfDNA fragments, across the genome. The cancer can be colorectal cancer, lung cancer, breast cancer, bile duct cancer, pancreatic cancer, gastric cancer, or ovarian cancer. The step of comparing can include comparing the cfDNA fragmentation profile to a reference cfDNA fragmentation profile in windows across the whole genome. The step of comparing can include comparing the cfDNA fragmentation profile to a reference cfDNA fragmentation profile over a subgenomic interval (e.g., an interval in a portion of a chromosome). The mammal can have been previously administered a cancer treatment to treat the cancer. The cancer treatment can be surgery, adjuvant chemotherapy, neoadjuvant chemotherapy, radiation therapy, hormone therapy, cytotoxic therapy, immunotherapy, adoptive T cell therapy, targeted therapy, or any combinations thereof. The method also can include administering to the mammal a cancer treatment (e.g., surgery, adjuvant chemotherapy, neoadjuvant chemotherapy, radiation therapy, hormone therapy, cytotoxic therapy, immunotherapy, adoptive T cell therapy, targeted therapy, or any combinations thereof). The mammal can be monitored for the presence of cancer after administration of the cancer treatment.

In another aspect, this document features methods for treating a mammal having cancer. The methods can include, or consist essentially of, identifying the mammal as having cancer, where the identifying includes determining a cfDNA fragmentation profile in a sample obtained from the mammal, comparing the cfDNA fragmentation profile to a reference cfDNA fragmentation profile, and identifying the mammal as having cancer when the cfDNA fragmentation profile obtained from the mammal is different from the reference cfDNA fragmentation profile; and administering a cancer treatment to the mammal. The mammal can be a human. The cancer can be colorectal cancer, lung cancer, breast cancer, gastric cancers, pancreatic cancers, bile duct cancers, or ovarian cancer. The cancer treatment can be surgery, adjuvant chemotherapy, neoadjuvant chemotherapy, radiation therapy, hormone therapy, cytotoxic therapy, immunotherapy, adoptive T cell therapy, targeted therapy, or combinations thereof. The reference cfDNA fragmentation profile can be a cfDNA fragmentation profile of a healthy mammal. The reference cfDNA fragmentation profile can be generated by determining a cfDNA fragmentation profile in a sample obtained from a healthy mammal. The reference DNA fragmentation pattern can be a reference nucleosome cfDNA fragmentation profile. The cfDNA fragmentation profile can include a median fragment size, where a median fragment size of the cfDNA fragmentation profile is shorter than a median fragment size of the reference cfDNA fragmentation profile. The cfDNA fragmentation profile can include a fragment size distribution, where a fragment size distribution of the cfDNA fragmentation profile differs by at least 10 nucleotides as compared to a fragment size distribution of the reference cfDNA fragmentation profile. The cfDNA fragmentation profile can include a ratio of small cfDNA fragments to large cfDNA fragments in the windows of mapped sequences, where a small cfDNA fragment is 100 bp to 150 bp in length, where a large cfDNA fragments is 151 bp to 220 bp in length, and where a correlation of fragment ratios in the cfDNA fragmentation profile is lower than a correlation of fragment ratios of the reference cfDNA fragmentation profile. The cfDNA fragmentation profile can include the sequence coverage of small cfDNA fragments in windows across the genome. The cfDNA fragmentation profile can include the sequence coverage of large cfDNA fragments in windows across the genome. The cfDNA fragmentation profile can include the sequence coverage of small and large cfDNA fragments in windows across the genome. The step of comparing can include comparing the cfDNA fragmentation profile to a reference cfDNA fragmentation profile over the whole genome. The step of comparing can include comparing the cfDNA fragmentation profile to a reference cfDNA fragmentation profile over a subgenomic interval. The mammal can have previously been administered a cancer treatment to treat the cancer. The cancer treatment can be surgery, adjuvant chemotherapy, neoadjuvant chemotherapy, radiation therapy, hormone therapy, cytotoxic therapy, immunotherapy, adoptive T cell therapy, targeted therapy, or combinations thereof. The method also can include monitoring the mammal for the presence of cancer after administration of the cancer treatment.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the descrip-

DESCRIPTION OF THE DRAWINGS

FIGS. 7A-7F. cfDNA fragmentation profiles in healthy individuals and patients with cancer. A, Genome-wide cfDNA fragmentation profiles (defined as the ratio of short to long fragments) from ~9x whole genome sequencing are shown in 5 Mb bins for 30 healthy individuals (top) and 8 lung cancer patients (bottom). B, An analysis of healthy cfDNA (top), lung cancer cfDNA (middle), and healthy lymphocyte (bottom) fragmentation profiles and lymphocyte profiles from chromosome 1 at 1 Mb resolution. The healthy lymphocyte profiles were scaled with a standard deviation equal to that of the median healthy cfDNA profiles. Healthy cfDNA patterns closely mirrored those in healthy lymphocytes while lung cancer cfDNA profiles were more varied and differed from both healthy and lymphocyte profiles. C, Smoothed median distances between adjacent nucleosome centered at zero using 100 kb bins from healthy cfDNA (top) and nuclease-digested healthy lymphocytes (middle) are depicted together with the first eigenvector for the genome contact matrix obtained through previously reported Hi-C analyses of lymphoblastoid cells (bottom). Healthy cfDNA nucleosome distances closely mirrored those in nuclease-digested lymphocytes as well as those from lymphoblastoid Hi-C analyses. cfDNA fragmentation profiles from healthy individuals (n=30) had high correlations while patients with lung cancer had lower correlations to median fragmentation profiles of lymphocytes (D), healthy cfDNA (E), and lymphocyte nucleosome (F) distances.

FIGS. 12A and 12B. Profiles of cfDNA fragment lengths in copy neutral regions in healthy individuals and one patient with colorectal cancer. A, The fragmentation profile in 211 copy neutral windows in chromosomes 1-6 for 25 randomly selected healthy individuals (gray). For a patient with colorectal cancer (CGCRC291) with an estimated mutant allele fraction of 20%, the cancer fragment length profile was diluted to an approximate 10% tumor contribution (blue). A and B, While the marginal densities of the fragment profiles for the healthy samples and cancer patient show substantial overlap (A, right), the fragmentation profiles are different as can be seen visualization of the fragmentation profiles (A, left) and by the separation of the colorectal cancer patient from the healthy samples in a principal component analysis (B).

FIG. 20. Detection of cancer using DELFI and mutation-based cfDNA approaches. DELFI (green) and targeted sequencing for mutation identification (blue) were performed independently in a cohort of 126 patients with breast, bile duct, colorectal, gastric, lung, or ovarian cancers. The number of individuals detected by each approach and in combination are indicated for DELFI detection with a specificity of 98%, targeted sequencing specificity at >99%, and a combined specificity of 98%. ND indicates not detected.

DETAILED DESCRIPTION

Figure 1:
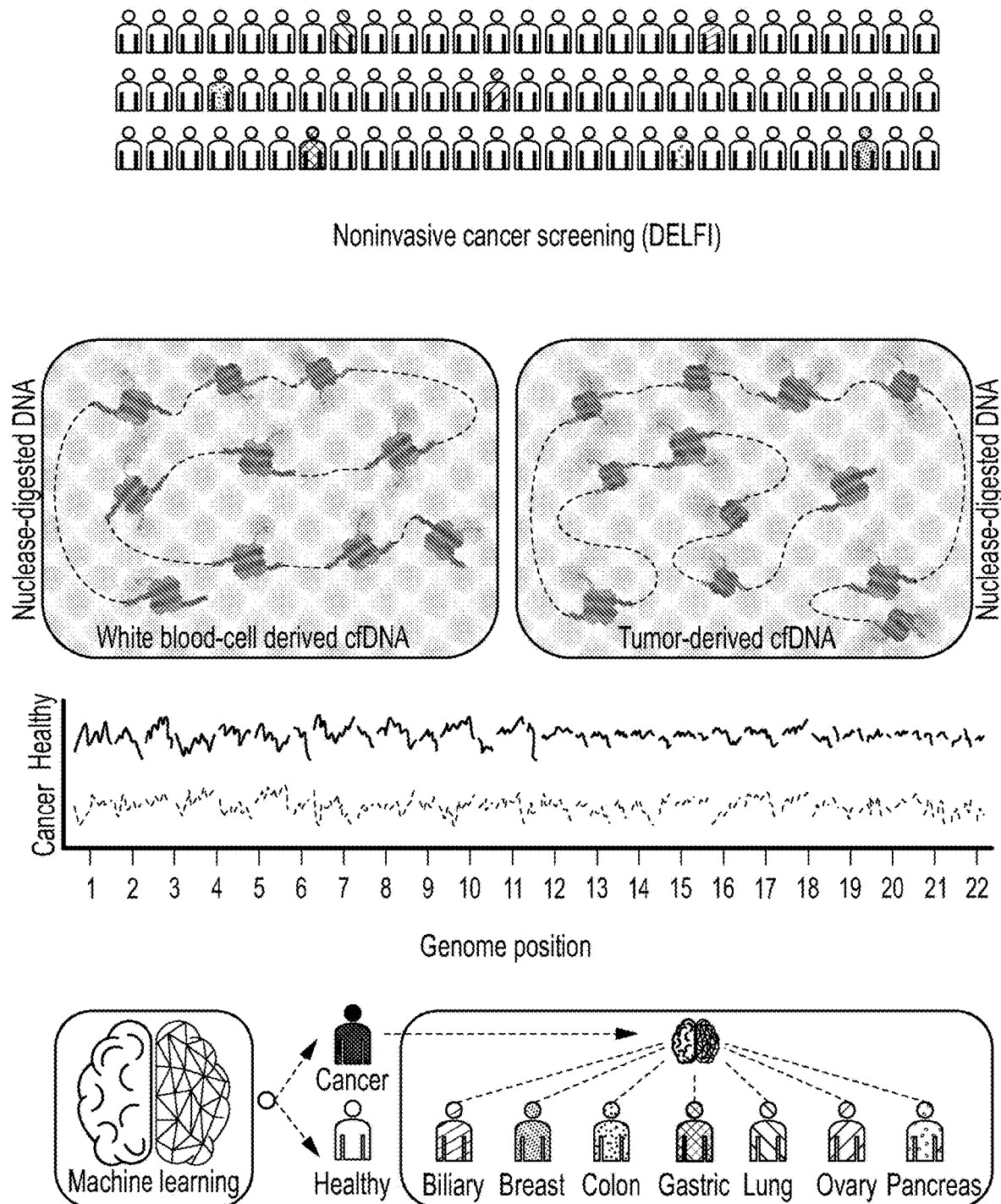
FIG. 1. Schematic of an exemplary DELFI approach. Blood is collected from a cohort of healthy individuals and patients with cancer. Nucleosome protected cfDNA is extracted from the plasma fraction, processed into sequencing libraries, examined through whole genome sequencing, mapped to the genome, and analyzed to determine cfDNA fragment profiles in different windows across the genome. Machine learning approaches are used to categorize individuals as healthy or as having cancer and to identify the tumor tissue of origin using genome-wide cfDNA fragmentation patterns.

This document provides methods and materials for determining a cfDNA fragmentation profile in a mammal (e.g., in a sample obtained from a mammal). As used herein, the terms "fragmentation profile," "position dependent differences in fragmentation patterns," and "differences in fragment size and coverage in a position dependent manner across the genome" are equivalent and can be used interchangeably. In some cases, determining a cfDNA fragmentation profile in a mammal can be used for identifying a mammal as having cancer. For example, cfDNA fragments obtained from a mammal (e.g., from a sample obtained from a mammal) can be subjected to low coverage whole-genome sequencing, and the sequenced fragments can be mapped to the genome (e.g., in non-overlapping windows) and assessed to determine a cfDNA fragmentation profile. As described herein, a cfDNA fragmentation profile of a mammal having cancer is more heterogeneous (e.g., in fragment lengths) than a cfDNA fragmentation profile of a healthy mammal (e.g., a mammal not having cancer). As such, this document also provides methods and materials for assessing, monitoring, and/or treating mammals (e.g., humans) having, or suspected of having, cancer. In some cases, this document provides methods and materials for identifying a mammal as having cancer. For example, a sample (e.g., a blood sample) obtained from a mammal can be assessed to determine the presence and, optionally, the tissue of origin of the cancer in the mammal based, at least in part, on the cfDNA fragmentation profile of the mammal. In some cases, this document provides methods and materials for monitoring a mammal as having cancer. For example, a sample (e.g., a blood sample) obtained from a mammal can be assessed to determine the presence of the cancer in the mammal based, at least in part, on the cfDNA fragmentation profile of the mammal. In some cases, this document provides methods and materials for identifying a mammal as having cancer, and administering one or more cancer treatments to the mammal to treat the mammal. For example, a sample (e.g., a blood sample) obtained from a mammal can be assessed to determine if the mammal has cancer based, at least in part, on the cfDNA fragmentation profile of the mammal, and one or more cancer treatments can be administered to the mammal.

A cfDNA fragmentation profile can include one or more cfDNA fragmentation patterns. A cfDNA fragmentation pattern can include any appropriate cfDNA fragmentation pattern. Examples of cfDNA fragmentation patterns include, without limitation, median fragment size, fragment size distribution, ratio of small cfDNA fragments to large cfDNA fragments, and the coverage of cfDNA fragments. In some cases, a cfDNA fragmentation pattern includes two or more (e.g., two, three, or four) of median fragment size, fragment size distribution, ratio of small cfDNA fragments to large cfDNA fragments, and the coverage of cfDNA fragments. In some cases, cfDNA fragmentation profile can be a genome-wide cfDNA profile (e.g., a genome-wide cfDNA profile in windows across the genome). In some cases, cfDNA fragmentation profile can be a targeted region profile. A targeted region can be any appropriate portion of the genome (e.g., a chromosomal region). Examples of chromosomal regions for which a cfDNA fragmentation profile can be determined as described herein include, without limitation, a portion of a chromosome (e.g., a portion of 2q, 4p, 5p, 6q, 7p, 8q, 9q, 10q, 11q, 12q, and/or 14q) and a chromosomal arm (e.g., a chromosomal arm of 8q, 13q, 11q, and/or 3p). In some cases, a cfDNA fragmentation profile can include two or more targeted region profiles.

In some cases, a cfDNA fragmentation profile can be used to identify changes (e.g., alterations) in cfDNA fragment lengths. An alteration can be a genome-wide alteration or an alteration in one or more targeted regions/loci. A target region can be any region containing one or more cancer-specific alterations. Examples of cancer-specific alterations, and their chromosomal locations, include, without limitation, those shown in Table 3 (Appendix C) and those shown in Table 6 (Appendix F). In some cases, a cfDNA fragmentation profile can be used to identify (e.g., simultaneously identify) from about 10 alterations to about 500 alterations (e.g., from about 25 to about 500, from about 50 to about 500, from about 100 to about 500, from about 200 to about 500, from about 300 to about 500, from about 10 to about 400, from about 10 to about 300, from about 10 to about 200, from about 10 to about 100, from about 10 to about 50, from about 20 to about 400, from about 30 to about 300, from about 40 to about 200, from about 50 to about 100, from about 20 to about 100, from about 25 to about 75, from about 50 to about 250, or from about 100 to about 200, alterations).

In some cases, a cfDNA fragmentation profile can be used to detect tumor-derived DNA. For example, a cfDNA fragmentation profile can be used to detect tumor-derived DNA by comparing a cfDNA fragmentation profile of a mammal having, or suspected of having, cancer to a reference cfDNA fragmentation profile (e.g., a cfDNA fragmentation profile of a healthy mammal and/or a nucleosomal DNA fragmentation profile of healthy cells from the mammal having, or suspected of having, cancer). In some cases, a reference cfDNA fragmentation profile is a previously generated profile from a healthy mammal. For example, methods provided herein can be used to determine a reference cfDNA fragmentation profile in a healthy mammal, and that reference cfDNA fragmentation profile can be stored (e.g., in a computer or other electronic storage medium) for future comparison to a test cfDNA fragmentation profile in mammal having, or suspected of having, cancer. In some cases, a reference cfDNA fragmentation profile (e.g., a stored cfDNA fragmentation profile) of a healthy mammal is determined over the whole genome. In some cases, a reference cfDNA fragmentation profile (e.g., a stored cfDNA fragmentation profile) of a healthy mammal is determined over a subgenomic interval.

In some cases, a cfDNA fragmentation profile can be used to identify a mammal (e.g., a human) as having cancer (e.g., a colorectal cancer, a lung cancer, a breast cancer, a gastric cancer, a pancreatic cancer, a bile duct cancer, and/or an ovarian cancer).

A cfDNA fragmentation profile can include a cfDNA fragment size pattern. cfDNA fragments can be any appropriate size. For example, cfDNA fragment can be from about 50 base pairs (bp) to about 400 bp in length. As described herein, a mammal having cancer can have a cfDNA fragment size pattern that contains a shorter median cfDNA fragment size than the median cfDNA fragment size in a healthy mammal. A healthy mammal (e.g., a mammal not having cancer) can have cfDNA fragment sizes having a median cfDNA fragment size from about 166.6 bp to about 167.2 bp (e.g., about 166.9 bp). In some cases, a mammal having cancer can have cfDNA fragment sizes that are, on average, about 1.28 bp to about 2.49 bp (e.g., about 1.88 bp) shorter than cfDNA fragment sizes in a healthy mammal. For example, a mammal having cancer can have cfDNA fragment sizes having a median cfDNA fragment size of about 164.11 bp to about 165.92 bp (e.g., about 165.02 bp).

A cfDNA fragmentation profile can include a cfDNA fragment size distribution. As described herein, a mammal having cancer can have a cfDNA size distribution that is more variable than a cfDNA fragment size distribution in a healthy mammal. In some case, a size distribution can be within a targeted region. A healthy mammal (e.g., a mammal not having cancer) can have a targeted region cfDNA fragment size distribution of about 1 or less than about 1. In some cases, a mammal having cancer can have a targeted region cfDNA fragment size distribution that is longer (e.g., 10, 15, 20, 25, 30, 35, 40, 45, 50 or more bp longer, or any number of base pairs between these numbers) than a targeted region cfDNA fragment size distribution in a healthy mammal. In some cases, a mammal having cancer can have a targeted region cfDNA fragment size distribution that is shorter (e.g., 10, 15, 20, 25, 30, 35, 40, 45, 50 or more bp shorter, or any number of base pairs between these numbers) than a targeted region cfDNA fragment size distribution in a healthy mammal. In some cases, a mammal having cancer can have a targeted region cfDNA fragment size distribution that is about 47 bp smaller to about 30 bp longer than a targeted region cfDNA fragment size distribution in a healthy mammal. In some cases, a mammal having cancer can have a targeted region cfDNA fragment size distribution of, on average, a 10, 11, 12, 13, 14, 15, 15, 17, 18, 19, 20 or more bp difference in lengths of cfDNA fragments. For example, a mammal having cancer can have a targeted region cfDNA fragment size distribution of, on average, about a 13 bp difference in lengths of cfDNA fragments. In some case, a size distribution can be a genome-wide size distribution. A healthy mammal (e.g., a mammal not having cancer) can have very similar distributions of short and long cfDNA fragments genome-wide. In some cases, a mammal having cancer can have, genome-wide, one or more alterations (e.g., increases and decreases) in cfDNA fragment sizes. The one or more alterations can be any appropriate chromosomal region of the genome. For example, an alteration can be in a portion of a chromosome. Examples of portions of chromosomes that can contain one or more alterations in cfDNA fragment sizes include, without limitation, portions of 2q, 4p, 5p, 6q, 7p, 8q, 9q, 10q, 11q, 12q, and 14q. For example, an alteration can be across a chromosome arm (e.g., an entire chromosome arm).

A cfDNA fragmentation profile can include a ratio of small cfDNA fragments to large cfDNA fragments and a correlation of fragment ratios to reference fragment ratios. As used herein, with respect to ratios of small cfDNA fragments to large cfDNA fragments, a small cfDNA fragment can be from about 100 bp in length to about 150 bp in length. As used herein, with respect to ratios of small cfDNA fragments to large cfDNA fragments, a large cfDNA fragment can be from about 151 bp in length to 220 bp in length. As described herein, a mammal having cancer can have a correlation of fragment ratios (e.g., a correlation of cfDNA fragment ratios to reference DNA fragment ratios such as DNA fragment ratios from one or more healthy mammals) that is lower (e.g., 2-fold lower, 3-fold lower, 4-fold lower, 5-fold lower, 6-fold lower, 7-fold lower, 8-fold lower, 9-fold lower, 10-fold lower, or more) than in a healthy mammal. A healthy mammal (e.g., a mammal not having cancer) can have a correlation of fragment ratios (e.g., a correlation of cfDNA fragment ratios to reference DNA fragment ratios such as DNA fragment ratios from one or more healthy mammals) of about 1 (e.g., about 0.96). In some cases, a mammal having cancer can have a correlation of fragment ratios (e.g., a correlation of cfDNA fragment ratios to reference DNA fragment ratios such as DNA fragment ratios from one or more healthy mammals) that is, on average, about 0.19 to about 0.30 (e.g., about 0.25) lower than a correlation of fragment ratios (e.g., a correlation of cfDNA fragment ratios to reference DNA fragment ratios such as DNA fragment ratios from one or more healthy mammals) in a healthy mammal.

A cfDNA fragmentation profile can include coverage of all fragments. Coverage of all fragments can include windows (e.g., non-overlapping windows) of coverage. In some cases, coverage of all fragments can include windows of small fragments (e.g., fragments from about 100 bp to about 150 bp in length). In some cases, coverage of all fragments can include windows of large fragments (e.g., fragments from about 151 bp to about 220 bp in length).

In some cases, a cfDNA fragmentation profile can be used to identify the tissue of origin of a cancer (e.g., a colorectal cancer, a lung cancer, a breast cancer, a gastric cancer, a pancreatic cancer, a bile duct cancer, or an ovarian cancer). For example, a cfDNA fragmentation profile can be used to identify a localized cancer. When a cfDNA fragmentation profile includes a targeted region profile, one or more alterations described herein (e.g., in Table 3 (Appendix C) and/or in Table 6 (Appendix F)) can be used to identify the tissue of origin of a cancer. In some cases, one or more alterations in chromosomal regions can be used to identify the tissue of origin of a cancer.

A cfDNA fragmentation profile can be obtained using any appropriate method. In some cases, cfDNA from a mammal (e.g., a mammal having, or suspected of having, cancer) can be processed into sequencing libraries which can be subjected to whole genome sequencing (e.g., low-coverage whole genome sequencing), mapped to the genome, and analyzed to determine cfDNA fragment lengths. Mapped sequences can be analyzed in non-overlapping windows covering the genome. Windows can be any appropriate size. For example, windows can be from thousands to millions of bases in length. As one non-limiting example, a window can be about 5 megabases (Mb) long. Any appropriate number of windows can be mapped. For example, tens to thousands of windows can be mapped in the genome. For example, hundreds to thousands of windows can be mapped in the genome. A cfDNA fragmentation profile can be determined within each window. In some cases, a cfDNA fragmentation profile can be obtained as described in Example 1. In some cases, a cfDNA fragmentation profile can be obtained as shown in FIG. 1.

In some cases, methods and materials described herein also can include machine learning. For example, machine learning can be used for identifying an altered fragmentation profile (e.g., using coverage of cfDNA fragments, fragment size of cfDNA fragments, coverage of chromosomes, and mtDNA).

In some cases, methods and materials described herein can be the sole method used to identify a mammal (e.g., a human) as having cancer (e.g., a colorectal cancer, a lung cancer, a breast cancer, a gastric cancer, a pancreatic cancer, a bile duct cancer, and/or an ovarian cancer). For example, determining a cfDNA fragmentation profile can be the sole method used to identify a mammal as having cancer.

In some cases, methods and materials described herein can be used together with one or more additional methods used to identify a mammal (e.g., a human) as having cancer (e.g., a colorectal cancer, a lung cancer, a breast cancer, a gastric cancer, a pancreatic cancer, a bile duct cancer, and/or an ovarian cancer). Examples of methods used to identify a mammal as having cancer include, without limitation, identifying one or more cancer-specific sequence alterations, identifying one or more chromosomal alterations (e.g., aneuploidies and rearrangements), and identifying other cfDNA alterations. For example, determining a cfDNA fragmentation profile can be used together with identifying one or more cancer-specific mutations in a mammal's genome to identify a mammal as having cancer. For example, determining a cfDNA fragmentation profile can be used together with identifying one or more aneuploidies in a mammal's genome to identify a mammal as having cancer.

In some aspects, this document also provides methods and materials for assessing, monitoring, and/or treating mammals (e.g., humans) having, or suspected of having, cancer. In some cases, this document provides methods and materials for identifying a mammal as having cancer. For example, a sample (e.g., a blood sample) obtained from a mammal can be assessed to determine if the mammal has cancer based, at least in part, on the cfDNA fragmentation profile of the mammal. In some cases, this document provides methods and materials for identifying the location (e.g., the anatomic site or tissue of origin) of a cancer in a mammal. For example, a sample (e.g., a blood sample) obtained from a mammal can be assessed to determine the tissue of origin of the cancer in the mammal based, at least in part, on the cfDNA fragmentation profile of the mammal. In some cases, this document provides methods and materials for identifying a mammal as having cancer, and administering one or more cancer treatments to the mammal to treat the mammal. For example, a sample (e.g., a blood sample) obtained from a mammal can be assessed to determine if the mammal has cancer based, at least in part, on the cfDNA fragmentation profile of the mammal, and administering one or more cancer treatments to the mammal. In some cases, this document provides methods and materials for treating a mammal having cancer. For example, one or more cancer treatments can be administered to a mammal identified as having cancer (e.g., based, at least in part, on the cfDNA fragmentation profile of the mammal) to treat the mammal. In some cases, during or after the course of a cancer treatment (e.g., any of the cancer treatments described herein), a mammal can undergo monitoring (or be selected for increased monitoring) and/or further diagnostic testing. In some cases, monitoring can include assessing mammals having, or suspected of having, cancer by, for example, assessing a sample (e.g., a blood sample) obtained from the mammal to determine the cfDNA fragmentation profile of the mammal as described herein, and changes in the cfDNA fragmentation profiles over time can be used to identify response to treatment and/or identify the mammal as having cancer (e.g., a residual cancer).

Any appropriate mammal can be assessed, monitored, and/or treated as described herein. A mammal can be a mammal having cancer. A mammal can be a mammal suspected of having cancer. Examples of mammals that can be assessed, monitored, and/or treated as described herein include, without limitation, humans, primates such as monkeys, dogs, cats, horses, cows, pigs, sheep, mice, and rats. For example, a human having, or suspected of having, cancer can be assessed to determine a cfDNA fragmentation profiled as described herein and, optionally, can be treated with one or more cancer treatments as described herein.

Any appropriate sample from a mammal can be assessed as described herein (e.g., assessed for a DNA fragmentation pattern). In some cases, a sample can include DNA (e.g., genomic DNA). In some cases, a sample can include cfDNA (e.g., circulating tumor DNA (ctDNA)). In some cases, a sample can be fluid sample (e.g., a liquid biopsy). Examples of samples that can contain DNA and/or polypeptides include, without limitation, blood (e.g., whole blood, serum, or plasma), amnion, tissue, urine, cerebrospinal fluid, saliva, sputum, broncho-alveolar lavage, bile, lymphatic fluid, cyst fluid, stool, ascites, pap smears, breast milk, and exhaled breath condensate. For example, a plasma sample can be assessed to determine a cfDNA fragmentation profiled as described herein.

A sample from a mammal to be assessed as described herein (e.g., assessed for a DNA fragmentation pattern) can include any appropriate amount of cfDNA. In some cases, a sample can include a limited amount of DNA. For example, a cfDNA fragmentation profile can be obtained from a sample that includes less DNA than is typically required for other cfDNA analysis methods, such as those described in, for example, Phallen et al., 2017 *Sci Transl Med* 9; Cohen et al., 2018 *Science* 359:926; Newman et al., 2014 *Nat Med* 20:548; and Newman et al., 2016 *Nat Biotechnol* 34:547).

In some cases, a sample can be processed (e.g., to isolate and/or purify DNA and/or polypeptides from the sample). For example, DNA isolation and/or purification can include cell lysis (e.g., using detergents and/or surfactants), protein removal (e.g., using a protease), and/or RNA removal (e.g., using an RNase). As another example, polypeptide isolation and/or purification can include cell lysis (e.g., using detergents and/or surfactants), DNA removal (e.g., using a DNase), and/or RNA removal (e.g., using an RNase).

A mammal having, or suspected of having, any appropriate type of cancer can be assessed (e.g., to determine a cfDNA fragmentation profile) and/or treated (e.g., by administering one or more cancer treatments to the mammal) using the methods and materials described herein. A cancer can be any stage cancer. In some cases, a cancer can be an early stage cancer. In some cases, a cancer can be an asymptomatic cancer. In some cases, a cancer can be a residual disease and/or a recurrence (e.g., after surgical resection and/or after cancer therapy). A cancer can be any type of cancer. Examples of types of cancers that can be assessed, monitored, and/or treated as described herein include, without limitation, colorectal cancers, lung cancers, breast cancers, gastric cancers, pancreatic cancers, bile duct cancers, and ovarian cancers.

When treating a mammal having, or suspected of having, cancer as described herein, the mammal can be administered one or more cancer treatments. A cancer treatment can be any appropriate cancer treatment. One or more cancer treatments described herein can be administered to a mammal at any appropriate frequency (e.g., once or multiple times over a period of time ranging from days to weeks). Examples of cancer treatments include, without limitation adjuvant chemotherapy, neoadjuvant chemotherapy, radiation therapy, hormone therapy, cytotoxic therapy, immunotherapy, adoptive T cell therapy (e.g., chimeric antigen receptors and/or T cells having wild-type or modified T cell receptors), targeted therapy such as administration of kinase inhibitors (e.g., kinase inhibitors that target a particular genetic lesion, such as a translocation or mutation), (e.g. a kinase inhibitor, an antibody, a bispecific antibody), signal transduction inhibitors, bispecific antibodies or antibody fragments (e.g., BiTEs), monoclonal antibodies, immune checkpoint inhibitors, surgery (e.g., surgical resection), or any combination of the above. In some cases, a cancer treatment can reduce the severity of the cancer, reduce a symptom of the cancer, and/or to reduce the number of cancer cells present within the mammal.

In some cases, a cancer treatment can include an immune checkpoint inhibitor. Non-limiting examples of immune checkpoint inhibitors include nivolumab (Opdivo), pembrolizumab (Keytruda), atezolizumab (tecentriq), avelumab (bavencio), durvalumab (imfinzi), ipilimumab (yervoy). See, e.g., Pardoll (2012) Nat. Rev Cancer 12: 252-264; Sun et al. (2017) Eur Rev Med Pharmacol Sci 21(6): 1198-1205; Hamanishi et al. (2015) J. Clin. Oncol. 33(34): 4015-22; Brahmer et al. (2012) N Engl J Med 366(26): 2455-65; Ricciuti et al. (2017) J. Thorac Oncol. 12(5): e51-e55; Ellis et al. (2017) Clin Lung Cancer pii: S1525-7304(17)30043-8; Zou and Awad (2017) Ann Oncol 28(4): 685-687; Sorscher (2017) N Engl J Med 376(10: 996-7; Hui et al. (2017) Ann Oncol 28(4): 874-881; Vansteenkiste et al. (2017) Expert Opin Biol Ther 17(6): 781-789; Hellmann et al. (2017) Lancet Oncol. 18(1): 31-41; Chen (2017) J. Chin Med Assoc 80(1): 7-14.

In some cases, a cancer treatment can be an adoptive T cell therapy (e.g., chimeric antigen receptors and/or T cells having wild-type or modified T cell receptors). See, e.g., Rosenberg and Restifo (2015) Science 348(6230): 62-68; Chang and Chen (2017) Trends Mol Med 23(5): 430-450; Yee and Lizee (2016) Cancer J. 23(2): 144-148; Chen et al.

(2016) Oncoimmunology 6(2): e1273302; US 2016/0194404; US 2014/0050788; US 2014/0271635; U.S. Pat. No. 9,233,125; incorporated by reference in their entirety herein.

In some cases, a cancer treatment can be a chemotherapeutic agent. Non-limiting examples of chemotherapeutic agents include: amsacrine, azacitidine, axathioprine, bevacizumab (or an antigen-binding fragment thereof), bleomycin, busulfan, carboplatin, capecitabine, chlorambucil, cisplatin, cyclophosphamide, cytarabine, dacarbazine, daunorubicin, docetaxel, doxifluridine, doxorubicin, epirubicin, erlotinib hydrochlorides, etoposide, fiudarabine, floxuridine, fludarabine, fluorouracil, gemcitabine, hydroxyurea, idarubicin, ifosfamide, irinotecan, lomustine, mechlorethamine, melphalan, mercaptopurine, methotrxate, mitomycin, mitoxantrone, oxaliplatin, paclitaxel, pemetrexed, procarbazine, all-trans retinoic acid, streptozocin, tafluposide, temozolomide, teniposide, tioguanine, topotecan, uramustine, valrubicin, vinblastine, vincristine, vindesine, vinorelbine, and combinations thereof. Additional examples of anti-cancer therapies are known in the art; see, e.g. the guidelines for therapy from the American Society of Clinical Oncology (ASCO), European Society for Medical Oncology (ESMO), or National Comprehensive Cancer Network (NCCN).

When monitoring a mammal having, or suspected of having, cancer as described herein (e.g., based, at least in part, on the cfDNA fragmentation profile of the mammal), the monitoring can be before, during, and/or after the course of a cancer treatment. Methods of monitoring provided herein can be used to determine the efficacy of one or more cancer treatments and/or to select a mammal for increased monitoring. In some cases, the monitoring can include identifying a cfDNA fragmentation profile as described herein. For example, a cfDNA fragmentation profile can be obtained before administering one or more cancer treatments to a mammal having, or suspected or having, cancer, one or more cancer treatments can be administered to the mammal, and one or more cfDNA fragmentation profiles can be obtained during the course of the cancer treatment. In some cases, a cfDNA fragmentation profile can change during the course of cancer treatment (e.g., any of the cancer treatments described herein). For example, a cfDNA fragmentation profile indicative that the mammal has cancer can change to a cfDNA fragmentation profile indicative that the mammal does not have cancer. Such a cfDNA fragmentation profile change can indicate that the cancer treatment is working. Conversely, a cfDNA fragmentation profile can remain static (e.g., the same or approximately the same) during the course of cancer treatment (e.g., any of the cancer treatments described herein). Such a static cfDNA fragmentation profile can indicate that the cancer treatment is not working. In some cases, the monitoring can include conventional techniques capable of monitoring one or more cancer treatments (e.g., the efficacy of one or more cancer treatments). In some cases, a mammal selected for increased monitoring can be administered a diagnostic test (e.g., any of the diagnostic tests disclosed herein) at an increased frequency compared to a mammal that has not been selected for increased monitoring. For example, a mammal selected for increased monitoring can be administered a diagnostic test at a frequency of twice daily, daily, bi-weekly, weekly, bi-monthly, monthly, quarterly, semi-annually, annually, or any at frequency therein. In some cases, a mammal selected for increased monitoring can be administered a one or more additional diagnostic tests compared to a mammal that has not been selected for increased monitoring. For example, a mammal selected for increased monitoring can be administered two diagnostic tests, whereas a mammal that has not been selected for increased monitoring is administered only a single diagnostic test (or no diagnostic tests). In some cases, a mammal that has been selected for increased monitoring can also be selected for further diagnostic testing. Once the presence of a tumor or a cancer (e.g., a cancer cell) has been identified (e.g., by any of the variety of methods disclosed herein), it may be beneficial for the mammal to undergo both increased monitoring (e.g., to assess the progression of the tumor or cancer in the mammal and/or to assess the development of one or more cancer biomarkers such as mutations), and further diagnostic testing (e.g., to determine the size and/or exact location (e.g., tissue of origin) of the tumor or the cancer). In some cases, one or more cancer treatments can be administered to the mammal that is selected for increased monitoring after a cancer biomarker is detected and/or after the cfDNA fragmentation profile of the mammal has not improved or deteriorated. Any of the cancer treatments disclosed herein or known in the art can be administered. For example, a mammal that has been selected for increased monitoring can be further monitored, and a cancer treatment can be administered if the presence of the cancer cell is maintained throughout the increased monitoring period. Additionally or alternatively, a mammal that has been selected for increased monitoring can be administered a cancer treatment, and further monitored as the cancer treatment progresses. In some cases, after a mammal that has been selected for increased monitoring has been administered a cancer treatment, the increased monitoring will reveal one or more cancer biomarkers (e.g., mutations). In some cases, such one or more cancer biomarkers will provide cause to administer a different cancer treatment (e.g., a resistance mutation may arise in a cancer cell during the cancer treatment, which cancer cell harboring the resistance mutation is resistant to the original cancer treatment).

When a mammal is identified as having cancer as described herein (e.g., based, at least in part, on the cfDNA fragmentation profile of the mammal), the identifying can be before and/or during the course of a cancer treatment. Methods of identifying a mammal as having cancer provided herein can be used as a first diagnosis to identify the mammal (e.g., as having cancer before any course of treatment) and/or to select the mammal for further diagnostic testing. In some cases, once a mammal has been determined to have cancer, the mammal may be administered further tests and/or selected for further diagnostic testing. In some cases, methods provided herein can be used to select a mammal for further diagnostic testing at a time period prior to the time period when conventional techniques are capable of diagnosing the mammal with an early-stage cancer. For example, methods provided herein for selecting a mammal for further diagnostic testing can be used when a mammal has not been diagnosed with cancer by conventional methods and/or when a mammal is not known to harbor a cancer. In some cases, a mammal selected for further diagnostic testing can be administered a diagnostic test (e.g., any of the diagnostic tests disclosed herein) at an increased frequency compared to a mammal that has not been selected for further diagnostic testing. For example, a mammal selected for further diagnostic testing can be administered a diagnostic test at a frequency of twice daily, daily, bi-weekly, weekly, bi-monthly, monthly, quarterly, semi-annually, annually, or any at frequency therein. In some cases, a mammal selected for further diagnostic testing can be administered a one or more additional diagnostic tests compared to a mammal that has not been selected for further diagnostic testing. For example, a mammal selected for further diagnostic testing can be administered two diagnostic tests, whereas a mammal that has not been selected for further diagnostic testing is administered only a single diagnostic test (or no diagnostic tests). In some cases, the diagnostic testing method can determine the presence of the same type of cancer (e.g., having the same tissue or origin) as the cancer that was originally detected (e.g., based, at least in part, on the cfDNA fragmentation profile of the mammal). Additionally or alternatively, the diagnostic testing method can determine the presence of a different type of cancer as the cancer that was original detected. In some cases, the diagnostic testing method is a scan. In some cases, the scan is a computed tomography (CT), a CT angiography (CTA), a esophagram (a Barium swallom), a Barium enema, a magnetic resonance imaging (MRI), a PET scan, an ultrasound (e.g., an endobronchial ultrasound, an endoscopic ultrasound), an X-ray, a DEXA scan. In some cases, the diagnostic testing method is a physical examination, such as an anoscopy, a bronchoscopy (e.g., an autofluorescence bronchoscopy, a white-light bronchoscopy, a navigational bronchoscopy), a colonoscopy, a digital breast tomosynthesis, an endoscopic retrograde cholangiopancreatography (ERCP), an ensophagogastroduodenoscopy, a mammography, a Pap smear, a pelvic exam, a positron emission tomography and computed tomography (PET-CT) scan. In some cases, a mammal that has been selected for further diagnostic testing can also be selected for increased monitoring. Once the presence of a tumor or a cancer (e.g., a cancer cell) has been identified (e.g., by any of the variety of methods disclosed herein), it may be beneficial for the mammal to undergo both increased monitoring (e.g., to assess the progression of the tumor or cancer in the mammal and/or to assess the development of one or more cancer biomarkers such as mutations), and further diagnostic testing (e.g., to determine the size and/or exact location of the tumor or the cancer). In some cases, a cancer treatment is administered to the mammal that is selected for further diagnostic testing after a cancer biomarker is detected and/or after the cfDNA fragmentation profile of the mammal has not improved or deteriorated. Any of the cancer treatments disclosed herein or known in the art can be administered. For example, a mammal that has been selected for further diagnostic testing can be administered a further diagnostic test, and a cancer treatment can be administered if the presence of the tumor or the cancer is confirmed. Additionally or alternatively, a mammal that has been selected for further diagnostic testing can be administered a cancer treatment, and can be further monitored as the cancer treatment progresses. In some cases, after a mammal that has been selected for further diagnostic testing has been administered a cancer treatment, the additional testing will reveal one or more cancer biomarkers (e.g., mutations). In some cases, such one or more cancer biomarkers (e.g., mutations) will provide cause to administer a different cancer treatment (e.g., a resistance mutation may arise in a cancer cell during the cancer treatment, which cancer cell harboring the resistance mutation is resistant to the original cancer treatment).

The invention will be further described in the following examples, which do not limit the scope of the invention described in the claims.

EXAMPLES

Example 1: Cell-Free DNA Fragmentation in Patients with Cancer

Analyses of cell free DNA have largely focused on targeted sequencing of specific genes. Such studies permit detection of a small number of tumor-specific alterations in patients with cancer and not all patients, especially those with early stage disease, have detectable changes. Whole genome sequencing of cell-free DNA can identify chromosomal abnormalities and rearrangements in cancer patients but detection of such alterations has been challenging in part due to the difficulty in distinguishing a small number of abnormal from normal chromosomal changes (Leary et al., 2010 *Sci Transl Med* 2:20ra14; and Leary et al., 2012 *Sci Transl Med* 4:162ra154). Other efforts have suggested nucleosome patterns and chromatin structure may be different between cancer and normal tissues, and that cfDNA in patients with cancer may result in abnormal cfDNA fragment size as well as position (Snyder et al., 2016 *Cell* 164:57; Jahr et al., 2001 *Cancer Res* 61:1659; Ivanov et al., 2015 *BMC Genomics* 16(Suppl 13):S1). However, the amount of sequencing needed for nucleosome footprint analyses of cfDNA is impractical for routine analyses.

Figure 2:
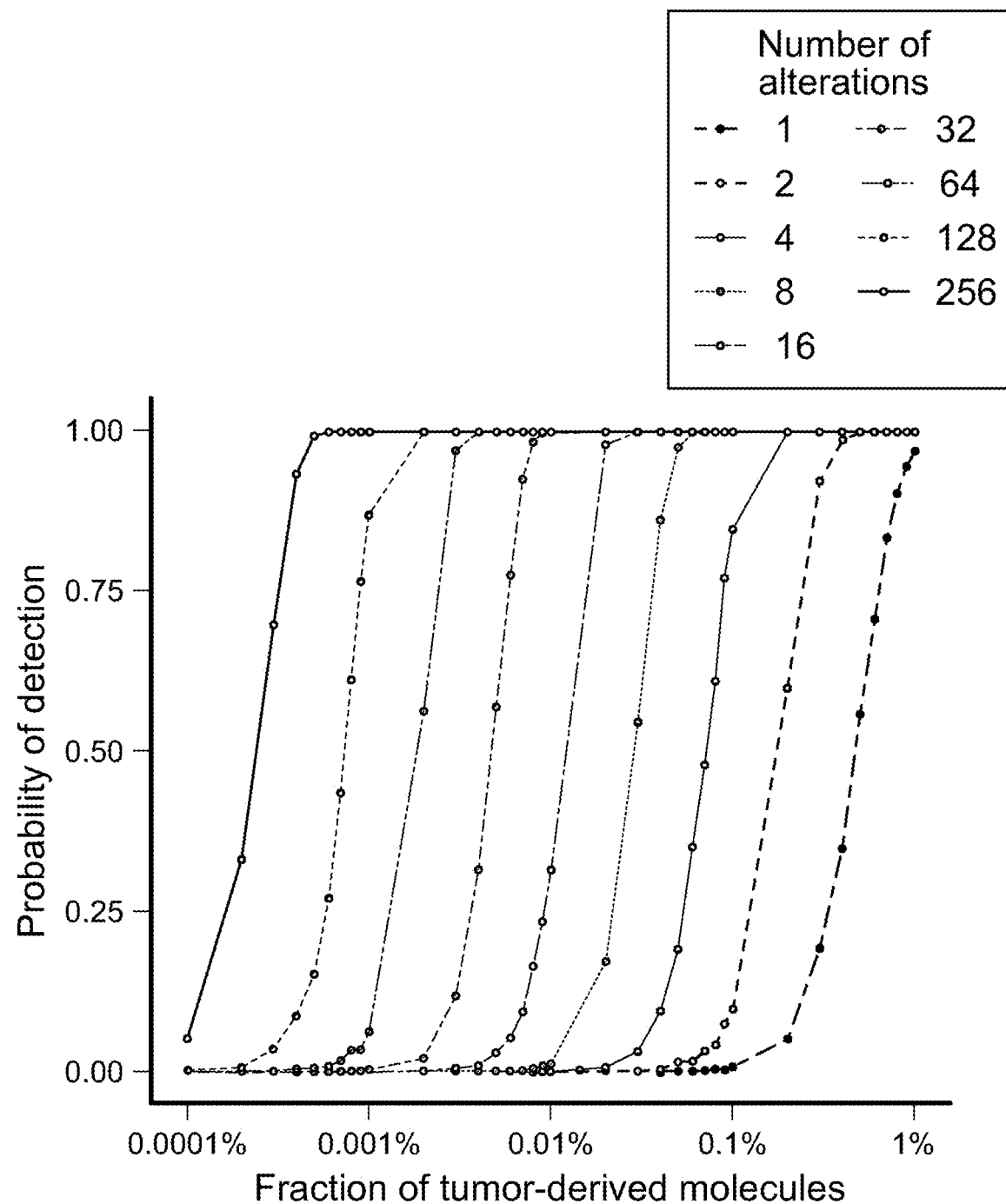
FIG. 2. Simulations of non-invasive cancer detection based on number of alterations analyzed and tumor-derived cfDNA fragment distributions. Monte Carlo simulations were performed using different numbers of tumor-specific alterations to evaluate the probability of detecting cancer alterations in cfDNA at the indicated fraction of tumor-derived molecules. The simulations were performed assuming an average of 2000 genome equivalents of cfDNA and the requirement of five or more observations of any alteration. These analyses indicate that increasing the number of tumor-specific alterations improves the sensitivity of detection of circulating tumor DNA.

The sensitivity of any cell-free DNA approach depends on the number of potential alterations examined as well as the technical and biological limitations of detecting such changes. As a typical blood sample contains ~2000 genome equivalents of cfDNA per milliliter of plasma (Phallen et al., 2017 *Sci Transl Med* 9), the theoretical limit of detection of a single alteration can be no better than one in a few thousand mutant to wild-type molecules. An approach that detects a larger number of alterations in the same number of genome equivalents would be more sensitive for detecting cancer in the circulation. Monte Carlo simulations show that increasing the number of potential abnormalities detected from only a few to tens or hundreds can potentially improve the limit of detection by orders of magnitude, similar to recent probability analyses of multiple methylation changes in cfDNA (FIG. 2).

This study presents a novel method called DELFI for detection of cancer and further identification of tissue of origin using whole genome sequencing (FIG. 1). The approach uses cfDNA fragmentation profiles and machine learning to distinguish patterns of healthy blood cell DNA from tumor-derived DNA and to identify the primary tumor tissue. DELFI was used for a retrospective analysis of cfDNA from 245 healthy individuals and 236 patients with breast, colorectal, lung, ovarian, pancreatic, gastric, or bile duct cancers, with most patients exhibiting localized disease. Assuming this approach had sensitivity≥0.80 for discriminating cancer patients from healthy individuals while maintaining a specificity of 0.95, a study of at least 200 cancer patients would enable estimation of the true sensitivity with a margin of error of 0.06 at the desired specificity of 0.95 or greater.

Materials and Methods

Patient and Sample Characteristics

Plasma samples from healthy individuals and plasma and tissue samples from patients with breast, lung, ovarian, colorectal, bile duct, or gastric cancer were obtained from ILSBio/Bioreclamation, Aarhus University, Herlev Hospital of the University of Copenhagen, Hvidovre Hospital, the University Medical Center of the University of Utrecht, the Academic Medical Center of the University of Amsterdam, the Netherlands Cancer Institute, and the University of California, San Diego. All samples were obtained under Institutional Review Board approved protocols with informed consent for research use at participating institutions. Plasma samples from healthy individuals were obtained at the time of routine screening, including for colonoscopies or Pap smears. Individuals were considered healthy if they had no previous history of cancer and negative screening results.

Plasma samples from individuals with breast, colorectal, gastric, lung, ovarian, pancreatic, and bile duct cancer were obtained at the time of diagnosis, prior to tumor resection or therapy. Nineteen lung cancer patients analyzed for change in cfDNA fragmentation profiles across multiple time points were undergoing treatment with anti-EGFR or anti-ERBB2 therapy (see, e.g., Phallen et cd, 2019 *Cancer Research* 15, 1204-1213). Clinical data for all patients included in this study are listed in Table 1 (Appendix A). Gender was confirmed through genomic analyses of X and Y chromosome representation. Pathologic staging of gastric cancer patients was performed after neoadjuvant therapy. Samples where the tumor stage was unknown were indicated as stage X or unknown.

Nucleosomal DNA Purification

Viably frozen lymphocytes were elutriated from leukocytes obtained from a healthy male (C0618) and female (D0808-L) (Advanced Biotechnologies Inc., Eldersburg, Md.). Aliquots of $1 \times 10^6$ cells were used for nucleosomal DNA purification using EZ Nucleosomal DNA Prep Kit (Zymo Research, Irvine, Calif.). Cells were initially treated with 100 µl of Nuclei Prep Buffer and incubated on ice for 5 minutes. After centrifugation at 200 g for 5 minutes, supernatant was discarded and pelleted nuclei were treated twice with 100 µl of Atlantis Digestion Buffer or with 100 µl of micrococcal nuclease (MN) Digestion Buffer. Finally, cellular nucleic DNA was fragmented with 0.5 U of Atlantis dsDNase at 42° C. for 20 minutes or 1.5 U of MNase at 37° C. for 20 minutes. Reactions were stopped using 5× MN Stop Buffer and DNA was purified using Zymo-Spin™ IIC Columns. Concentration and quality of eluted cellular nucleic DNA were analyzed using the Bioanalyzer 2100 (Agilent Technologies, Santa Clara, Calif.).

Sample Preparation and Sequencing of cfDNA

Whole blood was collected in EDTA tubes and processed immediately or within one day after storage at 4° C., or was collected in Streck tubes and processed within two days of collection for three cancer patients who were part of the monitoring analysis. Plasma and cellular components were separated by centrifugation at 800 g for 10 min at 4° C. Plasma was centrifuged a second time at 18,000 g at room temperature to remove any remaining cellular debris and stored at −80° C. until the time of DNA extraction. DNA was isolated from plasma using the Qiagen Circulating Nucleic Acids Kit (Qiagen GmbH) and eluted in LoBind tubes (Eppendorf AG). Concentration and quality of cfDNA were assessed using the Bioanalyzer 2100 (Agilent Technologies).

NGS cfDNA libraries were prepared for whole genome sequencing and targeted sequencing using 5 to 250 ng of cfDNA as described elsewhere (see, e.g., Phallen et al., 2017 *Sci Transl Med* 9:eaan2415). Briefly, genomic libraries were prepared using the NEBNext DNA Library Prep Kit for Illumina [New England Biolabs (NEB)] with four main modifications to the manufacturer's guidelines: (i) The library purification steps used the on-bead AMPure XP approach to minimize sample loss during elution and tube transfer steps (see, e.g., Fisher et al., 2011 *Genome Biol* 12:R1); (ii) NEBNext End Repair, A-tailing, and adapter ligation enzyme and buffer volumes were adjusted as appropriate to accommodate the on-bead AMPure XP purification strategy, (iii) a pool of eight unique Illumina dual index adapters with 8-base pair (bp) barcodes was used in the ligation reaction instead of the standard Illumina single or dual index adapters with 6- or 8-bp barcodes, respectively; and (iv) cfDNA libraries were amplified with Phusion Hot Start Polymerase.

Whole genome libraries were sequenced directly. For targeted libraries, capture was performed using Agilent SureSelect reagents and a custom set of hybridization probes targeting 58 genes (see, e.g., Phallen et al., 2017 *Sci Transl Med* 9:eaan2415) per the manufacturer's guidelines. The captured library was amplified with Phusion Hot Start Polymerase (NEB). Concentration and quality of captured cfDNA libraries were assessed on the Bioanalyzer 2100 using the DNA1000 Kit (Agilent Technologies). Targeted libraries were sequenced using 100-bp paired-end runs on the Illumina HiSeq 2000/2500 (Illumina).

Analyses of Targeted Sequencing Data from cfDNA

Analyses of targeted NGS data for cfDNA samples was performed as described elsewhere (see, e.g., Phallen et al., 2017 *Sci Transl Med* 9:eaan2415). Briefly, primary processing was completed using Illumina CASAVA (Consensus Assessment of Sequence and Variation) software (version 1.8), including demultiplexing and masking of dual-index adapter sequences. Sequence reads were aligned against the human reference genome (version hg18 or hg19) using NovoAlign with additional realignment of select regions using the Needleman-Wunsch method (see, e.g., Jones et al., 2015 *Sci Transl Med* 7:283ra53). The positions of the sequence alterations have not been affected by the different genome builds. Candidate mutations, consisting of point mutations, small insertions, and deletions, were identified using VariantDx (see, e.g., Jones et al., 2015 *Sci Transl Med* 7:283ra53) (Personal Genome Diagnostics, Baltimore, Md.) across the targeted regions of interest.

To analyze the fragment lengths of cfDNA molecules, each read pair from a cfDNA molecule was required to have a Phred quality score≥30. All duplicate cfDNA fragments, defined as having the same start, end, and index barcode were removed. For each mutation, only fragments for which one or both of the read pairs contained the mutated (or wild-type) base at the given position were included. This analysis was done using the R packages Rsamtools and GenomicAlignments.

For each genomic locus where a somatic mutation was identified, the lengths of fragments containing the mutant allele were compared to the lengths of fragments of the wild-type allele. If more than 100 mutant fragments were identified, Welch's two-sample t-test was used to compare the mean fragment lengths. For loci with fewer than 100 mutant fragments, a bootstrap procedure was implemented. Specifically, replacement N fragments containing the wild-type allele, where N denotes the number of fragments with the mutation, were sampled. For each bootstrap replicate of wild type fragments their median length was computed. The p-value was estimated as the fraction of bootstrap replicates with a median wild-type fragment length as or more extreme than the observed median mutant fragment length.

Analyses of Whole Genome Sequencing Data from cfDNA

Primary processing of whole genome NGS data for cfDNA samples was performed using Illumina CASAVA (Consensus Assessment of Sequence and Variation) software (version 1.8.2), including demultiplexing and masking of dual-index adapter sequences. Sequence reads were aligned against the human reference genome (version hg19) using ELAND.

Read pairs with a MAPQ score below 30 for either read and PCR duplicates were removed. hg19 autosomes were tiled into 26,236 adjacent, non-overlapping 100 kb bins. Regions of low mappability, indicated by the 10% of bins with the lowest coverage, were removed (see, e.g., Fortin et al, 2015 *Genome Biol* 16:180), as were reads falling in the Duke blacklisted regions (see, e.g., hgdownload.cse.ucsc.edu/goldenpath/hg19/encodeDCC/wgEncodeMapability/). Using this approach, 361 Mb (13%) of the hg19 reference genome was excluded, including centromeric and telomeric regions. Short fragments were defined as having a length between 100 and 150 bp and long fragments were defined has having a length between 151 and 220 bp.

To account for biases in coverage attributable to GC content of the genome, the locally weighted smoother loess with span ¾ was applied to the scatterplot of average fragment GC versus coverage calculated for each 100 kb bin. This loess regression was performed separately for short and long fragments to account for possible differences in GC effects on coverage in plasma by fragment length (see, e.g., Benjamini et al., 2012 *Nucleic Acids Res* 40:e72). The predictions for short and long coverage explained by GC from the loess model were subtracted, obtaining residuals for short and long that were uncorrelated with GC. The residuals were returned to the original scale by adding back the genome-wide median short and long estimates of coverage. This procedure was repeated for each sample to account for possible differences in GC effects on coverage between samples. To further reduce the feature space and noise, the total GC-adjusted coverage in 5 Mb bins was calculated.

To compare the variability of fragment lengths from healthy subjects to fragments in patients with cancer, the standard deviation of the short to long fragmentation profiles for each individual was calculated. The standard deviations in the two groups were compared by a Wilcoxon rank sum test.

Analyses of Chromosome Arm Copy Number Changes

To develop arm-level statistics for copy number changes, an approach for aneuploidy detection in plasma as described elsewhere (see, e.g., Leary et al., 2012 *Sci Transl Med* 4:162ra154) was adopted. This approach divides the genome into non-overlapping 50 KB bins for which GC-corrected log 2 read depth was obtained after correction by loess with span ¾. This loess-based correction is comparable to the approach outlined above, but is evaluated on a log 2 scale to increase robustness to outliers in the smaller bins and does not stratify by fragment length. To obtain an arm-specific Z-score for copy number changes, the mean GC-adjusted read depth for each arm (GR) was centered and scaled by the average and standard deviation, respectively, of GR scores obtained from an independent set of 50 healthy samples.

Analyses of Mitochondrial-Aligned Reads from cfDNA

Whole genome sequence reads that initially mapped to the mitochondrial genome were extracted from barn files and realigned to the hg19 reference genome in end-to-end mode with Bowtie2 as described elsewhere (see, e.g., Langmead et al., 2012 *Nat Methods* 9:357-359). The resulting aligned reads were filtered such that both mates aligned to the mitochondrial genome with MAPQ>=30. The number of fragments mapping to the mitochondrial genome was counted and converted to a percentage of the total number of fragments in the original barn files.

Prediction Model for Cancer Classification

To distinguish healthy from cancer patients using fragmentation profiles, a stochastic gradient boosting model was used (gbm; see, e.g., Friedman et al., 2001 *Ann Stat* 29:1189-1232; and Friedman et al., 2002 *Comput Stat Data An* 38:367-378). GC-corrected total and short fragment coverage for all 504 bins were centered and scaled for each sample to have mean 0 and unit standard deviation. Additional features included Z-scores for each of the 39 autosomal arms and mitochondrial representation (log 10-transformed proportion of reads mapped to the mitochondria). To estimate the prediction error of this approach, 10-fold cross-validation was used as described elsewhere (see, e.g., Efron et al., 1997 *J Am Stat Assoc* 92, 548-560). Feature selection, performed only on the training data in each cross-validation run, removed bins that were highly correlated (correlation>0.9) or had near zero variance. Stochastic gradient boosted machine learning was implemented using the R package gbm package with parameters n.trees=150, interaction.depth=3, shrinkage=0.1, and n.minobsinside=10. To average over the prediction error from the randomization of patients to folds, the 10-fold cross validation procedure was repeated 10 times. Confidence intervals for sensitivity fixed at 98% and 95% specificity were obtained from 2000 bootstrap replicates.

Prediction Model for Tumor Tissue of Origin Classification

For samples correctly classified as cancer patients at 90% specificity (n=174), a separate stochastic gradient boosting model was trained to classify the tissue of origin. To account for the small number of lung samples used for prediction, 18 cfDNA baseline samples from late stage lung cancer patients were included from the monitoring analyses. Performance characteristics of the model were evaluated by 10-fold cross-validation repeated 10 times. This gbm model was trained using the same features as in the cancer classification model. As previously described, features that displayed correlation above 0.9 to each other or had near zero variance were removed within each training dataset during cross-validation. The tissue class probabilities were averaged across the 10 replicates for each patient and the class with the highest probability was taken as the predicted tissue.

Analyses of Nucleosomal DNA from Human Lymphocytes and cfDNA

From the nuclease treated lymphocytes, fragment sizes were analyzed in 5 Mb bins as described for whole genome cfDNA analyses. A genome-wide map of nucleosome positions was constructed from the nuclease treated lymphocyte cell-lines. This approach identified local biases in the coverage of circulating fragments, indicating a region protected from degradation. A "Window positioning score" (WPS) was used to score each base pair in the genome (see, e.g., Snyder et al., 2016 *Cell* 164:57). Using a sliding window of 60 bp centered around each base, the WPS was calculated as the number of fragments completely spanning the window minus the number of fragments with only one end in the window. Since fragments arising from nucleosomes have a median length of 167 bp, a high WPS indicated a possible nucleosomic position. WPS scores were centered at zero using a running median and smoothed using a Kolmogorov-Zurbenko filter (see, e.g., Zurbenko, *The spectral analysis of time series*. North-Holland series in statistics and probability; Elsevier, New York, N Y, 1986). For spans of positive WPS between 50 and 450 bp, a nucleosome peak was defined as the set of base pairs with a WPS above the median in that window. The calculation of nucleosome positions for cfDNA from 30 healthy individuals with sequence coverage of 9× was determined in the same manner as for lymphocyte DNA. To ensure that nucleosomes in healthy cfDNA were representative, a consensus track of nucleosomes was defined consisting only of nucleosomes identified in two or more individuals. Median distances between adjacent nucleosomes were calculated from the consensus track.

Monte Carlo Simulation of Detection Sensitivity

A Monte Carlo simulation was used to estimate the probability of detecting a molecule with a tumor-derived alteration. Briefly, 1 million molecules were generated from a multinomial distribution. For a simulation with m alterations, wild-type molecules were simulated with probability p and each of them tumor alterations were simulated with probability (1−p)/m. Next, g*m molecules were sampled randomly with replacement, where g denotes the number of genome equivalents in 1 ml of plasma. If a tumor alteration was sampled s or more times, the sample was classified as cancer-derived. The simulation was repeated 1000 times, estimating the probability that the in silico sample would be correctly classified as cancer by the mean of the cancer indicator. Setting g=2000 and s=5, the number of tumor alterations was varied by powers of 2 from 1 to 256 and the fraction of tumor-derived molecules from 0.0001% to 1%

Statistical Analyses

All statistical analyses were performed using R version 3.4.3. The R packages caret (version 6.0-79) and gbm (version 2.1-4) were used to implement the classification of healthy versus cancer and tissue of origin. Confidence intervals from the model output were obtained with the pROC (version 1.13) R package (see, e.g., Robin et al., 2011 *BMC bioinformatics* 12:77). Assuming the prevalence of undiagnosed cancer cases in this population is high (1 or 2 cases per 100 healthy), a genomic assay with a specificity of 0.95 and sensitivity of 0.8 would have useful operating characteristics (positive predictive value of 0.25 and negative predictive value near 1). Power calculations suggest that an analysis of more than 200 cancer patients and an approximately equal number of healthy controls, enable an estimation of the sensitivity with a margin of error of 0.06 at the desired specificity of 0.95 or greater.

Data and Code Availability

Sequence data utilized in this study have been deposited at the European Genome-phenome Archive under study accession nos. EGAS00001003611 and EGAS00001002577. Code for analyses is available at github.com/Cancer-Genomics/delfi_scripts.

Results

DELFI allows simultaneous analysis of a large number of abnormalities in cfDNA through genome-wide analysis of fragmentation patterns. The method is based on low coverage whole genome sequencing and analysis of isolated cfDNA. Mapped sequences are analyzed in non-overlapping windows covering the genome. Conceptually, windows may range in size from thousands to millions of bases, resulting in hundreds to thousands of windows in the genome. 5 Mb windows were used for evaluating cfDNA fragmentation patterns as these would provide over 20,000 reads per window even at a limited amount of 1-2× genome coverage. Within each window, the coverage and size distribution of cfDNA fragments was examined. This approach was used to evaluate the variation of genome-wide fragmentation profiles in healthy and cancer populations (Table 1; Appendix A). The genome-wide pattern from an individual can be compared to reference populations to determine if the pattern is likely healthy or cancer-derived. As genome-wide profiles reveal positional differences associated with specific tissues that may be missed in overall fragment size distributions, these patterns may also indicate the tissue source of cfDNA.

Figure 3:
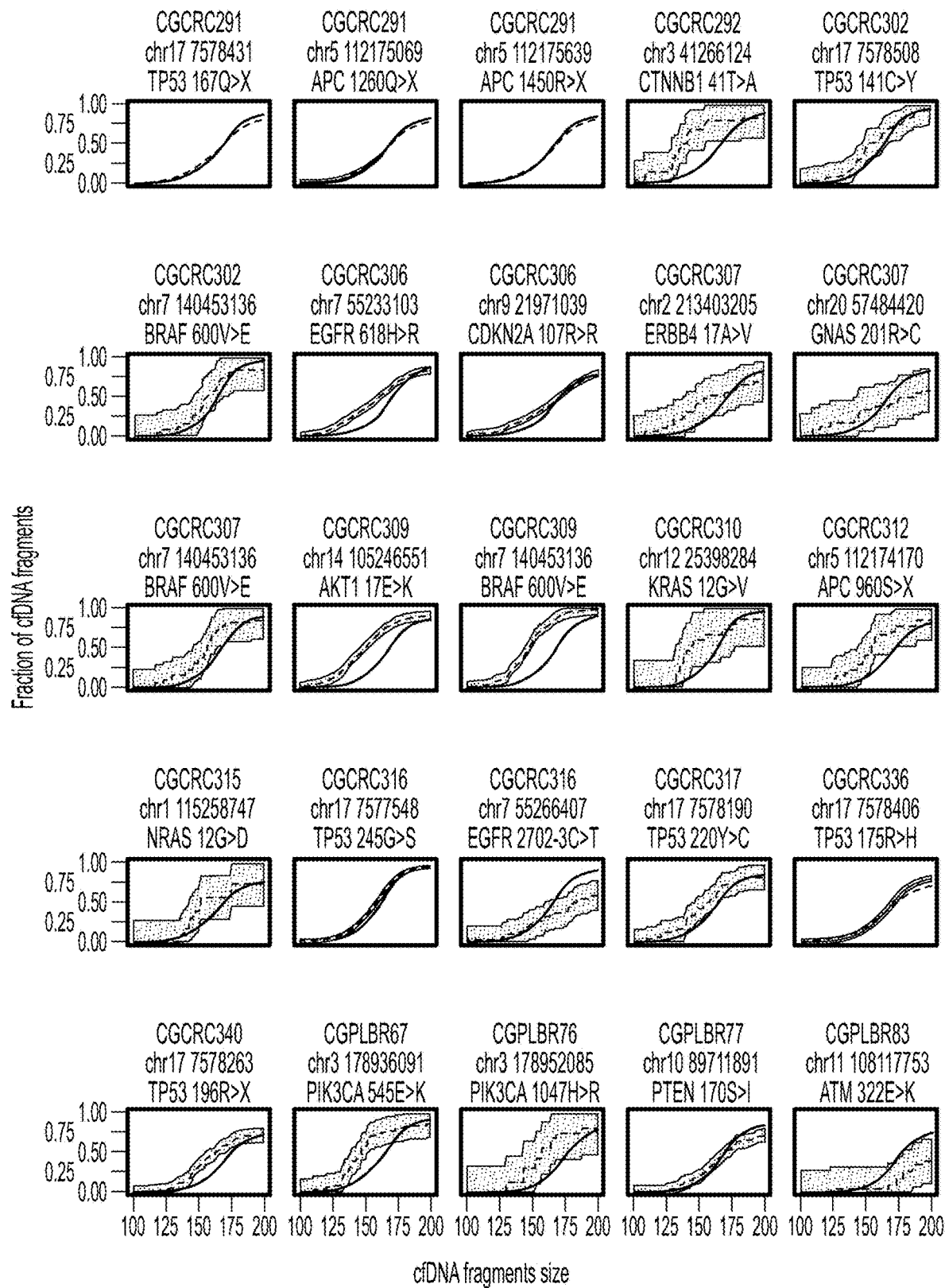
FIG. 3 Tumor-derived cfDNA fragment distributions. Cumulative density functions of cfDNA fragment lengths of 42 loci containing tumor-specific alterations from 30 patients with breast, colorectal, lung, or ovarian cancer are shown with 95% confidence bands (blue). Lengths of mutant cfDNA fragments were significantly different in size compared to wild-type cfDNA fragments (red) at these loci.
Figure 3:
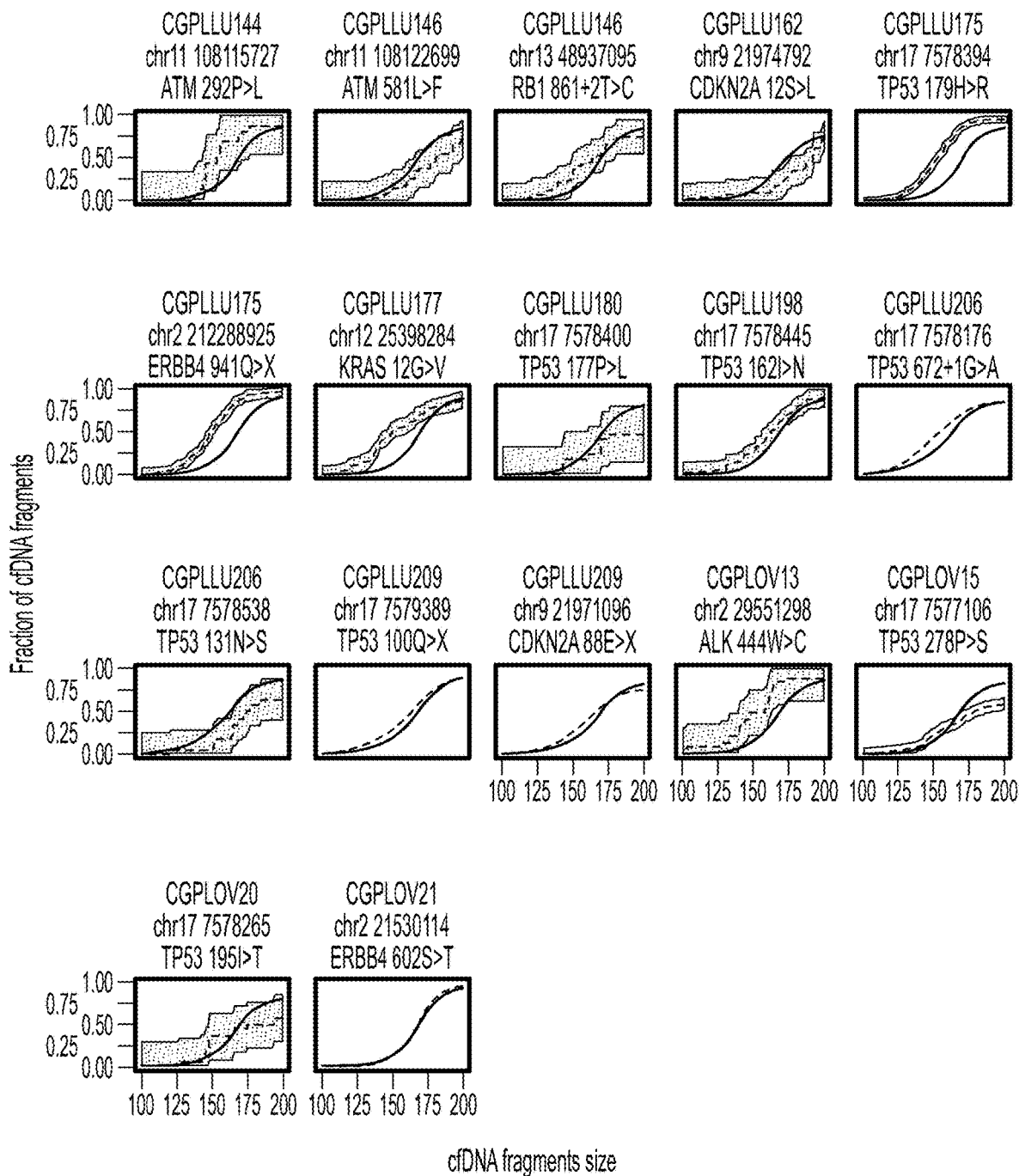
Figure 4A:
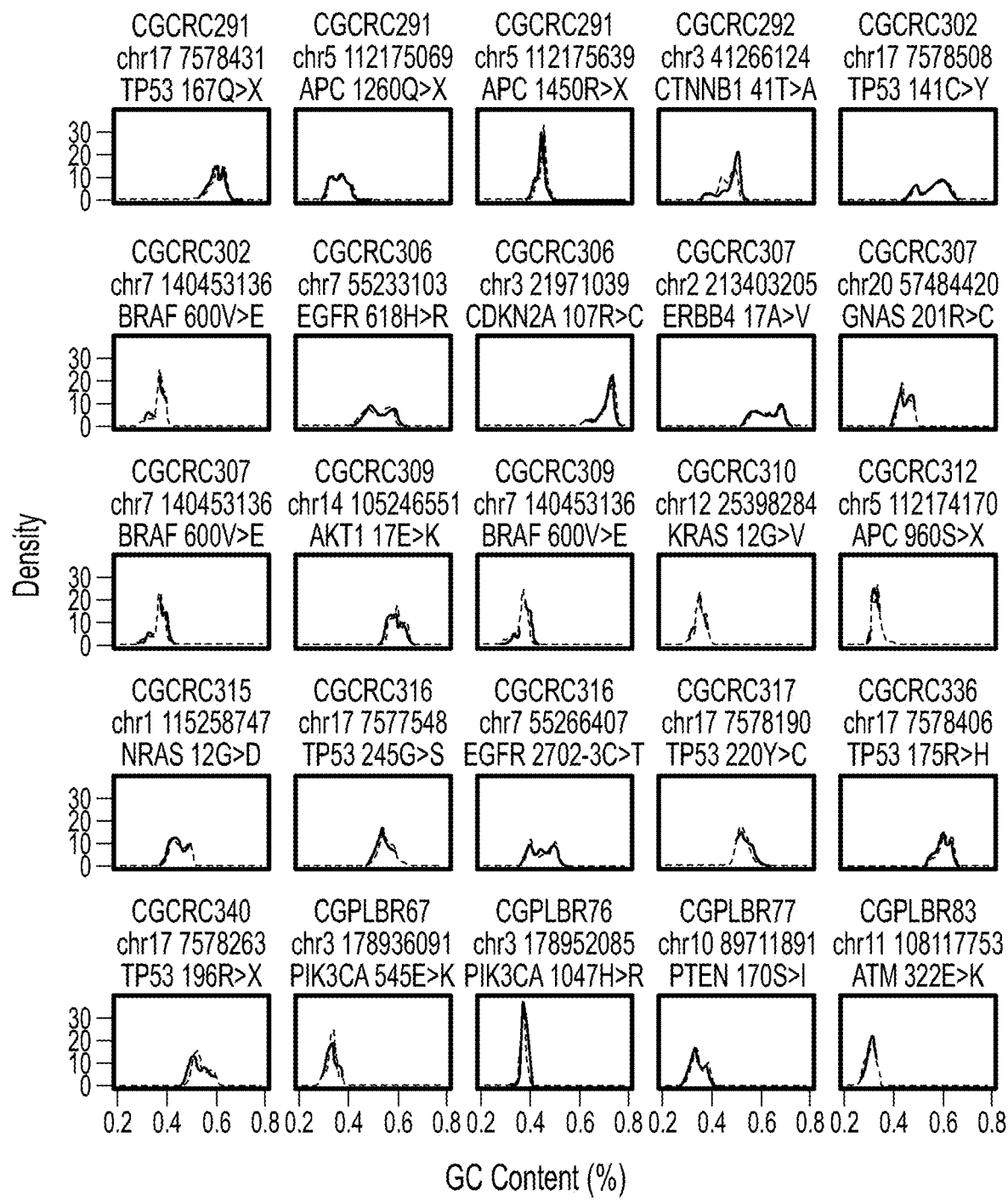
FIGS. 4A and 4B. Tumor-derived cfDNA GC content and fragment length. A, GC content was similar for mutated and non-mutated fragments. B, GC content was not correlated to fragment length.
Figure 4A:
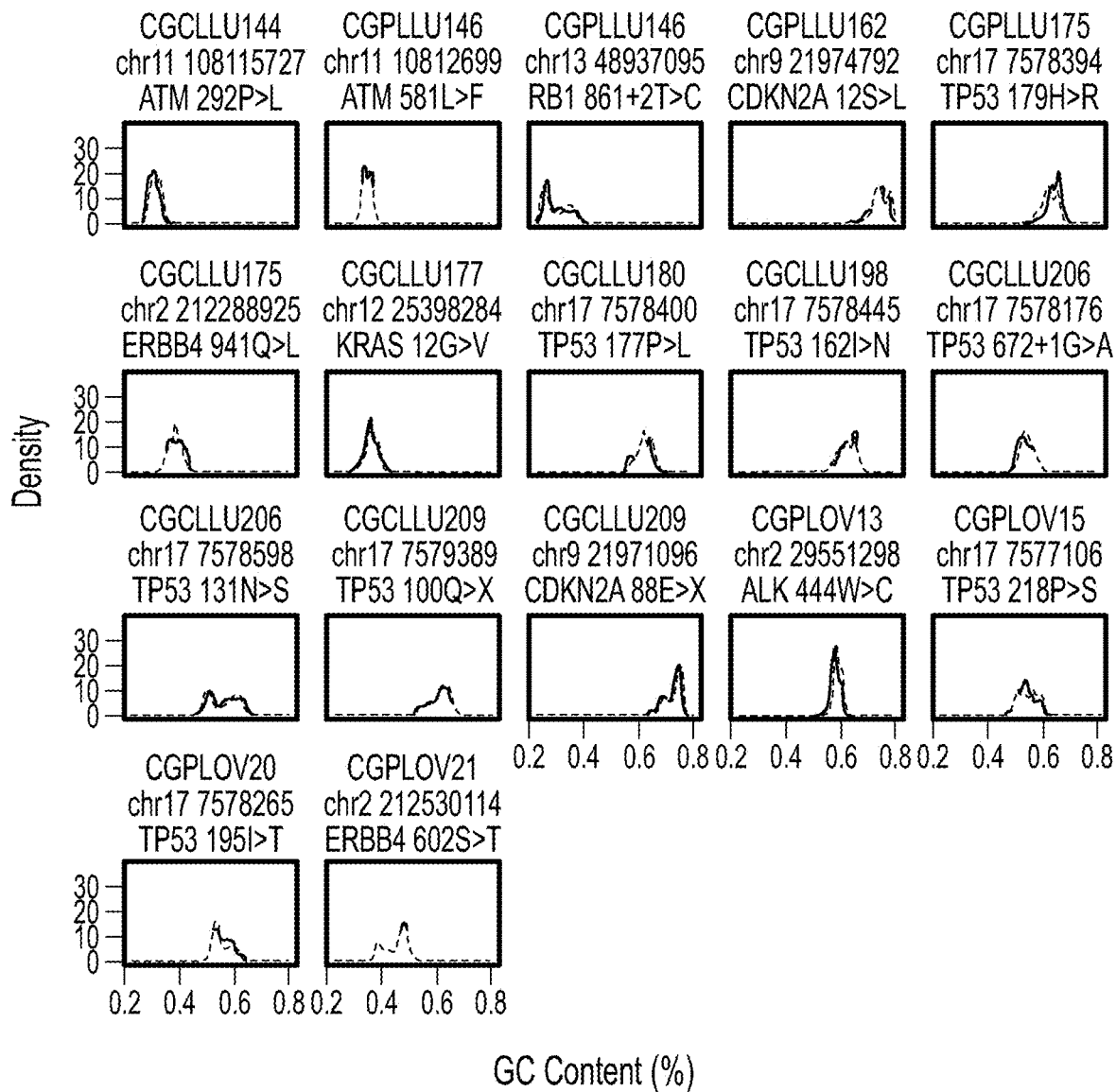
Figure 4B:
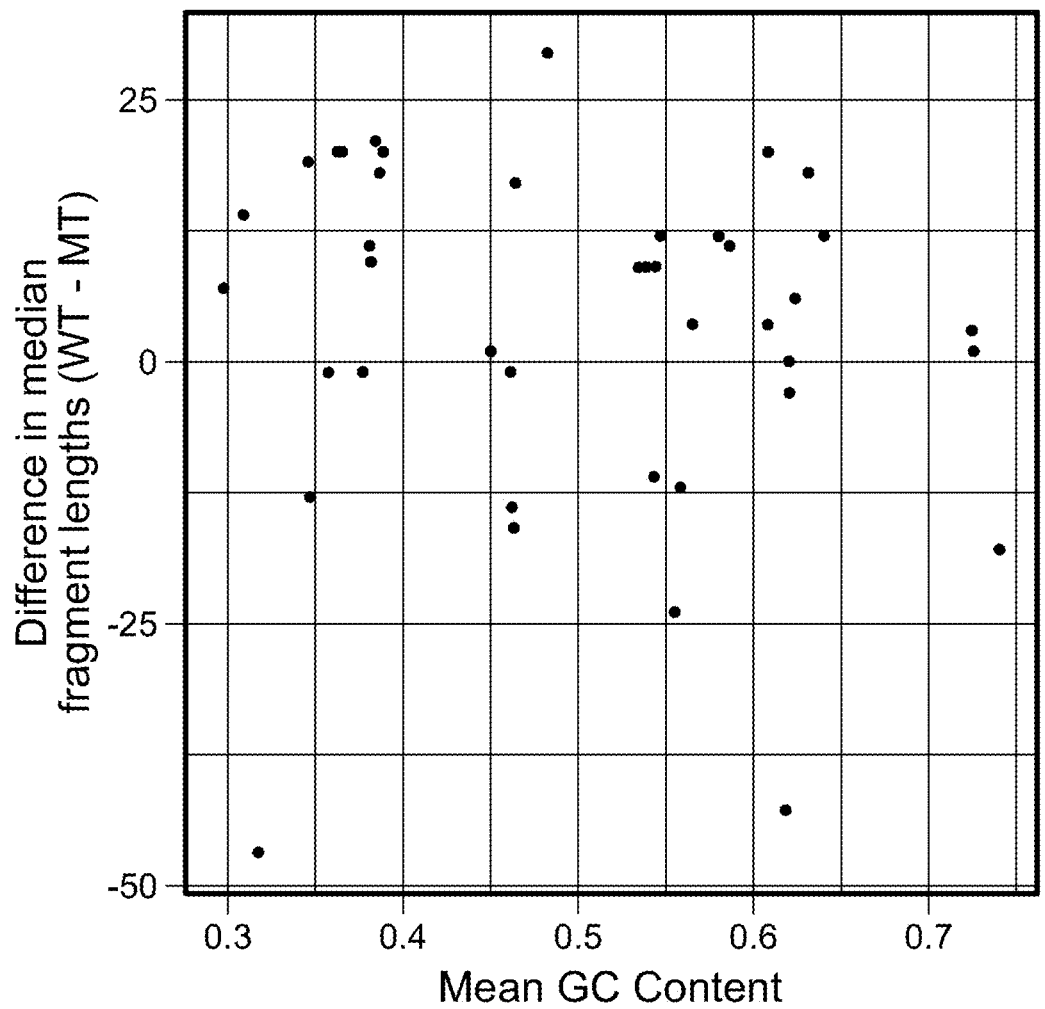
Figure 5:
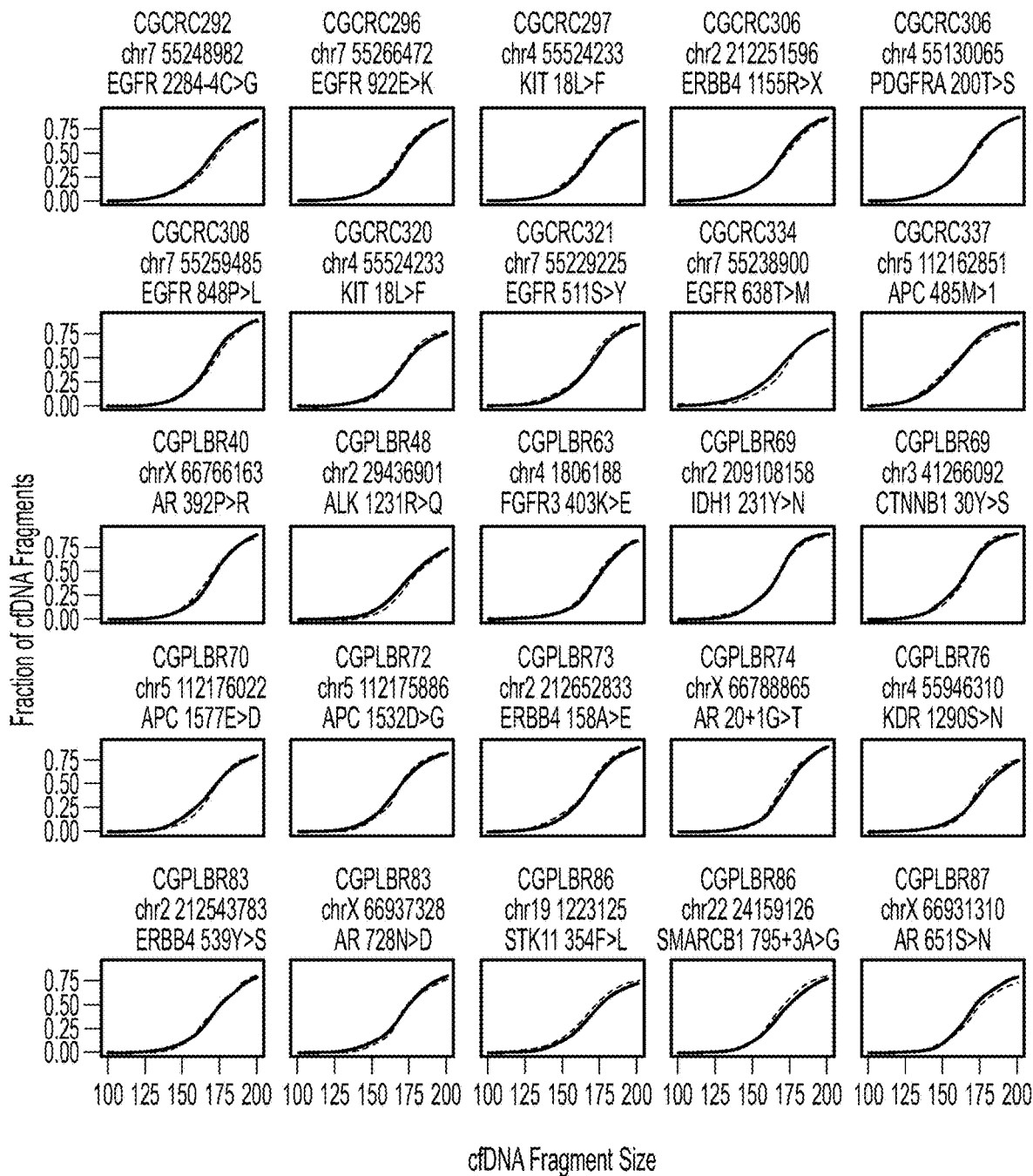
FIG. 5. Germline cfDNA fragment distributions. Cumulative density functions of fragment lengths of 44 loci containing germline alterations (non-tumor derived) from 38 patients with breast, colorectal, lung, or ovarian cancer are shown with 95% confidence bands. Fragments with germline mutations (blue) were comparable in length to wild-type cfDNA fragment lengths (red).
Figure 5:
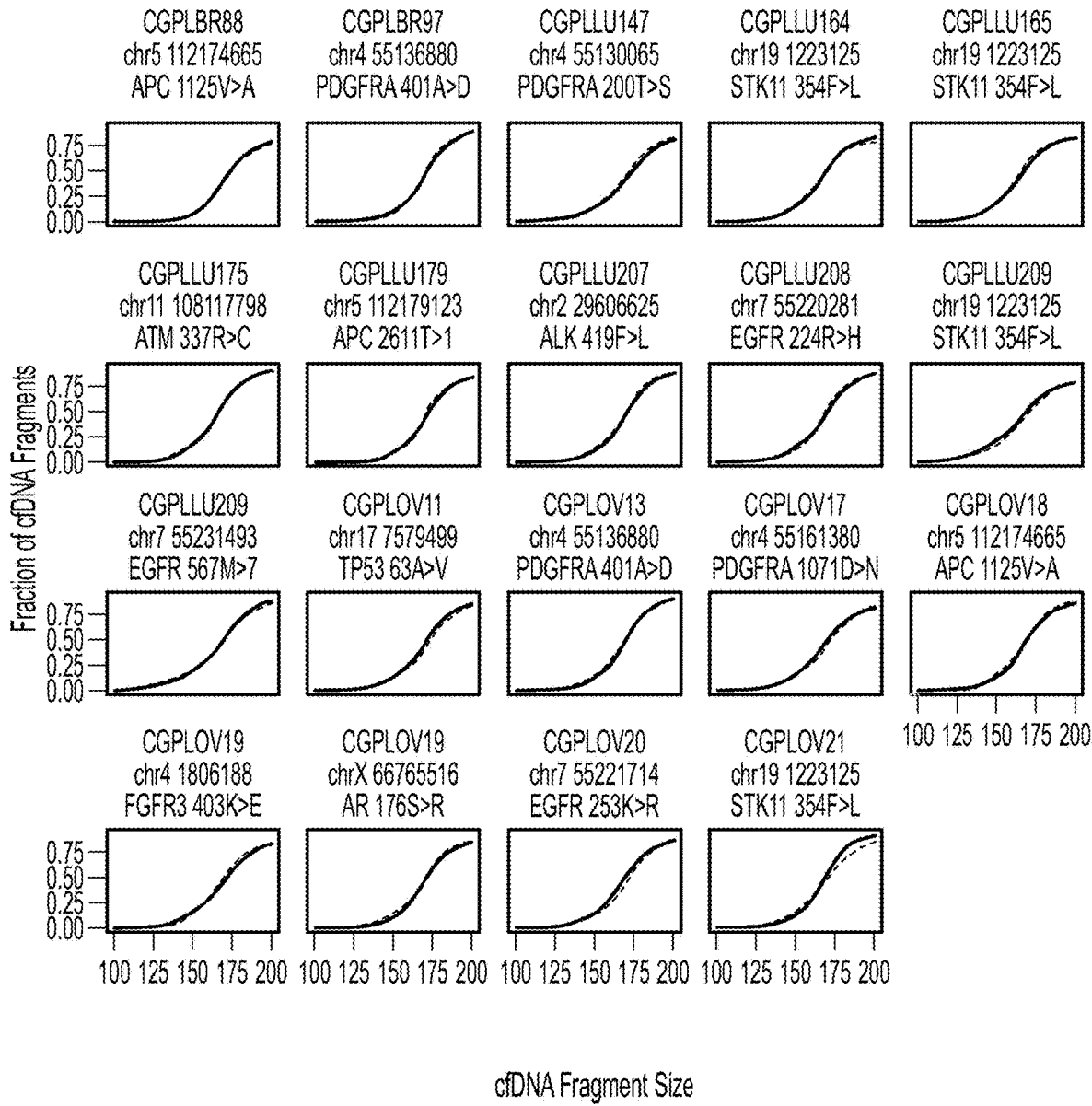
Figure 6:
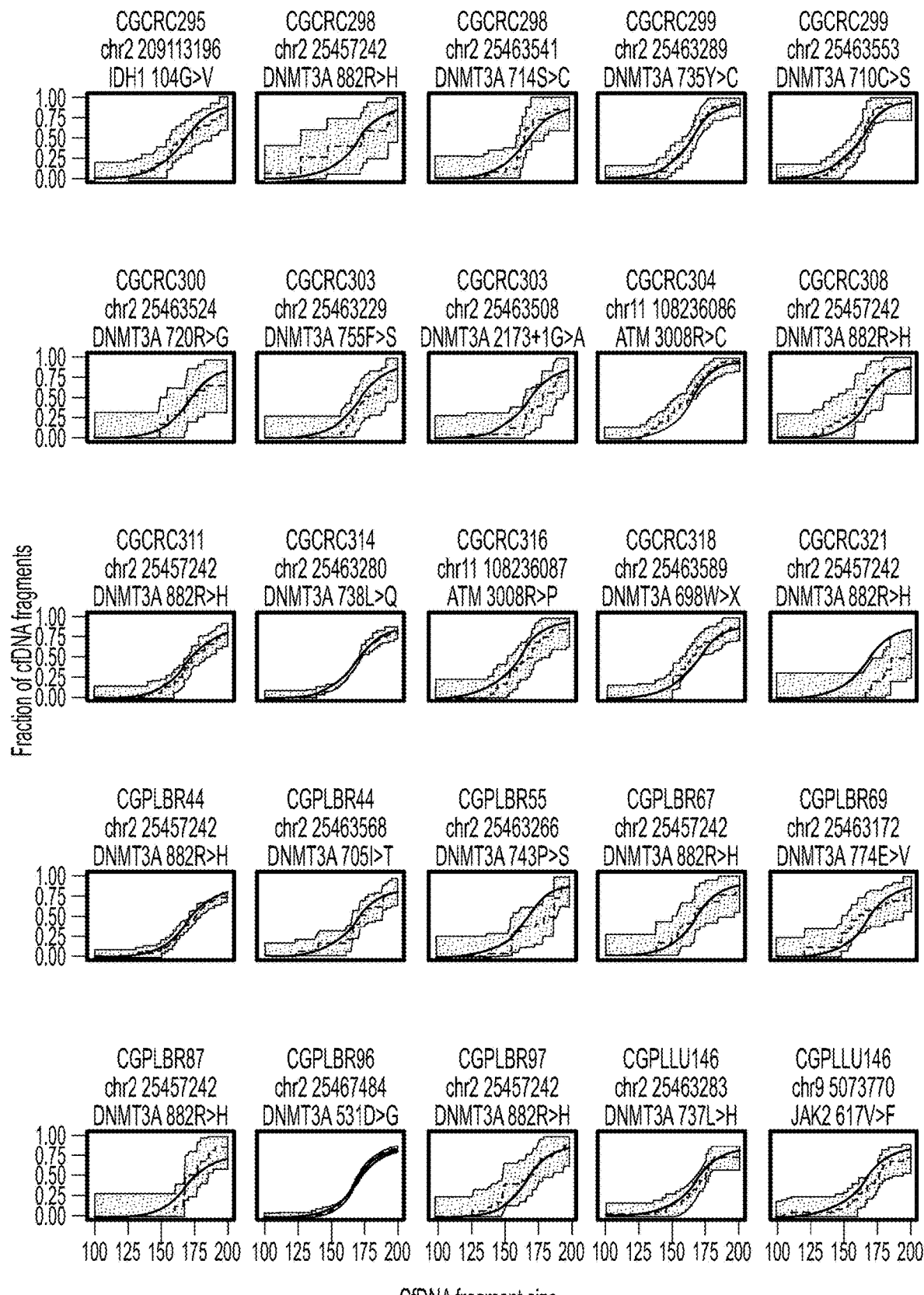
FIG. 6. Hematopoietic cfDNA fragment distributions. Cumulative density functions of fragment lengths of 41 loci containing hematopoietic alterations (non-tumor derived) from 28 patients with breast, colorectal, lung, or ovarian cancer are shown with 95% confidence bands. After correction for multiple testing, there were no significant differences ($\alpha=0.05$) in the size distributions of mutated hematopoietic cfDNA fragments (blue) and wild-type cfDNA fragments (red).
Figure 6:
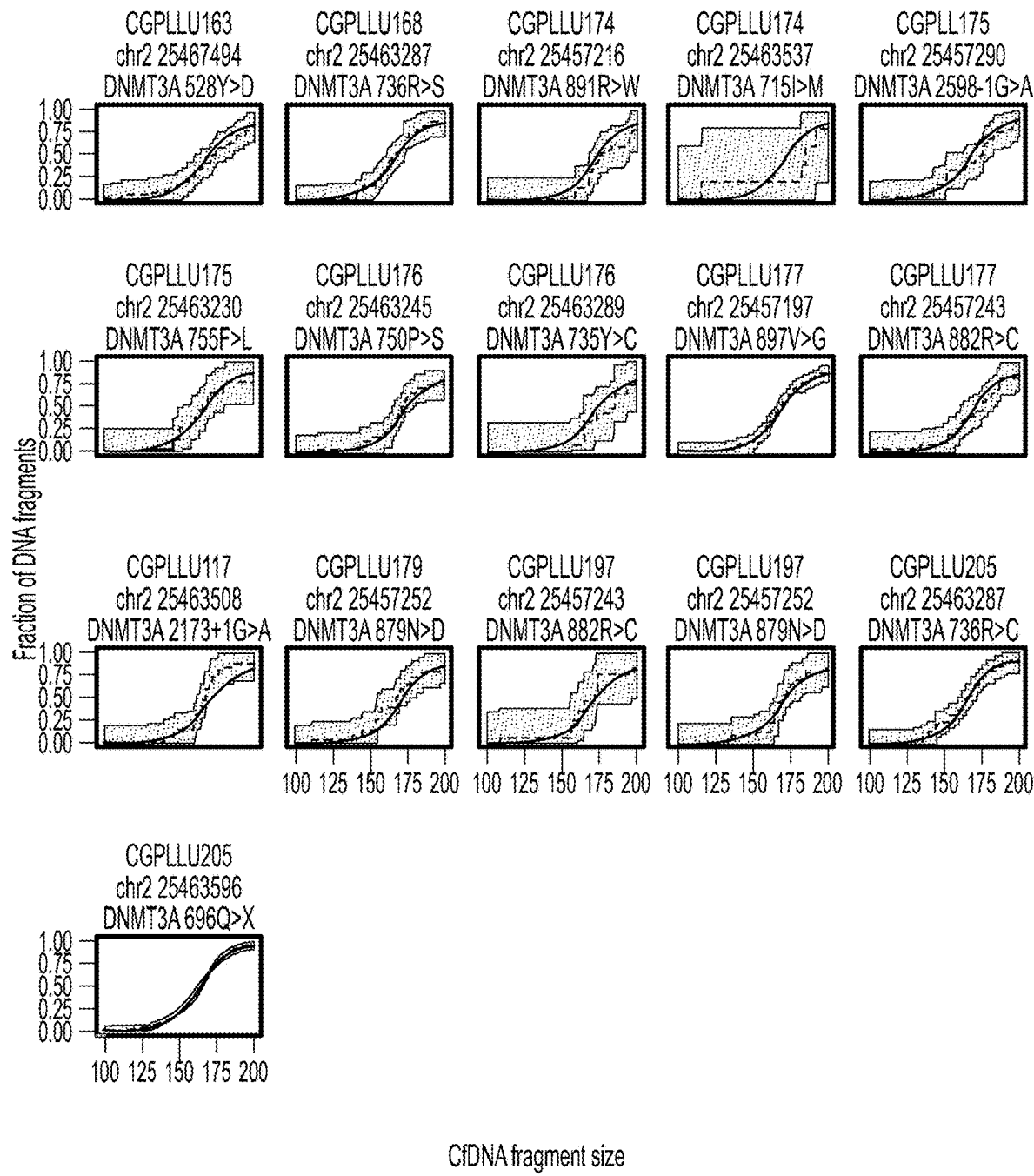

The fragmentation size of cfDNA was focused on as it was found that cancer-derived cfDNA molecules may be more variable in size than cfDNA derived from non-cancer cells. cfDNA fragments from targeted regions that were captured and sequenced at high coverage (43,706 total coverage, 8,044 distinct coverage) from patients with breast, colorectal, lung or ovarian cancer (Table 1 (Appendix A), Table 2 (Appendix B), and Table 3 (Appendix C)) were initially examined. Analyses of loci containing 165 tumor-specific alterations from 81 patients (range of 1-7 alterations per patient) revealed an average absolute difference of 6.5 bp (95% CI, 5.4-7.6 bp) between lengths of median mutant and wild-type cfDNA fragments is (FIG. 3, Table 3 (Appendix C)). The median size of mutant cfDNA fragments ranged from 30 bases smaller at chromosome 3 position 41,266,124 to 47 bases larger at chromosome 11 position 108,117,753 than the wild-type sequences at these regions (Table 3; Appendix C). GC content was similar for mutated and non-mutated fragments (FIG. 4*a*), and there was no correlation between GC content and fragment length (FIG. 4*b*). Similar analyses of 44 germline alterations from 38 patients identified median cfDNA size differences of less than 1 bp between fragment lengths of different alleles (FIG. 5, Table 3 (Appendix C)). Additionally, 41 alterations related to clonal hematopoiesis were identified through a previous sequence comparison of DNA from plasma, buffy coat, and tumors of the same individuals. Unlike tumor-derived fragments, there were no significant differences between fragments with hematopoietic alterations and wild type fragments (FIG. 6, Table 3 (Appendix C)). Overall, cancer-derived cfDNA fragment lengths were significantly more variable compared to non-cancer cfDNA fragments at certain genomic regions (p<0.001, variance ratio test). It was hypothesized that these differences may be due to changes in higher-order chromatin structure as well as other genomic and epigenomic abnormalities in cancer and that cfDNA fragmentation in a position-specific manner could therefore serve as a unique biomarker for cancer detection.

As targeted sequencing only analyzes a limited number of loci, larger-scale genome-wide analyses to detect additional abnormalities in cfDNA fragmentation were investigated. cfDNA was isolated from ~4 ml of plasma from 8 lung cancer patients with stage I-III disease, as well as from 30 healthy individuals (Table 1 (Appendix A), Table 4 (Appendix D), and Table 5 (Appendix E)). A high efficiency approach was used to convert cfDNA to next generation sequencing libraries and performed whole genome sequencing at ~9× coverage (Table 4; Appendix D). Overall cfDNA fragment lengths of healthy individuals were larger, with a median fragment size of 167.3 bp, while patients with cancer had median fragment sizes of 163.8 (p<0.01, Welch's t-test) (Table 5; Appendix E). To examine differences in fragment size and coverage in a position dependent manner across the genome, sequenced fragments were mapped to their genomic origin and fragment lengths were evaluated in 504 windows that were 5 Mb in size, covering ~2.6 Gb of the genome. For each window, the fraction of small cfDNA fragments (100 to 150 bp in length) to larger cfDNA fragments (151 to 220 bp) as well as overall coverage were determined and used to obtain genome-wide fragmentation profiles for each sample.

Figure 7A:
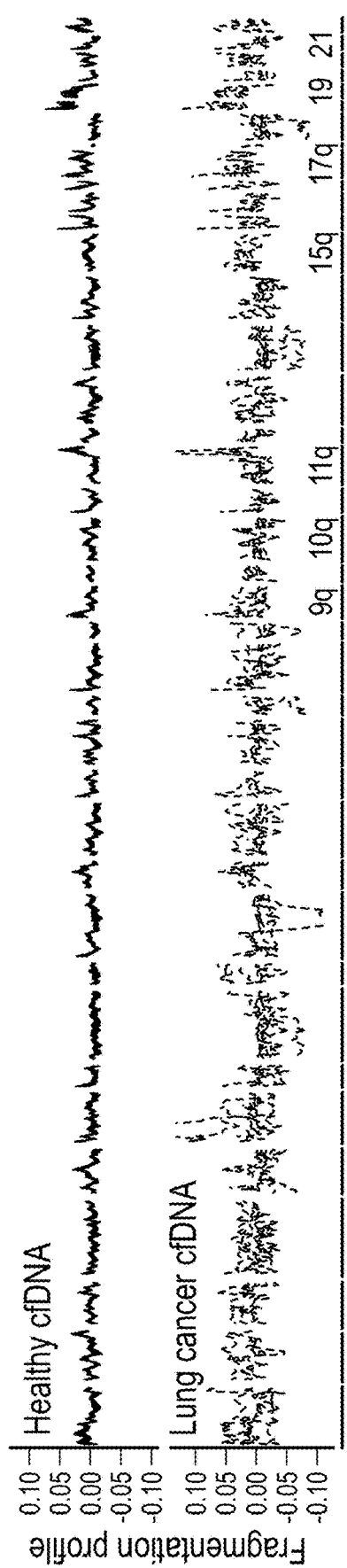
Figure 7B:
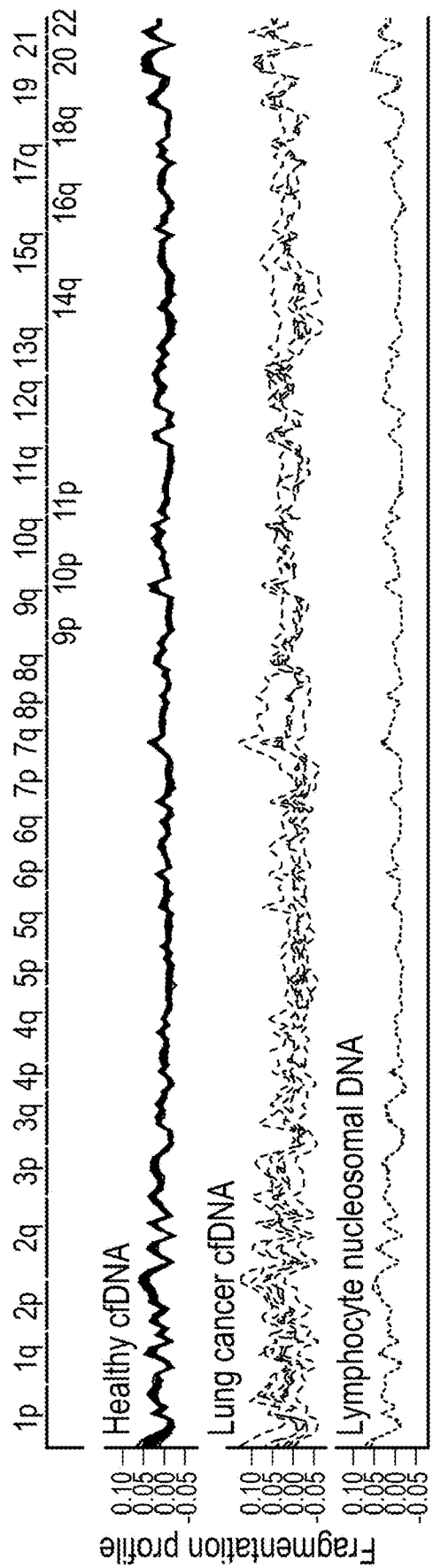
Figure 8:
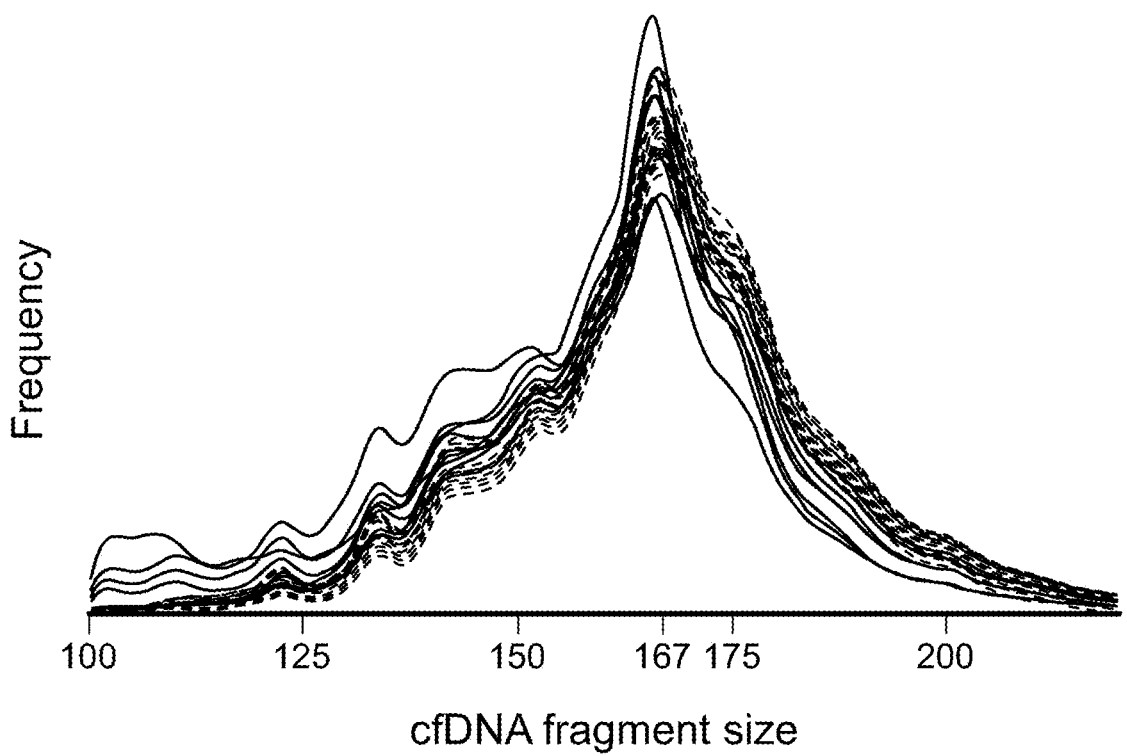
FIG. 8. Density of cfDNA fragment lengths in healthy individuals and patients with lung cancer. cfDNA fragments lengths are shown for healthy individuals (n=30, gray) and patients with lung cancer (n=8, blue).

Healthy individuals had very similar fragmentation profiles throughout the genome (FIG. 7 and FIG. 8). To examine the origins of fragmentation patterns normally observed in cfDNA, nuclei were isolated from elutriated lymphocytes of two healthy individuals and treated with DNA nucleases to obtain nucleosomal DNA fragments. Analyses of cfDNA patterns in observed healthy individuals revealed a high correlation to lymphocyte nucleosomal DNA fragmentation profiles (FIGS. 7*b* and 7*d*) and nucleosome distances (FIGS. 7*c* and 7*f*). Median distances between nucleosomes in lymphocytes were correlated to open (A) and closed (B) compartments of lymphoblastoid cells as revealed using the Hi-C method (see, e.g., Lieberman-Aiden et al., 2009 *Sci-* ence 326:289-293; and Fortin et al., 2015 *Genome Biol* 16:180) for examining the three-dimensional architecture of genomes (FIG. 7c). These analyses suggest that the fragmentation patterns of normal cfDNA are the result of nucleosomal DNA patterns that largely reflect the chromatin structure of normal blood cells.

In contrast to healthy cfDNA, patients with cancer had multiple distinct genomic differences with increases and decreases in fragment sizes at different regions (FIGS. 7a and 7b). Similar to our observations from targeted analyses, there was also greater variation in fragment lengths genome-wide for patients with cancer compared to healthy individuals.

To determine whether cfDNA fragment length patterns could be used to distinguish patients with cancer from healthy individuals, genome-wide correlation analyses were performed of the fraction of short to long cfDNA fragments for each sample compared to the median fragment length profile calculated from healthy individuals (FIGS. 7a, 7b, and 7e). While the profiles of cfDNA fragments were remarkably consistent among healthy individuals (median correlation of 0.99), the median correlation of genome-wide fragment ratios among cancer patients was 0.84 (0.15 lower, 95% CI 0.07-0.50, p<0.001, Wilcoxon rank sum test; Table 5 (Appendix E)). Similar differences were observed when comparing fragmentation profiles of cancer patients to fragmentation profiles or nucleosome distances in healthy lymphocytes (FIGS. 7c, 7d, and 7f). To account for potential biases in the fragmentation profiles attributable to GC content, a locally weighted smoother was applied independently to each sample and found that differences in fragmentation profiles between healthy individuals and cancer patients remained after this adjustment (median correlation of cancer patients to healthy=0.83) (Table 5; Appendix E).

Figure 9A:
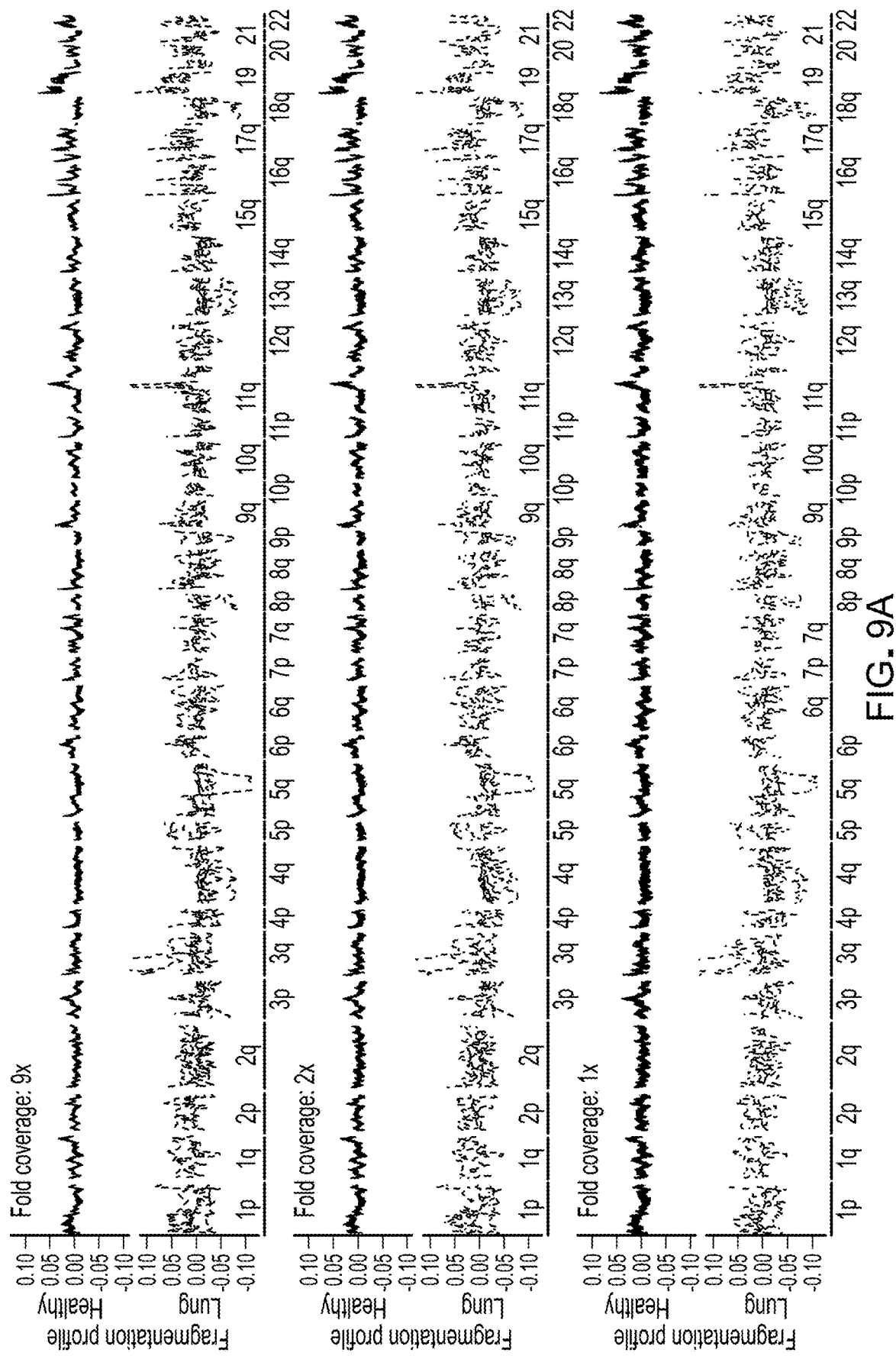
FIGS. 9A and 9B. Subsampling of whole genome sequence data for analysis of cfDNA fragmentation profiles. A, high coverage (9x) whole-genome sequencing data were subsampled to 2x, 1x, 0.5x, 0.2x, and 0.1x fold coverage. Mean centered genome-wide fragmentation profiles in 5 Mb bins for 30 healthy individuals and 8 patients with lung cancer are depicted for each subsampled fold coverage with median profiles shown in blue. B, Pearson correlation of subsampled profiles to initial profile at 9x coverage for healthy individuals and patients with lung cancer.
Figure 9A:
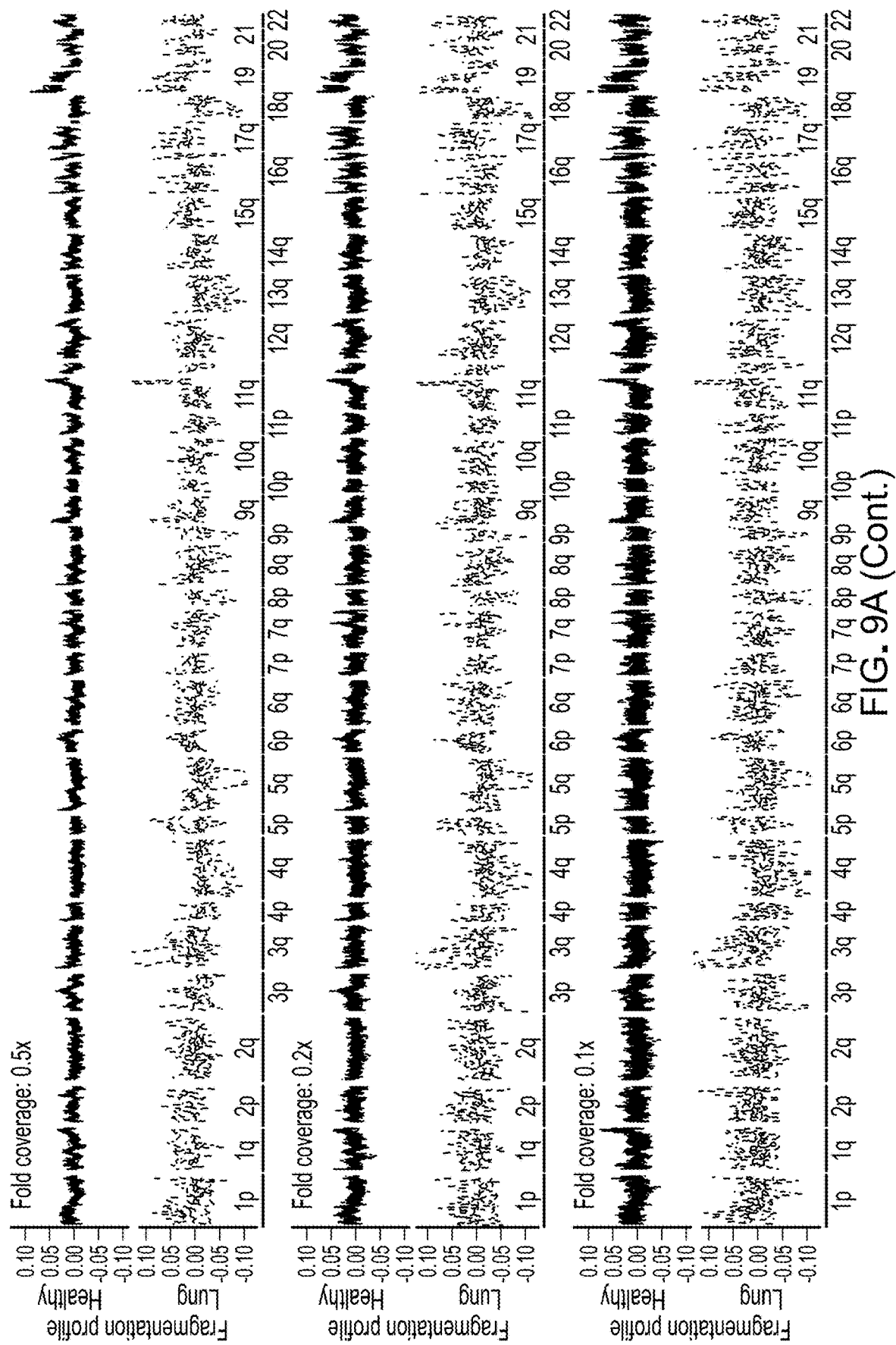
Figure 9B:
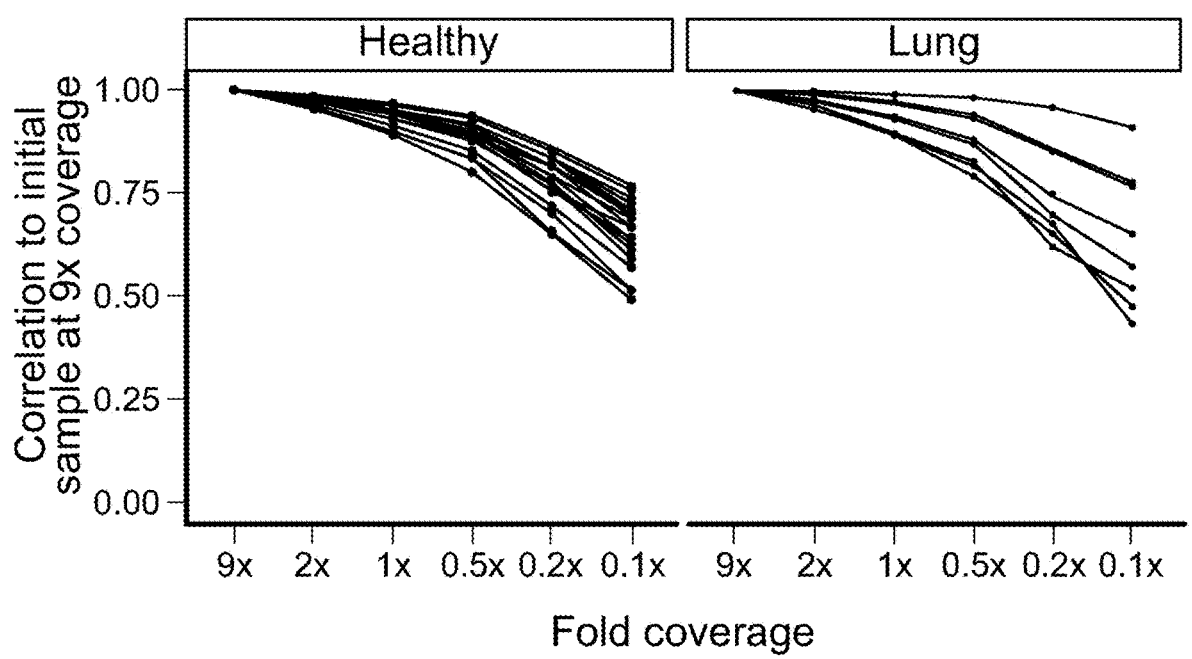
Figure 10:
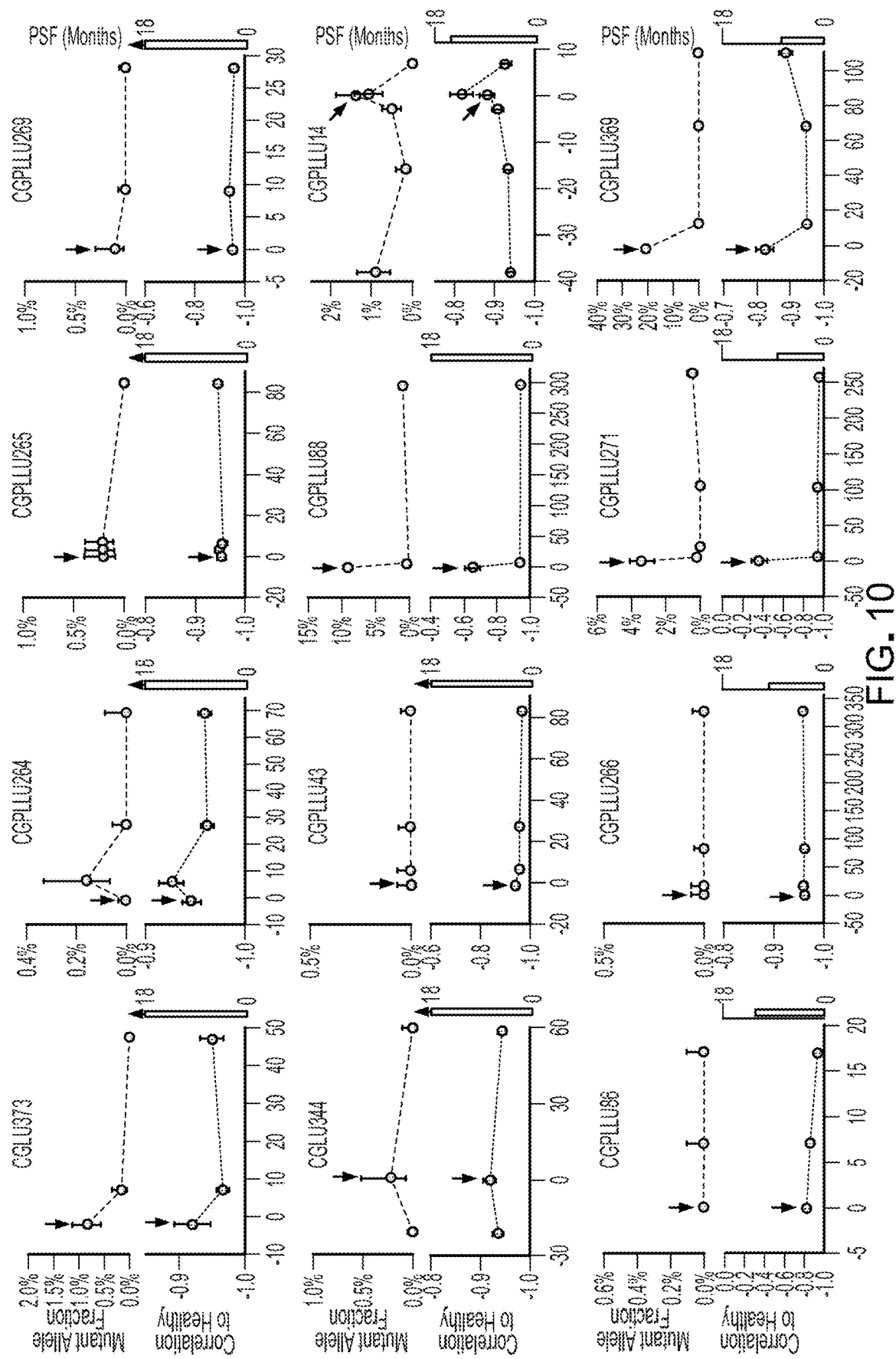
FIG. 10. cfDNA fragmentation profiles and sequence alterations during therapy. Detection and monitoring of cancer in serial blood draws from NSCLC patients (n=19) undergoing treatment with targeted tyrosine kinase inhibitors (black arrows) was performed using targeted sequencing (top) and genome-wide fragmentation profiles (bottom). For each case, the vertical axis of the lower panel displays −1 times the correlation of each sample to the median healthy cfDNA fragmentation profile. Error bars depict confidence intervals from binomial tests for mutant allele fractions and confidence intervals calculated using Fisher transformation for genome-wide fragmentation profiles. Although the approaches analyze different aspects of cfDNA (whole genome compared to specific alterations) the targeted sequencing and fragmentation profiles were similar for patients responding to therapy as well as those with stable or progressive disease. As fragmentation profiles reflect both genomic and epigenomic alterations, while mutant allele fractions only reflect individual mutations, mutant allele fractions alone may not reflect the absolute level of correlation of fragmentation profiles to healthy individuals.
Figure 10:
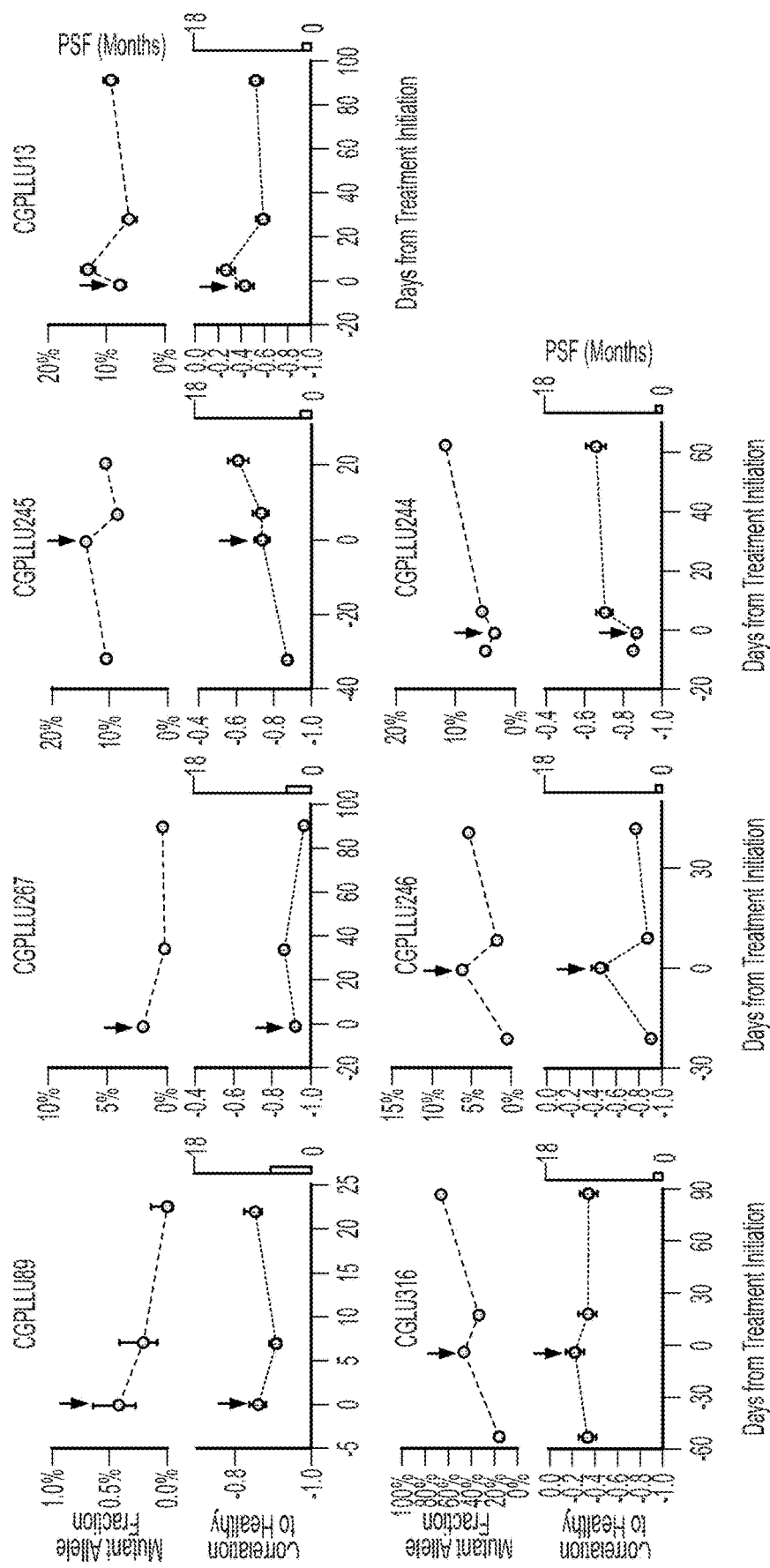

Subsampling analyses of whole genome sequence data was performed at 9× coverage from cfDNA of patients with cancer at ~2×, ~1×, ~0.5×, ~0.2×, and ~0.1× genome coverage, and it was determined that altered fragmentation profiles were readily identified even at 0.5× genome coverage (FIG. 9). Based on these observations, whole genome sequencing was performed with coverage of 1-2× to evaluate whether fragmentation profiles may change during the course of targeted therapy in a manner similar to monitoring of sequence alterations. cfDNA from 19 non-small cell lung cancer patients including 5 with partial radiographic response, 8 with stable disease, 4 with progressive disease, and 2 with unmeasurable disease, during the course of anti-EGFR or anti-ERBB2 therapy was evaluated (Table 6; Appendix F). As shown in FIG. 10, the degree of abnormality in the fragmentation profiles during therapy closely matched levels of EGFR or ERBB2 mutant allele fractions as determined using targeted sequencing (Spearman correlation of mutant allele fractions to fragmentation profiles=0.74). This correlation is remarkable as genome-wide and mutation-based methods are orthogonal and examine different cfDNA alterations that may be suppressed in these patients due to prior therapy. Notably all cases that had progression free survival of six or more months displayed a drop of or had extremely low levels of ctDNA after initiation of therapy as determined by fragmentation profiles, while cases with poor clinical outcome had increases in ctDNA. These results demonstrate the feasibility of fragmentation analyses for detecting the presence of tumor-derived cfDNA, and suggests that such analyses may also be useful for quantitative monitoring of cancer patients during treatment.

Figure 11A:
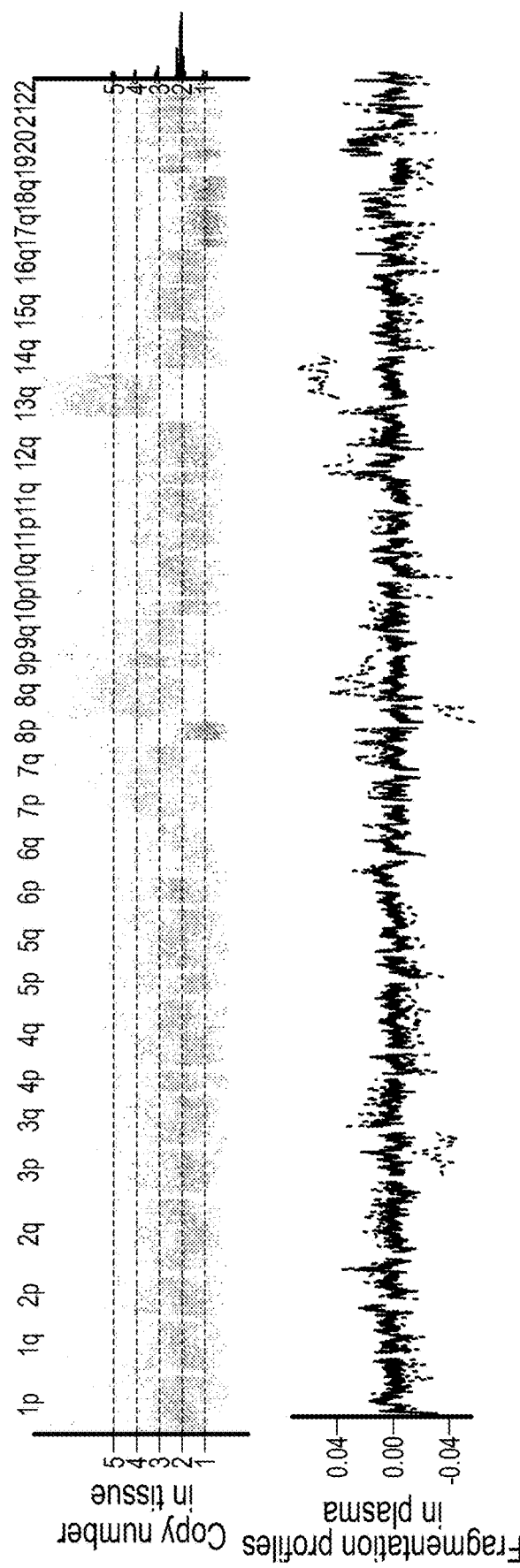
FIGS. 11A-11C. cfDNA fragmentation profiles in healthy individuals and patients with cancer. A, Fragmentation profiles (bottom) in the context of tumor copy number changes (top) in a colorectal cancer patient where parallel analyses of tumor tissue were performed. The distribution of segment means and integer copy numbers are shown at top right in the indicated colors. Altered fragmentation profiles were present in regions of the genome that were copy neutral and were further affected in regions with copy number changes. B, GC adjusted fragmentation profiles from 1-2x whole genome sequencing for healthy individuals and patients with cancer are depicted per cancer type using 5 Mb windows. The median healthy profile is indicated in black and the 98% confidence band is shown in gray. For patients with cancer, individual profiles are colored based on their correlation to the healthy median. C, Windows are indicated in orange if more than 10% of the cancer samples had a fragment ratio more than three standard deviations from the median healthy fragment ratio. These analyses highlight the multitude of position dependent alterations across the genome in cfDNA of individuals with cancer.

The fragmentation profiles were examined in the context of known copy number changes in a patient where parallel analyses of tumor tissue were obtained. These analyses demonstrated that altered fragmentation profiles were present in regions of the genome that were copy neutral and that these may be further affected in regions with copy number changes (FIG. 11a and FIG. 12a). Position dependent differences in fragmentation patterns could be used to distinguish cancer-derived cfDNA from healthy cfDNA in these regions (FIG. 12a, b), while overall cfDNA fragment size measurements would have missed such differences (FIG. 12a).

Figure 11B:
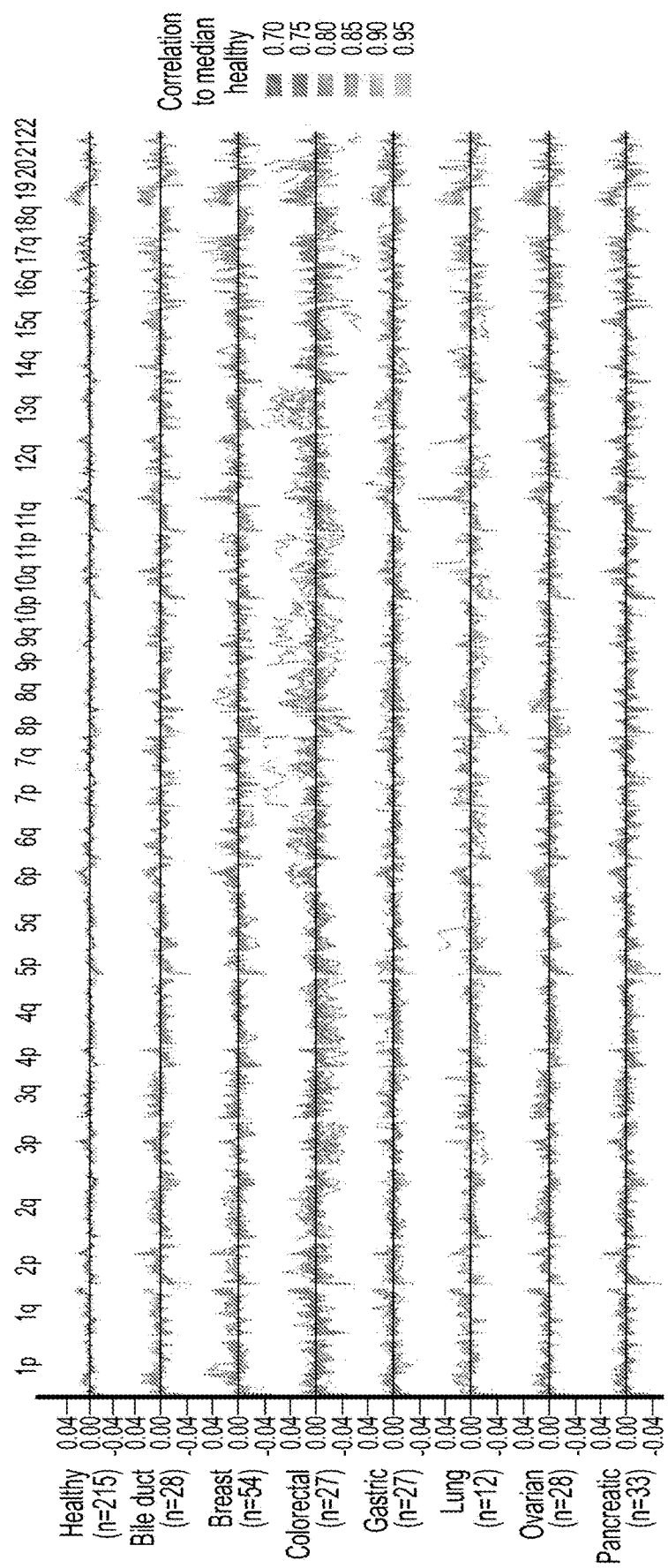
Figure 11C:
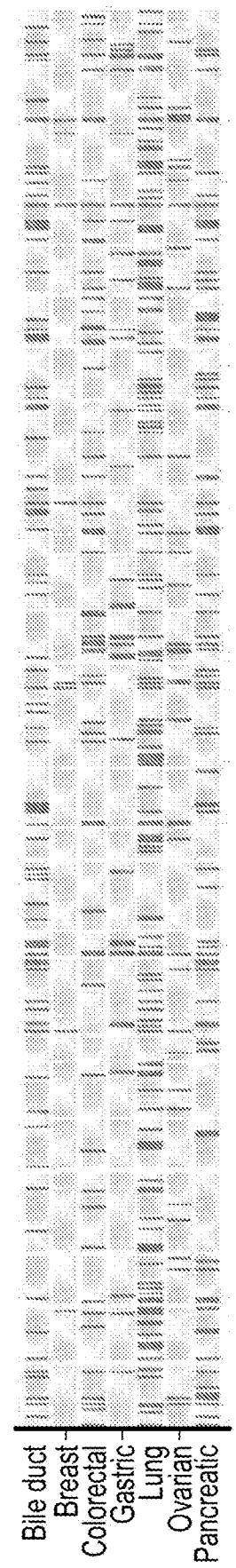
Figure 13A:
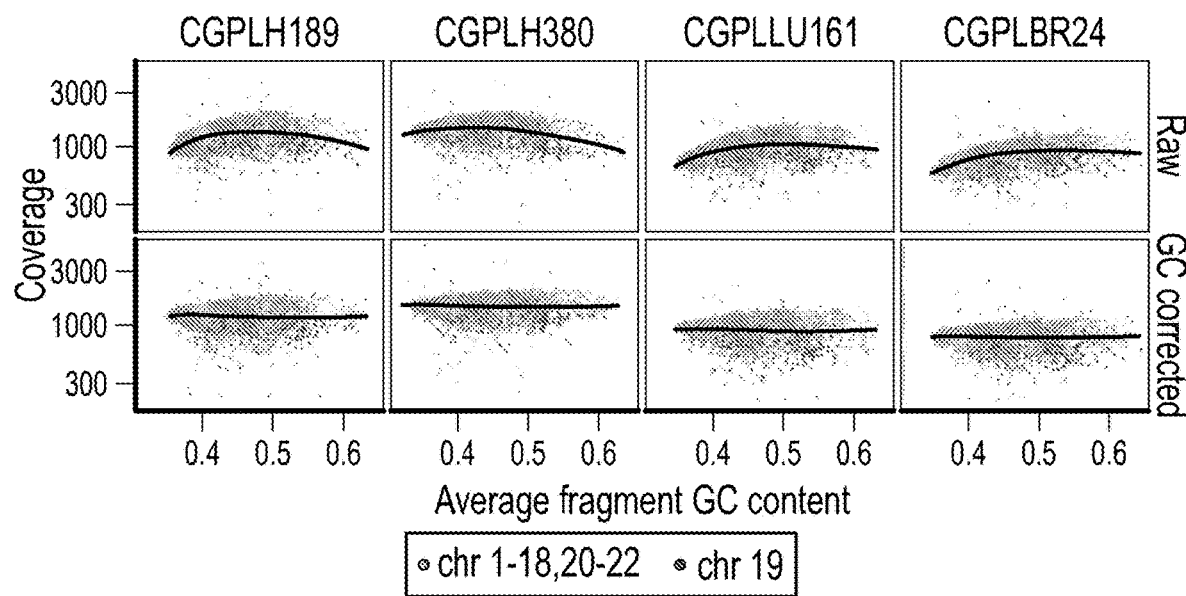
FIGS. 13A and 13B. Genome-wide GC correction of cfDNA fragments. To estimate and control for the effects of GC content on sequencing coverage, coverage in non-overlapping 100 kb genomic windows was calculated across the autosomes. For each window, the average GC of the aligned fragments was calculated. A, Loess smoothing of raw coverage (top row) for two randomly selected healthy subjects (CGPLH189 and CGPLH380) and two cancer patients (CGPLLU161 and CGPLBR24) with undetectable aneuploidy (PA score<2.35). After subtracting the average coverage predicted by the loess model, the residuals were rescaled to the median autosomal coverage (bottom row). As fragment length may also result in coverage biases, this GC correction procedure was performed separately for short ($\leq$150 bp) and long ($\geq$151 bp) fragments. While the 100 kb bins on chromosome 19 (blue points) consistently have less coverage than predicted by the loess model, we did not implement a chromosome-specific correction as such an approach would remove the effects of chromosomal copy number on coverage. B, Overall, a limited correlation was found between short or long fragment coverage and GC content after correction among healthy subjects and cancer patients with a PA score<3.
Figure 13B:
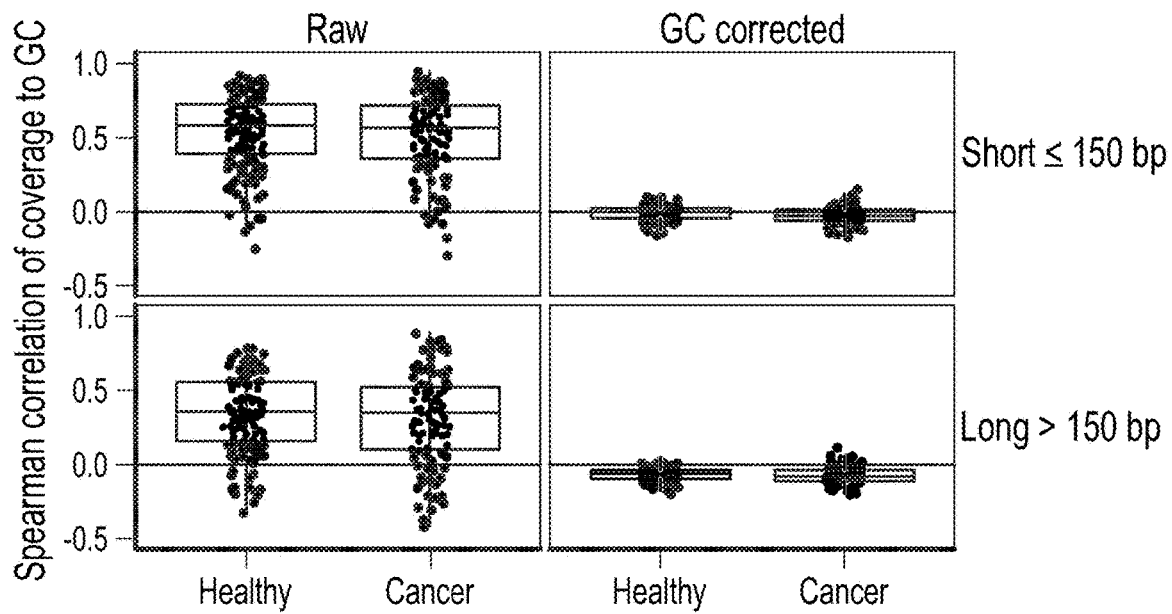

These analyses were extended to an independent cohort of cancer patients and healthy individuals. Whole genome sequencing of cfDNA at 1-2× coverage from a total of 208 patients with cancer, including breast (n=54), colorectal (n=27), lung (n=12), ovarian (n=28), pancreatic (n=34), gastric (n=27), or bile duct cancers (n=26), as well as 215 individuals without cancer was performed (Table 1 (Appendix A) and Table 4 (Appendix D)). All cancer patients were treatment naïve and the majority had resectable disease (n=183). After GC adjustment of short and long cfDNA fragment coverage (FIG. 13a), coverage and size characteristics of fragments in windows throughout the genome were examined (FIG. 11b, Table 4 (Appendix D) and Table 7 (Appendix G)). Genome-wide correlations of coverage to GC content were limited and no differences in these correlations between cancer patients and healthy individuals were observed (FIG. 13b). Healthy individuals had highly concordant fragmentation profiles, while patients with cancer had high variability with decreased correlation to the median healthy profile (Table 7; Appendix G). An analysis of the most commonly altered fragmentation windows in the genome among cancer patients revealed a median of 60 affected windows across the cancer types analyzed, highlighting the multitude of position dependent alterations in fragmentation of cfDNA in individuals with cancer (FIG. 11c).

Figure 14:
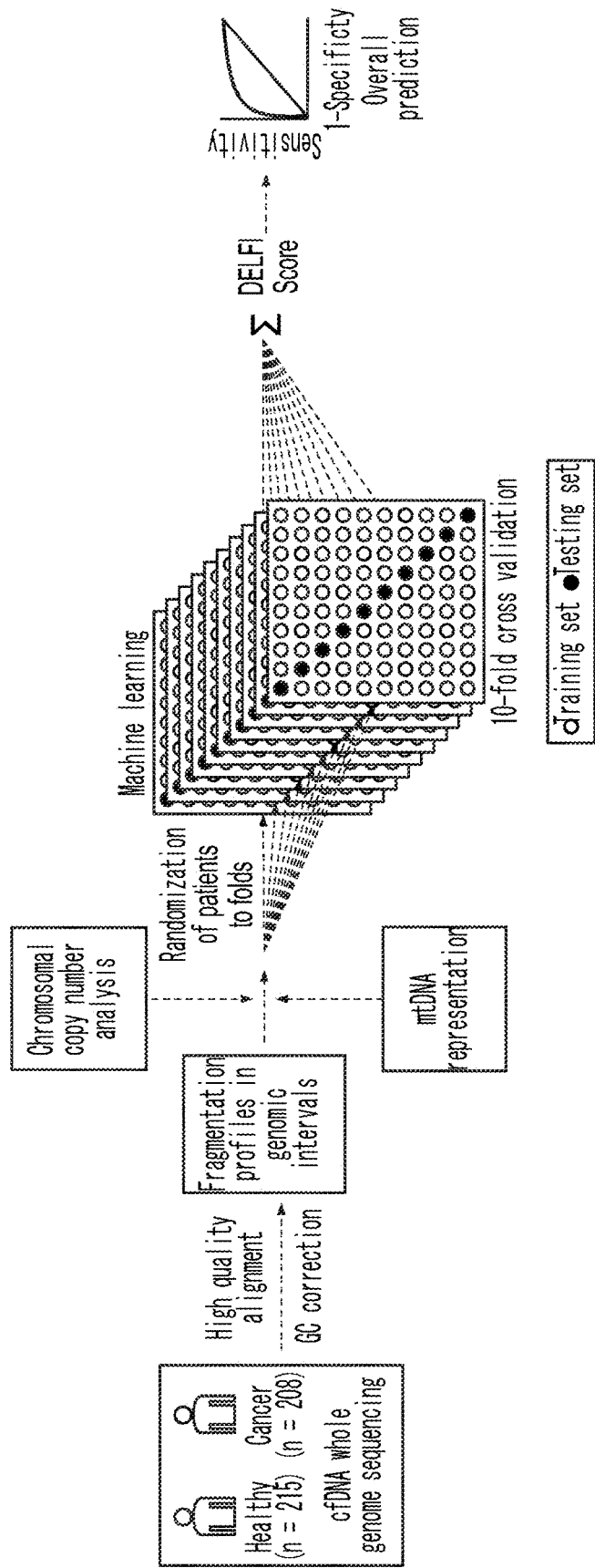
FIG. 14. Schematic of machine learning model. Gradient tree boosting machine learning was used to examine whether cfDNA can be categorized as having characteristics of a cancer patient or healthy individual. The machine learning model included fragmentation size and coverage characteristics in windows throughout the genome, as well as chromosomal arm and mitochondrial DNA copy numbers. A 10-fold cross validation approach was employed in which each sample is randomly assigned to a fold and 9 of the folds (90% of the data) are used for training and one fold (10% of the data) is used for testing. The prediction accuracy from a single cross validation is an average over the 10 possible combinations of test and training sets. As this prediction accuracy can reflect bias from the initial randomization of patients, the entire procedure was repeat, including the randomization of patients to folds, 10 times. For all cases, feature selection and model estimation were performed on training data and were validated on test data and the test data were never used for feature selection. Ultimately, a DELFI score was obtained that could be used to classify individuals as likely healthy or having cancer.
Figure 15:
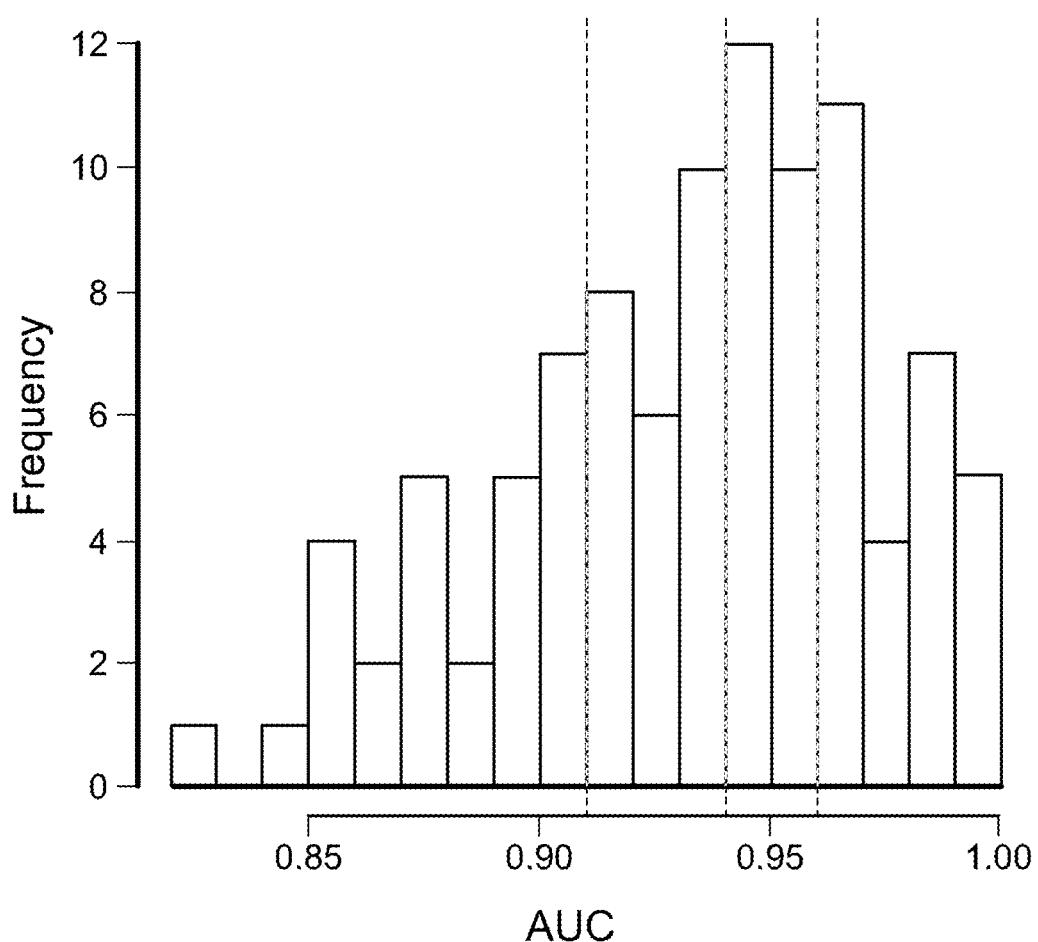
FIG. 15. Distribution of AUCs across the repeated 10-fold cross-validation. The $25^{th}$, $50^{th}$, and $75^{th}$ percentiles of the 100 AUCs for the cohort of 215 healthy individuals and 208 patients with cancer are indicated by dashed lines.
Figure 16A:
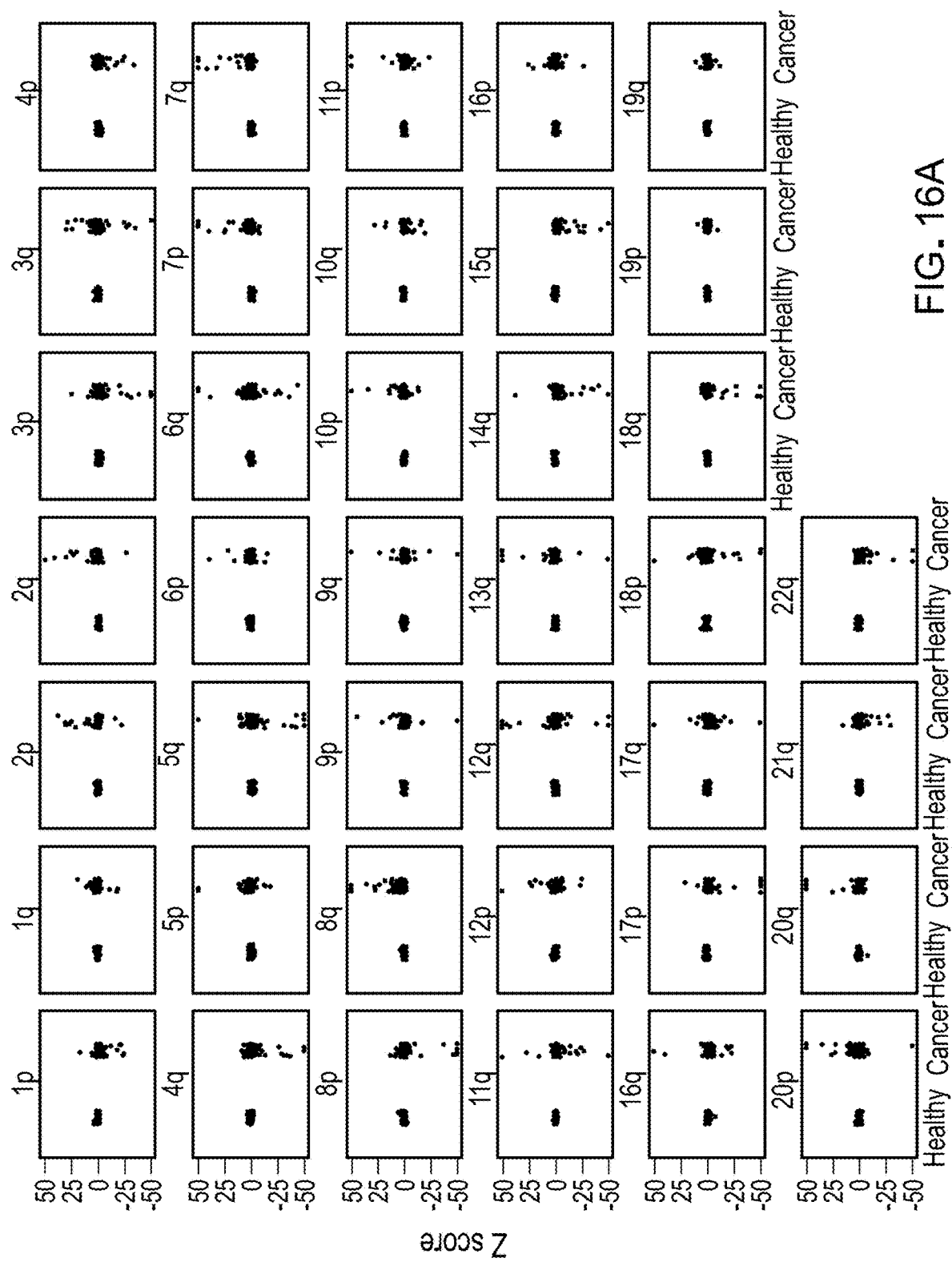
FIGS. 16A and 16B. Whole-genome analyses of chromosomal arm copy number changes and mitochondrial genome representation. A, Z scores for each autosome arm are depicted for healthy individuals (n=215) and patients with cancer (n=208). The vertical axis depicts normal copy at zero with positive and negative values indicating arm gains and losses, respectively. Z scores greater than 50 or less than −50 are thresholded at the indicated values. B, The fraction of reads mapping to the mitochondrial genome is depicted for healthy individuals and patients with cancer.
Figure 16B:
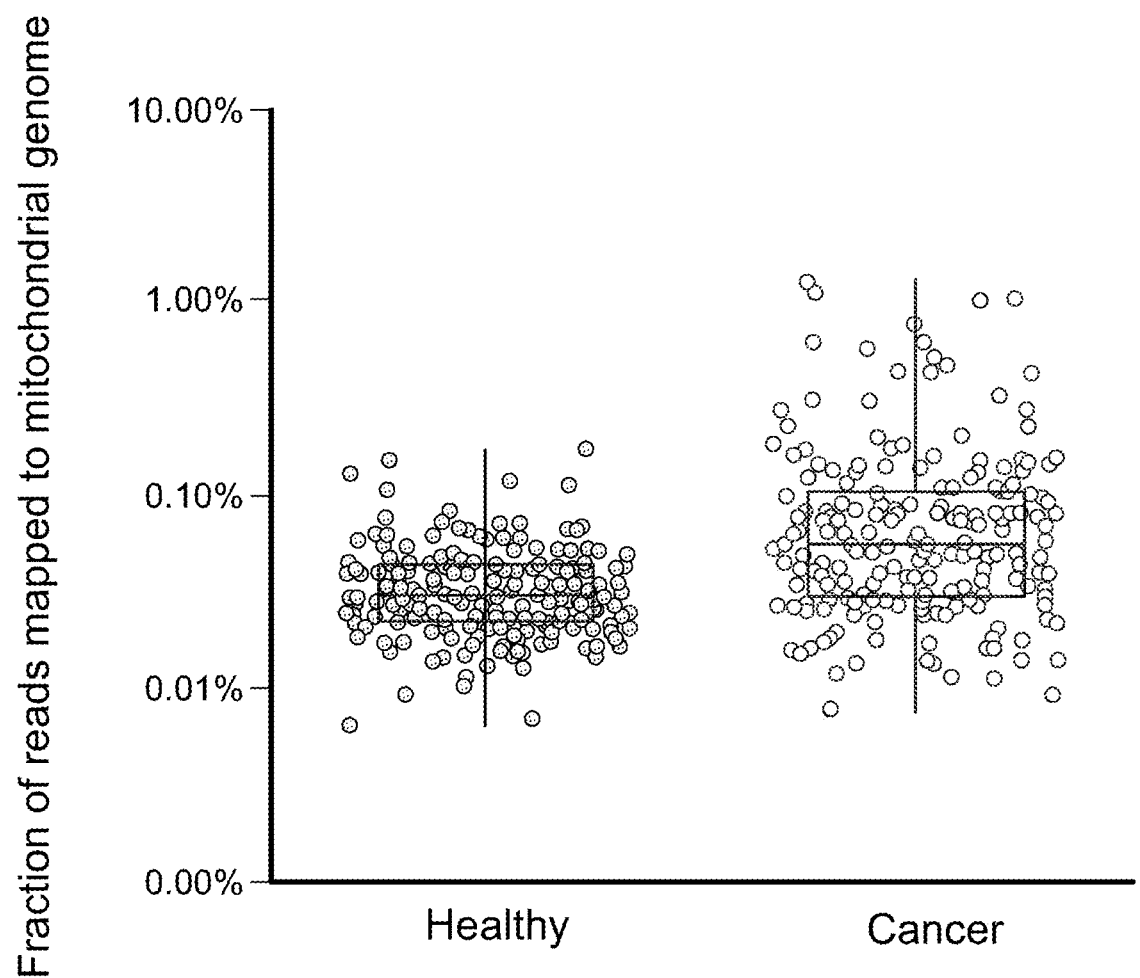
Figure 17A:
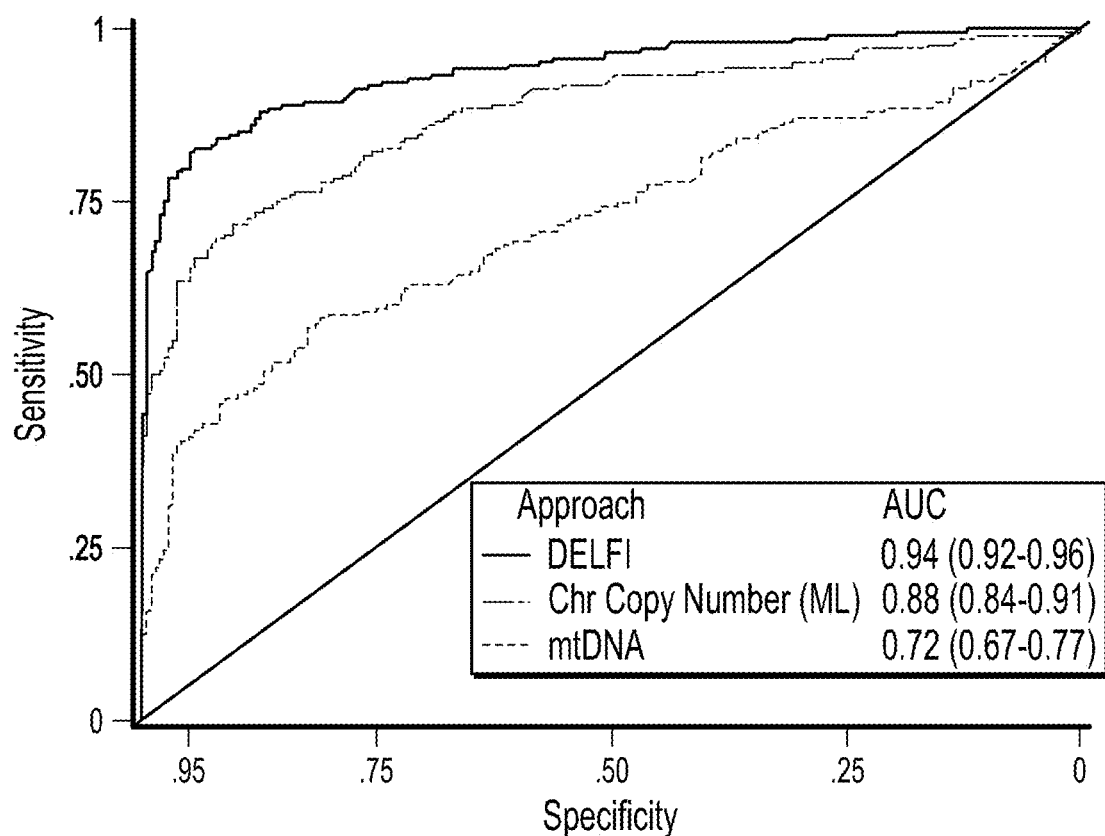
FIGS. 17A and 17B. Detection of cancer using DELFI. A, Receiver operator characteristics for detection of cancer using cfDNA fragmentation profiles and other genome-wide features in a machine learning approach are depicted for a cohort of 215 healthy individuals and 208 patients with cancer (DELFI, AUC=0.94), with $\geq$95% specificity shaded in blue. Machine learning analyses of chromosomal arm copy number (Chr copy number (ML)), and mitochondrial genome copy number (mtDNA), are shown in the indicated colors. B, Analyses of individual cancers types using the DELFI-combined approach had AUCs ranging from 0.86 to >0.99.
Figure 17B:
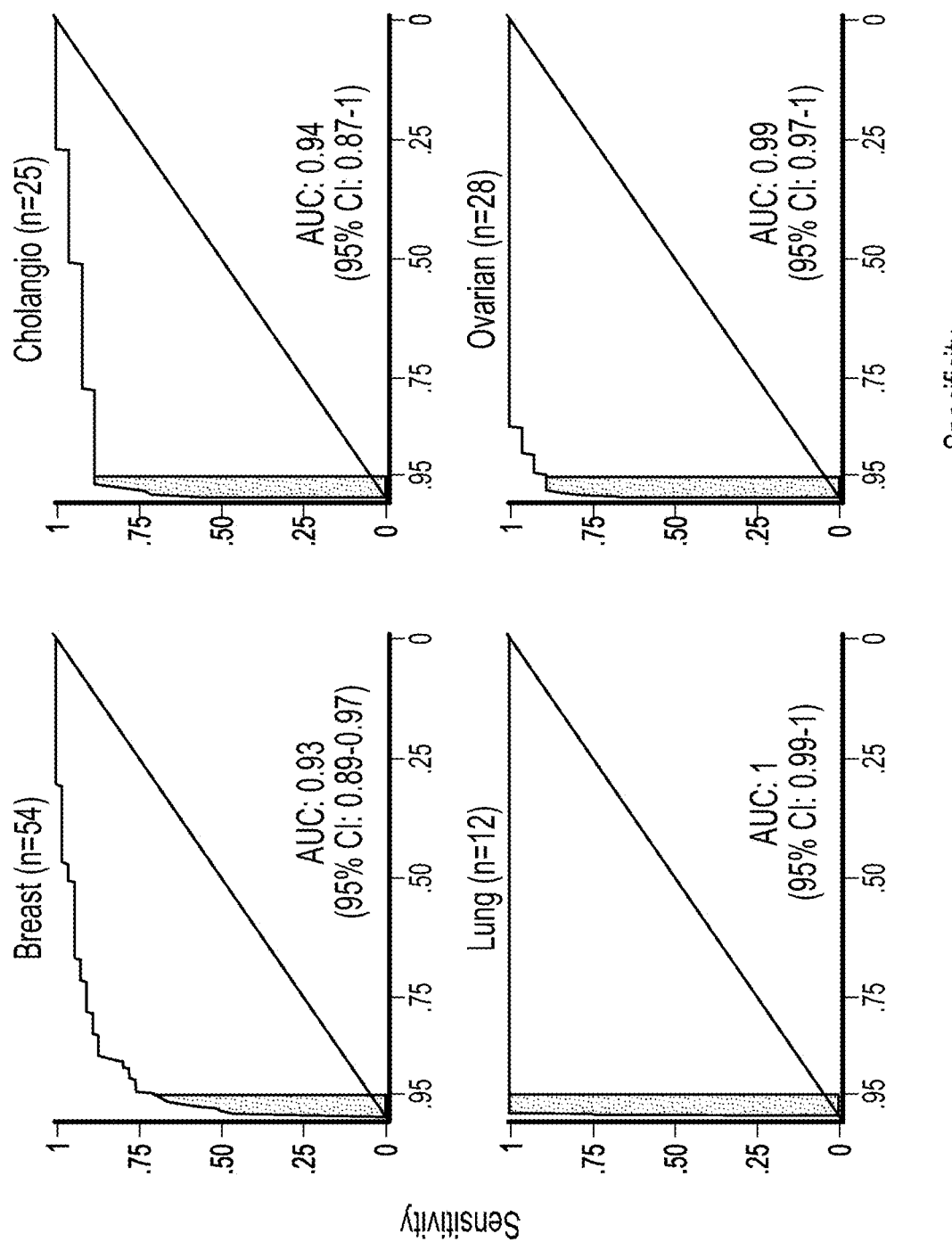
Figure 17B:
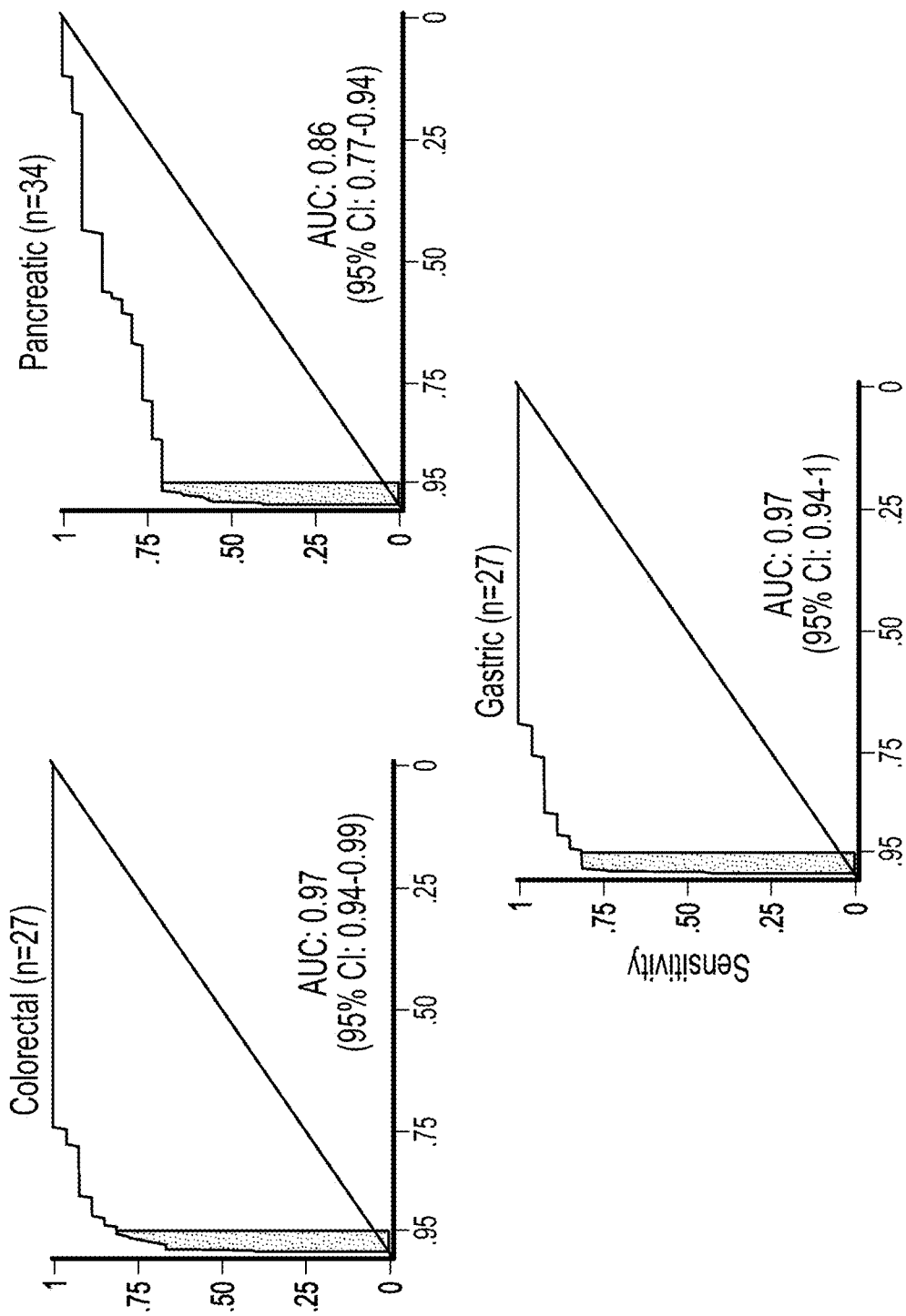
Figure 18:
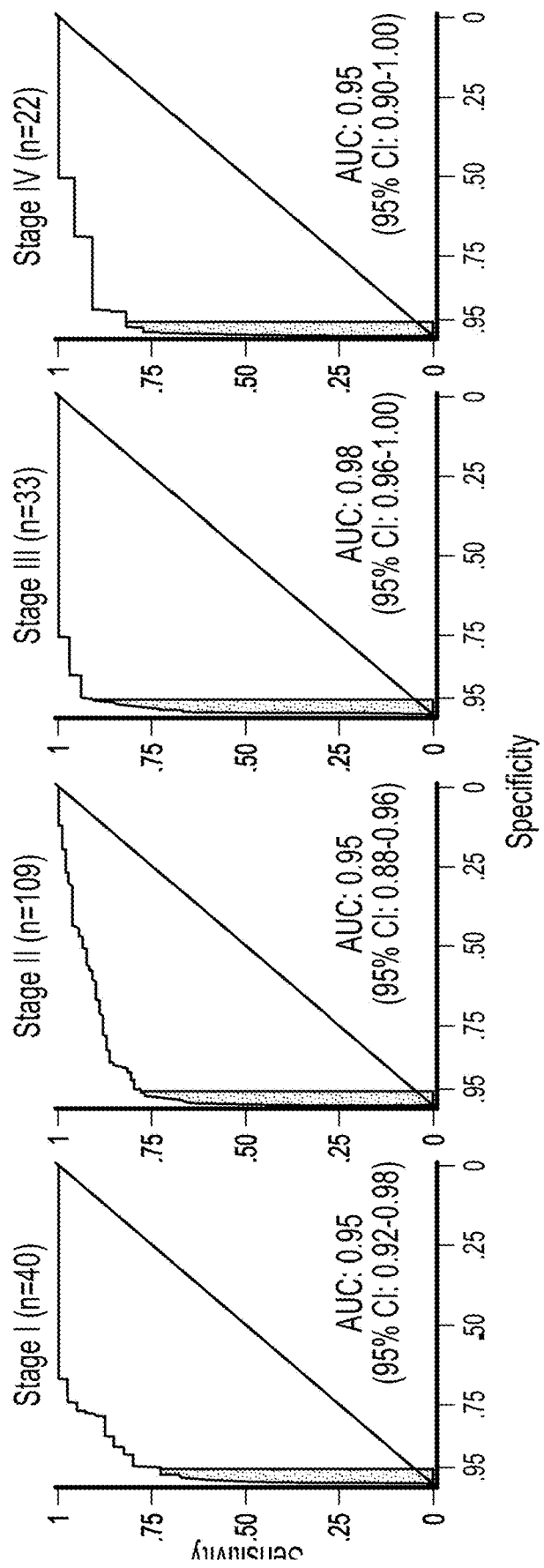
FIG. 18. DELFI detection of cancer by stage. Receiver operator characteristics for detection of cancer using cfDNA fragmentation profiles and other genome-wide features in a machine learning approach are depicted for a cohort of 215 healthy individuals and each stage of 208 patients with cancer with $\geq$95% specificity shaded in blue.

To determine if position dependent fragmentation changes can be used to detect individuals with cancer, a gradient tree boosting machine learning model was implemented to examine whether cfDNA can be categorized as having characteristics of a cancer patient or healthy individual and estimated performance characteristics of this approach by ten-fold cross validation repeated ten times (FIGS. 14 and 15). The machine learning model included GC-adjusted short and long fragment coverage characteristics in windows throughout the genome. A machine learning classifier for copy number changes from chromosomal arm dependent features rather than a single score was also developed (FIG. 16a and Table 8 (Appendix H)) and mitochondrial copy number changes were also included (FIG. 16b) as these could also help distinguish cancer from healthy individuals. Using this implementation of DELFI, a score was obtained that could be used to classify patients as healthy or having cancer. 152 of the 208 cancer patients were detected (73% sensitivity, 95% CI 67%-79%) while four of the 215 healthy individuals were misclassified (98% specificity) (Table 9). At a threshold of 95% specificity, 80% of patients with cancer were detected (95% CI, 74%-85%), including 79% of resectable (stage I-III) patients (145 of 183) and 82% of metastatic (stage IV) patients (18 out of 22) (Table 9). Receiver operator characteristic analyses for detection of patients with cancer had an AUC of 0.94 (95% CI 0.92-0.96), ranged among cancer types from 0.86 for pancreatic cancer to ≥0.99 for lung and ovarian cancers (FIGS. 17a and 17b), and had AUCs≥0.92 across all stages (FIG. 18). The DELFI classifier score did not differ with age among either cancer patients or healthy individuals (Table 1; Appendix A).

TABLE 9

DELFI performance for cancer detection.

| | | | 95% specificity | | | 98% specificity | |
|---|---|---|---|---|---|---|---|
| | Individuals analyzed | Individuals detected | Sensitivity | 95% CI | Individuals detected | Sensitivity | 95% CI |
| Healthy | 215 | 10 | — | — | 4 | — | — |
| Cancer | 208 | 166 | 80% | 74%-85% | 152 | 73% | 67%-79% |
| Type Breast | 54 | 38 | 70% | 56%-82% | 31 | 57% | 43%-71% |
| Bile duct | 26 | 23 | 88% | 70%-98% | 21 | 81% | 61%-93% |
| Colorectal | 27 | 22 | 81% | 62%-94% | 19 | 70% | 50%-86% |
| Gastric | 27 | 22 | 81% | 62%-94% | 22 | 81% | 62%-94% |
| Lung | 12 | 12 | 100% | 74%-100% | 12 | 100% | 74%-100% |
| Ovarian | 28 | 25 | 89% | 72%-98% | 25 | 89% | 72%-98% |
| Pancreatic | 34 | 24 | 71% | 53%-85% | 22 | 65% | 46%-80% |
| Stage I | 41 | 30 | 73% | 53%-86% | 28 | 68% | 52%-82% |
| II | 109 | 85 | 78% | 69%-85% | 78 | 72% | 62%-80% |
| III | 33 | 30 | 91% | 76%-98% | 26 | 79% | 61%-91% |
| IV | 22 | 18 | 82% | 60%-95% | 17 | 77% | 55%-92% |
| 0, X | 3 | 3 | 100% | 29%-100% | 3 | 100% | 29%-100% |

To assess the contribution of fragment size and coverage, chromosome arm copy number, or mitochondrial mapping to the predictive accuracy of the model, the repeated 10-fold cross-validation procedure was implemented to assess performance characteristics of these features in isolation. It was observed that fragment coverage features alone (AUC=0.94) were nearly identical to the classifier that combined all features (AUC=0.94) (FIG. 17a). In contrast, analyses of chromosomal copy number changes had lower performance (AUC=0.88) but were still more predictive than copy number changes based on individual scores (AUC=0.78) or mitochondrial mapping (AUC=0.72) (FIG. 17a). These results suggest that fragment coverage is the major contributor to our classifier. Including all features in the prediction model may contribute in a complementary fashion for detection of patients with cancer as they can be obtained from the same genome sequence data.

Figure 19:
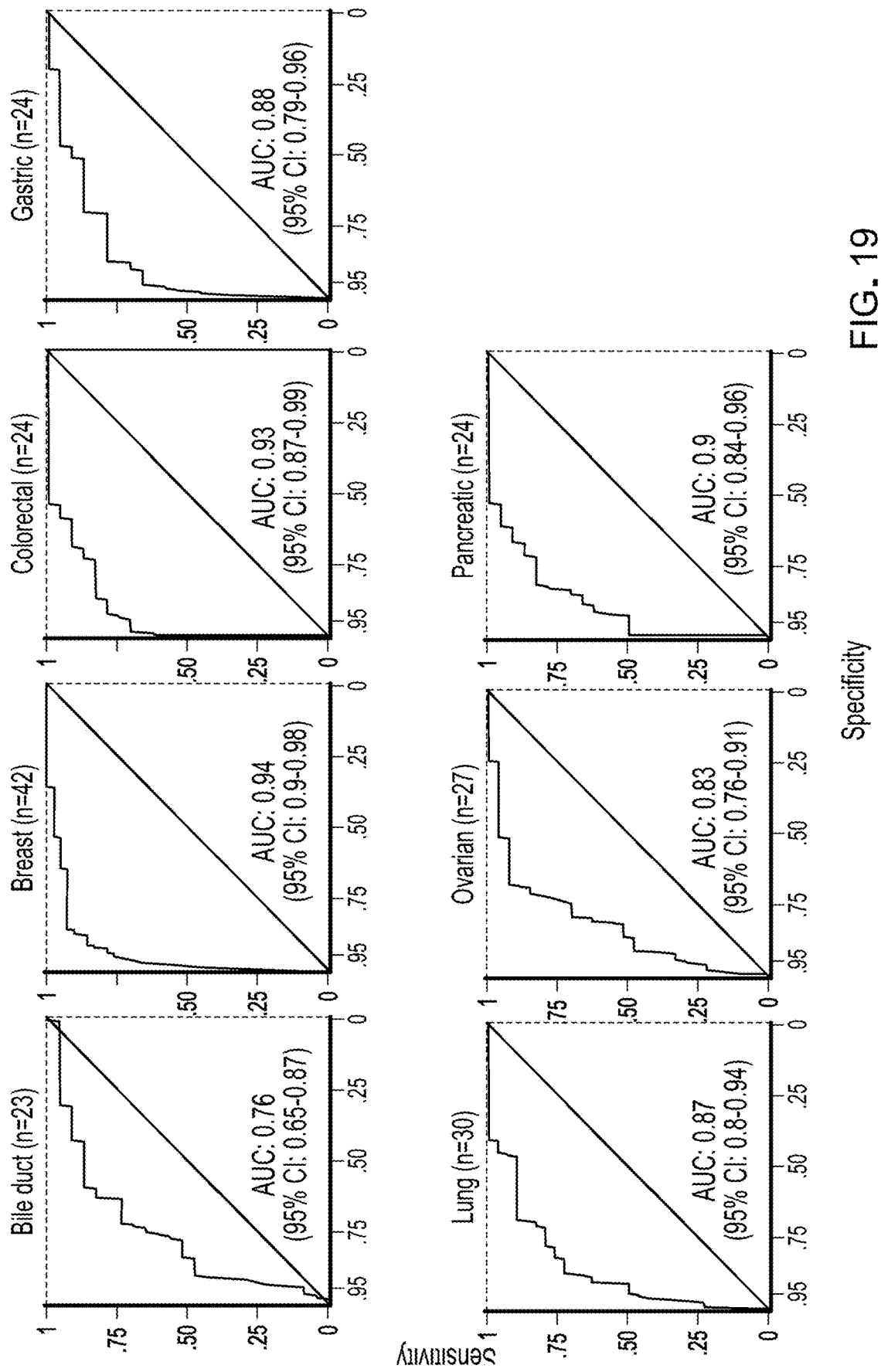
FIG. 19. DELFI tissue of origin prediction. Receiver operator characteristics for DELFI tissue prediction of bile duct, breast, colorectal, gastric, lung, ovarian, and pancreatic cancers are depicted. In order to increase sample sizes within cancer type classes, cases detected with a 90% specificity were included, and the lung cancer cohort was supplemented with the addition of baseline cfDNA data from 18 lung cancer patients with prior treatment (see, e.g., Shen et al., 2018 Nature, 563:579-583).

As fragmentation profiles reveal regional differences in fragmentation that may differ between tissues, a similar machine learning approach was used to examine whether cfDNA patterns could identify the tissue of origin of these tumors. It was found that this approach had a 61% accuracy (95% CI 53%-67%), including 76% for breast, 44% for bile duct, 71% for colorectal, 67% for gastric, 53% for lung, 48% for ovarian, and 50% for pancreatic cancers (FIG. 19, Table 10). The accuracy increased to 75% (95% CI 69%-81%) when considering assigning patients with abnormal cfDNA to one of two sites of origin (Table 10). For all tumor types, the classification of the tissue of origin by DELFI was significantly higher than determined by random assignment (p<0.01, binomial test, Table 10).

TABLE 10

DELFI tissue of origin prediction

| Cancer Type | Patients Detected* | Top Prediction | | Top Two Predictions | | Random Assignment | |
|---|---|---|---|---|---|---|---|
| | | Patients | Accuracy (95% CI) | Patients | Accuracy (95% CI) | Patients | Accuracy |
| Breast | 42 | 32 | 76% (61%-88%) | 38 | 91% (77%-97%) | 9 | 22% |
| Bile Duct | 23 | 10 | 44% (23%-66%) | 15 | 65% (43%-84%) | 3 | 12% |
| Colorectal | 24 | 17 | 71% (49%-87%) | 19 | 79% (58%-93%) | 3 | 12% |
| Gastric | 24 | 16 | 67% (45%-84%) | 19 | 79% (58%-93%) | 3 | 12% |
| Lung | 30 | 16 | 53% (34%-72%) | 23 | 77% (58%-90%) | 2 | 6% |
| Ovarian | 27 | 13 | 48% (29%-68%) | 16 | 59% (38%-78%) | 4 | 14% |
| Pancreatic | 24 | 12 | 50% (29%-71%) | 16 | 67% (45%-84%) | 3 | 12% |
| Total | 194 | 116 | 61% (53%-67%) | 146 | 75% (69%-81%) | 26 | 13% |

*Patients detected are based on DELFI detection at 90% specificity. Lung cohort includes additional lung cancer patients with prior therapy.

As cancer-specific sequence alterations can be used to identify patients with cancer, it was evaluated whether combining DELFI with this approach could increase the sensitivity of cancer detection (FIG. 20). An analysis of cfDNA from a subset of the treatment naïve cancer patients using both DELFI and targeted sequencing revealed that 82% (103 of 126) of patients had fragmentation profile alterations, while 66% (83 of 126) had sequence alterations. Over 89% of cases with mutant allele fractions>1% were detected by DELFI while for cases With mutant allele fractions<1% the fraction detected by DELFI was 80%, including for cases that were undetectable using targeted sequencing (Table 7; Appendix G). When these approaches were used together, the combined sensitivity of detection increased to 91% (115 of 126 patients) with a specificity of 98% (FIG. 20).

Overall, genome-wide cfDNA fragmentation profiles are different between cancer patients and healthy individuals. The variability in fragment lengths and coverage in a position dependent manner throughout the genome may explain the apparently contradictory observations of previous analyses of cfDNA at specific loci or of overall fragment sizes. In patients with cancer, heterogeneous fragmentation patterns in cfDNA appear to be a result of mixtures of nucleosomal DNA from both blood and neoplastic cells. These studies provide a method for simultaneous analysis of tens to potentially hundreds of tumor-specific abnormalities from minute amounts of cfDNA, overcoming a limitation that has precluded the possibility of more sensitive analyses of cfDNA. DELFI analyses detected a higher fraction of cancer patients than previous cfDNA analysis methods that have focused on sequence or overall fragmentation sizes (see, e.g., Phallen et al., 2017 *Sci Transl Med* 9:eaan2415; Cohen et al., 2018 *Science* 359:926; Newman et al., 2014 *Nat Med* 20:548, Bettegowda et al., 2014 *Sci Transl Med* 6:224ra24; Newman et al., 2016 *Nat Biotechnol* 34:547). As demonstrated in this Example, combining DELFI with analyses of other cfDNA alterations may further increase the sensitivity of detection. As fragmentation profiles appear related to nucleosomal DNA patterns, DELFI may be used for determining the primary source of tumor-derived cfDNA. The identification of the source of circulating tumor DNA in over half of patients analyzed may be further improved by including clinical characteristics, other biomarkers, including methylation changes, and additional diagnostic approaches (Ruibal Morell, 1992 *The International journal of biological markers* 7:160; Galli et al., 2013 *Clinical chemistry and laboratory medicine* 51:1369; Sikaris, 2011 *Heart, lung & circulation* 20:634; Cohen et al., 2018 *Science* 359:926). Finally, this approach requires only a small amount of whole genome sequencing, without the need for deep sequencing typical of approaches that focus on specific alterations. The performance characteristics and limited amount of sequencing needed for DELFI suggests that our approach could be broadly applied for screening and management of patients with cancer.

These results demonstrate that genome-wide cfDNA fragmentation profiles are different between cancer patients and healthy individuals. As such, cfDNA fragmentation profiles can have important implications for future research and applications of non-invasive approaches for detection of human cancer.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 1

APPENDIX A: Summary of patients and samples analyzed

| Patient | Patient Type | Sample Type | Timepoint | Age at Diagnosis | Gender | Stage | TNM Staging | Site of Primary Tumor |
|---|---|---|---|---|---|---|---|---|
| CGCRC321 | Colorectal Cancer | cfDNA | Preoperative treatment naive | 69 | F | IV | T3N2M1 | Coecum |
| CGCRC232 | Colorectal Cancer | cfDNA | Preoperative treatment naive | 51 | M | IV | T3N2M1 | Sigmoid Colon |
| CGCRC293 | Colorectal Cancer | cfDNA | Preoperative treatment naive | 55 | M | IV | T3N2M1 | Rectum |
| CGCRC294 | Colorectal Cancer | cfDNA | Preoperative treatment naive | 67 | F | II | T3N0M0 | Sigmoid Colon |
| CGCRC296 | Colorectal Cancer | cfDNA | Preoperative treatment naive | 76 | F | II | T4N0M0 | Coecum |
| CGCRC299 | Colorectal Cancer | cfDNA | Preoperative treatment naive | 71 | M | I | T1N0M0 | Rectum |
| CGCRC300 | Colorectal Cancer | cfDNA | Preoperative treatment naive | 65 | M | I | T2N0M0 | Rectum |
| CGCRC301 | Colorectal Cancer | cfDNA | Preoperative treatment naive | 76 | F | I | T2N0M0 | Rectum |
| CGCRC302 | Colorectal Cancer | cfDNA | Preoperative treatment naive | 73 | M | II | T3N0M0 | Transverse Colon |
| CGCRC304 | Colorectal Cancer | cfDNA | Preoperative treatment naive | 86 | F | II | T3N0M0 | Rectum |
| CGCRC305 | Colorectal Cancer | cfDNA | Preoperative treatment naive | 83 | F | II | T3N0M0 | Transverse Colon |
| CGCRC306 | Colorectal Cancer | cfDNA | Preoperative treatment naive | 80 | F | II | T4N0M0 | Ascending Colon |
| CGCRC307 | Colorectal Cancer | cfDNA | Preoperative treatment naive | 78 | F | II | T3N0M0 | Ascending Colon |
| CGCRC308 | Colorectal Cancer | cfDNA | Preoperative treatment naive | 72 | F | III | T4N2M0 | Ascending Colon |
| CGCRC311 | Colorectal Cancer | cfDNA | Preoperative treatment naive | 59 | M | I | T2N0M0 | Sigmoid Colon |
| CGCRC315 | Colorectal Cancer | cfDNA | Preoperative treatment naive | 74 | M | III | T3N1M0 | Sigmoid Colon |
| CGCRC316 | Colorectal Cancer | cfDNA | Preoperative treatment naive | 80 | M | III | T3N2M0 | Transverse Colon |
| CGCRC317 | Colorectal Cancer | cfDNA | Preoperative treatment naive | 74 | M | III | T3N2M0 | Descending Colon |
| CGCRC318 | Colorectal Cancer | cfDNA | Preoperative treatment naive | 81 | M | I | T2N0M0 | Coecum |
| CGCRC319 | Colorectal Cancer | cfDNA | Preoperative treatment naive | 80 | F | III | T2N1M0 | Descending Colon |
| CGCRC320 | Colorectal Cancer | cfDNA | Preoperative treatment naive | 73 | F | I | T2N0M0 | Ascending Colon |
| CGCRC321 | Colorectal Cancer | cfDNA | Preoperative treatment naive | 68 | M | I | T2N0M0 | Rectum |
| CGCRC333 | Colorectal Cancer | cfDNA | Preoperative treatment naive | NA | F | IV | NA | Colon/Rectum |
| CGCRC336 | Colorectal Cancer | cfDNA | Preoperative treatment naive | NA | M | IV | NA | Colon/Rectum |
| CGCRC338 | Colorectal Cancer | cfDNA | Preoperative treatment naive | NA | F | IV | NA | Colon/Rectum |
| CGCRC341 | Colorectal Cancer | cfDNA | Preoperative treatment naive | NA | F | IV | NA | Colon/Rectum |
| CGCRC342 | Colorectal Cancer | cfDNA | Preoperative treatment naive | NA | M | IV | NA | Colon/Rectum |
| CGLU316 | Lung Cancer | cfDNA | Pre-treatment, Day −53 | 50 | F | IV | T3N2M0 | Left Upper Lobe of Lung |
| CGLU316 | Lung Cancer | cfDNA | Pre-treatment, Day −4 | 50 | F | IV | T3N2M0 | Left Upper Lobe of Lung |
| CGLU316 | Lung Cancer | cfDNA | Post-treatment, Day 18 | 50 | F | IV | T3N2M0 | Left Upper Lobe of Lung |
| CGLU316 | Lung Cancer | cfDNA | Post-treatment, Day 87 | 50 | F | IV | T3N2M0 | Left Upper Lobe of Lung |
| CGLU344 | Lung Cancer | cfDNA | Pre-treatment, Day −21 | 65 | F | IV | T2N2M1 | Right Upper Lobe of Lung |
| CGLU344 | Lung Cancer | cfDNA | Pre-treatment, Day 0 | 65 | F | IV | T2N2M1 | Right Upper Lobe of Lung |
| CGLU344 | Lung Cancer | cfDNA | Post-treatment, Day 0.1875 | 65 | F | IV | T2N2M1 | Right Upper Lobe of Lung |
| CGLU344 | Lung Cancer | cfDNA | Post-treatment, Day 59 | 65 | F | IV | T2N2M1 | Right Upper Lobe of Lung |
| CGLU369 | Lung Cancer | cfDNA | Pre-treatment, Day −2 | 48 | F | IV | T2NxM1 | Right Upper Lobe of Lung |
| CGLU369 | Lung Cancer | cfDNA | Post-treatment, Day 12 | 48 | F | IV | T2NxM1 | Right Upper Lobe of Lung |
| CGLU369 | Lung Cancer | cfDNA | Post-treatment, Day 68 | 48 | F | IV | T2NxM1 | Right Upper Lobe of Lung |
| CGLU369 | Lung Cancer | cfDNA | Post-treatment, Day 110 | 48 | F | IV | T2NxM1 | Right Upper Lobe of Lung |
| CGLU373 | Lung Cancer | cfDNA | Pre-treatment, Day −2 | 56 | F | IV | T3N1M0 | Right Upper Lobe of Lung |
| CGLU373 | Lung Cancer | cfDNA | Post-treatment, Day 0.125 | 56 | F | IV | T3N1M0 | Right Upper Lobe of Lung |
| CGLU373 | Lung Cancer | cfDNA | Post-treatment, Day 7 | 56 | F | IV | T3N1M0 | Right Upper Lobe of Lung |
| CGLU373 | Lung Cancer | cfDNA | Post-treatment, Day 47 | 56 | F | IV | T3N1M0 | Right Upper Lobe of Lung |

TABLE 1-continued

APPENDIX A: Summary of patients and samples analyzed

| | | | | | | | | |
|---|---|---|---|---|---|---|---|---|
| CGPLBR100 | Breast Cancer | cfDNA | Preoperative treatment naive | 44 | F | III | T2N2M0 | Left Breast |
| CGPLBR101 | Breast Cancer | cfDNA | Preoperative treatment naive | 46 | F | II | T2N1M0 | Left Breast |
| CGPLBR102 | Breast Cancer | cfDNA | Preoperative treatment naive | 47 | F | II | T2N1M0 | Right Breast |
| CGPLBR103 | Breast Cancer | cfDNA | Preoperative treatment naive | 48 | F | II | T2N1M0 | Left Breast |
| CGPLBR104 | Breast Cancer | cfDNA | Preoperative treatment naive | 68 | F | II | T2N0M0 | Right Breast |
| CGPLBR12 | Breast Cancer | cfDNA | Preoperative treatment naive | NA | F | III | NA | Breast |
| CGPLBR18 | Breast Cancer | cfDNA | Preoperative treatment naive | NA | F | III | NA | Breast |
| CGPLBR23 | Breast Cancer | cfDNA | Preoperative treatment naive | 53 | F | II | NA | Breast |
| CGPLBR24 | Breast Cancer | cfDNA | Preoperative treatment naive | 52 | F | II | NA | Breast |
| CGPLBR28 | Breast Cancer | cfDNA | Preoperative treatment naive | 59 | F | III | NA | Breast |
| CGPLBR30 | Breast Cancer | cfDNA | Preoperative treatment naive | 61 | F | II | NA | Breast |
| CGPLBR31 | Breast Cancer | cfDNA | Preoperative treatment naive | 54 | F | II | NA | Breast |
| CGPLBR32 | Breast Cancer | cfDNA | Preoperative treatment naive | NA | F | II | NA | Breast |
| CGPLBR33 | Breast Cancer | cfDNA | Preoperative treatment naive | 47 | F | II | NA | Breast |
| CGPLBR34 | Breast Cancer | cfDNA | Preoperative treatment naive | 60 | F | II | NA | Breast |
| CGPLBR35 | Breast Cancer | cfDNA | Preoperative treatment naive | 43 | F | II | NA | Breast |
| CGPLBR36 | Breast Cancer | cfDNA | Preoperative treatment naive | 36 | F | II | NA | Breast |
| CGPLBR37 | Breast Cancer | cfDNA | Preoperative treatment naive | 58 | F | II | NA | Breast |
| CGPLBR38 | Breast Cancer | cfDNA | Preoperative treatment naive | 54 | F | I | T1N0M0 | Left Breast |
| CGPLBR40 | Breast Cancer | cfDNA | Preoperative treatment naive | 66 | F | III | T2N2M0 | Left Breast |
| CGPLBR41 | Breast Cancer | cfDNA | Preoperative treatment naive | 51 | F | III | T3N1M0 | Left Breast |
| CGPLBR45 | Breast Cancer | cfDNA | Preoperative treatment naive | 57 | F | II | NA | Breast |
| CGPLBR46 | Breast Cancer | cfDNA | Preoperative treatment naive | 54 | F | III | NA | Breast |
| CGPLBR47 | Breast Cancer | cfDNA | Preoperative treatment naive | 54 | F | I | NA | Breast |
| CGPLBR48 | Breast Cancer | cfDNA | Preoperative treatment naive | 47 | F | II | T2N1M0 | Left Breast |
| CGPLBR49 | Breast Cancer | cfDNA | Preoperative treatment naive | 37 | F | II | T2N1M0 | Left Breast |
| CGPLBR50 | Breast Cancer | cfDNA | Preoperative treatment naive | 51 | F | I | NA | Breast |
| CGPLBR51 | Breast Cancer | cfDNA | Preoperative treatment naive | 53 | F | II | NA | Breast |
| CGPLBR52 | Breast Cancer | cfDNA | Preoperative treatment naive | 68 | F | III | NA | Breast |
| CGPLBR55 | Breast Cancer | cfDNA | Preoperative treatment naive | 53 | F | III | T3N1M0 | Right Breast |
| CGPLBR56 | Breast Cancer | cfDNA | Preoperative treatment naive | 56 | F | II | NA | Breast |
| CGPLBR57 | Breast Cancer | cfDNA | Preoperative treatment naive | 54 | F | III | T2N2M0 | Left Breast |
| CGPLBR59 | Breast Cancer | cfDNA | Preoperative treatment naive | 42 | F | I | T1N0M0 | Left Breast |
| CGPLBR60 | Breast Cancer | cfDNA | Preoperative treatment naive | 61 | F | II | NA | Left Breast |
| CGPLBR61 | Breast Cancer | cfDNA | Preoperative treatment naive | 67 | F | II | T2N1M0 | Left Breast |
| CGPLBR63 | Breast Cancer | cfDNA | Preoperative treatment naive | 48 | F | II | T2N1M0 | Left Breast |
| CGPLBR65 | Breast Cancer | cfDNA | Preoperative treatment naive | 50 | F | II | NA | Left Breast |
| CGPLBR68 | Breast Cancer | cfDNA | Preoperative treatment naive | 64 | F | III | T4N1M0 | Breast |
| CGPLBR69 | Breast Cancer | cfDNA | Preoperative treatment naive | 43 | F | II | T2N0M0 | Breast |
| CGPLBR70 | Breast Cancer | cfDNA | Preoperative treatment naive | 60 | F | II | T2N1M0 | Breast |
| CGPLBR71 | Breast Cancer | cfDNA | Preoperative treatment naive | 65 | F | II | T2N0M0 | Breast |
| CGPLBR72 | Breast Cancer | cfDNA | Preoperative treatment naive | 67 | F | II | T2N0M0 | Breast |
| CGPLBR73 | Breast Cancer | cfDNA | Preoperative treatment naive | 60 | F | II | T2N1M0 | Breast |
| CGPLBR76 | Breast Cancer | cfDNA | Preoperative treatment naive | 53 | F | II | T2N0M0 | Right Breast |
| CGPLBR81 | Breast Cancer | cfDNA | Preoperative treatment naive | 54 | F | II | NA | Breast |
| CGPLBR82 | Breast Cancer | cfDNA | Preoperative treatment naive | 70 | F | I | T1N0M0 | Right Breast |
| CGPLBR83 | Breast Cancer | cfDNA | Preoperative treatment naive | 53 | F | II | T2N1M0 | Right Breast |
| CGPLBR84 | Breast Cancer | cfDNA | Preoperative treatment naive | NA | F | III | NA | Breast |
| CGPLBR87 | Breast Cancer | cfDNA | Preoperative treatment naive | 80 | F | II | T2N1M0 | Right Breast |
| CGPLBR88 | Breast Cancer | cfDNA | Preoperative treatment naive | 48 | F | II | T1N1M0 | Left Breast |
| CGPLBR90 | Breast Cancer | cfDNA | Preoperative treatment naive | 51 | F | II | NA | Right Breast |
| CGPLBR91 | Breast Cancer | cfDNA | Preoperative treatment naive | 62 | F | III | T2N2M0 | Breast |
| CGPLBR92 | Breast Cancer | cfDNA | Preoperative treatment naive | 58 | F | II | T2N1M0 | Breast |
| CGPLBR93 | Breast Cancer | cfDNA | Preoperative treatment naive | 59 | F | II | T1N0M0 | Breast |
| CGPLH189 | Healthy | cfDNA | Preoperative treatment naive | 74 | M | NA | NA | NA |
| CGPLH190 | Healthy | cfDNA | Preoperative treatment naive | 67 | M | NA | NA | NA |
| CGPLH192 | Healthy | cfDNA | Preoperative treatment naive | 74 | M | NA | NA | NA |
| CGPLH193 | Healthy | cfDNA | Preoperative treatment naive | 72 | F | NA | NA | NA |
| CGPLH194 | Healthy | cfDNA | Preoperative treatment naive | 75 | F | NA | NA | NA |
| CGPLH196 | Healthy | cfDNA | Preoperative treatment naive | 64 | M | NA | NA | NA |
| CGPLH197 | Healthy | cfDNA | Preoperative treatment naive | 74 | M | NA | NA | NA |
| CGPLH198 | Healthy | cfDNA | Preoperative treatment naive | 66 | M | NA | NA | NA |
| CGPLH199 | Healthy | cfDNA | Preoperative treatment naive | 75 | F | NA | NA | NA |
| CGPLH200 | Healthy | cfDNA | Preoperative treatment naive | 51 | M | NA | NA | NA |
| CGPLH201 | Healthy | cfDNA | Preoperative treatment naive | 68 | F | NA | NA | NA |
| CGPLH202 | Healthy | cfDNA | Preoperative treatment naive | 73 | M | NA | NA | NA |
| CGPLH203 | Healthy | cfDNA | Preoperative treatment naive | 59 | M | NA | NA | NA |
| CGPLH205 | Healthy | cfDNA | Preoperative treatment naive | 68 | F | NA | NA | NA |
| CGPLH208 | Healthy | cfDNA | Preoperative treatment naive | 75 | F | NA | NA | NA |
| CGPLH209 | Healthy | cfDNA | Preoperative treatment naive | 74 | M | NA | NA | NA |
| CGPLH210 | Healthy | cfDNA | Preoperative treatment naive | 75 | M | NA | NA | NA |
| CGPLH211 | Healthy | cfDNA | Preoperative treatment naive | 75 | F | NA | NA | NA |
| CGPLH300 | Healthy | cfDNA | Preoperative treatment naive | 72 | F | NA | NA | NA |
| CGPLH307 | Healthy | cfDNA | Preoperative treatment naive | 53 | M | NA | NA | NA |
| CGPLH308 | Healthy | cfDNA | Preoperative treatment naive | 60 | M | NA | NA | NA |
| CGPLH309 | Healthy | cfDNA | Preoperative treatment naive | 61 | F | NA | NA | NA |
| CGPLH310 | Healthy | cfDNA | Preoperative treatment naive | 55 | F | NA | NA | NA |
| CGPLH311 | Healthy | cfDNA | Preoperative treatment naive | 50 | M | NA | NA | NA |

TABLE 1-continued

APPENDIX A: Summary of patients and samples analyzed

| | | | | | | | | |
|---|---|---|---|---|---|---|---|---|
| CGPLH314 | Healthy | cfDNA | Preoperative treatment naive | 59 | M | NA | NA | NA |
| CGPLH314 | Healthy | cfDNA, technical replicate | Preoperative treatment naive | 59 | M | NA | NA | NA |
| CGPLH315 | Healthy | cfDNA | Preoperative treatment naive | 59 | F | NA | NA | NA |
| CGPLH316 | Healthy | cfDNA | Preoperative treatment naive | 64 | M | NA | NA | NA |
| CGPLH317 | Healthy | cfDNA | Preoperative treatment naive | 53 | F | NA | NA | NA |
| CGPLH319 | Healthy | cfDNA | Preoperative treatment naive | 60 | F | NA | NA | NA |
| CGPLH320 | Healthy | cfDNA | Preoperative treatment naive | 75 | F | NA | NA | NA |
| CGPLH322 | Healthy | cfDNA | Preoperative treatment naive | 53 | F | NA | NA | NA |
| CGPLH324 | Healthy | cfDNA | Preoperative treatment naive | 59 | F | NA | NA | NA |
| CGPLH325 | Healthy | cfDNA | Preoperative treatment naive | 54 | M | NA | NA | NA |
| CGPLH326 | Healthy | cfDNA | Preoperative treatment naive | 67 | F | NA | NA | NA |
| CGPLH327 | Healthy | cfDNA | Preoperative treatment naive | 50 | M | NA | NA | NA |
| CGPLH328 | Healthy | cfDNA | Preoperative treatment naive | 68 | F | NA | NA | NA |
| CGPLH328 | Healthy | cfDNA, technical replicate | Preoperative treatment naive | 68 | F | NA | NA | NA |
| CGPLH329 | Healthy | cfDNA | Preoperative treatment naive | 59 | M | NA | NA | NA |
| CGPLH330 | Healthy | cfDNA | Preoperative treatment naive | 75 | M | NA | NA | NA |
| CGPLH331 | Healthy | cfDNA | Preoperative treatment naive | 55 | M | NA | NA | NA |
| CGPLH331 | Healthy | cfDNA, technical replicate | Preoperative treatment naive | 55 | M | NA | NA | NA |
| CGPLH333 | Healthy | cfDNA | Preoperative treatment naive | 60 | M | NA | NA | NA |
| CGPLH335 | Healthy | cfDNA | Preoperative treatment naive | 74 | M | NA | NA | NA |
| CGPLH336 | Healthy | cfDNA | Preoperative treatment naive | 53 | F | NA | NA | NA |
| CGPLH337 | Healthy | cfDNA | Preoperative treatment naive | 53 | F | NA | NA | NA |
| CGPLH338 | Healthy | cfDNA | Preoperative treatment naive | 75 | M | NA | NA | NA |
| CGPLH339 | Healthy | cfDNA | Preoperative treatment naive | 70 | M | NA | NA | NA |
| CGPLH340 | Healthy | cfDNA | Preoperative treatment naive | 62 | M | NA | NA | NA |
| CGPLH341 | Healthy | cfDNA | Preoperative treatment naive | 61 | F | NA | NA | NA |
| CGPLH342 | Healthy | cfDNA | Preoperative treatment naive | 49 | F | NA | NA | NA |
| CGPLH343 | Healthy | cfDNA | Preoperative treatment naive | 58 | M | NA | NA | NA |
| CGPLH344 | Healthy | cfDNA | Preoperative treatment naive | 50 | M | NA | NA | NA |
| CGPLH345 | Healthy | cfDNA | Preoperative treatment naive | 55 | F | NA | NA | NA |
| CGPLH346 | Healthy | cfDNA | Preoperative treatment naive | 50 | F | NA | NA | NA |
| CGPLH35 | Healthy | cfDNA | Preoperative treatment naive | 48 | F | NA | NA | NA |
| CGPLH350 | Healthy | cfDNA | Preoperative treatment naive | 65 | M | NA | NA | NA |
| CGPLH351 | Healthy | cfDNA | Preoperative treatment naive | 71 | M | NA | NA | NA |
| CGPLH352 | Healthy | cfDNA | Preoperative treatment naive | 50 | F | NA | NA | NA |
| CGPLH353 | Healthy | cfDNA | Preoperative treatment naive | 50 | F | NA | NA | NA |
| CGPLH354 | Healthy | cfDNA | Preoperative treatment naive | 50 | F | NA | NA | NA |
| CGPLH355 | Healthy | cfDNA | Preoperative treatment naive | 70 | M | NA | NA | NA |
| CGPLH356 | Healthy | cfDNA | Preoperative treatment naive | 50 | F | NA | NA | NA |
| CGPLH357 | Healthy | cfDNA | Preoperative treatment naive | 52 | F | NA | NA | NA |
| CGPLH358 | Healthy | cfDNA | Preoperative treatment naive | 55 | M | NA | NA | NA |
| CGPLH36 | Healthy | cfDNA | Preoperative treatment naive | 36 | F | NA | NA | NA |
| CGPLH360 | Healthy | cfDNA | Preoperative treatment naive | 60 | M | NA | NA | NA |
| CGPLH361 | Healthy | cfDNA | Preoperative treatment naive | 50 | M | NA | NA | NA |
| CGPLH362 | Healthy | cfDNA | Preoperative treatment naive | 72 | F | NA | NA | NA |
| CGPLH363 | Healthy | cfDNA | Preoperative treatment naive | 68 | F | NA | NA | NA |
| CGPLH364 | Healthy | cfDNA | Preoperative treatment naive | 50 | F | NA | NA | NA |
| CGPLH365 | Healthy | cfDNA | Preoperative treatment naive | 68 | F | NA | NA | NA |
| CGPLH366 | Healthy | cfDNA | Preoperative treatment naive | 61 | M | NA | NA | NA |
| CGPLH367 | Healthy | cfDNA | Preoperative treatment naive | 50 | F | NA | NA | NA |
| CGPLH368 | Healthy | cfDNA | Preoperative treatment naive | 50 | M | NA | NA | NA |
| CGPLH369 | Healthy | cfDNA | Preoperative treatment naive | 55 | F | NA | NA | NA |
| CGPLH369 | Healthy | cfDNA, technical replicate | Preoperative treatment naive | 55 | F | NA | NA | NA |
| CGPLH37 | Healthy | cfDNA | Preoperative treatment naive | 39 | F | NA | NA | NA |
| CGPLH370 | Healthy | cfDNA | Preoperative treatment naive | 50 | F | NA | NA | NA |
| CGPLH371 | Healthy | cfDNA | Preoperative treatment naive | 57 | F | NA | NA | NA |
| CGPLH380 | Healthy | cfDNA | Preoperative treatment naive | 53 | F | NA | NA | NA |
| CGPLH381 | Healthy | cfDNA | Preoperative treatment naive | 56 | F | NA | NA | NA |
| CGPLH382 | Healthy | cfDNA | Preoperative treatment naive | 53 | F | NA | NA | NA |
| CGPLH383 | Healthy | cfDNA | Preoperative treatment naive | 62 | F | NA | NA | NA |
| CGPLH384 | Healthy | cfDNA | Preoperative treatment naive | 50 | M | NA | NA | NA |
| CGPLH385 | Healthy | cfDNA | Preoperative treatment naive | 69 | M | NA | NA | NA |
| CGPLH386 | Healthy | cfDNA | Preoperative treatment naive | 62 | M | NA | NA | NA |
| CGPLH386 | Healthy | cfDNA technical replicate | Preoperative treatment naive | 62 | M | NA | NA | NA |
| CGPLH387 | Healthy | cfDNA | Preoperative treatment naive | 71 | F | NA | NA | NA |
| CGPLH388 | Healthy | cfDNA | Preoperative treatment naive | 57 | F | NA | NA | NA |
| CGPLH389 | Healthy | cfDNA | Preoperative treatment naive | 73 | F | NA | NA | NA |
| CGPLH390 | Healthy | cfDNA | Preoperative treatment naive | 50 | F | NA | NA | NA |

TABLE 1-continued

APPENDIX A: Summary of patients and samples analyzed

| | | | | | | | | |
|---|---|---|---|---|---|---|---|---|
| CGPLH391 | Healthy | cfDNA | Preoperative treatment naive | 58 | M | NA | NA | NA |
| CGPLH391 | Healthy | cfDNA technical replicate | Preoperative treatment naive | 58 | M | NA | NA | NA |
| CGPLH392 | Healthy | cfDNA | Preoperative treatment naive | 57 | F | NA | NA | NA |
| CGPLH393 | Healthy | cfDNA | Preoperative treatment naive | 54 | M | NA | NA | NA |
| CGPLH394 | Healthy | cfDNA | Preoperative treatment naive | 55 | F | NA | NA | NA |
| CGPLH395 | Healthy | cfDNA | Preoperative treatment naive | 56 | F | NA | NA | NA |
| CGPLH395 | Healthy | cfDNA technical replicate | Preoperative treatment naive | 56 | F | NA | NA | NA |
| CGPLH396 | Healthy | cfDNA | Preoperative treatment naive | 50 | M | NA | NA | NA |
| CGPLH398 | Healthy | cfDNA | Preoperative treatment naive | 68 | M | NA | NA | NA |
| CGPLH399 | Healthy | cfDNA | Preoperative treatment naive | 62 | F | NA | NA | NA |
| CGPLH400 | Healthy | cfDNA | Preoperative treatment naive | 64 | M | NA | NA | NA |
| CGPLH400 | Healthy | cfDNA technical replicate | Preoperative treatment naive | 64 | M | NA | NA | NA |
| CGPLH401 | Healthy | cfDNA | Preoperative treatment naive | 50 | M | NA | NA | NA |
| CGPLH401 | Healthy | cfDNA technical replicate | Preoperative treatment naive | 50 | M | NA | NA | NA |
| CGPLH402 | Healthy | cfDNA | Preoperative treatment naive | 57 | F | NA | NA | NA |
| CGPLH403 | Healthy | cfDNA | Preoperative treatment naive | 64 | M | NA | NA | NA |
| CGPLH404 | Healthy | cfDNA | Preoperative treatment naive | 50 | M | NA | NA | NA |
| CGPLH405 | Healthy | cfDNA | Preoperative treatment naive | 50 | F | NA | NA | NA |
| CGPLH406 | Healthy | cfDNA | Preoperative treatment naive | 57 | M | NA | NA | NA |
| CGPLH407 | Healthy | cfDNA | Preoperative treatment naive | 75 | F | NA | NA | NA |
| CGPLH408 | Healthy | cfDNA | Preoperative treatment naive | 50 | F | NA | NA | NA |
| CGPLH409 | Healthy | cfDNA | Preoperative treatment naive | 53 | M | NA | NA | NA |
| CGPLH410 | Healthy | cfDNA | Preoperative treatment naive | 52 | M | NA | NA | NA |
| CGPLH411 | Healthy | cfDNA | Preoperative treatment naive | 50 | F | NA | NA | NA |
| CGPLH412 | Healthy | cfDNA | Preoperative treatment naive | 53 | F | NA | NA | NA |
| CGPLH413 | Healthy | cfDNA | Preoperative treatment naive | 54 | F | NA | NA | NA |
| CGPLH414 | Healthy | cfDNA | Preoperative treatment naive | 56 | M | NA | NA | NA |
| CGPLH415 | Healthy | cfDNA | Preoperative treatment naive | 59 | M | NA | NA | NA |
| CGPLH416 | Healthy | cfDNA | Preoperative treatment naive | 58 | F | NA | NA | NA |
| CGPLH417 | Healthy | cfDNA | Preoperative treatment naive | 70 | M | NA | NA | NA |
| CGPLH418 | Healthy | cfDNA | Preoperative treatment naive | 70 | F | NA | NA | NA |
| CGPLH419 | Healthy | cfDNA | Preoperative treatment naive | 65 | F | NA | NA | NA |
| CGPLH42 | Healthy | cfDNA | Preoperative treatment naive | 54 | F | NA | NA | NA |
| CGPLH420 | Healthy | cfDNA | Preoperative treatment naive | 51 | M | NA | NA | NA |
| CGPLH422 | Healthy | cfDNA | Preoperative treatment naive | 68 | F | NA | NA | NA |
| CGPLH423 | Healthy | cfDNA | Preoperative treatment naive | 54 | M | NA | NA | NA |
| CGPLH424 | Healthy | cfDNA | Preoperative treatment naive | 53 | F | NA | NA | NA |
| CGPLH425 | Healthy | cfDNA | Preoperative treatment naive | 53 | F | NA | NA | NA |
| CGPLH426 | Healthy | cfDNA | Preoperative treatment naive | 68 | M | NA | NA | NA |
| CGPLH427 | Healthy | cfDNA | Preoperative treatment naive | 68 | M | NA | NA | NA |
| CGPLH428 | Healthy | cfDNA | Preoperative treatment naive | 50 | F | NA | NA | NA |
| CGPLH429 | Healthy | cfDNA | Preoperative treatment naive | 63 | F | NA | NA | NA |
| CGPLH43 | Healthy | cfDNA | Preoperative treatment naive | 49 | F | NA | NA | NA |
| CGPLH430 | Healthy | cfDNA | Preoperative treatment naive | 69 | F | NA | NA | NA |
| CGPLH431 | Healthy | cfDNA | Preoperative treatment naive | 59 | F | NA | NA | NA |
| CGPLH432 | Healthy | cfDNA | Preoperative treatment naive | 59 | F | NA | NA | NA |
| CGPLH434 | Healthy | cfDNA | Preoperative treatment naive | 59 | M | NA | NA | NA |
| CGPLH435 | Healthy | cfDNA | Preoperative treatment naive | 50 | M | NA | NA | NA |
| CGPLH436 | Healthy | cfDNA | Preoperative treatment naive | 50 | F | NA | NA | NA |
| CGPLH437 | Healthy | cfDNA | Preoperative treatment naive | 56 | M | NA | NA | NA |
| CGPLH438 | Healthy | cfDNA | Preoperative treatment naive | 69 | M | NA | NA | NA |
| CGPLH439 | Healthy | cfDNA | Preoperative treatment naive | 50 | F | NA | NA | NA |
| CGPLH440 | Healthy | cfDNA | Preoperative treatment naive | 72 | M | NA | NA | NA |
| CGPLH441 | Healthy | cfDNA | Preoperative treatment naive | 50 | F | NA | NA | NA |
| CGPLH442 | Healthy | cfDNA | Preoperative treatment naive | 59 | F | NA | NA | NA |
| CGPLH443 | Healthy | cfDNA | Preoperative treatment naive | 52 | F | NA | NA | NA |
| CGPLH444 | Healthy | cfDNA | Preoperative treatment naive | 60 | F | NA | NA | NA |
| CGPLH445 | Healthy | cfDNA | Preoperative treatment naive | 53 | F | NA | NA | NA |
| CGPLH446 | Healthy | cfDNA | Preoperative treatment naive | 51 | F | NA | NA | NA |
| CGPLH447 | Healthy | cfDNA | Preoperative treatment naive | 50 | F | NA | NA | NA |
| CGPLH448 | Healthy | cfDNA | Preoperative treatment naive | 51 | F | NA | NA | NA |
| CGPLH449 | Healthy | cfDNA | Preoperative treatment naive | 51 | F | NA | NA | NA |
| CGPLH45 | Healthy | cfDNA | Preoperative treatment naive | 58 | F | NA | NA | NA |
| CGPLH450 | Healthy | cfDNA | Preoperative treatment naive | 50 | F | NA | NA | NA |
| CGPLH451 | Healthy | cfDNA | Preoperative treatment naive | 54 | F | NA | NA | NA |
| CGPLH452 | Healthy | cfDNA | Preoperative treatment naive | 69 | M | NA | NA | NA |
| CGPLH453 | Healthy | cfDNA | Preoperative treatment naive | 53 | F | NA | NA | NA |
| CGPLH455 | Healthy | cfDNA | Preoperative treatment naive | 55 | F | NA | NA | NA |

TABLE 1-continued

APPENDIX A: Summary of patients and samples analyzed

| | | | | | | | | |
|---|---|---|---|---|---|---|---|---|
| CGPLH455 | Healthy | cfDNA technical replicate | Preoperative treatment naive | 55 | F | NA | NA | NA |
| CGPLH456 | Healthy | cfDNA | Preoperative treatment naive | 54 | F | NA | NA | NA |
| CGPLH457 | Healthy | cfDNA | Preoperative treatment naive | 54 | F | NA | NA | NA |
| CGPLH458 | Healthy | cfDNA | Preoperative treatment naive | 52 | F | NA | NA | NA |
| CGPLH459 | Healthy | cfDNA | Preoperative treatment naive | 50 | F | NA | NA | NA |
| CGPLH46 | Healthy | cfDNA | Preoperative treatment naive | 35 | F | NA | NA | NA |
| CGPLH460 | Healthy | cfDNA | Preoperative treatment naive | 50 | F | NA | NA | NA |
| CGPLH463 | Healthy | cfDNA | Preoperative treatment naive | 53 | F | NA | NA | NA |
| CGPLH464 | Healthy | cfDNA | Preoperative treatment naive | 50 | F | NA | NA | NA |
| CGPLH465 | Healthy | cfDNA | Preoperative treatment naive | 50 | F | NA | NA | NA |
| CGPLH466 | Healthy | cfDNA | Preoperative treatment naive | 50 | F | NA | NA | NA |
| CGPLH466 | Healthy | cfDNA technical replicate | Preoperative treatment naive | 50 | F | NA | NA | NA |
| CGPLH467 | Healthy | cfDNA | Preoperative treatment naive | 50 | F | NA | NA | NA |
| CGPLH468 | Healthy | cfDNA | Preoperative treatment naive | 53 | M | NA | NA | NA |
| CGPLH469 | Healthy | cfDNA | Preoperative treatment naive | 50 | F | NA | NA | NA |
| CGPLH47 | Healthy | cfDNA | Preoperative treatment naive | 50 | F | NA | NA | NA |
| CGPLH470 | Healthy | cfDNA | Preoperative treatment naive | 68 | F | NA | NA | NA |
| CGPLH471 | Healthy | cfDNA | Preoperative treatment naive | 70 | F | NA | NA | NA |
| CGPLH472 | Healthy | cfDNA | Preoperative treatment naive | 69 | F | NA | NA | NA |
| CGPLH473 | Healthy | cfDNA | Preoperative treatment naive | 62 | M | NA | NA | NA |
| CGPLH474 | Healthy | cfDNA | Preoperative treatment naive | 63 | M | NA | NA | NA |
| CGPLH475 | Healthy | cfDNA | Preoperative treatment naive | 67 | F | NA | NA | NA |
| CGPLH476 | Healthy | cfDNA | Preoperative treatment naive | 65 | F | NA | NA | NA |
| CGPLH477 | Healthy | cfDNA | Preoperative treatment naive | 61 | F | NA | NA | NA |
| CGPLH478 | Healthy | cfDNA | Preoperative treatment naive | 51 | F | NA | NA | NA |
| CGPLH479 | Healthy | cfDNA | Preoperative treatment naive | 52 | M | NA | NA | NA |
| CGPLH48 | Healthy | cfDNA | Preoperative treatment naive | 38 | F | NA | NA | NA |
| CGPLH480 | Healthy | cfDNA | Preoperative treatment naive | 50 | F | NA | NA | NA |
| CGPLH481 | Healthy | cfDNA | Preoperative treatment naive | 53 | F | NA | NA | NA |
| CGPLH482 | Healthy | cfDNA | Preoperative treatment naive | 50 | M | NA | NA | NA |
| CGPLH483 | Healthy | cfDNA | Preoperative treatment naive | 66 | M | NA | NA | NA |
| CGPLH484 | Healthy | cfDNA | Preoperative treatment naive | 72 | M | NA | NA | NA |
| CGPLH485 | Healthy | cfDNA | Preoperative treatment naive | 50 | F | NA | NA | NA |
| CGPLH486 | Healthy | cfDNA | Preoperative treatment naive | 50 | F | NA | NA | NA |
| CGPLH487 | Healthy | cfDNA | Preoperative treatment naive | 50 | M | NA | NA | NA |
| CGPLH488 | Healthy | cfDNA | Preoperative treatment naive | 50 | F | NA | NA | NA |
| CGPLH49 | Healthy | cfDNA | Preoperative treatment naive | 39 | F | NA | NA | NA |
| CGPLH490 | Healthy | cfDNA | Preoperative treatment naive | 50 | F | NA | NA | NA |
| CGPLH491 | Healthy | cfDNA | Preoperative treatment naive | 50 | F | NA | NA | NA |
| CGPLH492 | Healthy | cfDNA | Preoperative treatment naive | 51 | F | NA | NA | NA |
| CGPLH493 | Healthy | cfDNA | Preoperative treatment naive | 64 | M | NA | NA | NA |
| CGPLH494 | Healthy | cfDNA | Preoperative treatment naive | 53 | F | NA | NA | NA |
| CGPLH495 | Healthy | cfDNA | Preoperative treatment naive | 50 | F | NA | NA | NA |
| CGPLH496 | Healthy | cfDNA | Preoperative treatment naive | 74 | M | NA | NA | NA |
| CGPLH497 | Healthy | cfDNA | Preoperative treatment naive | 68 | F | NA | NA | NA |
| CGPLH497 | Healthy | cfDNA technical replicate | Preoperative treatment naive | 68 | F | NA | NA | NA |
| CGPLH498 | Healthy | cfDNA | Preoperative treatment naive | 54 | F | NA | NA | NA |
| CGPLH499 | Healthy | cfDNA | Preoperative treatment naive | 52 | F | NA | NA | NA |
| CGPLH50 | Healthy | cfDNA | Preoperative treatment naive | 55 | F | NA | NA | NA |
| CGPLH500 | Healthy | cfDNA | Preoperative treatment naive | 51 | F | NA | NA | NA |
| CGPLH501 | Healthy | cfDNA | Preoperative treatment naive | 50 | F | NA | NA | NA |
| CGPLH502 | Healthy | cfDNA | Preoperative treatment naive | 53 | F | NA | NA | NA |
| CGPLH503 | Healthy | cfDNA | Preoperative treatment naive | 67 | M | NA | NA | NA |
| CGPLH504 | Healthy | cfDNA | Preoperative treatment naive | 57 | F | NA | NA | NA |
| CGPLH504 | Healthy | cfDNA technical replicate | Preoperative treatment naive | 57 | F | NA | NA | NA |
| CGPLH505 | Healthy | cfDNA | Preoperative treatment naive | 50 | F | NA | NA | NA |
| CGPLH506 | Healthy | cfDNA | Preoperative treatment naive | 51 | F | NA | NA | NA |
| CGPLH507 | Healthy | cfDNA | Preoperative treatment naive | 56 | M | NA | NA | NA |
| CGPLH508 | Healthy | cfDNA | Preoperative treatment naive | 54 | F | NA | NA | NA |
| CGPLH508 | Healthy | cfDNA technical replicate | Preoperative treatment naive | 54 | F | NA | NA | NA |
| CGPLH509 | Healthy | cfDNA | Preoperative treatment naive | 60 | M | NA | NA | NA |
| CGPLH51 | Healthy | cfDNA | Preoperative treatment naive | 48 | F | NA | NA | NA |
| CGPLH510 | Healthy | cfDNA | Preoperative treatment naive | 67 | M | NA | NA | NA |
| CGPLH511 | Healthy | cfDNA | Preoperative treatment naive | 75 | M | NA | NA | NA |
| CGPLH512 | Healthy | cfDNA | Preoperative treatment naive | 52 | M | NA | NA | NA |
| CGPLH513 | Healthy | cfDNA | Preoperative treatment naive | 57 | M | NA | NA | NA |
| CGPLH514 | Healthy | cfDNA | Preoperative treatment naive | 55 | F | NA | NA | NA |
| CGPLH515 | Healthy | cfDNA | Preoperative treatment naive | 68 | F | NA | NA | NA |

TABLE 1-continued

APPENDIX A: Summary of patients and samples analyzed

| | | | | | | | | |
|---|---|---|---|---|---|---|---|---|
| CGPLH516 | Healthy | cfDNA | Preoperative treatment naive | 65 | F | NA | NA | NA |
| CGPLH517 | Healthy | cfDNA | Preoperative treatment naive | 54 | F | NA | NA | NA |
| CGPLH517 | Healthy | cfDNA technical replicate | Preoperative treatment naive | 54 | F | NA | NA | NA |
| CGPLH518 | Healthy | cfDNA | Preoperative treatment naive | 50 | F | NA | NA | NA |
| CGPLH519 | Healthy | cfDNA | Preoperative treatment naive | 54 | M | NA | NA | NA |
| CGPLH522 | Healthy | cfDNA | Preoperative treatment naive | 40 | F | NA | NA | NA |
| CGPLH520 | Healthy | cfDNA | Preoperative treatment naive | 51 | F | NA | NA | NA |
| CGPLH54 | Healthy | cfDNA | Preoperative treatment naive | 47 | F | NA | NA | NA |
| CGPLH55 | Healthy | cfDNA | Preoperative treatment naive | 46 | F | NA | NA | NA |
| CGPLH56 | Healthy | cfDNA | Preoperative treatment naive | 42 | F | NA | NA | NA |
| CGPLH57 | Healthy | cfDNA | Preoperative treatment naive | 39 | F | NA | NA | NA |
| CGPLH59 | Healthy | cfDNA | Preoperative treatment naive | 34 | F | NA | NA | NA |
| CGPLH625 | Healthy | cfDNA | Preoperative treatment naive | 53 | F | NA | NA | NA |
| CGPLH625 | Healthy | cfDNA | Preoperative treatment naive | 53 | F | NA | NA | NA |
| CGPLH626 | Healthy | cfDNA technical replicate | Preoperative treatment naive | 50 | F | NA | NA | NA |
| CGPLH63 | Healthy | cfDNA | Preoperative treatment naive | 47 | F | NA | NA | NA |
| CGPLH639 | Healthy | cfDNA | Preoperative treatment naive | 50 | F | NA | NA | NA |
| CGPLH64 | Healthy | cfDNA | Preoperative treatment naive | 55 | F | NA | NA | NA |
| CGPLH640 | Healthy | cfDNA | Preoperative treatment naive | 50 | F | NA | NA | NA |
| CGPLH642 | Healthy | cfDNA | Preoperative treatment naive | 54 | F | NA | NA | NA |
| CGPLH643 | Healthy | cfDNA | Preoperative treatment naive | 55 | F | NA | NA | NA |
| CGPLH644 | Healthy | cfDNA | Preoperative treatment naive | 50 | F | NA | NA | NA |
| CGPLH646 | Healthy | cfDNA | Preoperative treatment naive | 50 | F | NA | NA | NA |
| CGPLH75 | Healthy | cfDNA | Preoperative treatment naive | 46 | F | NA | NA | NA |
| CGPLH76 | Healthy | cfDNA | Preoperative treatment naive | 53 | F | NA | NA | NA |
| CGPLH77 | Healthy | cfDNA | Preoperative treatment naive | 46 | F | NA | NA | NA |
| CGPLH78 | Healthy | cfDNA | Preoperative treatment naive | 34 | F | NA | NA | NA |
| CGPLH79 | Healthy | cfDNA | Preoperative treatment naive | 37 | F | NA | NA | NA |
| CGPLH80 | Healthy | cfDNA | Preoperative treatment naive | 37 | F | NA | NA | NA |
| CGPLH81 | Healthy | cfDNA | Preoperative treatment naive | 54 | F | NA | NA | NA |
| CGPLH82 | Healthy | cfDNA | Preoperative treatment naive | 38 | F | NA | NA | NA |
| CGPLH83 | Healthy | cfDNA | Preoperative treatment naive | 60 | F | NA | NA | NA |
| CGPLH84 | Healthy | cfDNA | Preoperative treatment naive | 45 | F | NA | NA | NA |
| CGPLLU13 | Lung Cancer | cfDNA | Pre treatment, Day 2 | 72 | F | IV | T1BN2bM1a | Right Lung |
| CGPLLU13 | Lung Cancer | cfDNA | Post-treatment, Day 5 | 72 | F | IV | T1BN2bM1a | Right Lung |
| CGPLLU13 | Lung Cancer | cfDNA | Post-treatment, Day 28 | 72 | F | IV | T1BN2bM1a | Right Lung |
| CGPLLU13 | Lung Cancer | cfDNA | Post-treatment, Day 91 | 72 | F | IV | T1BN2bM1a | Right Lung |
| CGPLLU14 | Lung Cancer | cfDNA | Pre-treatment, Day −38 | 55 | F | IV | T1N1M0 | Right Lower Lobe of Lung |
| CGPLLU14 | Lung Cancer | cfDNA | Pre-treatment, Day −16 | 55 | F | IV | T1N1M0 | Right Lower Lobe of Lung |
| CGPLLU14 | Lung Cancer | cfDNA | Pre-treatment, Day −3 | 55 | F | IV | T1N1M0 | Right Lower Lobe of Lung |
| CGPLLU14 | Lung Cancer | cfDNA | Pre-treatment, Day 0 | 55 | F | IV | T1N1M0 | Right Lower Lobe of Lung |
| CGPLLU14 | Lung Cancer | cfDNA | Post-treatment, Day 0.33 | 55 | F | IV | T1N1M0 | Right Lower Lobe of Lung |
| CGPLLU14 | Lung Cancer | cfDNA | Post-treatment, Day 7 | 55 | F | IV | T1N1M0 | Right Lower Lobe of Lung |
| CGPLLU144 | Lung Cancer | cfDNA | Preoperative treatment naive | 52 | M | II | T2aN1M0 | Lung |
| CGPLLU147 | Lung Cancer | cfDNA | Preoperative treatment naive | 60 | M | III | T3N2M0 | Lung |
| CGPLLU161 | Lung Cancer | cfDNA | Preoperative treatment naive | 41 | F | II | T3N0M0 | Lung |
| CGPLLU162 | Lung Cancer | cfDNA | Preoperative treatment naive | 38 | M | II | T1N1M0 | Right Lung |
| CGPLLU163 | Lung Cancer | cfDNA | Preoperative treatment naive | 66 | M | II | T1N1M0 | Left Lung |
| CGPLLU165 | Lung Cancer | cfDNA | Preoperative treatment naive | 68 | F | II | T1N1M0 | Right Lung |
| CGPLLU168 | Lung Cancer | cfDNA | Preoperative treatment naive | 70 | F | I | T2aN0M0 | Lung |
| CGPLLU169 | Lung Cancer | cfDNA | Preoperative treatment naive | 64 | M | I | T1bN0M0 | Lung |
| CGPLLU175 | Lung Cancer | cfDNA | Preoperative treatment naive | 47 | M | I | T2N0M0 | Lung |
| CGPLLU176 | Lung Cancer | cfDNA | Preoperative treatment naive | 58 | M | I | T2N0M0 | Lung |
| CGPLLU177 | Lung Cancer | cfDNA | Preoperative treatment naive | 45 | M | II | T3N0M0 | Right Lung |
| CGPLLU180 | Lung Cancer | cfDNA | Preoperative treatment naive | 57 | M | I | T2N0M0 | Right Lung |
| CGPLLU198 | Lung Cancer | cfDNA | Preoperative treatment naive | 49 | F | I | T2N0M0 | Left Lung |
| CGPLLU202 | Lung Cancer | cfDNA | Preoperative treatment naive | 68 | M | I | T2N0M0 | Right Lung |
| CGPLLU203 | Lung Cancer | cfDNA | Preoperative treatment naive | 66 | M | II | T3N0M0 | Right Lung |
| CGPLLU205 | Lung Cancer | cfDNA | Preoperative treatment naive | 65 | M | II | T3N0M0 | Left Lung |
| CGPLLU206 | Lung Cancer | cfDNA | Preoperative treatment naive | 55 | M | III | T3N1M0 | Right Lung |
| CGPLLU207 | Lung Cancer | cfDNA | Preoperative treatment naive | 60 | F | II | T2N1M0 | Lung |
| CGPLLU208 | Lung Cancer | cfDNA | Preoperative treatment naive | 56 | M | II | T2N1M0 | Lung |
| CGPLLU209 | Lung Cancer | cfDNA | Preoperative treatment naive | 65 | M | II | T2aN0M0 | Lung |
| CGPLLU244 | Lung Cancer | cfDNA | Pre-treatment, Day −7 | 66 | F | IV | NA | Right Upper Lobe of Lung |
| CGPLLU244 | Lung Cancer | cfDNA | Pre-treatment, Day −1 | 66 | F | IV | NA | Right Upper Lobe of Lung |
| CGPLLU244 | Lung Cancer | cfDNA | Post-treatment, Day 6 | 66 | F | IV | NA | Right Upper Lobe of Lung |
| CGPLLU244 | Lung Cancer | cfDNA | Post-treatment, Day 62 | 66 | F | IV | NA | Right Upper Lobe of Lung |
| CGPLLU245 | Lung Cancer | cfDNA | Pre-treatment, Day 32 | 49 | M | IV | T2aN2M1B | Left Upper Lobe of Lung |
| CGPLLU245 | Lung Cancer | cfDNA | Pre-treatment, Day 0 | 49 | M | IV | T2aN2M1B | Left Upper Lobe of Lung |
| CGPLLU245 | Lung Cancer | cfDNA | Post-treatment, Day 7 | 49 | M | IV | T2aN2M1B | Left Upper Lobe of Lung |
| CGPLLU245 | Lung Cancer | cfDNA | Post-treatment, Day 21 | 49 | M | IV | T2aN2M1B | Left Upper Lobe of Lung |
| CGPLLU246 | Lung Cancer | cfDNA | Pre-treatment, Day −21 | 65 | F | IV | NA | Right Lower Lobe of Lung |
| CGPLLU246 | Lung Cancer | cfDNA | Pre-treatment, Day 0 | 65 | F | IV | NA | Right Lower Lobe of Lung |
| CGPLLU246 | Lung Cancer | cfDNA | Post-treatment, Day 9 | 65 | F | IV | NA | Right Lower Lobe of Lung |

TABLE 1-continued

APPENDIX A: Summary of patients and samples analyzed

| CGPLLU246 | Lung Cancer | cfDNA | Post-treatment, Day 42 | 65 | F | IV | NA | Right Lower Lobe of Lung |
|---|---|---|---|---|---|---|---|---|
| CGPLLU264 | Lung Cancer | cfDNA | Pre-treatment, Day −1 | 84 | M | IV | T1N2BM1 | Left Middle Lung |
| CGPLLU264 | Lung Cancer | cfDNA | Post-treatment, Day 6 | 84 | M | IV | T1N2BM1 | Left Middle Lung |
| CGPLLU264 | Lung Cancer | cfDNA | Post-treatment, Day 27 | 84 | M | IV | T1N2BM1 | Left Middle Lung |
| CGPLLU264 | Lung Cancer | cfDNA | Post-treatment, Day 69 | 84 | M | IV | T1N2BM1 | Left Middle Lung |
| CGPLLU265 | Lung Cancer | cfDNA | Pre-treatment, Day 0 | 71 | F | IV | T1N0Mx | Left Lower Lobe of Lung |
| CGPLLU265 | Lung Cancer | cfDNA | Post-treatment, Day 3 | 71 | F | IV | T1N0Mx | Left Lower Lobe of Lung |
| CGPLLU265 | Lung Cancer | cfDNA | Post-treatment, Day 7 | 71 | F | IV | T1N0Mx | Left Lower Lobe of Lung |
| CGPLLU265 | Lung Cancer | cfDNA | Post-treatment, Day 84 | 71 | F | IV | T1N0Mx | Left Lower Lobe of Lung |
| CGPLLU266 | Lung Cancer | cfDNA | Pre-treatment, Day 0 | 78 | M | IV | T2aN1 | Left Lower Lobe of Lung |
| CGPLLU266 | Lung Cancer | cfDNA | Post-treatment, Day 16 | 78 | M | IV | T2aN1 | Left Lower Lobe of Lung |
| CGPLLU266 | Lung Cancer | cfDNA | Post-treatment, Day 83 | 78 | M | IV | T2aN1 | Left Lower Lobe of Lung |
| CGPLLU266 | Lung Cancer | cfDNA | Post-treatment, Day 328 | 78 | M | IV | T2aN1 | Left Lower Lobe of Lung |
| CGPLLU267 | Lung Cancer | cfDNA | Pre-treatment, Day −1 | 55 | F | IV | T3NxM1a | Right Upper Lobe of Lung |
| CGPLLU267 | Lung Cancer | cfDNA | Post-treatment, Day 34 | 55 | F | IV | T3NxM1a | Right Upper Lobe of Lung |
| CGPLLU267 | Lung Cancer | cfDNA | Post-treatment, Day 90 | 55 | F | IV | T3NxM1a | Right Upper Lobe of Lung |
| CGPLLU269 | Lung Cancer | cfDNA | Pre-treatment, Day 0 | 52 | F | IV | T1CNxM1C | Right Paratracheal Lesion |
| CGPLLU269 | Lung Cancer | cfDNA | Post-treatment, Day 9 | 52 | F | IV | T1CNxM1C | Right Paratracheal Lesion |
| CGPLLU269 | Lung Cancer | cfDNA | Post-treatment, Day 28 | 52 | F | IV | T1CNxM1C | Right Paratracheal Lesion |
| CGPLLU271 | Lung Cancer | cfDNA | Post-treatment, Day 259 | 73 | M | IV | T1aNxM1 | Left Upper Lobe of Lung |
| CGPLLU271 | Lung Cancer | cfDNA | Pre-treatment, Day 0 | 73 | M | IV | T1aNxM1 | Left Upper Lobe of Lung |
| CGPLLU271 | Lung Cancer | cfDNA | Post-treatment, Day 6 | 73 | M | IV | T1aNxM1 | Left Upper Lobe of Lung |
| CGPLLU271 | Lung Cancer | cfDNA | Post-treatment, Day 20 | 73 | M | IV | T1aNxM1 | Left Upper Lobe of Lung |
| CGPLLU271 | Lung Cancer | cfDNA | Post-treatment, Day 104 | 73 | M | IV | T1aNxM1 | Left Upper Lobe of Lung |
| CGPLLU43 | Lung Cancer | cfDNA | Pre-treatment, Day −1 | 57 | F | IV | T1BN0M0 | Right Lower Lobe of Lung |
| CGPLLU43 | Lung Cancer | cfDNA | Post-treatment, Day 6 | 57 | F | IV | T1BN0M0 | Right Lower Lobe of Lung |
| CGPLLU43 | Lung Cancer | cfDNA | Post-treatment, Day 27 | 57 | F | IV | T1BN0M0 | Right Lower Lobe of Lung |
| CGPLLU43 | Lung Cancer | cfDNA | Post-treatment, Day 83 | 57 | F | IV | T1BN0M0 | Right Lower Lobe of Lung |
| CGPLLU86 | Lung Cancer | cfDNA | Pre-treatment, Day 0 | 55 | M | IV | NA | Left Upper Lobe of Lung |
| CGPLLU86 | Lung Cancer | cfDNA | Post-treatment, Day 0.5 | 55 | M | IV | NA | Left Upper Lobe of Lung |
| CGPLLU86 | Lung Cancer | cfDNA | Post-treatment, Day 7 | 55 | M | IV | NA | Left Upper Lobe of Lung |
| CGPLLU86 | Lung Cancer | cfDNA | Post-treatment, Day 17 | 55 | M | IV | NA | Left Upper Lobe of Lung |
| CGPLLU88 | Lung Cancer | cfDNA | Pre-treatment, Day 0 | 59 | M | IV | NA | Right Middle Lobe of Lung |
| CGPLLU88 | Lung Cancer | cfDNA | Post-treatment, Day 7 | 59 | M | IV | NA | Right Middle Lobe of Lung |
| CGPLLU88 | Lung Cancer | cfDNA | Post-treatment, Day 297 | 59 | M | IV | NA | Right Middle Lobe of Lung |
| CGPLLU89 | Lung Cancer | cfDNA | Pre-treatment, Day 0 | 54 | F | IV | NA | Right Upper Lobe of Lung |
| CGPLLU89 | Lung Cancer | cfDNA | Post-treatment, Day 7 | 54 | F | IV | NA | Right Upper Lobe of Lung |
| CGPLLU89 | Lung Cancer | cfDNA | Post-treatment, Day 22 | 54 | F | IV | NA | Right Upper Lobe of Lung |
| CGPLOV11 | Ovarian Cancer | cfDNA | Preoperative treatment naive | 51 | F | IV | T3cN0M1 | Right Ovary |
| CGPLOV12 | Ovarian Cancer | cfDNA | Preoperative treatment naive | 45 | F | I | T1aN0MX | Ovary |
| CGPLOV13 | Ovarian Cancer | cfDNA | Preoperative treatment naive | 62 | F | IV | T1bN0M1 | Right Ovary |
| CGPLOV15 | Ovarian Cancer | cfDNA | Preoperative treatment naive | 54 | F | III | T3N1M0 | Ovary |
| CGPLOV16 | Ovarian Cancer | cfDNA | Preoperative treatment naive | 40 | F | III | T3aN0M0 | Ovary |
| CGPLOV19 | Ovarian Cancer | cfDNA | Preoperative treatment naive | 52 | F | II | T2aN0M0 | Ovary |
| CGPLOV20 | Ovarian Cancer | cfDNA | Preoperative treatment naive | 52 | F | II | T2aN0M0 | Left Ovary |
| CGPLOV21 | Ovarian Cancer | cfDNA | Preoperative treatment naive | 51 | M | IV | TanyN1M1 | Ovary |
| CGPLOV22 | Ovarian Cancer | cfDNA | Preoperative treatment naive | 54 | F | III | T1cNXMX | Left Ovary |
| CGPLOV23 | Ovarian Cancer | cfDNA | Preoperative treatment naive | 47 | F | I | T1aN0M0 | Ovary |
| CGPLOV24 | Ovarian Cancer | cfDNA | Preoperative treatment naive | 14 | F | I | T1aN0M0 | Ovary |
| CGPLOV25 | Ovarian Cancer | cfDNA | Preoperative treatment naive | 18 | F | I | T1aN0M0 | Ovary |
| CGPLOV26 | Ovarian Cancer | cfDNA | Preoperative treatment naive | 35 | F | I | T1aN0M0 | Ovary |
| CGPLOV28 | Ovarian Cancer | cfDNA | Preoperative treatment naive | 63 | F | I | T1aNxM0 | Right Ovary |
| CGPLOV31 | Ovarian Cancer | cfDNA | Preoperative treatment naive | 45 | F | III | T3aNxM0 | Right Ovary |
| CGPLOV32 | Ovarian Cancer | cfDNA | Preoperative treatment naive | 53 | F | I | T1aNxM0 | Left Ovary |
| CGPLOV37 | Ovarian Cancer | cfDNA | Preoperative treatment naive | 40 | F | I | T1cN0M0 | Ovary |
| CGPLOV38 | Ovarian Cancer | cfDNA | Preoperative treatment naive | 46 | F | I | T1cN0M0 | Ovary |
| CGPLOV40 | Ovarian Cancer | cfDNA | Preoperative treatment naive | 53 | F | IV | T3aN0M0 | Ovary |
| CGPLOV41 | Ovarian Cancer | cfDNA | Preoperative treatment naive | 57 | F | IV | T3N0M1 | Ovary |
| CGPLOV42 | Ovarian Cancer | cfDNA | Preoperative treatment naive | 52 | F | I | T3N0M1 | Ovary |
| CGPLOV43 | Ovarian Cancer | cfDNA | Preoperative treatment naive | 30 | F | I | T3aN0M0 | Ovary |
| CGPLOV44 | Ovarian Cancer | cfDNA | Preoperative treatment naive | 69 | F | I | T1aN0M0 | Ovary |
| CGPLOV46 | Ovarian Cancer | cfDNA | Preoperative treatment naive | 58 | F | I | T1bN0M0 | Ovary |
| CGPLOV47 | Ovarian Cancer | cfDNA | Preoperative treatment naive | 41 | F | I | T1aN0M0 | Ovary |
| CGPLOV48 | Ovarian Cancer | cfDNA | Preoperative treatment naive | 52 | F | I | T1bN0M0 | Ovary |
| CGPLOV49 | Ovarian Cancer | cfDNA | Preoperative treatment naive | 68 | F | III | T3bN0M0 | Ovary |
| CGPLOV50 | Ovarian Cancer | cfDNA | Preoperative treatment naive | 30 | F | III | T3bN0M0 | Ovary |
| CGPLPA112 | Pancreatic Cancer | cfDNA | Preoperative treatment naive | 58 | M | II | NA | Intra Pancreatic Bile Duct |
| CGPLPA113 | Duodenal Cancer | cfDNA | Preoperative treatment naive | 71 | M | I | NA | Intra Pancreatic Bile Duct |
| CGPLPA114 | Bile Duct Cancer | cfDNA | Preoperative treatment naive | NA | F | II | NA | Intra Pancreatic Bile Duct |
| CGPLPA115 | Bile Duct Cancer | cfDNA | Preoperative treatment naive | NA | M | IV | NA | Intra Hepatic Bile Duct |
| CGPLPA117 | Bile Duct Cancer | cfDNA | Preoperative treatment naive | NA | M | II | NA | Intra Pancreatic Bile Duct |
| CGPLPA118 | Bile Duct Cancer | cfDNA | Preoperative treatment naive | 68 | F | I | NA | Bile Duct |
| CGPLPA122 | Bile Duct Cancer | cfDNA | Preoperative treatment naive | 62 | F | II | NA | Bile Duct |
| CGPLPA124 | Bile Duct Cancer | cfDNA | Preoperative treatment naive | 83 | F | II | NA | Bile Duct |
| CGPLPA125 | Bile Duct Cancer | cfDNA | Preoperative treatment naive | 58 | M | II | NA | Bile Duct |
| CGPLPA126 | Bile Duct Cancer | cfDNA | Preoperative treatment naive | 68 | M | II | NA | Bile Duct |
| CGPLPA127 | Bile Duct Cancer | cfDNA | Preoperative treatment naive | 71 | F | IV | NA | Bile Duct |
| CGPLPA128 | Bile Duct Cancer | cfDNA | Preoperative treatment naive | 67 | M | II | NA | Bile Duct |

TABLE 1-continued

APPENDIX A: Summary of patients and samples analyzed

| | | | | | | | | |
|---|---|---|---|---|---|---|---|---|
| CGPLPA129 | Bile Duct Cancer | cfDNA | Preoperative treatment naive | 56 | F | II | NA | Bile Duct |
| CGPLPA130 | Bile Duct Cancer | cfDNA | Preoperative treatment naive | 82 | F | II | NA | Bile Duct |
| CGPLPA131 | Bile Duct Cancer | cfDNA | Preoperative treatment naive | 71 | M | II | NA | Bile Duct |
| CGPLPA134 | Bile Duct Cancer | cfDNA | Preoperative treatment naive | 68 | M | II | NA | Bile Duct |
| CGPLPA135 | Bile Duct Cancer | cfDNA | Preoperative treatment naive | 67 | F | I | NA | Bile Duct |
| CGPLPA136 | Bile Duct Cancer | cfDNA | Preoperative treatment naive | 69 | F | II | NA | Bile Duct |
| CGPLPA137 | Bile Duct Cancer | cfDNA | Preoperative treatment naive | NA | M | II | NA | Bile Duct |
| CGPLPA139 | Bile Duct Cancer | cfDNA | Preoperative treatment naive | NA | M | IV | NA | Bile Duct |
| CGPLPA14 | Pancreatic Cancer | cfDNA | Preoperative treatment naive | 68 | M | II | NA | Pancreas |
| CGPLPA140 | Bile Duct Cancer | cfDNA | Preoperative treatment naive | 52 | M | II | NA | Extra Hepatic Bile Duct |
| CGPLPA141 | Bile Duct Cancer | cfDNA | Preoperative treatment naive | 68 | F | II | NA | Extra Hepatic Bile Duct |
| CGPLPA15 | Pancreatic Cancer | cfDNA | Preoperative treatment naive | 70 | F | II | NA | Pancreas |
| CGPLPA155 | Bile Duct Cancer | cfDNA | Preoperative treatment naive | NA | F | II | NA | NA |
| CGPLPA156 | Pancreatic Cancer | cfDNA | Preoperative treatment naive | 73 | F | II | NA | Pancreas |
| CGPLPA165 | Bile Duct Cancer | cfDNA | Preoperative treatment naive | 42 | M | I | NA | Bile Duct |
| CGPLPA168 | Bile Duct Cancer | cfDNA | Preoperative treatment naive | 58 | M | II | NA | Bile Duct |
| CGPLPA17 | Pancreatic Cancer | cfDNA | Preoperative treatment naive | 65 | M | II | NA | Pancreas |
| CGPLPA184 | Bile Duct Cancer | cfDNA | Preoperative treatment naive | 75 | F | II | NA | Bile Duct |
| CGPLPA187 | Bile Duct Cancer | cfDNA | Preoperative treatment naive | 67 | F | II | NA | Bile Duct |
| CGPLPA23 | Pancreatic Cancer | cfDNA | Preoperative treatment naive | 58 | F | II | NA | Pancreas |
| CGPLPA25 | Pancreatic Cancer | cfDNA | Preoperative treatment naive | 65 | F | II | NA | Pancreas |
| CGPLPA26 | Pancreatic Cancer | cfDNA | Preoperative treatment naive | 64 | M | II | NA | Pancreas |
| CGPLPA28 | Pancreatic Cancer | cfDNA | Preoperative treatment naive | 79 | F | II | NA | Pancreas |
| CGPLPA33 | Pancreatic Cancer | cfDNA | Preoperative treatment naive | 67 | F | II | NA | Pancreas |
| CGPLPA34 | Pancreatic Cancer | cfDNA | Preoperative treatment naive | 73 | M | II | NA | Pancreas |
| CGPLPA37 | Pancreatic Cancer | cfDNA | Preoperative treatment naive | 67 | F | II | NA | Pancreas |
| CGPLPA38 | Pancreatic Cancer | cfDNA | Preoperative treatment naive | 65 | M | II | NA | Pancreas |
| CGPLPA39 | Pancreatic Cancer | cfDNA | Preoperative treatment naive | 67 | F | II | NA | Pancreas |
| CGPLPA40 | Pancreatic Cancer | cfDNA | Preoperative treatment naive | 64 | M | II | NA | Pancreas |
| CGPLPA42 | Pancreatic Cancer | cfDNA | Preoperative treatment naive | 73 | M | II | NA | Pancreas |
| CGPLPA46 | Pancreatic Cancer | cfDNA | Preoperative treatment naive | 59 | F | II | NA | Pancreas |
| CGPLPA47 | Pancreatic Cancer | cfDNA | Preoperative treatment naive | 67 | M | II | NA | Pancreas |
| CGPLPA48 | Pancreatic Cancer | cfDNA | Preoperative treatment naive | 72 | F | I | NA | Pancreas |
| CGPLPA52 | Pancreatic Cancer | cfDNA | Preoperative treatment naive | 63 | M | II | NA | Pancreas |
| CGPLPA53 | Pancreatic Cancer | cfDNA | Preoperative treatment naive | 46 | M | I | NA | Pancreas |
| CGPLPA58 | Pancreatic Cancer | cfDNA | Preoperative treatment naive | 74 | F | II | NA | Pancreas |
| CGPLPA59 | Pancreatic Cancer | cfDNA | Preoperative treatment naive | 59 | F | II | NA | Pancreas |
| CGPLPA67 | Pancreatic Cancer | cfDNA | Preoperative treatment naive | 55 | M | III | NA | Pancreas |
| CGPLPA69 | Pancreatic Cancer | cfDNA | Preoperative treatment naive | 70 | M | I | NA | Pancreas |
| CGPLPA71 | Pancreatic Cancer | cfDNA | Preoperative treatment naive | 64 | M | II | NA | Pancreas |
| CGPLPA74 | Pancreatic Cancer | cfDNA | Preoperative treatment naive | 71 | F | II | NA | Pancreas |
| CGPLPA76 | Pancreatic Cancer | cfDNA | Preoperative treatment naive | 69 | M | II | NA | Pancreas |
| CGPLPA85 | Pancreatic Cancer | cfDNA | Preoperative treatment naive | 77 | F | II | NA | Pancreas |
| CGPLPA86 | Pancreatic Cancer | cfDNA | Preoperative treatment naive | 66 | M | II | NA | Pancreas |
| CGPLPA92 | Pancreatic Cancer | cfDNA | Preoperative treatment naive | 72 | M | II | NA | Pancreas |
| CGPLPA93 | Pancreatic Cancer | cfDNA | Preoperative treatment naive | 48 | M | II | NA | Pancreas |
| CGPLPA94 | Pancreatic Cancer | cfDNA | Preoperative treatment naive | 72 | F | II | NA | Pancreas |
| CGPLPA95 | Pancreatic Cancer | cfDNA | Preoperative treatment naive | 64 | F | II | NA | Pancreas |
| CGST102 | Gastric cancer | cfDNA | Preoperative treatment naive | 76 | F | II | T3N0M0 | Stomach |
| CGST11 | Gastric cancer | cfDNA | Preoperative treatment naive | 49 | M | IV | TXNXM1 | Stomach |
| CGST110 | Gastric cancer | cfDNA | Preoperative treatment naive | 77 | M | III | T4AN3aM0 | Stomach |
| CGST114 | Gastric cancer | cfDNA | Preoperative treatment naive | 65 | M | III | T4AN1M0 | Stomach |
| CGST13 | Gastric cancer | cfDNA | Preoperative treatment naive | 72 | F | II | T1AN2M0 | Stomach |
| CGST131 | Gastric cancer | cfDNA | Preoperative treatment naive | 63 | M | III | T2N3aM0 | Stomach |
| CGST141 | Gastric cancer | cfDNA | Preoperative treatment naive | 38 | F | III | T3N2M0 | Stomach |
| CGST16 | Gastric cancer | cfDNA | Preoperative treatment naive | 78 | M | III | T4AN3aM0 | Stomach |
| CGST18 | Gastric cancer | cfDNA | Preoperative treatment naive | 56 | M | II | T3N0M0 | Stomach |
| CGST21 | Gastric cancer | cfDNA | Preoperative treatment naive | 39 | M | II | T2N1 (mi)M0 | Stomach |
| CGST26 | Gastric cancer | cfDNA | Preoperative treatment naive | 51 | M | IV | TXNXM1 | Stomach |
| CGST28 | Gastric cancer | cfDNA | Preoperative treatment naive | 55 | M | X | TXNXMx | Stomach |
| CGST30 | Gastric cancer | cfDNA | Preoperative treatment naive | 64 | F | III | T3N2M0 | Stomach |
| CGST32 | Gastric cancer | cfDNA | Preoperative treatment naive | 67 | M | II | T3N1M0 | Stomach |
| CGST33 | Gastric cancer | cfDNA | Preoperative treatment naive | 61 | M | I | T2N0M0 | Stomach |
| CGST38 | Gastric cancer | cfDNA | Preoperative treatment naive | 71 | F | 0 | T0N0M0 | Stomach |
| CGST39 | Gastric cancer | cfDNA | Preoperative treatment naive | 51 | M | IV | TXNXM1 | Stomach |
| CGST41 | Gastric cancer | cfDNA | Preoperative treatment naive | 66 | F | IV | TXNXM1 | Stomach |
| CGST45 | Gastric cancer | cfDNA | Preoperative treatment naive | 41 | F | II | T3N0M0 | Stomach |
| CGST47 | Gastric cancer | cfDNA | Preoperative treatment naive | 74 | F | I | T1AN0M0 | Stomach |
| CGST48 | Gastric cancer | cfDNA | Preoperative treatment naive | 62 | M | IV | TXNXM1 | Stomach |
| CGST53 | Gastric cancer | cfDNA | Preoperative treatment naive | 70 | M | 0 | T0N0M0 | Stomach |
| CGST58 | Gastric cancer | cfDNA | Preoperative treatment naive | 58 | M | III | T4AN3bM0 | Stomach |
| CGST67 | Gastric cancer | cfDNA | Preoperative treatment naive | 69 | M | I | T1BN0M0 | Stomach |
| CGST77 | Gastric cancer | cfDNA | Preoperative treatment naive | 70 | M | IV | TXNXM1 | Stomach |
| CGST80 | Gastric cancer | cfDNA | Preoperative treatment naive | 58 | M | III | T3N3aM0 | Stomach |
| CGST81 | Gastric cancer | cfDNA | Preoperative treatment naive | 64 | F | I | T2N0Mx | Stomach |
| CGH14 | Healthy | nan adult elutriated | NA | NA | M | NA | NA | NA |

TABLE 1-continued

APPENDIX A: Summary of patients and samples analyzed

| Patient | Histopathological Diagnosis | | | | | | | | | |
|---|---|---|---|---|---|---|---|---|---|---|
| CGH15 | Healthy | nan adult elutriated | NA | | NA | F | NA | NA | | NA |

| Patient | Histopathological Diagnosis | Degree of Differentiation | Location of Metastases at Diagnosis | Volume of Plasma (ml) | cfDNA Extracted (ng/ml) | cfDNA Input (ng/ml) | Whole Genome Fragment Profile Analysis | Targeted Fragment Profile Analysis | Targeted Mutation Analysis |
|---|---|---|---|---|---|---|---|---|---|
| CGCRC321 | Adenocarcinoma | Moderate | Synchronous Liver | 7.9 | 7.80 | 7.80 | Y | Y | Y |
| CGCRC232 | Adenocarcinoma | Moderate | Synchronous liver, Lung | 7.9 | 6.73 | 6.73 | Y | Y | Y |
| CGCRC293 | Adenocarcinoma | Moderate | Synchronous Liver | 7.2 | 3.83 | 3.83 | Y | Y | Y |
| CGCRC294 | Adenocarcinoma | Moderate | None | 8.4 | 18.87 | 18.87 | Y | Y | Y |
| CGCRC296 | Adenocarcinoma | Poor | None | 4.3 | 31.24 | 31.24 | Y | Y | Y |
| CGCRC299 | Adenocarcinoma | Moderate | None | 8.8 | 10.18 | 10.18 | Y | Y | Y |
| CGCRC300 | Adenocarcinoma | Moderate | None | 4.3 | 10.48 | 10.48 | Y | Y | Y |
| CGCRC301 | Adenocarcinoma | Moderate | None | 4.1 | 6.51 | 6.51 | Y | Y | Y |
| CGCRC302 | Adenocarcinoma | Moderate | None | 4.3 | 52.13 | 52.13 | Y | Y | Y |
| CGCRC304 | Adenocarcinoma | Moderate | None | 4.1 | 30.19 | 30.19 | Y | Y | Y |
| CGCRC305 | Adenocarcinoma | Moderate | None | 8.6 | 9.10 | 9.10 | Y | Y | Y |
| CGCRC306 | Adenocarcinoma | Moderate | None | 4.5 | 24.31 | 24.31 | Y | Y | Y |
| CGCRC307 | Adenocarcinoma | Moderate | None | 8.5 | 14.26 | 14.26 | Y | Y | Y |
| CGCRC308 | Adenocarcinoma | Moderate | None | 4.3 | 46.87 | 46.87 | Y | Y | Y |
| CGCRC311 | Adenocarcinoma | Moderate | None | 8.5 | 3.91 | 3.91 | Y | Y | Y |
| CGCRC315 | Adenocarcinoma | Moderate | None | 8.6 | 9.67 | 9.67 | Y | Y | Y |
| CGCRC316 | Adenocarcinoma | Moderate | None | 4.9 | 52.16 | 52.16 | Y | Y | Y |
| CGCRC317 | Adenocarcinoma | Moderate | None | 8.8 | 16.08 | 16.08 | Y | Y | Y |
| CGCRC318 | Adenocarcinoma | Moderate | None | 9.8 | 18.24 | 18.24 | Y | Y | Y |
| CGCRC319 | Adenocarcinoma | Moderate | None | 4.2 | 53.54 | 53.54 | Y | N | Y |
| CGCRC320 | Adenocarcinoma | Moderate | None | 4.5 | 30.37 | 30.37 | Y | Y | Y |
| CGCRC321 | Adenocarcinoma | Moderate | None | 9.3 | 4.25 | 4.25 | Y | Y | Y |
| CGCRC333 | Adenocarcinoma | NA | Liver | 4.0 | 113.88 | 113.88 | Y | Y | Y |
| CGCRC336 | Adenocarcinoma | NA | Liver | 4.4 | 211.74 | 211.74 | Y | Y | Y |
| CGCRC338 | Adenocarcinoma | NA | Liver | 2.3 | 109.76 | 109.76 | Y | Y | Y |
| CGCRC341 | Adenocarcinoma | NA | Liver | 4.6 | 156.62 | 156.62 | Y | N | Y |
| CGCRC342 | Adenocarcinoma | NA | Liver | 3.9 | 56.09 | 56.09 | Y | N | Y |
| CGLU316 | Adeno, Squamous, Small Cell Carcinoma | Poor | Lung | 5.0 | 2.38 | 2.38 | Y | N | Y |
| CGLU316 | Adeno, Squamous, Small Cell Carcinoma | Poor | Lung | 5.0 | 2.11 | 2.11 | Y | N | Y |
| CGLU316 | Adeno, Squamous, Small Cell Carcinoma | Poor | Lung | 5.0 | 0.87 | 1.07 | Y | N | Y |
| CGLU316 | Adeno, Squamous, Small Cell Carcinoma | Poor | Lung | 2.0 | 8.74 | 8.75 | Y | N | Y |
| CGLU344 | Adenocarcinoma | NA | Pleura, Liver, Peritoneum | 5.0 | 34.77 | 25.00 | Y | N | Y |
| CGLU344 | Adenocarcinoma | NA | Pleura, Liver, Peritoneum | 5.0 | 15.63 | 15.64 | Y | N | Y |
| CGLU344 | Adenocarcinoma | NA | Pleura, Liver, Peritoneum | 5.0 | 9.22 | 9.22 | Y | N | Y |
| CGLU344 | Adenocarcinoma | NA | Pleura, Liver, Peritoneum | 5.0 | 5.31 | 5.32 | Y | N | Y |
| CGLU369 | Adenocarcinoma | NA | Brain | 2.0 | 11.28 | 11.28 | Y | N | Y |
| CGLU369 | Adenocarcinoma | NA | Brain | 5.0 | 10.09 | 10.09 | Y | N | Y |
| CGLU369 | Adenocarcinoma | NA | Brain | 5.0 | 6.69 | 6.70 | Y | N | Y |
| CGLU369 | Adenocarcinoma | NA | Brain | 5.0 | 8.41 | 8.42 | Y | N | Y |
| CGLU373 | Adenocarcinoma | Moderate | None | 5.0 | 6.35 | 6.35 | Y | N | Y |
| CGLU373 | Adenocarcinoma | Moderate | None | 5.0 | 6.28 | 6.28 | Y | N | Y |
| CGLU373 | Adenocarcinoma | Moderate | None | 5.0 | 3.82 | 3.82 | Y | N | Y |
| CGLU373 | Adenocarcinoma | Moderate | None | 3.5 | 5.55 | 5.55 | Y | N | Y |
| CGPLBR100 | Infiltration Ductal Carcinoma | NA | None | 4.0 | 4.25 | 4.25 | Y | N | Y |
| CGPLBR101 | Infiltration Lobular Carcinoma | Moderate | None | 4.0 | 37.88 | 37.88 | Y | N | Y |
| CGPLBR102 | Infiltration Ductal Carcinoma | Moderate | None | 3.6 | 13.67 | 13.67 | Y | N | Y |
| CGPLBR103 | Infiltration Ductal Carcinoma | Moderate | None | 3.6 | 7.11 | 7.11 | Y | N | Y |
| CGPLBR104 | Infiltration Lobular Carcinoma | Moderate | None | 4.7 | 19.89 | 19.89 | Y | N | Y |
| CGPLBR12 | Ductal Carcinoma insitu with Microinvasion | NA | NA | 4.3 | 4.21 | 4.21 | Y | N | N |
| CGPLBR18 | Infiltration Lobular Carcinoma | NA | NA | 4.1 | 40.39 | 30.49 | Y | N | N |
| CGPLBR23 | Infiltration Ductal Carcinoma | NA | None | 4.7 | 20.09 | 20.09 | Y | N | N |
| CGPLBR24 | Infiltration Ductal Carcinoma | NA | None | 3.6 | 58.33 | 34.72 | Y | N | N |
| CGPLBR28 | Infiltration Ductal Carcinoma | NA | None | 4.2 | 12.86 | 12.86 | Y | N | N |
| CGPLBR30 | Infiltration Ductal Carcinoma | NA | None | 4.1 | 59.73 | 30.49 | Y | N | N |
| CGPLBR31 | Infiltration Ductal Carcinoma | NA | None | 3.4 | 23.94 | 23.94 | Y | N | N |
| CGPLBR32 | Infiltration Ductal Carcinoma | NA | None | 4.4 | 71.23 | 28.41 | Y | N | N |
| CGPLBR33 | Infiltration Lobular Carcinoma | NA | None | 4.4 | 11.00 | 11.00 | Y | N | N |
| CGPLBR34 | Infiltration Lobular Carcinoma | NA | None | 4.4 | 23.61 | 23.61 | Y | N | N |

TABLE 1-continued

APPENDIX A: Summary of patients and samples analyzed

| | | | | | | | | | |
|---|---|---|---|---|---|---|---|---|---|
| CGPLBR35 | Ductal Carcinoma insitu with Microinvasion | NA | None | 4.5 | 22.58 | 22.58 | Y | N | N |
| CGPLBR36 | Infiltration Ductal Carcinoma | NA | None | 4.4 | 17.23 | 17.73 | Y | N | N |
| CGPLBR37 | Infiltration Ductal Carcinoma | NA | None | 4.4 | 9.39 | 9.39 | Y | N | N |
| CGPLBR38 | Infiltration Ductal Carcinoma | Moderate | None | 4.0 | 5.77 | 5.77 | Y | Y | Y |
| CGPLBR40 | Infiltration Ductal Carcinoma | Poor | None | 4.6 | 15.69 | 15.69 | Y | Y | Y |
| CGPLBR41 | Infiltration Ductal Carcinoma | Moderate | None | 4.5 | 11.56 | 11.56 | Y | N | Y |
| CGPLBR45 | Infiltration Ductal Carcinoma | NA | None | 4.5 | 20.36 | 20.36 | Y | N | N |
| CGPLBR46 | Infiltration Ductal Carcinoma | NA | None | 3.5 | 20.17 | 20.17 | Y | N | N |
| CGPLBR47 | Infiltration Ductal Carcinoma | NA | None | 4.5 | 13.89 | 13.89 | Y | N | N |
| CGPLBR48 | Infiltration Ductal Carcinoma | Poor | None | 3.9 | 7.07 | 7.07 | Y | Y | Y |
| CGPLBR49 | Infiltration Ductal Carcinoma | Poor | None | 4.0 | 5.74 | 5.74 | Y | N | Y |
| CGPLBR50 | Infiltration Ductal Carcinoma | NA | None | 4.5 | 45.58 | 27.78 | Y | N | N |
| CGPLBR51 | Infiltration Ductal Carcinoma | NA | None | 4.0 | 8.83 | 8.83 | Y | N | N |
| CGPLBR52 | Infiltration Ductal Carcinoma | NA | None | 4.5 | 80.71 | 27.78 | Y | N | N |
| CGPLBR55 | Infiltration Ductal Carcinoma | Poor | None | 4.3 | 4.57 | 4.57 | Y | Y | Y |
| CGPLBR56 | Infiltration Ductal Carcinoma | NA | None | 4.5 | 22.16 | 22.16 | Y | N | N |
| CGPLBR57 | Infiltration Ductal Carcinoma | NA | None | 4.3 | 4.02 | 4.02 | Y | N | Y |
| CGPLBR59 | Infiltration Ductal Carcinoma | Moderate | None | 4.1 | 8.24 | 8.24 | Y | N | Y |
| CGPLBR60 | Infiltration Ductal Carcinoma | NA | None | 4.5 | 11.09 | 11.09 | Y | N | N |
| CGPLBR61 | Infiltration Ductal Carcinoma | Moderate | None | 4.1 | 13.25 | 13.25 | Y | N | Y |
| CGPLBR63 | Infiltration Ductal Carcinoma | Moderate | None | 4.0 | 6.19 | 6.19 | Y | Y | Y |
| CGPLBR65 | Infiltration Ductal Carcinoma | NA | None | 3.5 | 41.75 | 35.71 | Y | N | N |
| CGPLBR68 | Infiltration Ductal Carcinoma | Poor | None | 3.4 | 10.41 | 10.41 | Y | N | Y |
| CGPLBR69 | Infiltration Ductal Carcinoma | Moderate | None | 4.4 | 4.07 | 4.07 | Y | Y | Y |
| CGPLBR70 | Infiltration Ductal Carcinoma | Moderate | None | 3.4 | 11.94 | 11.94 | Y | Y | Y |
| CGPLBR71 | Infiltration Ductal Carcinoma | Poor | None | 3.1 | 7.64 | 7.64 | Y | Y | Y |
| CGPLBR72 | Infiltration Ductal Carcinoma | Well | None | 3.9 | 4.43 | 4.43 | Y | Y | Y |
| CGPLBR73 | Infiltration Ductal Carcinoma | Moderate | None | 3.3 | 14.69 | 14.69 | Y | Y | Y |
| CGPLBR76 | Infiltration Ductal Carcinoma | Well | None | 4.9 | 8.71 | 8.71 | Y | Y | Y |
| CGPLBR81 | Infiltration Ductal Carcinoma | NA | None | 2.5 | 83.14 | 50.00 | Y | N | N |
| CGPLBR82 | Infiltration Lobular Carcinoma | Moderate | None | 4.8 | 23.39 | 23.39 | Y | N | Y |
| CGPLBR83 | Infiltration Ductal Carcinoma | Moderate | None | 3.7 | 100.17 | 100.17 | Y | Y | Y |
| CGPLBR84 | Infiltration Ductal Carcinoma | NA | NA | 3.6 | 16.95 | 16.95 | Y | N | N |
| CGPLBR87 | Papillary Carcinoma | Well | None | 3.6 | 277.39 | 69.44 | Y | Y | Y |
| CGPLBR88 | Infiltration Ductal Carcinoma | Poor | None | 3.6 | 49.75 | 49.75 | Y | Y | Y |
| CGPLBR90 | Infiltration Ductal Carcinoma | NA | None | 3.0 | 14.24 | 14.24 | Y | N | N |
| CGPLBR91 | Infiltration Lobular Carcinoma | Poor | None | 3.2 | 22.41 | 22.41 | Y | N | Y |
| CGPLBR92 | Infiltration Medullary Carcinoma | Poor | None | 3.1 | 81.00 | 81.00 | Y | Y | Y |
| CGPLBR93 | Infiltration Ductal Carcinoma | Moderate | None | 3.3 | 27.94 | 27.94 | Y | N | Y |
| CGPLH189 | NA | NA | NA | 5.0 | 5.84 | 5.84 | Y | N | N |
| CGPLH190 | NA | NA | NA | 4.7 | 18.07 | 18.07 | Y | N | N |
| CGPLH192 | NA | NA | NA | 4.7 | 12.19 | 12.19 | Y | N | N |
| CGPLH193 | NA | NA | NA | 5.0 | 5.47 | 5.47 | Y | N | N |
| CGPLH194 | NA | NA | NA | 5.0 | 9.98 | 9.98 | Y | N | N |
| CGPLH196 | NA | NA | NA | 5.0 | 11.69 | 11.69 | Y | N | N |
| CGPLH197 | NA | NA | NA | 5.0 | 5.69 | 5.69 | Y | N | N |
| CGPLH198 | NA | NA | NA | 5.0 | 4.36 | 4.36 | Y | N | N |
| CGPLH199 | NA | NA | NA | 5.0 | 9.77 | 9.77 | Y | N | N |
| CGPLH200 | NA | NA | NA | 5.0 | 5.40 | 5.60 | Y | N | N |
| CGPLH201 | NA | NA | NA | 5.0 | 8.82 | 8.82 | v | N | N |
| CGPLH202 | NA | NA | NA | 5.0 | 5.54 | 5.54 | Y | N | N |
| CGPLH203 | NA | NA | NA | 5.0 | 9.03 | 9.03 | Y | N | N |
| CGPLH205 | NA | NA | NA | 5.0 | 4.74 | 4.74 | Y | N | N |
| CGPLH208 | NA | NA | NA | 5.0 | 4.67 | 4.67 | Y | N | N |
| CGPLH209 | NA | NA | NA | 5.0 | 5.15 | 5.15 | Y | N | N |
| CGPLH210 | NA | NA | NA | 5.0 | 5.41 | 5.41 | Y | N | N |
| CGPLH211 | NA | NA | NA | 5.0 | 6.24 | 6.24 | Y | N | N |
| CGPLH300 | NA | NA | NA | 4.4 | 6.75 | 6.75 | Y | N | N |
| CGPLH307 | NA | NA | NA | 4.5 | 3.50 | 3.50 | Y | N | N |
| CGPLH308 | NA | NA | NA | 4.5 | 6.01 | 6.01 | Y | N | N |
| CGPLH309 | NA | NA | NA | 4.5 | 5.21 | 5.21 | Y | N | N |
| CGPLH310 | NA | NA | NA | 4.5 | 15.25 | 15.25 | Y | N | N |
| CGPLH311 | NA | NA | NA | 4.5 | 4.47 | 4.47 | Y | N | N |
| CGPLH314 | NA | NA | NA | 4.5 | 9.62 | 9.62 | Y | N | N |
| CGPLH314 | NA | NA | NA | 4.4 | 16.24 | 16.24 | Y | N | N |
| CGPLH315 | NA | NA | NA | 4.2 | 11.55 | 11.55 | Y | N | N |
| CGPLH316 | NA | NA | NA | 4.5 | 28.12 | 27.78 | Y | N | N |
| CGPLH317 | NA | NA | NA | 4.5 | 7.62 | 7.62 | Y | N | N |
| CGPLH319 | NA | NA | NA | 4.2 | 4.41 | 4.41 | Y | N | N |
| CGPLH320 | NA | NA | NA | 4.5 | 6.93 | 6.93 | Y | N | N |
| CGPLH322 | NA | NA | NA | 4.2 | 8.17 | 8.17 | Y | N | N |
| CGPLH324 | NA | NA | NA | 5.0 | 6.63 | 6.63 | Y | N | N |
| CGPLH325 | NA | NA | NA | 4.6 | 4.15 | 4.15 | Y | N | N |
| CGPLH326 | NA | NA | NA | 4.5 | 6.06 | 6.06 | Y | N | N |
| CGPLH327 | NA | NA | NA | 1.8 | 1.24 | 1.24 | Y | N | N |
| CGPLH328 | NA | NA | NA | 4.4 | 3.42 | 3.42 | Y | N | N |
| CGPLH328 | NA | NA | NA | 4.9 | 5.47 | 5.47 | Y | N | N |

TABLE 1-continued

APPENDIX A: Summary of patients and samples analyzed

| | | | | | | | | | |
|---|---|---|---|---|---|---|---|---|---|
| CGPLH329 | NA | | NA | NA | 4.5 | 5.27 | 5.27 | Y | N | N |
| CGPLH330 | NA | | NA | NA | 4.3 | 10.21 | 10.21 | Y | N | N |
| CGPLH331 | NA | | NA | NA | 4.6 | 2.63 | 2.63 | Y | N | N |
| CGPLH331 | NA | | NA | NA | 4.3 | 4.15 | 4.15 | Y | N | N |
| CGPLH333 | NA | | NA | NA | 4.7 | 4.06 | 4.06 | Y | N | N |
| CGPLH335 | NA | | NA | NA | 4.4 | 9.39 | 9.39 | Y | N | N |
| CGPLH336 | NA | | NA | NA | 4.6 | 6.64 | 6.64 | Y | N | N |
| CGPLH337 | NA | | NA | NA | 4.2 | 4.48 | 4.48 | Y | N | N |
| CGPLH338 | NA | | NA | NA | 4.5 | 59.44 | 27.78 | Y | N | N |
| CGPLH339 | NA | | NA | NA | 4.5 | 12.27 | 12.27 | Y | N | N |
| CGPLH340 | NA | | NA | NA | 4.5 | 4.86 | 4.86 | Y | N | N |
| CGPLH341 | NA | | NA | NA | 4.1 | 7.62 | 7.62 | Y | N | N |
| CGPLH342 | NA | | NA | NA | 4.2 | 18.29 | 18.29 | Y | N | N |
| CGPLH343 | NA | | NA | NA | 4.5 | 3.49 | 3.49 | Y | N | N |
| CGPLH344 | NA | | NA | NA | 4.2 | 8.41 | 8.41 | Y | N | N |
| CGPLH345 | NA | | NA | NA | 4.5 | 9.73 | 9.73 | Y | N | N |
| CGPLH346 | NA | | NA | NA | 4.5 | 7.86 | 7.86 | Y | N | N |
| CGPLH35 | NA | | NA | NA | 4.0 | 13.15 | 13.15 | Y | N | Y |
| CGPLH350 | NA | | NA | NA | 3.5 | 6.09 | 6.09 | Y | N | N |
| CGPLH351 | NA | | NA | NA | 4.0 | 15.91 | 15.91 | Y | N | N |
| CGPLH352 | NA | | NA | NA | 4.2 | 6.47 | 6.47 | Y | N | N |
| CGPLH353 | NA | | NA | NA | 4.2 | 4.47 | 4.47 | Y | N | N |
| CGPLH354 | NA | | NA | NA | 4.2 | 17.49 | 17.49 | Y | N | N |
| CGPLH355 | NA | | NA | NA | 4.2 | 11.58 | 11.58 | Y | N | N |
| CGPLH356 | NA | | NA | NA | 4.5 | 314 | 3.94 | Y | N | N |
| CGPLH357 | NA | | NA | NA | 4.2 | 11/9 | 11.79 | Y | N | N |
| CGPLH358 | NA | | NA | NA | 4.2 | 2116 | 2116 | Y | N | N |
| CGPLH36 | NA | | NA | NA | 4.0 | 1310 | 13.0O | Y | N | Y |
| CGPLH360 | NA | | NA | NA | 4.2 | 3.48 | 3.48 | Y | N | N |
| CGPLH361 | NA | | NA | NA | 4.3 | 618 | 6.98 | Y | N | N |
| CGPLH362 | NA | | NA | NA | 4.4 | 8.49 | 8.49 | Y | N | N |
| CGPLH363 | NA | | NA | NA | 4.5 | 4.44 | 4.44 | Y | N | N |
| CGPLH364 | NA | | NA | NA | 4.5 | 1731 | 17.31 | Y | N | N |
| CGPLH365 | NA | | NA | NA | 4.5 | 0.55 | 0.55 | Y | N | N |
| CGPLH366 | NA | | NA | NA | 4.5 | 4.88 | 4.88 | Y | N | N |
| CGPLH367 | NA | | NA | NA | 4.4 | 6.48 | 6.48 | Y | N | N |
| CGPLH368 | NA | | NA | NA | 4.3 | 2.63 | 2.63 | Y | N | N |
| CGPLH369 | NA | | NA | NA | 4.3 | 10.18 | 10.18 | Y | N | N |
| CGPLH369 | NA | | NA | NA | 4.4 | 10.71 | 10.71 | Y | N | N |
| CGPLH37 | NA | | NA | NA | 4.0 | 9.73 | 9.73 | Y | N | Y |
| CGPLH370 | NA | | NA | NA | 4.5 | 7.22 | 7.22 | Y | N | N |
| CGPLH371 | NA | | NA | NA | 4.6 | 5.62 | 5.62 | Y | N | N |
| CGPLH380 | NA | | NA | NA | 4.2 | 6.61 | 6.61 | Y | N | N |
| CGPLH381 | NA | | NA | NA | 4.2 | 27.38 | 27.33 | Y | N | N |
| CGPLH382 | NA | | NA | NA | 4.5 | 11.58 | 11.58 | Y | N | N |
| CGPLH383 | NA | | NA | NA | 4.5 | 25.50 | 25.50 | Y | N | N |
| CGPLH384 | NA | | NA | NA | 4.5 | 1516 | 15.66 | Y | N | N |
| CGPLH385 | NA | | NA | NA | 4.5 | 19.35 | 19.35 | Y | N | N |
| CGPLH386 | NA | | NA | NA | 4.5 | 6.46 | 6.46 | Y | N | N |
| CGPLH386 | NA | | NA | NA | 4.6 | 6.54 | 6.54 | Y | N | N |
| CGPLH387 | NA | | NA | NA | 4.5 | 6.19 | 6.19 | Y | N | N |
| CGPLH388 | NA | | NA | NA | 4.5 | 6.62 | 6.62 | Y | N | N |
| CGPLH389 | NA | | NA | NA | 4.6 | 14.78 | 14.78 | Y | N | N |
| CGPLH390 | NA | | NA | NA | 4.5 | 12.14 | 12.14 | Y | N | N |
| CGPLH391 | NA | | NA | NA | 4.5 | 8.88 | 8.88 | Y | N | N |
| CGPLH391 | NA | | NA | NA | 4.5 | 8.37 | 8.37 | Y | N | N |
| CGPLH392 | NA | | NA | NA | 4.5 | 8.39 | 8.39 | Y | N | N |
| CGPLH393 | NA | | NA | NA | 4.5 | 5.27 | 5.27 | Y | N | N |
| CGPLH394 | NA | | NA | NA | 4.4 | 3.79 | 3.79 | Y | N | N |
| CGPLH395 | NA | | NA | NA | 4.4 | 9.56 | 9.56 | Y | N | N |
| CGPLH395 | NA | | NA | NA | 4.4 | 5.40 | 5.40 | Y | N | N |
| CGPLH396 | NA | | NA | NA | 4.4 | 20.31 | 20.31 | Y | N | N |
| CGPLH398 | NA | | NA | NA | 4.3 | 13.01 | 13.01 | Y | N | N |
| CGPLH399 | NA | | NA | NA | 4.4 | 4.79 | 4.79 | Y | N | N |
| CGPLH400 | NA | | NA | NA | 4.4 | 7.70 | 7.70 | Y | N | N |
| CGPLH400 | NA | | NA | NA | 4.4 | 6.26 | 6.26 | Y | N | N |
| CGPLH401 | NA | | NA | NA | 4.3 | 13.01 | 13.01 | Y | N | N |
| CGPLH401 | NA | | NA | NA | 4.4 | 11.13 | 11.13 | Y | N | N |
| CGPLH402 | NA | | NA | NA | 4.5 | 2.89 | 2.89 | Y | N | N |
| CGPLH403 | NA | | NA | NA | 4.3 | 4.41 | 4.41 | Y | N | N |
| CGPLH404 | NA | | NA | NA | 4.2 | 6.38 | 6.38 | Y | N | N |
| CGPLH405 | NA | | NA | NA | 4.4 | 7.28 | 7.28 | Y | N | N |
| CGPLH406 | NA | | NA | NA | 4.2 | 5.40 | 5.40 | Y | N | N |
| CGPLH407 | NA | | NA | NA | 4.0 | 13.30 | 13.30 | Y | N | N |
| CGPLH408 | NA | | NA | NA | 4.2 | 5.18 | 5.18 | Y | N | N |
| CGPLH409 | NA | | NA | NA | 3.7 | 3.98 | 3.98 | Y | N | N |
| CGPLH410 | NA | | NA | NA | 4.1 | 6.91 | 6.91 | Y | N | N |
| CGPLH411 | NA | | NA | NA | 4.1 | 3.30 | 3.30 | Y | N | N |

TABLE 1-continued

APPENDIX A: Summary of patients and samples analyzed

| | | | | | | | | | |
|---|---|---|---|---|---|---|---|---|---|
| CGPLH412 | NA | NA | NA | 4.1 | 5.55 | 5.55 | Y | N | N |
| CGPLH413 | NA | NA | NA | 4.5 | 8.18 | 8.18 | Y | N | N |
| CGPLH414 | NA | NA | NA | 3.8 | 5.85 | 5.85 | Y | N | N |
| CGPLH415 | NA | NA | NA | 4.7 | 10.20 | 10.20 | Y | N | N |
| CGPLH416 | NA | NA | NA | 4.5 | 11.73 | 11.73 | Y | N | N |
| CGPLH417 | NA | NA | NA | 4.2 | 10.98 | 10.98 | Y | N | N |
| CGPLH418 | NA | NA | NA | 4.5 | 10.96 | 10.96 | Y | N | N |
| CGPLH419 | NA | NA | NA | 4.5 | 10.17 | 10.17 | Y | N | N |
| CGPLH42 | NA | NA | NA | 4.0 | 14.30 | 14.30 | Y | N | Y |
| CGPLH420 | NA | NA | NA | 4.2 | 12.32 | 12.32 | Y | N | N |
| CGPLH422 | NA | NA | NA | 4.6 | 5.42 | 5.42 | Y | N | N |
| CGPLH423 | NA | NA | NA | 4.2 | 2.85 | 2.85 | Y | N | N |
| CGPLH424 | NA | NA | NA | 4.7 | 1.66 | 1.66 | Y | N | N |
| CGPLH425 | NA | NA | NA | 4.4 | 5.98 | 5.98 | Y | N | N |
| CGPLH426 | NA | NA | NA | 4.4 | 2.84 | 2.84 | Y | N | N |
| CGPLH427 | NA | NA | NA | 4.4 | 10.86 | 10.86 | Y | N | N |
| CGPLH428 | NA | NA | NA | 4.5 | 6.27 | 6.27 | Y | N | N |
| CGPLH429 | NA | NA | NA | 4.5 | 3.89 | 3.89 | Y | N | N |
| CGPLH43 | NA | NA | NA | 4.0 | 8.50 | 8.50 | Y | N | Y |
| CGPLH430 | NA | NA | NA | 4.2 | 10.33 | 10.33 | Y | N | N |
| CGPLH431 | NA | NA | NA | 4.8 | 12.81 | 12.81 | Y | N | N |
| CGPLH432 | NA | NA | NA | 4.8 | 2.42 | 2.42 | Y | N | N |
| CGPLH434 | NA | NA | NA | 4.6 | 8.83 | 8.83 | Y | N | N |
| CGPLH435 | NA | NA | NA | 4.5 | 8.95 | 8.95 | Y | N | N |
| CGPLH436 | NA | NA | NA | 4.5 | 4.29 | 4.29 | Y | N | N |
| CGPLH437 | NA | NA | NA | 4.6 | 18.07 | 18.07 | Y | N | N |
| CGPLH438 | NA | NA | NA | 4.8 | 16.62 | 16.62 | Y | N | N |
| CGPLH439 | NA | NA | NA | 4.7 | 4.38 | 4.38 | Y | N | N |
| CGPLH440 | NA | NA | NA | 4.7 | 4.32 | 4.32 | Y | N | N |
| CGPLH441 | NA | NA | NA | 4.7 | 7.80 | 7.80 | Y | N | N |
| CGPLH442 | NA | NA | NA | 4.5 | 6.15 | 6.15 | Y | N | N |
| CGPLH443 | NA | NA | NA | 4.4 | 3.44 | 3.44 | Y | N | N |
| CGPLH444 | NA | NA | NA | 4.4 | 4.12 | 4.12 | Y | N | N |
| CGPLH445 | NA | NA | NA | 4.4 | 4.38 | 4.38 | Y | N | N |
| CGPLH446 | NA | NA | NA | 4.4 | 2.92 | 2.92 | Y | N | N |
| CGPLH447 | NA | NA | NA | 4.6 | 3.87 | 3.87 | Y | N | N |
| CGPLH448 | NA | NA | NA | 4.4 | 5.29 | 5.29 | Y | Y | N |
| CGPLH449 | NA | NA | NA | 4.5 | 3.77 | 3.77 | Y | N | N |
| CGPLH45 | NA | NA | NA | 4.0 | 10.85 | 10.85 | Y | N | Y |
| CGPLH450 | NA | NA | NA | 4.5 | 5.62 | 5.62 | Y | N | N |
| CGPLH451 | NA | NA | NA | 4.6 | 7.24 | 7.24 | Y | N | N |
| CGPLH452 | NA | NA | NA | 4.4 | 2.54 | 2.54 | Y | N | N |
| CGPLH453 | NA | NA | NA | 4.6 | 9.11 | 9.11 | Y | N | N |
| CGPLH455 | NA | NA | NA | 4.4 | 2.64 | 2.64 | Y | N | N |
| CGPLH455 | NA | NA | NA | 4.5 | 2.42 | 2.42 | Y | N | N |
| CGPLH456 | NA | NA | NA | 4.5 | 3.11 | 3.11 | Y | N | N |
| CGPLH457 | NA | NA | NA | 4.4 | 5.92 | 5.92 | Y | N | N |
| CGPLH458 | NA | NA | NA | 4.5 | 16.04 | 16.04 | Y | N | N |
| CGPLH459 | NA | NA | NA | 4.4 | 6.52 | 6.52 | Y | N | N |
| CGPLH46 | NA | NA | NA | 4.0 | 8.25 | 8.25 | Y | N | Y |
| CGPLH460 | NA | NA | NA | 4.6 | 5.24 | 5.24 | Y | N | N |
| CGPLH463 | NA | NA | NA | 4.5 | 22.77 | 22.77 | Y | N | N |
| CGPLH464 | NA | NA | NA | 4.4 | 2.90 | 2.90 | Y | N | N |
| CGPLH465 | NA | NA | NA | 4.5 | 4.76 | 4.76 | Y | N | N |
| CGPLH466 | NA | NA | NA | 4.6 | 5.68 | 5.68 | Y | N | N |
| CGPLH466 | NA | NA | NA | 4.5 | 6.75 | 6.75 | Y | N | N |
| CGPLH467 | NA | NA | NA | 4.5 | 4.59 | 4.59 | Y | N | N |
| CGPLH468 | NA | NA | NA | 4.5 | 11.19 | 11.19 | Y | N | N |
| CGPLH469 | NA | NA | NA | 4.5 | 3.25 | 3.25 | Y | N | N |
| CGPLH47 | NA | NA | NA | 4.0 | 7.43 | 7.43 | Y | N | Y |
| CGPLH470 | NA | NA | NA | 4.5 | 13.64 | 13.64 | Y | N | N |
| CGPLH471 | NA | NA | NA | 4.3 | 13.00 | 13.00 | Y | N | N |
| CGPLH472 | NA | NA | NA | 4.2 | 10.17 | 10.17 | Y | N | N |
| CGPLH473 | NA | NA | NA | 4.3 | 2.98 | 2.98 | Y | N | N |
| CGPLH474 | NA | NA | NA | 4.3 | 29.15 | 29.15 | Y | N | N |
| CGPLH475 | NA | NA | NA | 4.0 | 7.26 | 7.26 | Y | N | N |
| CGPLH476 | NA | NA | NA | 4.3 | 6.16 | 6.16 | Y | N | N |
| CGPLH477 | NA | NA | NA | 4.3 | 15.21 | 15.21 | Y | N | N |
| CGPLH478 | NA | NA | NA | 4.4 | 7.29 | 7.29 | Y | N | N |
| CGPLH479 | NA | NA | NA | 4.5 | 8.73 | 8.73 | Y | N | N |
| CGPLH48 | NA | NA | NA | 4.0 | 6.38 | 6.38 | Y | N | Y |
| CGPLH480 | NA | NA | NA | 4.4 | 10.62 | 10.62 | Y | N | N |
| CGPLH481 | NA | NA | NA | 4.3 | 6.75 | 6.75 | Y | N | N |
| CGPLH482 | NA | NA | NA | 4.3 | 23.58 | 23.58 | Y | N | N |
| CGPLH483 | NA | NA | NA | 4.4 | 14.44 | 14.44 | Y | N | N |
| CGPLH484 | NA | NA | NA | 4.2 | 14.32 | 14.32 | Y | N | N |
| CGPLH485 | NA | NA | NA | 4.3 | 9.64 | 9.64 | Y | N | N |
| CGPLH486 | NA | NA | NA | 4.3 | 10.16 | 10.16 | Y | N | N |

TABLE 1-continued

APPENDIX A: Summary of patients and samples analyzed

| | | | | | | | | | |
|---|---|---|---|---|---|---|---|---|---|
| CGPLH487 | NA | NA | NA | 4.4 | 6.11 | 6.11 | Y | N | N |
| CGPLH488 | NA | NA | NA | 4.5 | 7.88 | 7.88 | Y | N | N |
| CGPLH49 | NA | NA | NA | 4.0 | 6.60 | 6.60 | Y | N | Y |
| CGPLH490 | NA | NA | NA | 4.5 | 4.18 | 4.18 | Y | N | N |
| CGPLH491 | NA | NA | NA | 4.5 | 13.16 | 13.16 | Y | N | N |
| CGPLH492 | NA | NA | NA | 4.5 | 3.83 | 3.83 | Y | N | N |
| CGPLH493 | NA | NA | NA | 4.5 | 25.06 | 25.06 | Y | N | N |
| CGPLH494 | NA | NA | NA | 4.4 | 5.24 | 5.24 | Y | N | N |
| CGPLH495 | NA | NA | NA | 4.4 | 5.03 | 5.03 | Y | N | N |
| CGPLH496 | NA | NA | NA | 4.5 | 34.01 | 27.78 | Y | N | N |
| CGPLH497 | NA | NA | NA | 4.5 | 8.24 | 8.24 | Y | N | N |
| CGPLH497 | NA | NA | NA | 4.4 | 5.88 | 5.88 | Y | N | N |
| CGPLH498 | NA | NA | NA | 4.4 | 5.33 | 5.33 | Y | N | N |
| CGPLH499 | NA | NA | NA | 4.5 | 7.85 | 7.85 | Y | N | N |
| CGPLH50 | NA | NA | NA | 4.0 | 7.05 | 7.05 | Y | N | Y |
| CGPLH500 | NA | NA | NA | 4.5 | 3.49 | 3.49 | Y | N | N |
| CGPLH501 | NA | NA | NA | 4.3 | 6.29 | 6.29 | Y | N | N |
| CGPLH502 | NA | NA | NA | 4.5 | 2.74 | 2.24 | Y | N | N |
| CGPLH503 | NA | NA | NA | 4.5 | 11.01 | 11.01 | Y | N | N |
| CGPLH504 | NA | NA | NA | 4.3 | 6.60 | 6.60 | Y | N | N |
| CGPLH504 | NA | NA | NA | 4.2 | 10.02 | 10.02 | Y | N | N |
| CGPLH505 | NA | NA | NA | 4.1 | 5.23 | 5.23 | Y | N | N |
| CGPLH506 | NA | NA | NA | 4.5 | 12.23 | 12.23 | Y | N | N |
| CGPLH507 | NA | NA | NA | 4.1 | 9.89 | 9.89 | Y | N | N |
| CGPLH508 | NA | NA | NA | 4.5 | 8.88 | 8.88 | Y | N | N |
| CGPLH508 | NA | NA | NA | 4.4 | 9.55 | 9.55 | Y | N | N |
| CGPLH509 | NA | NA | NA | 4.0 | 9.79 | 9.79 | Y | N | N |
| CGPLH51 | NA | NA | NA | 4.0 | 7.85 | 7.85 | Y | N | Y |
| CGPLH510 | NA | NA | NA | 4.2 | 14.20 | 14.20 | Y | N | N |
| CGPLH511 | NA | NA | NA | 4.5 | 12.94 | 12.94 | Y | N | N |
| CGPLH512 | NA | NA | NA | 4.3 | 8.60 | 8.60 | Y | N | N |
| CGPLH513 | NA | NA | NA | 4.3 | 6.54 | 6.54 | Y | N | N |
| CGPLH514 | NA | NA | NA | 4.4 | 10.94 | 10.94 | Y | N | N |
| CGPLH515 | NA | NA | NA | 4.5 | 8.71 | 8.71 | Y | N | N |
| CGPLH516 | NA | NA | NA | 4.5 | 7.32 | 7.32 | Y | N | N |
| CGPLH517 | NA | NA | NA | 4.6 | 5.16 | 5.16 | Y | N | N |
| CGPLH517 | NA | NA | NA | 4.5 | 9.74 | 9.74 | Y | N | N |
| CGPLH518 | NA | NA | NA | 4.4 | 5.92 | 5.92 | Y | N | N |
| CGPLH519 | NA | NA | NA | 4.4 | 6.96 | 6.96 | Y | N | N |
| CGPLH522 | NA | NA | NA | 4.0 | 9.90 | 9.90 | Y | N | Y |
| CGPLH520 | NA | NA | NA | 4.3 | 8.27 | 8.27 | Y | N | N |
| CGPLH54 | NA | NA | NA | 4.0 | 14.18 | 14.18 | Y | N | Y |
| CGPLH55 | NA | NA | NA | 4.0 | 7.35 | 7.35 | Y | N | Y |
| CGPLH56 | NA | NA | NA | 4.0 | 5.20 | 5.20 | Y | N | Y |
| CGPLH57 | NA | NA | NA | 4.0 | 7.15 | 7.15 | Y | N | Y |
| CGPLH59 | NA | NA | NA | 4.0 | 6.03 | 6.03 | Y | N | Y |
| CGPLH625 | NA | NA | NA | 4.5 | 2.64 | 2.64 | Y | N | N |
| CGPLH625 | NA | NA | NA | 4.5 | 2.69 | 2.69 | Y | N | N |
| CGPLH626 | NA | NA | NA | 4.0 | 11.12 | 11.12 | Y | N | N |
| CGPLH63 | NA | NA | NA | 4.0 | 10.10 | 10.10 | Y | N | Y |
| CGPLH639 | NA | NA | NA | 4.5 | 2.00 | 2.00 | Y | N | N |
| CGPLH64 | NA | NA | NA | 4.0 | 8.03 | 8.03 | Y | N | Y |
| CGPLH640 | NA | NA | NA | 4.5 | 9.36 | 9.36 | Y | N | N |
| CGPLH642 | NA | NA | NA | 4.5 | 4.99 | 4.99 | Y | N | N |
| CGPLH643 | NA | NA | NA | 4.4 | 7.12 | 7.12 | Y | N | N |
| CGPLH644 | NA | NA | NA | 4.4 | 5.06 | 5.06 | Y | N | N |
| CGPLH646 | NA | NA | NA | 4.4 | 6.75 | 6.75 | Y | N | N |
| CGPLH75 | NA | NA | NA | 4.0 | 3.87 | 3.87 | Y | N | Y |
| CGPLH76 | NA | NA | NA | 4.0 | 4.03 | 4.03 | Y | N | Y |
| CGPLH77 | NA | NA | NA | 4.0 | 5.89 | 5.89 | Y | N | Y |
| CGPLH78 | NA | NA | NA | 4.0 | 2.51 | 2.51 | Y | N | Y |
| CGPLH79 | NA | NA | NA | 4.0 | 3.68 | 3.68 | Y | N | Y |
| CGPLH80 | NA | NA | NA | 4.0 | 1.94 | 1.94 | Y | N | Y |
| CGPLH81 | NA | NA | NA | 4.0 | 5.16 | 5.16 | Y | N | Y |
| CGPLH82 | NA | NA | NA | 4.0 | 3.30 | 3.30 | Y | N | Y |
| CGPLH83 | NA | NA | NA | 4.0 | 5.04 | 5.04 | Y | N | Y |
| CGPLH84 | NA | NA | NA | 4.0 | 3.33 | 3.33 | Y | N | Y |
| CGPLLU13 | Adenocarcinoma | NA | Bone | 5.0 | 7.67 | 7.67 | Y | N | Y |
| CGPLLU13 | Adenocarcinoma | NA | Bone | 4.5 | 8.39 | 8.39 | Y | N | Y |
| CGPLLU13 | Adenocarcinoma | NA | Bone | 3.2 | 8.66 | 8.66 | Y | N | Y |
| CGPLLU13 | Adenocarcinoma | NA | Bone | 5.0 | 5.97 | 5.97 | Y | N | Y |
| CGPLLU14 | Adenocarcinoma | Moderate | NA | 2.0 | 2.55 | 2.55 | Y | N | Y |
| CGPLLU14 | Adenocarcinoma | Moderate | NA | 2.0 | 2.55 | 2.55 | Y | N | Y |
| CGPLLU14 | Adenocarcinoma | Moderate | NA | 2.0 | 2.55 | 2.55 | Y | N | Y |
| CGPLLU14 | Adenocarcinoma | Moderate | NA | 2.0 | 2.55 | 2.55 | Y | N | Y |
| CGPLLU14 | Adenocarcinoma | Moderate | NA | 2.0 | 2.55 | 2.55 | Y | N | Y |
| CGPLLU144 | Adenocarcinoma | Poor | None | 3.5 | 31.51 | 31.51 | Y | Y | Y |

TABLE 1-continued

APPENDIX A: Summary of patients and samples analyzed

| | | | | | | | | | |
|---|---|---|---|---|---|---|---|---|---|
| CGPLLU147 | Adenosquamous Carcinoma | Poor | None | 3.8 | 6.72 | 6.72 | Y | Y | Y |
| CGPLLU161 | Adenocarcinoma | Well | None | 4.0 | 83.04 | 83.04 | Y | N | Y |
| CGPLLU162 | Adenocarcinoma | Moderate | None | 3.1 | 40.32 | 40.32 | Y | Y | Y |
| CGPLLU163 | Adenocarcinoma | Poor | None | 5.0 | 54.03 | 54.03 | Y | Y | Y |
| CGPLLU165 | Adenocarcinoma | Well | None | 4.5 | 20.13 | 20.13 | Y | Y | Y |
| CGPLLU168 | Adenocarcinoma | Poor | None | 4.3 | 19.38 | 19.38 | Y | Y | Y |
| CGPLLU169 | Squamous Cel Carcinoma | Moderate | None | 4.2 | 13.70 | 13.70 | Y | N | Y |
| CGPLLU175 | Squamous Cel Carcinoma | Moderate | None | 4.4 | 16.84 | 16.84 | Y | Y | Y |
| CGPLLU176 | Adenosquamous Carcinoma | Moderate | None | 3.2 | 7.86 | 7.86 | Y | Y | Y |
| CGPLLU177 | Adenocarcinoma | NA | None | 3.9 | 19.07 | 19.07 | Y | Y | Y |
| CGPLLU180 | Large Cel Carcinoma | Poor | None | 3.2 | 19.31 | 19.31 | Y | Y | Y |
| CGPLLU198 | Adenocarcinoma | Moderate | None | 4.2 | 14.09 | 14.09 | Y | Y | Y |
| CGPLLU202 | Adenocarcinoma | NA | None | 4.4 | 24.72 | 24.72 | Y | Y | Y |
| CGPLLU203 | Squamous Cel Carcinoma | Well | None | 4.2 | 26.24 | 26.24 | Y | N | Y |
| CGPLLU205 | Adenocarcinoma | Poor | None | 4.0 | 18.56 | 18.55 | Y | Y | Y |
| CGPLLU206 | Squamous Cel Carcinoma | Poor | None | 3.5 | 18.24 | 18.24 | Y | Y | Y |
| CGPLLU207 | Adenocarcinoma | Well | None | 4.0 | 17.29 | 17.29 | Y | Y | Y |
| CGPLLU208 | Adenocarcinoma | Moderate | None | 3.0 | 24.34 | 24.34 | Y | Y | Y |
| CGPLLU209 | Large Cel Carcinoma | Poor | None | 5.5 | 53.95 | 53.95 | Y | Y | Y |
| CGPLLU244 | Adenocarcinoma | Moderate/ Poor | Liver, Rib, Brain, Pleura | 4.5 | 17.84 | 17.48 | Y | N | Y |
| CGPLLU244 | Adenocarcinoma | Moderate/ Poor | Liver, Rib, Brain, Pleura | 4.5 | 17.84 | 17.84 | Y | N | Y |
| CGPLLU244 | Adenocarcinoma | Moderate/ Poor | Liver, Rib, Brain, Pleura | 4.5 | 17.84 | 17.84 | Y | N | Y |
| CGPLLU244 | Adenocarcinoma | Moderate/ Poor | Liver, Rib, Brain, Pleura | 4.5 | 17.84 | 17.84 | Y | N | Y |
| CGPLLU245 | Adenocarcinoma | NA | Brain | 4.7 | 19.42 | 19.42 | Y | N | Y |
| CGPLLU245 | Adenocarcinoma | NA | Brain | 4.7 | 19.42 | 19.42 | Y | N | Y |
| CGPLLU245 | Adenocarcinoma | NA | Brain | 4.7 | 19.42 | 19.42 | Y | N | Y |
| CGPLLU245 | Adenocarcinoma | NA | Brain | 4.7 | 19.42 | 19.42 | Y | N | Y |
| CGPLLU246 | Adenocarcinoma | Poor | Pleura | 5.5 | 18.51 | 18.51 | Y | N | Y |
| CGPLLU246 | Adenocarcinoma | Poor | Pleura | 5.5 | 18.51 | 18.51 | Y | N | Y |
| CGPLLU246 | Adenocarcinoma | Poor | Pleura | 5.5 | 18.51 | 18.51 | Y | N | Y |
| CGPLLU246 | Adenocarcinoma | Poor | Pleura | 5.5 | 18.51 | 18.51 | Y | N | Y |
| CGPLLU264 | Adenocarcinoma | NA | Lung | 4.0 | 22.97 | 22.97 | Y | N | Y |
| CGPLLU264 | Adenocarcinoma | NA | Lung | 4.5 | 10.53 | 10.53 | Y | N | Y |
| CGPLLU264 | Adenocarcinoma | NA | Lung | 3.0 | 7.15 | 7.15 | Y | N | Y |
| CGPLLU264 | Adenocarcinoma | NA | Lung | 4.0 | 9.60 | 9.60 | Y | N | Y |
| CGPLLU265 | Adenocarcinoma | NA | Lung | 4.2 | 7.16 | 7.16 | Y | N | Y |
| CGPLLU265 | Adenocarcinoma | NA | None | 4.0 | 8.11 | 8.11 | Y | N | Y |
| CGPLLU265 | Adenocarcinoma | NA | None | 4.2 | 7.53 | 7.53 | Y | N | Y |
| CGPLLU265 | Adenocarcinoma | NA | None | 5.0 | 16.17 | 16.17 | Y | N | Y |
| CGPLLU266 | Adenocarcinoma | Moderate | None | 5.0 | 5.32 | 5.32 | Y | N | Y |
| CGPLLU266 | Adenocarcinoma | Moderate | None | 3.5 | 6.31 | 6.31 | Y | N | Y |
| CGPLLU266 | Adenocarcinoma | Moderate | None | 5.0 | 7.64 | 7.64 | Y | N | Y |
| CGPLLU266 | Adenocarcinoma | Moderate | None | 5.0 | 14.39 | 14.39 | Y | N | Y |
| CGPLLU267 | Squamous Cel Carcinoma | Poor | Lung | 4.5 | 2.87 | 2.87 | Y | N | Y |
| CGPLLU267 | Squamous Cel Carcinoma | Poor | Lung | 4.5 | 3.34 | 3.34 | Y | N | Y |
| CGPLLU267 | Squamous Cel Carcinoma | Poor | Lung | 3.5 | 3.00 | 3.00 | Y | N | Y |
| CGPLLU269 | Adenocarcinoma | NA | Brain, Liver, Bone, Pleura | 5.0 | 11.40 | 11.40 | Y | N | Y |
| CGPLLU269 | Adenocarcinoma | NA | Brain, Liver, Bone, Pleura | 5.0 | 8.35 | 8.35 | Y | N | Y |
| CGPLLU269 | Adenocarcinoma | NA | Brain, Liver, Bone, Pleura | 3.5 | 17.79 | 17.79 | Y | N | Y |
| CGPLLU271 | Adenocarcinoma | NA | Pleura | 4.0 | 4.70 | 4.70 | Y | N | Y |
| CGPLLU271 | Adenocarcinoma | NA | Pleura | 5.0 | 18.16 | 18.16 | Y | N | Y |
| CGPLLU271 | Adenocarcinoma | NA | Pleura | 4.5 | 13.84 | 13.84 | Y | N | Y |
| CGPLLU271 | Adenocarcinoma | NA | Pleura | 3.5 | 13.46 | 13.46 | Y | N | Y |
| CGPLLU271 | Adenocarcinoma | NA | Pleura | 4.0 | 13.77 | 13.77 | Y | N | Y |
| CGPLLU43 | Adenocarcinoma | Moderate | None | 4.9 | 2.17 | 2.17 | Y | N | Y |
| CGPLLU43 | Adenocarcinoma | Moderate | None | 3.7 | 3.26 | 3.26 | Y | N | Y |
| CGPLLU43 | Adenocarcinoma | Moderate | None | 4.0 | 4.12 | 4.12 | Y | N | Y |
| CGPLLU43 | Adenocarcinoma | Moderate | None | 3.7 | 8.20 | 8.20 | Y | N | Y |
| CGPLLU86 | Adenocarcinoma | NA | Lung | 4.0 | 7.90 | 7.90 | Y | N | Y |
| CGPLLU86 | Adenocarcinoma | NA | Lung | 4.C | 7.90 | 7.90 | Y | N | Y |
| CGPLLU86 | Adenocarcinoma | NA | Lung | 4.0 | 7.90 | 7.90 | Y | N | Y |
| CGPLLU86 | Adenocarcinoma | NA | Lung | 4.0 | 7.90 | 7.90 | Y | N | Y |
| CGPLLU88 | Adenocarcinoma | NA | None | 5.0 | 27.16 | 27.16 | Y | N | Y |
| CGPLLU88 | Adenocarcinoma | NA | None | 5.0 | 6.49 | 6.49 | Y | N | Y |
| CGPLLU88 | Adenocarcinoma | NA | None | 4.0 | 3.04 | 3.04 | Y | N | Y |
| CGPLLU89 | Adenocarcinoma | NA | Brain, Bone, Lung | 8.0 | 8.43 | 8.43 | Y | N | Y |
| CGPLLU89 | Adenocarcinoma | NA | Brain, Bone, Lung | 8.0 | 8.43 | 8.43 | Y | N | Y |
| CGPLLU89 | Adenocarcinoma | NA | Brain, Bone, Lung | 8.0 | 8.43 | 8.43 | Y | N | Y |
| CGPLOV11 | Endometrioid Adenocarcinoma | Moderate | Omentum | 3.4 | 17.35 | 17.35 | Y | Y | Y |
| CGPLOV12 | Endometrioid Adenocarcinoma | NA | None | 3.2 | 12.44 | 12.44 | Y | N | Y |
| CGPLOV13 | Endometrioid Adenocarcinoma | Poor | Omentum | 3.8 | 27.00 | 27.00 | Y | Y | Y |

TABLE 1-continued

APPENDIX A: Summary of patients and samples analyzed

| | | | | | | | | | |
|---|---|---|---|---|---|---|---|---|---|
| CGPLOV15 | Adenocarcinoma | Poor | None | 5.0 | 4.77 | 4.77 | Y | Y | Y |
| CGPLOV16 | Serous Adenocarcinoma | Moderate | None | 4.5 | 27.28 | 27.28 | Y | | Y |
| CGPLOV19 | Endometrioid Adenocarcinoma | Moderate | None | 5.0 | 23.46 | 23.46 | Y | Y | Y |
| CGPLOV20 | Endometrioid Adenocarcinoma | Poor | None | 4.2 | 5.67 | 5.67 | Y | Y | Y |
| CGPLOV21 | Serous Adenocarcinoma | Poor | Omentum, Appendix | 4.3 | 56.32 | 56.32 | Y | Y | Y |
| CGPLOV22 | Serous Adenocarcinoma | Well | None | 4.6 | 17.42 | 17.42 | Y | Y | Y |
| CGPLOV23 | Serous Adenocarcinoma | Poor | None | 5.0 | 26.73 | 26.73 | Y | N | Y |
| CGPLOV24 | Germ Cell Tumor | Poor | None | 4.2 | 10.71 | 10.71 | Y | N | Y |
| CGPLOV25 | Germ Cell Tumor | Poor | None | 4.8 | 6.78 | 6.78 | Y | N | Y |
| CGPLOV26 | Germ Cell Tumor | Poor | None | 4.5 | 27.90 | 27.90 | Y | N | Y |
| CGPLOV28 | Serous Carcinoma | NA | None | 3.2 | 10.74 | 10.74 | Y | N | Y |
| CGPLOV31 | Clear Cell adenocarcinoma | NA | None | 4.0 | 14.45 | 14.45 | Y | N | Y |
| CGPLOV32 | Mucinous Cystadenoma | NA | None | 3.2 | 27.36 | 27.36 | Y | N | Y |
| CGPLOV37 | Serous Carcinoma | NA | None | 3.2 | 46.88 | 46.88 | Y | N | Y |
| CGPLOV38 | Serous Carcinoma | NA | None | 2.4 | 34.29 | 34.29 | Y | N | Y |
| CGPLOV40 | Serous Carcinoma | NA | Omentum, Uterus, Appendix | 1.1 | 193.60 | 156.25 | Y | N | Y |
| CGPLOV41 | Serous Carcinoma | NA | Omentum, Uterus, Cervix | 4.4 | 10.03 | 10.03 | Y | N | Y |
| CGPLOV42 | Serous Carcinoma | NA | None | 4.2 | 49.51 | 49.51 | Y | N | Y |
| CGPLOV43 | Mucinous Cystadenocarcinoma | NA | None | 4.4 | 9.09 | 9.09 | Y | N | Y |
| CGPLOV44 | Mucinous Adenocarcinoma | NA | None | 4.5 | 8.79 | 8.79 | Y | N | Y |
| CGPLOV46 | Serous Carcinoma | NA | None | 4.1 | 8.97 | 8.97 | Y | N | Y |
| CGPLOV47 | Serous Cystadenoma | NA | None | 4.5 | 19.35 | 19.35 | Y | N | Y |
| CGPLOV48 | Serous Carcinoma | NA | None | 3.5 | 22.80 | 22.80 | Y | N | Y |
| CGPLOV49 | Serous Carcinoma | NA | None | 4.2 | 16.48 | 16.48 | Y | N | Y |
| CGPLOV50 | Serous Carcinoma | NA | None | 4.5 | 8.89 | 8.89 | Y | N | Y |
| CGPLPA112 | NA | NA | None | 35 | 18.52 | 18.52 | Y | N | N |
| CGPLPA113 | NA | NA | None | 4.8 | 8.24 | 8.24 | Y | N | N |
| CGPLPA114 | NA | NA | None | 4.8 | 26.43 | 26.43 | Y | N | N |
| CGPLPA115 | NA | NA | NA | 5.0 | 31.41 | 31.41 | Y | N | N |
| CGPLPA117 | NA | NA | None | 3.4 | 2.29 | 2.29 | Y | N | N |
| CGPLPA118 | Intra-Ampullary Bile Duct | NA | None | 3.8 | 9.93 | 9.93 | Y | N | Y |
| CGPLPA122 | Intra-Pancreatic Bile Duct | NA | None | 3.8 | 66.54 | 32.89 | Y | N | Y |
| CGPLPA124 | Intra-Ampullary Bile Duct | moderate | None | 4.6 | 29.24 | 27.17 | Y | N | Y |
| CGPLPA125 | Intra-Pancreatic Bile Duct | poor | None | 2.7 | 8.31 | 8.31 | Y | N | N |
| CGPLPA126 | Intra-Pancreatic Bile Duct | NA | None | 4.3 | 80.56 | 29.07 | Y | N | Y |
| CGPLPA127 | Extra-Pancreatic Bile Duct | NA | NA | 3.0 | 20.60 | 20.60 | Y | N | N |
| CGPLPA128 | Intra-Pancreatic Bile Duct | NA | None | 3.9 | 5.91 | 5.91 | Y | N | Y |
| CGPLPA129 | Intra-Pancreatic Bile Duct | NA | None | 4.6 | 27.07 | 27.07 | Y | N | Y |
| CGPLPA130 | Intra-Ampullary Bile Duct | well | None | 4.0 | 4.34 | 4.34 | Y | N | Y |
| CGPLPA131 | Intra-Pancreatic Bile Duct | NA | None | 3.9 | 68.95 | 32.05 | Y | N | Y |
| CGPLPA134 | Intra-Pancreatic Bile Duct | NA | None | 4.1 | 58.08 | 30.49 | Y | N | Y |
| CGPLPA135 | Intra-Pancreatic Bile Duct | NA | NA | 3.9 | 4.22 | 4.22 | Y | N | N |
| CGPLPA136 | Intra-Pancreatic Bile Duct | NA | None | 4.1 | 20.23 | 20.23 | Y | N | Y |
| CGPLPA137 | NA | NA | NA | 4.0 | 5.75 | 5.75 | Y | N | N |
| CGPLPA139 | NA | NA | NA | 4.0 | 14.89 | 14.89 | Y | N | N |
| CGPLPA14 | Ductal Adenocarcinoma | Poor | None | 4.0 | 1.30 | 1.30 | Y | N | N |
| CGPLPA140 | Intra Pancreatic Bile Duct | Poor | None | 4.7 | 29.34 | 26.60 | Y | N | Y |
| CGPLPA141 | Intra Pancreatic Bile Duct | Moderate | None | 2.8 | 53.67 | 44.64 | Y | N | N |
| CGPLPA15 | Ductal Acenocarcinoma | Well | Lymph Node | 4.0 | 1.92 | 1.92 | Y | N | N |
| CGPLPA155 | NA | NA | NA | 4.0 | 25.72 | 25.72 | Y | N | N |
| CGPLPA156 | Ductal Adenocarcinoma | Poor | Lymph Node | 4.5 | 7.54 | 7.54 | Y | N | N |
| CGPLPA165 | Intra-Pancreatic Bile Duck with Medullary Features | well | None | 3.9 | 10.48 | 10.48 | Y | N | N |
| CGPLPA168 | Extra-Pancreatic Bile Duct | NA | NA | 3.0 | 139.12 | 34.72 | Y | N | N |
| CGPLPA17 | Ductal Adenocarcinoma | Well | Lymph Node | 4.0 | 13.08 | 13.08 | Y | N | N |
| CGPLPA184 | Intra-Pancreatic Bile Duct | NA | None | NA | NA | NA | Y | N | N |
| CGPLPA187 | Intra-Pancreatic Bile Duct | NA | None | NA | NA | NA | Y | N | N |
| CGPLPA23 | Ductal Adenocarcinoma | Moderate | Lymph Node | 4.0 | 16.62 | 16.62 | Y | N | N |
| CGPLPA25 | Ductal Adenocarcinoma | Poor | Lymph Node | 4.0 | 8.71 | 8.71 | Y | N | N |
| CGPLPA26 | Ductal Adenocarcinoma | Well | Lymph Node | 4.0 | 6.97 | 6.97 | Y | N | N |
| CGPLPA28 | Ductal Adenocarcinoma | Well | Lymph Node | 4.0 | 18.13 | 18.13 | Y | N | N |
| CGPLPA33 | Ductal Adenocarcinoma | Well | Lymph Node | 4.0 | IMO | IMO | Y | N | N |
| CGPLPA34 | Ductal Adenocarcinoma | Well | Lymph Node | 4.0 | 3.36 | 3.36 | Y | N | N |
| CGPLPA37 | Ductal Adenocarcinoma | NA | Lymph Node | 4.0 | 21.83 | 21.83 | Y | N | N |
| CGPLPA38 | Ductal Adenocarcinoma | Moderate | None | 4.0 | 5.29 | 5.29 | Y | N | N |
| CGPLPA39 | Ductal Adenocarcinoma | Well | Lymph Node | 4.0 | 11.73 | 11.73 | Y | N | N |
| CGPLPA40 | Ductal Adenocarcinoma | Well | Lymph Node | 4.0 | 4.78 | 4.78 | Y | N | N |
| CGPLPA42 | Ductal Adenocarcinoma | Moderate | Lymph Node | 4.0 | 3.41 | 3.41 | Y | N | N |
| CGPLPA46 | Ductal Adenocarcinoma | Poor | Lymph Node | 4.0 | 0.74 | 0.74 | Y | N | N |
| CGPLPA47 | Ductal Adenocarcinoma | Well | Lymph Node | 4.0 | 6.01 | 6.01 | Y | N | N |
| CGPLPA48 | Ductal Adenocarcinoma | Well | None | NA | NA | NA | Y | N | N |
| CGPLPA52 | Ductal Adenocarcinoma | Moderate | None | 2.5 | 9.86 | 9.86 | Y | N | N |
| CGPLPA53 | Ductal Adenocarcinoma | Poor | Lymph Node | 3.0 | 14.48 | 14.48 | Y | N | N |
| CGPLPA58 | Ductal Adenocarcinoma | NA | None | 3.0 | 6.87 | 6.87 | Y | N | N |
| CGPLPA59 | Ductal Adenocarcinoma or | Well | Lymph Node | NA | NA | NA | Y | N | N |

TABLE 1-continued

APPENDIX A: Summary of patients and samples analyzed

| | Adenome | | | | | | | | |
|---|---|---|---|---|---|---|---|---|---|
| CGPLPA67 | Ductal Adenocarcinoma | Well | Lymph Node | 3.2 | 9.72 | 9.72 | Y | N | N |
| CGPLPA69 | Ductal Adenocarcinoma | Well | None | 2.0 | 1.72 | 1.72 | Y | N | N |
| CGPLPA71 | Ductal Adenocarcinoma | Well | Lymph Node | 2.2 | 39.07 | 39.07 | Y | N | N |
| CGPLPA74 | Ductal Adenocarcinoma | Moderate | Lymph Node | 2.5 | 4.99 | 4.99 | Y | N | N |
| CGPLPA76 | Ductal Adenocarcinoma | Poor | None | 2.5 | 23.19 | 23.19 | Y | N | N |
| CGPLPA85 | Ductal Adenocarcinoma | Poor | Lymph Node | 3.0 | 152.46 | 41.67 | Y | N | N |
| CGPLPA86 | Ductal Adenocarcinoma | Moderate | Lymph Node | 2.5 | 11.02 | 11.02 | Y | N | N |
| CGPLPA92 | Ductal Adenocarcinoma | NA | Lymph Node | 2.0 | 5.34 | 5.34 | Y | N | N |
| CGPLPA93 | Ductal Adenocarcinoma | Poor | None | 3.0 | 96.28 | 41.67 | Y | N | N |
| CGPLPA94 | Ductal Adenocarcinoma | NA | Lymph Node | 3.0 | 29.66 | 29.65 | Y | N | N |
| CGPLPA95 | Ductal Adenocarcinoma | Well | Lymph Node | NA | NA | NA | Y | N | N |
| CGST102 | Tubular Adenocarcinoma | Moderate | None | 4.1 | 8.03 | 8.03 | Y | N | Y |
| CGST11 | Mixed Carcinoma | Moderate | None | 3.8 | 3.57 | 3.57 | Y | N | N |
| CGST110 | Tubular Adenocarcinoma | Moderate | None | 3.8 | 5.00 | 5.00 | Y | N | Y |
| CGST114 | Tubular Adenocarcinoma | Poor | None | 4.4 | 10.35 | 10.35 | Y | N | Y |
| CGST13 | Signet Ring Cell Carcinoma | Poor | None | 4.4 | 24.33 | 24.33 | Y | N | Y |
| CGST131 | Signet ring cel carcinoma | Poor | None | 4.0 | 4.28 | 4.28 | Y | N | N |
| CGST141 | Signet Cell Carcinoma | Poor | None | 4.4 | 10.84 | 10.84 | Y | N | Y |
| CGST16 | Tubular Adenocarcinoma | Poor | None | 4.0 | 40.69 | 40.69 | Y | N | Y |
| CGST18 | Mucinous Adenocarcinoma | Well | None | 4.3 | 9.78 | 9.78 | Y | N | Y |
| CGST21 | Papillary Adenocarcinoma | Moderate | None | 4.0 | 0.83 | 0.83 | Y | N | N |
| CGST26 | Signet ring cel carcinoma | Poor | None | 3.5 | 5.56 | 5.56 | Y | N | N |
| CGST28 | Undifferentiated Carcinoma | Poor | None | 4.0 | 5.86 | 5.86 | Y | N | Y |
| CGST30 | Signet Ring Cell Carcinoma | Poor | None | 3.0 | 4.22 | 4.22 | Y | N | Y |
| CGST32 | Tubular Adenocarcinoma | Moderate | None | 4.0 | 11.49 | 11.49 | Y | N | Y |
| CGST33 | Tubular Adenocarcinoma | Moderate | None | 3.5 | 5.71 | 5.71 | Y | N | Y |
| CGST38 | Mucinous adenocarcinoma | NA | None | 4.0 | NA | NA | Y | N | N |
| CGST39 | Signet Ring Cell Carcinoma | Poor | None | 3.5 | 20.69 | 20.69 | Y | N | Y |
| CGST41 | Signet Ring Cell Carcinoma | Poor | None | 3.5 | 7.83 | 7.83 | Y | N | Y |
| CGST45 | Signet Ring Cell Carcinoma | Poor | None | 3.8 | 7.14 | 7.14 | Y | N | Y |
| CGST47 | Tubular Adenocarcinoma | Moderate | None | 4.0 | 4.55 | 4.55 | Y | N | Y |
| CGST48 | Tubular Adenocarcinoma | Poor | None | 4.5 | 8.79 | 8.79 | Y | N | Y |
| CGST53 | NA | NA | None | 3.8 | 15.82 | 15.82 | V | N | N |
| CGST58 | Signet Ring Cell Carcinoma | Poor | None | 3.8 | 19.81 | 19.81 | Y | N | Y |
| CGST67 | Tubular adenocarcinoma | Moderate | None | 3.0 | 23.01 | 23.01 | Y | N | N |
| CGST77 | Tubular adenocarcinoma | Moderate | None | 4.5 | 15.09 | 15.09 | Y | N | N |
| CGST80 | Mucinous Adenocarcinoma | Poor | None | 4.5 | 8.56 | 8.56 | Y | N | Y |
| CGST81 | Signet Ring Cell Carcinoma | Poor | None | 3.5 | 37.32 | 37.32 | Y | N | Y |
| CGH14 | NA | NA | NA | NA | NA | NA | Y | N | N |
| CGH15 | NA | NA | NA | NA | NA | NA | Y | N | N |

NA denotes data not available or not applicable for healthy individuals.

TABLE 2

APPENDIX B: Summary of targeted cfDNA analyses

| Patient | Patient Type | Timepoint | Fragment Profile Analysis | Mutation Analysis | Read Length | Bases in Target Region | Bases Mapped to Genome | Bases Mapped to Target Regions | Percent Mapped to Target Regions | Total Coverage | Distinct Coverage |
|---|---|---|---|---|---|---|---|---|---|---|---|
| CGCRC291 | Colorectal Cancer | Preoperative, Treatment naïve | Y | Y | 100 | 80930 | 7501485600 | 3771359756 | 50% | 44345 | 10359 |
| CGCRC292 | Colorectal Cancer | Preoperative, Treatment naïve | Y | Y | 100 | 80930 | 6736035200 | 3098886973 | 46% | 36448 | 8603 |
| CGCRC293 | Colorectal Cancer | Preoperative, Treatment naïve | Y | Y | 100 | 80930 | 6300244000 | 2818734206 | 45% | 33117 | 5953 |
| CGCRC294 | Colorectal Cancer | Preoperative, Treatment naïve | Y | Y | 100 | 80930 | 7786872600 | 3911796709 | 50% | 46016 | 12071 |
| CGCRC295 | Colorectal Cancer | Preoperative, Treatment naïve | Y | N | 100 | 80930 | 8240660200 | 3478059753 | 42% | 40787 | 5826 |
| CGCRC296 | Colorectal Cancer | Preoperative, Treatment naïve | Y | Y | 100 | 80930 | 5718556500 | 2895549356 | 51% | 33912 | 10180 |
| CGCRC297 | Colorectal Cancer | Preoperative, Treatment naïve | Y | N | 100 | 80930 | 7550826100 | 3717222432 | 49% | 43545 | 5870 |
| CGCRC298 | Colorectal Cancer | Preoperative, Treatment naïve | Y | N | 100 | 80930 | 12501036400 | 6096393764 | 49% | 71196 | 9617 |
| CGCRC299 | Colorectal Cancer | Preoperative, Treatment naïve | Y | Y | 100 | 80930 | 7812602900 | 4121569690 | 53% | 48098 | 10338 |
| CGCRC300 | Colorectal Cancer | Preoperative, Treatment naïve | Y | Y | 100 | 80930 | 8648090300 | 3962285136 | 46% | 46364 | 5756 |
| CGCRC301 | Colorectal Cancer | Preoperative, Treatment naïve | Y | Y | 100 | 80930 | 7538758100 | 3695480348 | 49% | 43024 | 6618 |
| CGCRC302 | Colorectal Cancer | Preoperative, Treatment naïve | Y | Y | 100 | 80930 | 8573658300 | 4349420574 | 51% | 51006 | 13799 |
| CGCRC303 | Colorectal Cancer | Preoperative, Treatment naïve | Y | Y | 100 | 80930 | 5224046400 | 2505714343 | 48% | 29365 | 8372 |
| CGCRC304 | Colorectal Cancer | Preoperative, Treatment naïve | Y | Y | 100 | 80930 | 5762112600 | 2942170530 | 51% | 34462 | 10208 |
| CGCRC305 | Colorectal Cancer | Preoperative, Treatment naïve | Y | Y | 100 | 80930 | 7213384100 | 3726953480 | 52% | 43516 | 8589 |
| CGCRC306 | Colorectal Cancer | Preoperative, Treatment naïve | Y | Y | 100 | 80930 | 7075579700 | 3552441899 | 50% | 41507 | 7372 |
| CGCRC307 | Colorectal Cancer | Preoperative, Treatment naïve | Y | Y | 100 | 80930 | 7572687100 | 3492191519 | 46% | 40793 | 9680 |
| CGCRC308 | Colorectal Cancer | Preoperative, Treatment naïve | Y | Y | 100 | 80930 | 7945738000 | 3895908986 | 49% | 45224 | 11809 |
| CGCRC309 | Colorectal Cancer | Preoperative, Treatment naïve | Y | Y | 100 | 80930 | 8487455800 | 3921079811 | 46% | 45736 | 10739 |
| CGCRC310 | Colorectal Cancer | Preoperative, Treatment naïve | Y | Y | 100 | 80930 | 9003580500 | 4678812441 | 52% | 54713 | 11139 |
| CGCRC311 | Colorectal Cancer | Preoperative, Treatment naïve | Y | Y | 100 | 80930 | 6528162700 | 3276653864 | 50% | 38324 | 6044 |
| CGCRC312 | Colorectal Cancer | Preoperative, Treatment naïve | Y | N | 100 | 80930 | 7683294300 | 3316719187 | 43% | 38652 | 4622 |
| CGCRC313 | Colorectal Cancer | Preoperative, Treatment naïve | Y | N | 100 | 80930 | 5874099200 | 2896148722 | 49% | 33821 | 6506 |
| CGCRC314 | Colorectal Cancer | Preoperative, Treatment naïve | Y | N | 100 | 80930 | 6883148500 | 3382767492 | 49% | 39414 | 6664 |
| CGCRC315 | Colorectal Cancer | Preoperative, Treatment naïve | Y | Y | 100 | 80930 | 7497252500 | 3775556051 | 50% | 44034 | 8666 |
| CGCRC317 | Colorectal Cancer | Preoperative, Treatment naïve | Y | Y | 100 | 80930 | 10684720400 | 5533857153 | 52% | 64693 | 14289 |
| CGCRC318 | Colorectal Cancer | Preoperative, Treatment naïve | Y | Y | 100 | 80930 | 7086877600 | 3669434216 | 52% | 43538 | 10944 |
| CGCRC319 | Colorectal Cancer | Preoperative, Treatment naïve | Y | Y | 100 | 80930 | 6880041100 | 3326357413 | 48% | 39077 | 11571 |
| CGCRC320 | Colorectal Cancer | Preoperative, Treatment naïve | N | Y | 100 | 80930 | 7485342900 | 3982677483 | 53% | 47327 | 10502 |
| CGCRC321 | Colorectal Cancer | Preoperative, Treatment naïve | Y | Y | 100 | 80930 | 7056703200 | 3450648135 | 49% | 40888 | 10198 |
| CGCRC332 | Colorectal Cancer | Preoperative, Treatment naïve | Y | Y | 100 | 80930 | 7203625900 | 3633396892 | 50% | 43065 | 6499 |
| CGCRC333 | Colorectal Cancer | Preoperative, Treatment naïve | Y | N | 100 | 80930 | 7202969100 | 3758323705 | 52% | 44580 | 3243 |
| CGCRC334 | Colorectal Cancer | Preoperative, Treatment naïve | Y | Y | 100 | 80930 | 8767144700 | 4199126827 | 48% | 49781 | 8336 |
| CGCRC335 | Colorectal Cancer | Preoperative, Treatment naïve | Y | Y | 100 | 80930 | 7771869100 | 3944578280 | 51% | 46518 | 5014 |
| CGCRC336 | Colorectal Cancer | Preoperative, Treatment naïve | Y | N | 100 | 80930 | 7972524600 | 4064901201 | 51% | 48308 | 6151 |
| CGCRC337 | Colorectal Cancer | Preoperative, Treatment naïve | Y | N | 100 | 80930 | 8597346400 | 4333410573 | 50% | 51390 | 7551 |
| CGCRC338 | Colorectal Cancer | Preoperative, Treatment naïve | Y | N | 100 | 80930 | 7399611700 | 3800666199 | 51% | 45083 | 8092 |
| CGCRC339 | Colorectal Cancer | Preoperative, Treatment naïve | Y | N | 100 | 80930 | 8029493700 | 4179383804 | 52% | 49380 | 5831 |
| CGCRC340 | Colorectal Cancer | Preoperative, Treatment naïve | Y | Y | 100 | 80930 | 7938963600 | 4095555110 | 52% | 48397 | 3808 |
| CGCRC341 | Colorectal Cancer | Preoperative, Treatment naïve | Y | N | 100 | 80930 | 7214889500 | 3706643098 | 51% | 43805 | 3014 |
| CGCRC342 | Colorectal Cancer | Preoperative, Treatment naïve | N | Y | 100 | 80930 | 8803159200 | 3668208527 | 42% | 43106 | 11957 |
| CGCRC344 | Colorectal Cancer | Preoperative, Treatment naïve | N | Y | 100 | 80930 | 8478811500 | 3425540889 | 40% | 40328 | 9592 |
| CGCRC345 | Colorectal Cancer | Preoperative, Treatment naïve | N | Y | 100 | 80930 | 6942167800 | 3098232737 | 45% | 36823 | 2300 |
| CGGRC345 | Colorectal Cancer | Preoperative, Treatment naïve | N | Y | 100 | 80930 | 8182868200 | 2383173431 | 29% | 28233 | 7973 |
| CGGRC346 | Colorectal Cancer | Preoperative, Treatment naïve | N | Y | 100 | 80930 | 7448272300 | 3925056341 | 53% | 46679 | 5582 |

TABLE 2-continued

APPENDIX B: Summary of targeted cfDNA analyses

| Patient | Patient Type | Timepoint | Fragment Profile Analysis | Mutation Analysis | Read Length | Bases in Target Region | Bases Mapped to Genome | Bases Mapped to Target Regions | Percent Mapped to Target Regions | Total Coverage | Distinct Coverage |
|---|---|---|---|---|---|---|---|---|---|---|---|
| CGCRC347 | Colorectal Cancer | Preoperative, Treatment naïve | N | Y | 100 | 80930 | 5804744500 | 2968809912 | 51% | 35490 | 4141 |
| CGCRC349 | Colorectal Cancer | Preoperative, Treatment naïve | N | Y | 100 | 80930 | 6943451600 | 3533145275 | 51% | 41908 | 5762 |
| CGCRC350 | Colorectal Cancer | Preoperative, Treatment naïve | N | Y | 100 | 80930 | 7434818400 | 3848923016 | 52% | 45678 | 4652 |
| CGCRC351 | Colorectal Cancer | Preoperative, Treatment naïve | N | Y | 100 | 80930 | 7306546400 | 3636910409 | 50% | 43162 | 5205 |
| CGCRC352 | Colorectal Cancer | Preoperative, Treatment naïve | N | Y | 100 | 80930 | 7864655600 | 3336939252 | 42% | 39587 | 4502 |
| CGCRC353 | Colorectal Cancer | Preoperative, Treatment naïve | N | Y | 100 | 80930 | 7501674800 | 3642919375 | 49% | 43379 | 4666 |
| CGCRC354 | Colorectal Cancer | Preoperative, Treatment naïve | N | Y | 100 | 80930 | 7938270200 | 2379068977 | 30% | 28256 | 4858 |
| CGCRC356 | Colorectal Cancer | Preoperative, Treatment naïve | N | Y | 100 | 80930 | 6013175900 | 3046754994 | 51% | 36127 | 3425 |
| CGGRC357 | Colorectal Cancer | Preoperative, Treatment naïve | N | Y | 100 | 80930 | 6013464600 | 3022035300 | 50% | 35813 | 4259 |
| CGCRC358 | Colorectal Cancer | Preoperative, Treatment naïve | N | Y | 100 | 80930 | 7227212400 | 3188723303 | 44% | 37992 | 5286 |
| CGCRC359 | Colorectal Cancer | Preoperative, Treatment naïve | N | Y | 100 | 80930 | 7818567700 | 425110101 | 5% | 5040 | 2566 |
| CGCRC367 | Colorectal Cancer | Preoperative, Treatment naïve | N | Y | 100 | 80930 | 6582043200 | 3363063597 | 51% | 39844 | 5839 |
| CGCRC368 | Colorectal Cancer | Preoperative, Treatment naïve | N | Y | 100 | 80930 | 8042242400 | 4101646000 | 51% | 48636 | 11471 |
| CGCRC370 | Colorectal Cancer | Preoperative, Treatment naïve | N | Y | 100 | 80930 | 6940330100 | 3198954121 | 46% | 38153 | 4826 |
| CGCRC373 | Colorectal Cancer | Preoperative, Treatment naïve | N | Y | 100 | 80930 | 6587201700 | 3120088035 | 47% | 37234 | 5190 |
| CGCRC376 | Colorectal Cancer | Preoperative, Treatment naïve | N | Y | 100 | 80930 | 6727983100 | 3162416807 | 47% | 37735 | 3445 |
| CGCRC377 | Colorectal Cancer | Preoperative, Treatment naïve | N | Y | 100 | 80930 | 6716339200 | 3131415570 | 47% | 37160 | 4524 |
| CGCRC378 | Colorectal Cancer | Preoperative, Treatment naïve | N | Y | 100 | 80930 | 6523969900 | 2411096720 | 37% | 28728 | 3239 |
| CGCRC379 | Colorectal Cancer | Preoperative, Treatment naïve | N | Y | 100 | 80930 | 6996252100 | 3371081103 | 48% | 39999 | 2891 |
| CGCRC380 | Colorectal Cancer | Preoperative, Treatment naïve | N | Y | 100 | 80930 | 7097496300 | 2710244446 | 38% | 32020 | 3261 |
| CGCRC381 | Colorectal Cancer | Preoperative, Treatment naïve | N | Y | 100 | 80930 | 6951936100 | 3287050681 | 47% | 38749 | 9357 |
| CGCRC382 | Colorectal Cancer | Preoperative, Treatment naïve | N | Y | 100 | 80930 | 6959048700 | 2552325859 | 37% | 30040 | 5148 |
| CGCRC384 | Colorectal Cancer | Preoperative, Treatment naïve | N | Y | 100 | 80930 | 7012798900 | 3293884583 | 47% | 39158 | 3653 |
| CGCRC385 | Colorectal Cancer | Preoperative, Treatment naïve | N | Y | 100 | 80930 | 7542017900 | 3356570505 | 45% | 39884 | 3686 |
| CGCRC386 | Colorectal Cancer | Preoperative, Treatment naïve | N | Y | 100 | 80930 | 6876069600 | 3064412286 | 45% | 36431 | 2787 |
| CGCRC387 | Colorectal Cancer | Preoperative, Treatment naïve | N | Y | 100 | 80930 | 7399564700 | 3047254560 | 41% | 36141 | 6675 |
| CGCRC388 | Colorectal Cancer | Preoperative, Treatment naïve | N | Y | 100 | 80930 | 6532692900 | 3137284885 | 48% | 37285 | 5114 |
| CGCRC389 | Colorectal Cancer | Preoperative, Treatment naïve | N | Y | 100 | 80930 | 6651206300 | 3102100941 | 47% | 36764 | 6123 |
| CGCRC390 | Colorectal Cancer | Preoperative, Treatment naïve | N | Y | 100 | 80930 | 7260616800 | 3376667585 | 47% | 40048 | 4368 |
| CGCRC531 | Colorectal Cancer | Preoperative, Treatment naïve | N | Y | 100 | 80930 | 6883624500 | 3202877881 | 47% | 37978 | 5029 |
| CGLU316 | Lung Cancer | Pre-treatment, Day −53 | Y | N | 100 | 80930 | 7864415100 | 1991331171 | 25% | 23601 | 3565 |
| CGLU316 | Lung Cancer | Pre-treatment, Day −53 | Y | N | 100 | 80930 | 7502591600 | 3730963390 | 50% | 44262 | 3966 |
| CGLU316 | Lung Cancer | Pre-treatment, Day −53 | Y | N | 100 | 80930 | 6582515900 | 3187059470 | 48% | 37813 | 3539 |
| CGLU316 | Lung Cancer | Pre-treatment, Day −53 | Y | N | 100 | 80930 | 6587281800 | 1947630979 | 30% | 23094 | 4439 |
| CGLU344 | Lung Cancer | Pre-treatment, Day −21 | Y | N | 100 | 80930 | 6151628500 | 2748983603 | 45% | 32462 | 8063 |
| CGLU344 | Lung Cancer | Pre-treatment, Day −21 | Y | N | 100 | 80930 | 7842910900 | 1147703178 | 15% | 13565 | 4303 |
| CGLU344 | Lung Cancer | Pre-treatment, Day −21 | Y | N | 100 | 80930 | 5838083100 | 2291108925 | 39% | 27067 | 4287 |
| CGLU344 | Lung Cancer | Pre-treatment, Day −21 | Y | N | 100 | 80930 | 7685989200 | 3722274529 | 48% | 43945 | 3471 |
| CGLU369 | Lung Cancer | Pre-treatment, Day −2 | Y | N | 100 | 80930 | 7080245300 | 1271457982 | 18% | 15109 | 2364 |
| CGLU369 | Lung Cancer | Pre-treatment, Day −2 | Y | N | 100 | 80930 | 7078131900 | 1482448715 | 21% | 17583 | 4275 |
| CGLU369 | Lung Cancer | Pre-treatment, Day −2 | Y | N | 100 | 80930 | 6904701700 | 2124660124 | 31% | 25230 | 5278 |
| CGLU373 | Lung Cancer | Pre-treatment, Day −2 | Y | N | 100 | 80930 | 7003462200 | 3162195578 | 45% | 37509 | 6062 |
| CGLU373 | Lung Cancer | Pre-treatment, Day −2 | Y | N | 100 | 80930 | 6346267200 | 3053520676 | 48% | 36137 | 6251 |
| CGLU373 | Lung Cancer | Pre-treatment, Day −2 | Y | N | 100 | 80930 | 6517189900 | 3192984468 | 49% | 38066 | 8040 |
| CGLU373 | Lung Cancer | Pre-treatment, Day −2 | Y | N | 100 | 80930 | 7767146300 | 3572598842 | 46% | 42378 | 5306 |
| CGLU373 | Lung Cancer | Pre-treatment, Day −2 | Y | N | 100 | 80930 | 7190999100 | 3273648804 | 46% | 38784 | 4454 |
| CGPLBR100 | Breast Cancer | Preoperative, Treatment naïve | N | Y | 100 | 80930 | 7299964400 | 3750278051 | 51% | 44794 | 3249 |

TABLE 2-continued

APPENDIX B: Summary of targeted cfDNA analyses

| Patient | Patient Type | Timepoint | Fragment Profile Analysis | Mutation Analysis | Read Length | Bases in Target Region | Bases Mapped to Genome | Bases Mapped to Target Regions | Percent Mapped to Target Regions | Total Coverage | Distinct Coverage |
|---|---|---|---|---|---|---|---|---|---|---|---|
| CGPLBR101 | Breast Cancer | Preoperative, Treatment naïve | N | Y | 100 | 80930 | 7420822800 | 3810365416 | 51% | 45565 | 9784 |
| CGPLBR102 | Breast Cancer | Preoperative, Treatment naïve | N | Y | 100 | 80930 | 6679304900 | 3269688319 | 49% | 38679 | 7613 |
| CGPLBR103 | Breast Cancer | Preoperative, Treatment naïve | N | Y | 100 | 80930 | 7040304400 | 3495542468 | 50% | 41786 | 6748 |
| CGPLBR104 | Breast Cancer | Preoperative, Treatment naïve | N | Y | 100 | 80930 | 7188389200 | 3716096781 | 52% | 44316 | 9448 |
| CGPLBR38 | Breast Cancer | Preoperative, Treatment naïve | Y | Y | 100 | 80930 | 7810293900 | 4057576306 | 52% | 48098 | 9868 |
| CGPLBR39 | Breast Cancer | Preoperative, Treatment naïve | N | Y | 100 | 80930 | 7745701500 | 3805623239 | 49% | 45084 | 11065 |
| CGPLBR40 | Breast Cancer | Preoperative, Treatment naïve | Y | Y | 100 | 80930 | 7558990500 | 3652442341 | 48% | 43333 | 12948 |
| CGPLBR41 | Breast Cancer | Preoperative, Treatment naïve | N | Y | 100 | 80930 | 7900994600 | 3836600101 | 49% | 45535 | 10847 |
| CGPLBR44 | Breast Cancer | Preoperative, Treatment naïve | Y | N | 100 | 80930 | 7017744200 | 3269110569 | 47% | 38672 | 8344 |
| CGPLBR48 | Breast Cancer | Preoperative, Treatment naïve | N | Y | 100 | 80930 | 5629044200 | 2611554623 | 46% | 30860 | 8652 |
| CGPLBR49 | Breast Cancer | Preoperative, Treatment naïve | Y | Y | 100 | 80930 | 5784711600 | 2673457893 | 46% | 31274 | 10429 |
| CGPLBR55 | Breast Cancer | Preoperative, Treatment naïve | N | Y | 100 | 80930 | 8309154900 | 4306956261 | 52% | 51143 | 8328 |
| CGPLBR57 | Breast Cancer | Preoperative, Treatment naïve | Y | Y | 100 | 80930 | 8636181000 | 4391502618 | 51% | 52108 | 5857 |
| CGPLBR59 | Breast Cancer | Preoperative, Treatment naïve | N | Y | 100 | 80930 | 8799457700 | 4152328555 | 47% | 49281 | 5855 |
| CGPLBR61 | Breast Cancer | Preoperative, Treatment naïve | Y | Y | 100 | 80930 | 8163706700 | 3952010628 | 48% | 46755 | 8522 |
| CGPLBR63 | Breast Cancer | Preoperative, Treatment naïve | N | N | 100 | 80930 | 7020533100 | 3542447304 | 50% | 41956 | 4773 |
| CGPLBR67 | Breast Cancer | Preoperative, Treatment naïve | Y | Y | 100 | 80930 | 8254353900 | 3686093696 | 45% | 43516 | 7752 |
| CGPLBR68 | Breast Cancer | Preoperative, Treatment naïve | N | Y | 100 | 80930 | 7629312300 | 4078969547 | 53% | 48389 | 7402 |
| CGPLBR69 | Breast Cancer | Preoperative, Treatment naïve | Y | Y | 100 | 80930 | 7571501500 | 3857354512 | 51% | 45322 | 7047 |
| CGPLBR70 | Breast Cancer | Preoperative, Treatment naïve | N | Y | 100 | 80930 | 7251760700 | 3641333708 | 50% | 43203 | 8884 |
| CGPLBR71 | Breast Cancer | Preoperative, Treatment naïve | Y | Y | 100 | 80930 | 8515402600 | 4496696391 | 53% | 53340 | 6805 |
| CGPLBR72 | Breast Cancer | Preoperative, Treatment naïve | N | Y | 100 | 80930 | 8556946900 | 4389761697 | 51% | 52081 | 5632 |
| CGPLBR73 | Breast Cancer | Preoperative, Treatment naïve | Y | Y | 100 | 80930 | 7959392300 | 4006933338 | 50% | 47555 | 8791 |
| CGPLBR74 | Breast Cancer | Preoperative, Treatment naïve | N | N | 100 | 80930 | 8524536400 | 4063900599 | 48% | 48252 | 7013 |
| CGPLBR75 | Breast Cancer | Preoperative, Treatment naïve | Y | Y | 100 | 80930 | 8250379100 | 3960599885 | 48% | 46955 | 6319 |
| CGPLBP76 | Breast Cancer | Preoperative, Treatment naïve | N | Y | 100 | 80930 | 7774235200 | 3893522420 | 50% | 46192 | 9628 |
| CGPLBR77 | Breast Cancer | Preoperative, Treatment naïve | Y | Y | 100 | 80930 | 7572797600 | 3255963429 | 43% | 38568 | 8263 |
| CGPLBR80 | Breast Cancer | Preoperative, Treatment naïve | N | N | 100 | 80930 | 6845325800 | 3147476693 | 46% | 37201 | 5595 |
| CGPLBR82 | Breast Cancer | Preoperative, Treatment naïve | Y | N | 100 | 80930 | 8236705200 | 4170465005 | 51% | 49361 | 12319 |
| CGPLBR83 | Breast Cancer | Preoperative, Treatment naïve | N | Y | 100 | 80930 | 7434568100 | 3676855019 | 49% | 43628 | 5458 |
| CGPLBR86 | Breast Cancer | Preoperative, Treatment naïve | Y | Y | 100 | 80930 | 7616282500 | 3644791327 | 48% | 43490 | 7048 |
| CGPLBR87 | Breast Cancer | Preoperative, Treatment naïve | N | Y | 100 | 80930 | 6194021300 | 3004882010 | 49% | 35765 | 5306 |
| CGPLBR88 | Breast Cancer | Preoperative, Treatment naïve | Y | Y | 100 | 80930 | 6071567200 | 2847926237 | 47% | 33945 | 10319 |
| CGPLBR91 | Breast Cancer | Preoperative, Treatment naïve | N | Y | 100 | 80930 | 7192457700 | 3480203404 | 48% | 41570 | 9912 |
| CGPLBR92 | Breast Cancer | Preoperative, Treatment naïve | Y | Y | 100 | 80930 | 7678981800 | 3600279233 | 47% | 42975 | 13580 |
| CGPLBR93 | Breast Cancer | Preoperative, Treatment naïve | N | Y | 100 | 80930 | 7605717800 | 3998713397 | 53% | 47866 | 10329 |
| CGPLBR96 | Breast Cancer | Preoperative, Treatment naïve | Y | Y | 100 | 80930 | 6297446700 | 2463064737 | 39% | 29341 | 7937 |
| CGPLBR97 | Breast Cancer | Preoperative, Treatment naïve | N | Y | 100 | 80930 | 7114921600 | 3557069027 | 50% | 42488 | 10712 |
| CGPLH35 | Healthy | Preoperative, Treatment naïve | Y | Y | 100 | 80930 | 6919126300 | 2312758764 | 33% | 25570 | 1989 |
| CGPLH36 | Healthy | Preoperative, Treatment naïve | N | Y | 100 | 80930 | 6089923400 | 2038548115 | 33% | 22719 | 1478 |
| CGPLH37 | Healthy | Preoperative, Treatment naïve | Y | Y | 100 | 80930 | 5557270200 | 1935301929 | 35% | 21673 | 2312 |
| CGPLH42 | Healthy | Preoperative, Treatment naïve | N | Y | 100 | 80930 | 5792045400 | 2388036949 | 41% | 27197 | 2523 |
| CGPLH43 | Healthy | Preoperative, Treatment naïve | Y | Y | 100 | 80930 | 5568321700 | 2017813329 | 36% | 23228 | 1650 |
| CGPLH45 | Healthy | Preoperative, Treatment naïve | N | Y | 100 | 80930 | 8485593200 | 2770176078 | 33% | 32829 | 3114 |
| CGPLH46 | Healthy | Preoperative, Treatment naïve | Y | Y | 100 | 80930 | 5083171100 | 1899395790 | 37% | 21821 | 1678 |
| CGPLH47 | Healthy | Preoperative, Treatment naïve | N | Y | 100 | 80930 | 6016388500 | 2062392156 | 34% | 23459 | 1431 |
| CGPLH48 | Healthy | Preoperative, Treatment naïve | N | Y | 100 | 80930 | 4958945900 | 1809825992 | 36% | 20702 | 1698 |

TABLE 2-continued

APPENDIX B: Summary of targeted cfDNA analyses

| Patient | Patient Type | Timepoint | Fragment Profile Analysis | Mutation Analysis | Read Length | Bases in Target Region | Bases Mapped to Genome | Bases Mapped to Target Regions | Percent Mapped to Target Regions | Total Coverage | Distinct Coverage |
|---|---|---|---|---|---|---|---|---|---|---|---|
| CGPLH49 | Healthy | Preoperative, Treatment naïve | N | Y | 100 | 80930 | 7953812200 | 2511365904 | 32% | 27006 | 1440 |
| CGPLH50 | Healthy | Preoperative, Treatment naïve | N | Y | 100 | 80930 | 6989407600 | 2561288100 | 37% | 29177 | 2591 |
| CGPLH51 | Healthy | Preoperative, Treatment naïve | N | Y | 100 | 80930 | 7862073200 | 2525091396 | 32% | 29999 | 1293 |
| CGPLH52 | Healthy | Preoperative, Treatment naïve | N | Y | 100 | 80930 | 6939636800 | 2397922699 | 35% | 27029 | 2501 |
| CGPLH54 | Healthy | Preoperative, Treatment naïve | N | Y | 100 | 80930 | 10611934700 | 2290823134 | 22% | 27175 | 3306 |
| CGPLH55 | Healthy | Preoperative, Treatment naïve | N | Y | 100 | 80930 | 9912569200 | 2521962244 | 25% | 27082 | 3161 |
| CGPLH56 | Healthy | Preoperative, Treatment naïve | N | Y | 100 | 80930 | 5777591900 | 2023874863 | 35% | 22916 | 1301 |
| CGPLH57 | Healthy | Preoperative, Treatment naïve | N | Y | 100 | 80930 | 9234904800 | 1493926244 | 16% | 15843 | 1655 |
| CGPLH59 | Healthy | Preoperative, Treatment naïve | N | Y | 100 | 80930 | 9726052100 | 2987875484 | 31% | 35427 | 2143 |
| CGPLH63 | Healthy | Preoperative, Treatment naïve | N | Y | 100 | 80930 | 8696405000 | 2521574759 | 29% | 26689 | 1851 |
| CGPLH64 | Healthy | Preoperative, Treatment naïve | N | Y | 100 | 80930 | 5438852600 | 996198502 | 18% | 11477 | 1443 |
| CGPLH75 | Healthy | Preoperative, Treatment naïve | Y | N | 100 | 80930 | 3446444000 | 1505718480 | 44% | 17805 | 3016 |
| CGPLH76 | Healthy | Preoperative, Treatment naïve | Y | N | 100 | 80930 | 7499116400 | 3685762725 | 49% | 43682 | 4643 |
| CGPLH77 | Healthy | Preoperative, Treatment naïve | Y | N | 100 | 80930 | 6512408400 | 2537359345 | 39% | 30280 | 3131 |
| CGPLH78 | Healthy | Preoperative, Treatment naïve | Y | Y | 100 | 80930 | 7642949300 | 3946069680 | 52% | 46316 | 5358 |
| CGPLH79 | Healthy | Preoperative, Treatment naïve | Y | Y | 100 | 80930 | 7785475700 | 3910639227 | 50% | 45280 | 6714 |
| CGPLH80 | Healthy | Preoperative, Treatment naïve | Y | N | 100 | 80930 | 7918361500 | 3558236955 | 45% | 42171 | 5062 |
| CGPLH81 | Healthy | Preoperative, Treatment naïve | Y | Y | 100 | 80930 | 6646268900 | 3112369850 | 47% | 37119 | 3678 |
| CGPLH82 | Healthy | Preoperative, Treatment naïve | Y | N | 100 | 80930 | 7744065000 | 3941700596 | 51% | 46820 | 5723 |
| CGPLH83 | Healthy | Preoperative, Treatment naïve | Y | N | 100 | 80930 | 6957686000 | 1447503106 | 21% | 17280 | 2875 |
| CGPLH84 | Healthy | Preoperative, Treatment naïve | Y | Y | 100 | 80930 | 8326493200 | 3969908122 | 48% | 47464 | 3647 |
| CGPLH86 | Healthy | Preoperative, Treatment naïve | Y | Y | 100 | 80930 | 8664194700 | 4470145091 | 52% | 53398 | 5094 |
| CGPLH90 | Healthy | Preoperative, Treatment naïve | Y | Y | 100 | 80930 | 7516078800 | 3841504088 | 51% | 45907 | 4414 |
| CGPLLU13 | Lung Cancer | Pre-treatment, Day −2 | N | Y | 100 | 80930 | 5659546100 | 1721618955 | 30% | 20587 | 6025 |
| CGPLLU13 | Lung Cancer | Pre-treatment, Day −2 | N | Y | 100 | 80930 | 6199049700 | 2563659840 | 41% | 30728 | 6514 |
| CGPLLU13 | Lung Cancer | Pre-treatment, Day −2 | N | Y | 100 | 80930 | 5864396500 | 1194237002 | 20% | 14331 | 3952 |
| CGPLLU13 | Lung Cancer | Pre-treatment, Day −38 | N | Y | 100 | 80930 | 5080197700 | 1373550586 | 27% | 16480 | 5389 |
| CGPLLU14 | Lung Cancer | Pre-treatment, Day −38 | N | Y | 100 | 80930 | 8668655700 | 3980731089 | 46% | 48628 | 3148 |
| CGPLLU14 | Lung Cancer | Pre-treatment, Day −16 | N | Y | 100 | 80930 | 8271043600 | 4105092738 | 50% | 50152 | 4497 |
| CGPLLU14 | Lung Cancer | Pre-treatment, Day −3 | N | Y | 100 | 80930 | 7149809200 | 3405754720 | 48% | 40382 | 6170 |
| CGPLLU14 | Lung Cancer | Pre-treatment, Day 0 | N | Y | 100 | 80930 | 6556332200 | 3289504484 | 50% | 39004 | 4081 |
| CGPLLU14 | Lung Cancer | Post-treatment, Day 0.33 | N | Y | 100 | 80930 | 7410378300 | 3464236558 | 47% | 41108 | 4259 |
| CGPLLU14 | Lung Cancer | Post-treatment, Day 7 | N | Y | 100 | 80930 | 7530190700 | 3752054349 | 50% | 45839 | 2469 |
| CGPLLU44 | Lung Cancer | Preoperative, Treatment naïve | N | Y | 100 | 80930 | 8716827400 | 4216576624 | 48% | 49370 | 10771 |
| CGPLLU46 | Lung Cancer | Preoperative, Treatment naïve | Y | Y | 100 | 80930 | 8506844200 | 4195033049 | 49% | 49084 | 6968 |
| CGPLLU47 | Lung Cancer | Preoperative, Treatment naïve | Y | Y | 100 | 80930 | 7416300600 | 3530746046 | 48% | 41302 | 4691 |
| CGPLLU161 | Lung Cancer | Preoperative, Treatment naïve | Y | N | 100 | 80930 | 7789148700 | 3280139772 | 42% | 38568 | 12229 |
| CGPLLU162 | Lung Cancer | Preoperative, Treatment naïve | Y | Y | 100 | 80930 | 7625462000 | 3470147667 | 46% | 40918 | 10099 |
| CGPLLU163 | Lung Cancer | Preoperative, Treatment naïve | Y | Y | 100 | 80930 | 8019293200 | 3946533983 | 49% | 46471 | 12108 |
| CGPLLU164 | Lung Cancer | Preoperative, Treatment naïve | Y | N | 100 | 80930 | 8110030900 | 3592748235 | 44% | 42161 | 6947 |
| CGPLLU165 | Lung Cancer | Preoperative, Treatment naïve | Y | Y | 100 | 80930 | 8389514600 | 4147501817 | 49% | 48770 | 8996 |
| CGPLLU168 | Lung Cancer | Preoperative, Treatment naïve | Y | N | 100 | 80930 | 7690630000 | 3868237773 | 50% | 45625 | 9711 |
| CGPLLU169 | Lung Cancer | Preoperative, Treatment naïve | Y | Y | 100 | 80930 | 9378353000 | 4800407624 | 51% | 56547 | 10261 |
| CGPLLU174 | Lung Cancer | Preoperative, Treatment naïve | Y | Y | 100 | 80930 | 7481844600 | 3067532518 | 41% | 36321 | 6137 |
| CGPLLU175 | Lung Cancer | Preoperative, Treatment naïve | Y | Y | 100 | 80930 | 8532324200 | 4002541569 | 47% | 47084 | 7862 |
| CGPLLU176 | Lung Cancer | Preoperative, Treatment naïve | Y | Y | 100 | 80930 | 8143905000 | 4054098929 | 50% | 47708 | 5588 |
| CGPLLU177 | Lung Cancer | Preoperative, Treatment naïve | Y | Y | 100 | 80930 | 8421611300 | 4197108809 | 50% | 49476 | 8780 |

TABLE 2-continued

APPENDIX B: Summary of targeted cfDNA analyses

| Patient | Patient Type | Timepoint | Fragment Profile Analysis | Mutation Analysis | Read Length | Bases in Target Region | Bases Mapped to Genome | Bases Mapped to Target Regions | Percent Mapped to Target Regions | Total Coverage | Distinct Coverage |
|---|---|---|---|---|---|---|---|---|---|---|---|
| CGPLLU178 | Lung Cancer | Preoperative, Treatment naïve | Y | N | 100 | 80930 | 8483124700 | 4169577489 | 49% | 48580 | 6445 |
| CGPLLU179 | Lung Cancer | Preoperative, Treatment naïve | Y | N | 100 | 80930 | 7774358700 | 3304915738 | 43% | 38768 | 6862 |
| CGPLLU180 | Lung Cancer | Preoperative, Treatment naïve | Y | N | 100 | 80930 | 8192813800 | 3937552475 | 48% | 46498 | 6568 |
| CGPLLU197 | Lung Cancer | Preoperative, Treatment naïve | Y | N | 100 | 80930 | 7996779200 | 3082397881 | 39% | 36381 | 5388 |
| CGPLLU198 | Lung Cancer | Preoperative, Treatment naïve | Y | N | 100 | 80930 | 7175247200 | 3545719100 | 49% | 42008 | 6817 |
| CGPLLU202 | Lung Cancer | Preoperative, Treatment naïve | Y | Y | 100 | 80930 | 6840112800 | 3427820669 | 50% | 40670 | 7951 |
| CGPLLU203 | Lung Cancer | Preoperative, Treatment naïve | Y | Y | 100 | 80930 | 7468749900 | 3762726574 | 50% | 44500 | 9917 |
| CGPLLU204 | Lung Cancer | Preoperative, Treatment naïve | Y | Y | 100 | 80930 | 7445026400 | 3703545153 | 50% | 44317 | 6856 |
| CGPLLU205 | Lung Cancer | Preoperative, Treatment naïve | N | N | 100 | 80930 | 9205429100 | 4350573991 | 47% | 51627 | 9810 |
| CGPLLU206 | Lung Cancer | Preoperative, Treatment naïve | Y | Y | 100 | 80930 | 7397914600 | 3635210205 | 49% | 43016 | 7124 |
| CGPLLU207 | Lung Cancer | Preoperative, Treatment naïve | Y | Y | 100 | 80930 | 7133043900 | 3736258011 | 52% | 44291 | 8499 |
| CGPLLU208 | Lung Cancer | Preoperative, Treatment naïve | Y | Y | 100 | 80930 | 7346976400 | 3858814032 | 52% | 45782 | 8940 |
| CGPLLU209 | Lung Cancer | Preoperative, Treatment naïve | Y | N | 100 | 80930 | 6723337800 | 3362944595 | 50% | 39531 | 11946 |
| CGPLLU244 | Lung Cancer | Pre-treatment, Day −7 | Y | N | 100 | 80930 | 8305560600 | 4182616104 | 50% | 50851 | 7569 |
| CGPLLU244 | Lung Cancer | Pre-treatment, Day −1 | Y | Y | 100 | 80930 | 7739951100 | 3788487116 | 49% | 45925 | 8552 |
| CGPLLU244 | Lung Cancer | Post-treatment, Day 6 | N | Y | 100 | 80930 | 8061928000 | 4225322272 | 52% | 51279 | 8646 |
| CGPLLU244 | Lung Cancer | Post-treatment, Day 62 | N | Y | 100 | 80930 | 8894936700 | 4437962639 | 50% | 53862 | 7361 |
| CGPLLU245 | Lung Cancer | Pre-treatment, Day −32 | N | Y | 100 | 80930 | 7679235200 | 3935822054 | 51% | 47768 | 7266 |
| CGPLLU245 | Lung Cancer | Pre-treatment, Day 0 | N | Y | 100 | 80930 | 8985252500 | 4824268339 | 54% | 58338 | 10394 |
| CGPLLU245 | Lung Cancer | Post-treatment, Day 7 | N | Y | 100 | 80930 | 8518229300 | 4480236927 | 53% | 54083 | 10125 |
| CGPLLU245 | Lung Cancer | Post-treatment, Day 21 | N | Y | 100 | 80930 | 9031131000 | 4824738475 | 53% | 58313 | 10598 |
| CGPLLU246 | Lung Cancer | Pre-treatment, Day −21 | N | Y | 100 | 80930 | 8520360800 | 3509660305 | 41% | 42349 | 8086 |
| CGPLLU246 | Lung Cancer | Pre-treatment, Day 0 | N | Y | 100 | 80930 | 5451467800 | 2826351657 | 52% | 34243 | 8256 |
| CGPLLU246 | Lung Cancer | Post-treatment, Day 9 | N | Y | 100 | 80930 | 8137616600 | 4135036174 | 51% | 50121 | 6466 |
| CGPLLU246 | Lung Cancer | Post-treatment, Day 42 | Y | Y | 100 | 80930 | 8385724600 | 4413323333 | 53% | 53495 | 7303 |
| CGPLLU264 | Lung Cancer | Pre-treatment, Day −1 | Y | N | 100 | 80930 | 3254777700 | 3016326208 | 48% | 36164 | 12138 |
| CGPLLU264 | Lung Cancer | Pre-treatment, Day 0 | Y | N | 100 | 80930 | 6185331000 | 8087883231 | 50% | 37003 | 8388 |
| CGPLLU264 | Lung Cancer | Post-treatment, Day −1 | Y | N | 100 | 80930 | 6274540300 | 2861143666 | 46% | 34308 | 6817 |
| CGPLLU264 | Lung Cancer | Pre-treatment, Day −1 | Y | N | 100 | 80930 | 5701274000 | 1241270938 | 22% | 14886 | 4273 |
| CGPLLU265 | Lung Cancer | Pre-treatment, Day −1 | Y | N | 100 | 80930 | 6091276800 | 2922585558 | 48% | 35004 | 7742 |
| CGPLLU265 | Lung Cancer | Pre-treatment, Day 0 | Y | Y | 100 | 80930 | 8430107900 | 2945953499 | 46% | 35219 | 8574 |
| CGPLLU266 | Lung Cancer | Pre-treatment, Day 0 | Y | Y | 100 | 80930 | 5869510300 | 2792208995 | 48% | 33423 | 8423 |
| CGPLLU266 | Lung Cancer | Pre-treatment, Day −1 | Y | N | 100 | 80930 | 5884330900 | 2588386038 | 44% | 30977 | 9803 |
| CGPLLU267 | Lung Cancer | Pre-treatment, Day 0 | Y | N | 100 | 80930 | 5807524900 | 2347651479 | 40% | 28146 | 5793 |
| CGPLLU267 | Lung Cancer | Pre-treatment, Day −1 | Y | N | 100 | 80930 | 6064269800 | 2086938782 | 34% | 24994 | 6221 |
| CGPLLU269 | Lung Cancer | Pre-treatment, Day 0 | Y | Y | 100 | 80930 | 6785913900 | 3458588505 | 51% | 41432 | 7765 |
| CGPLLU269 | Lung Cancer | Pre-treatment, Day −1 | Y | N | 100 | 80930 | 6513702000 | 2096370387 | 32% | 25142 | 6598 |
| CGPLLU271 | Lung Cancer | Pre-treatment, Day 0 | Y | Y | 100 | 80930 | 6610761200 | 2576886619 | 39% | 31095 | 4485 |
| CGPLLU271 | Lung Cancer | Post-treatment, Day 259 | Y | N | 100 | 80930 | 6156102000 | 2586081726 | 42% | 30714 | 5309 |
| CGPLLU271 | Lung Cancer | Post-treatment, Day 259 | Y | N | 100 | 80930 | 6180799700 | 2013434756 | 33% | 23902 | 3885 |
| CGPLLU271 | Lung Cancer | Post-treatment, Day 259 | Y | N | 100 | 80930 | 6221168600 | 1499602843 | 24% | 17799 | 6098 |
| CGPLLU271 | Lung Cancer | Post-treatment, Day 259 | Y | N | 100 | 80930 | 5353961600 | 1698331125 | 32% | 20094 | 5252 |
| CGPLLU271 | Lung Cancer | Post-treatment, Day 259 | Y | N | 100 | 80930 | 5831612800 | 1521114956 | 26% | 18067 | 6210 |
| CGPLLU271 | Lung Cancer | Post-treatment, Day 259 | Y | N | 100 | 80930 | 6229704000 | 1481468974 | 24% | 17608 | 4633 |
| CGPLLU271 | Lung Cancer | Post-treatment, Day 259 | Y | N | 100 | 80930 | 6134366400 | 1351029627 | 22% | 16170 | 7024 |
| CGPLLU271 | Lung Cancer | Post-treatment, Day 259 | Y | N | 100 | 80930 | 6491884900 | 1622578435 | 25% | 19433 | 5792 |
| CGPLLU271 | Lung Cancer | Post-treatment, Day 259 | Y | Y | 100 | 80930 | 5742881200 | 2349421128 | 41% | 28171 | 5723 |

TABLE 2-continued

APPENDIX B: Summary of targeted cfDNA analyses

| Patient | Patient Type | Timepoint | Fragment Profile Analysis | Mutation Analysis | Read Length | Bases in Target Region | Bases Mapped to Genome | Bases Mapped to Target Regions | Percent Mapped to Target Regions | Total Coverage | Distinct Coverage |
|---|---|---|---|---|---|---|---|---|---|---|---|
| CGPLLU271 | Lung Cancer | Post-treatment, Day 259 | Y | N | 100 | 80930 | 5503999300 | 1695782705 | 31% | 20320 | 5907 |
| CGPLLU43 | Lung Cancer | Pre-treatment, Day −1 | Y | N | 100 | 80930 | 6575907000 | 3002048491 | 46% | 35997 | 5445 |
| CGPLLU43 | Lung Cancer | Pre-treatment, Day −1 | Y | N | 100 | 80930 | 6204350900 | 3016077187 | 49% | 36162 | 5704 |
| CGPLLU43 | Lung Cancer | Pre-treatment, Day −1 | Y | N | 100 | 80930 | 5997724300 | 2989608757 | 50% | 35873 | 6228 |
| CGPLLU43 | Lung Cancer | Pre-treatment, Day −1 | Y | Y | 100 | 80930 | 6026261500 | 2881177658 | 48% | 34568 | 7221 |
| CGPLLU86 | Lung Cancer | Pre-treatment, Day 0 | N | Y | 100 | 80930 | 8222093400 | 3523035056 | 43% | 41165 | 3614 |
| CGPLLU86 | Lung Cancer | Post-treatment, Day 0.5 | N | Y | 100 | 80930 | 8305719500 | 4271264008 | 51% | 49508 | 6681 |
| CGPLLU86 | Lung Cancer | Post-treatment, Day 7 | N | Y | 100 | 80930 | 6787785300 | 3443658418 | 51% | 40132 | 3643 |
| CGPLLU86 | Lung Cancer | Post-treatment, Day 17 | N | N | 100 | 80930 | 6213229400 | 3120325926 | 50% | 36413 | 3560 |
| CGPLLU88 | Lung Cancer | Pre-treatment, Day 0 | Y | N | 100 | 80930 | 7252433900 | 3621678746 | 50% | 42719 | 8599 |
| CGPLLU88 | Lung Cancer | Pre-treatment, Day 0 | Y | N | 100 | 80930 | 7679995800 | 4004738253 | 52% | 46951 | 6387 |
| CGPLLU88 | Lung Cancer | Pre-treatment, Day 0 | Y | N | 100 | 80930 | 6509178000 | 3316053733 | 51% | 39274 | 2661 |
| CGPLLU89 | Lung Cancer | Pre-treatment, Day 0 | N | Y | 100 | 80930 | 7662496600 | 3781536306 | 49% | 44097 | 7909 |
| CGPLLU89 | Lung Cancer | Post-treatment, Day 7 | N | Y | 100 | 80930 | 7005599500 | 3339612564 | 48% | 38977 | 5034 |
| CGPLLU89 | Lung Cancer | Post-treatment, Day 22 | N | Y | 100 | 80930 | 8325998600 | 3094796789 | 37% | 36061 | 2822 |
| CGPLOV10 | Ovarian Cancer | Preoperative, Treatment naïve | Y | N | 100 | 80930 | 7073534200 | 3402308123 | 48% | 39820 | 4059 |
| CGPLOV11 | Ovarian Cancer | Preoperative, Treatment naïve | Y | Y | 100 | 80930 | 6924062200 | 3324593050 | 48% | 38796 | 7185 |
| CGPLOV12 | Ovarian Cancer | Preoperative, Treatment naïve | N | Y | 100 | 80930 | 6552080100 | 3181854993 | 49% | 37340 | 6114 |
| CGPLOV13 | Ovarian Cancer | Preoperative, Treatment naïve | Y | Y | 100 | 80930 | 6796755500 | 3264897084 | 48% | 38340 | 7931 |
| CGPLOV14 | Ovarian Cancer | Preoperative, Treatment naïve | N | Y | 100 | 80930 | 7856573900 | 3408425065 | 43% | 39997 | 7712 |
| CGPLOV15 | Ovarian Cancer | Preoperative, Treatment naïve | Y | Y | 100 | 80930 | 7239201500 | 3322285607 | 46% | 38953 | 6644 |
| CGPLOV16 | Ovarian Cancer | Preoperative, Treatment naïve | N | Y | 100 | 80930 | 8570755900 | 4344288233 | 51% | 51009 | 11947 |
| CGPLOV17 | Ovarian Cancer | Preoperative, Treatment naïve | Y | N | 100 | 80930 | 6910310400 | 2805243492 | 41% | 32828 | 4307 |
| CGPLOV18 | Ovarian Cancer | Preoperative, Treatment naïve | N | N | 100 | 80930 | 8173037600 | 4064432407 | 50% | 47714 | 5182 |
| CGPLOV19 | Ovarian Cancer | Preoperative, Treatment naïve | Y | Y | 100 | 80930 | 7732198900 | 3672564399 | 47% | 43020 | 11127 |
| CGPLOV20 | Ovarian Cancer | Preoperative, Treatment naïve | Y | Y | 100 | 80930 | 7559602000 | 3678700179 | 49% | 43230 | 4872 |
| CGPLOV21 | Ovarian Cancer | Preoperative, Treatment naïve | Y | Y | 100 | 80930 | 8949032900 | 4616255499 | 52% | 54012 | 12777 |
| CGPLOV22 | Ovarian Cancer | Preoperative, Treatment naïve | Y | Y | 100 | 80930 | 8680136500 | 4049934586 | 47% | 46912 | 9715 |
| CGPLOV23 | Ovarian Cancer | Preoperative, Treatment naïve | N | Y | 100 | 80930 | 6660096600 | 3422631774 | 51% | 40810 | 9460 |
| CGPLOV24 | Ovarian Cancer | Preoperative, Treatment naïve | N | Y | 100 | 80930 | 8634287200 | 4272258165 | 49% | 50736 | 8689 |
| CGPLOV25 | Ovarian Cancer | Preoperative, Treatment naïve | N | Y | 100 | 80930 | 6978295000 | 3390206388 | 49% | 40188 | 5856 |
| CGPLOV26 | Ovarian Cancer | Preoperative, Treatment naïve | N | Y | 100 | 80930 | 7041038300 | 3728879661 | 53% | 44341 | 8950 |
| CGPLOV28 | Ovarian Cancer | Preoperative, Treatment naïve | N | Y | 100 | 80930 | 7429236900 | 3753051715 | 51% | 45430 | 4155 |
| CGPLOV31 | Ovarian Cancer | Preoperative, Treatment naïve | N | Y | 100 | 80930 | 8981384000 | 4621838729 | 51% | 55429 | 5458 |
| CGPLOV32 | Ovarian Cancer | Preoperative, Treatment naïve | N | Y | 100 | 80930 | 9344536800 | 4737698323 | 51% | 57234 | 6165 |
| CGPLOV37 | Ovarian Cancer | Preoperative, Treatment naïve | N | Y | 100 | 80930 | 8158083200 | 4184432898 | 51% | 50648 | 6934 |
| CGPLOV38 | Ovarian Cancer | Preoperative, Treatment naïve | N | Y | 100 | 80930 | 8654435400 | 4492987085 | 52% | 53789 | 6124 |
| CGPLOV40 | Ovarian Cancer | Preoperative, Treatment naïve | N | Y | 100 | 80930 | 9868640700 | 4934400809 | 50% | 59049 | 7721 |
| CGPLOV41 | Ovarian Cancer | Preoperative, Treatment naïve | N | Y | 100 | 80930 | 7689013600 | 3861448829 | 50% | 46292 | 4469 |
| CGPLOV42 | Ovarian Cancer | Preoperative, Treatment naïve | N | Y | 100 | 80930 | 9836516300 | 4864154366 | 49% | 58302 | 7632 |
| CGPLOV43 | Ovarian Cancer | Preoperative, Treatment naïve | N | Y | 100 | 80930 | 8756507100 | 4515479918 | 52% | 54661 | 4310 |
| CGPLOV44 | Ovarian Cancer | Preoperative, Treatment naïve | N | Y | 100 | 80930 | 7576310800 | 4120933322 | 54% | 49903 | 4969 |
| CGPLOV46 | Ovarian Cancer | Preoperative, Treatment naïve | N | Y | 100 | 80930 | 9346036300 | 5037820346 | 54% | 61204 | 3927 |
| CGPLOV47 | Ovarian Cancer | Preoperative, Treatment naïve | N | Y | 100 | 80930 | 10880620200 | 5491357828 | 50% | 66363 | 6895 |
| CGPLOV48 | Ovarian Cancer | Preoperative, Treatment naïve | N | Y | 100 | 80930 | 7658787800 | 3335991337 | 44% | 40332 | 4066 |
| CGPLOV49 | Ovarian Cancer | Preoperative, Treatment naïve | N | Y | 100 | 80930 | 10076208000 | 5519656698 | 55% | 67117 | 5097 |
| CGPLOV50 | Ovarian Cancer | Preoperative, Treatment naïve | N | Y | 100 | 80930 | 8239290400 | 4472380276 | 54% | 54150 | 3836 |

TABLE 2-continued

APPENDIX B: Summary of targeted cfDNA analyses

| Patient | Patient Type | Timepoint | Fragment Profile Analysis | Mutation Analysis | Read Length | Bases in Target Region | Bases Mapped to Genome | Bases Mapped to Target Regions | Percent Mapped to Target Regions | Total Coverage | Distinct Coverage |
|---|---|---|---|---|---|---|---|---|---|---|---|
| CGPLPA118 | Bile Duct Cancer | Preoperative, Treatment naïve | N | Y | 100 | 80930 | 9094827600 | 4828332902 | 53% | 57021 | 4802 |
| CGPLPA122 | Bile Duct Cancer | Preoperative, Treatment naïve | N | Y | 100 | 80930 | 7303323100 | 3990160379 | 55% | 47240 | 7875 |
| CGPLPA124 | Bile Duct Cancer | Preoperative, Treatment naïve | N | Y | 100 | 80930 | 7573482800 | 3965807442 | 52% | 46388 | 8658 |
| CGPLPA126 | Bile Duct Cancer | Preoperative, Treatment naïve | N | Y | 100 | 80930 | 7904953600 | 4061463168 | 51% | 47812 | 10498 |
| CGPLPA128 | Bile Duct Cancer | Preoperative, Treatment naïve | N | Y | 100 | 80930 | 7249238300 | 2244188735 | 31% | 26436 | 3413 |
| CGPLPA129 | Bile Duct Cancer | Preoperative, Treatment naïve | N | Y | 100 | 80930 | 7559858900 | 4003725804 | 53% | 47182 | 5733 |
| CGPLPA130 | Bile Duct Cancer | Preoperative, Treatment naïve | N | Y | 100 | 80930 | 6973946500 | 1247144905 | 18% | 14691 | 1723 |
| CGPLPA131 | Bile Duct Cancer | Preoperative, Treatment naïve | N | Y | 100 | 80930 | 7226237900 | 3370664342 | 47% | 39661 | 5054 |
| CGPLPA134 | Bile Duct Cancer | Preoperative, Treatment naïve | N | Y | 100 | 80930 | 7268866100 | 3754945844 | 52% | 44306 | 7023 |
| CGPLPA136 | Bile Duct Cancer | Preoperative, Treatment naïve | N | Y | 100 | 80930 | 7476690700 | 4073978408 | 54% | 48134 | 5244 |
| CGPLPA140 | Bile Duct Cancer | Preoperative, Treatment naïve | N | Y | 100 | 80930 | 7364654600 | 3771765342 | 51% | 44479 | 7080 |
| CGST102 | Gastric Cancer | Preoperative, Treatment naïve | N | Y | 100 | 80930 | 5715504500 | 2644902854 | 46% | 31309 | 4503 |
| CGST110 | Gastric Cancer | Preoperative, Treatment naïve | N | Y | 100 | 80930 | 9179291500 | 4298269268 | 47% | 51666 | 3873 |
| CGST114 | Gastric Cancer | Preoperative, Treatment naïve | N | Y | 100 | 80930 | 7151572200 | 3254967293 | 46% | 38496 | 4839 |
| CGST13 | Gastric Cancer | Preoperative, Treatment naïve | N | Y | 100 | 80930 | 6449701500 | 3198545984 | 50% | 38515 | 6731 |
| CGST141 | Gastric Cancer | Preoperative, Treatment naïve | N | Y | 100 | 80930 | 6781001300 | 3440927391 | 51% | 40762 | 5404 |
| CGST16 | Gastric Cancer | Preoperative, Treatment naïve | N | Y | 100 | 80930 | 6396470600 | 2931380289 | 46% | 35354 | 8148 |
| CGST18 | Gastric Cancer | Preoperative, Treatment naïve | N | Y | 100 | 80930 | 6647324000 | 3138967777 | 47% | 37401 | 4992 |
| CGST28 | Gastric Cancer | Preoperative, Treatment naïve | N | Y | 100 | 80930 | 6288486100 | 2884997993 | 46% | 34538 | 2586 |
| CGST30 | Gastric Cancer | Preoperative, Treatment naïve | N | Y | 100 | 80930 | 6141213100 | 3109994564 | 51% | 37194 | 2555 |
| CGST32 | Gastric Cancer | Preoperative, Treatment naïve | N | Y | 100 | 80930 | 6969139300 | 3099120469 | 44% | 36726 | 3935 |
| CGST33 | Gastric Cancer | Preoperative, Treatment naïve | N | Y | 100 | 80930 | 6560309400 | 3168371917 | 48% | 37916 | 4597 |
| CGST39 | Gastric Cancer | Preoperative, Treatment naïve | N | Y | 100 | 80930 | 7043791400 | 2992801875 | 42% | 35620 | 6737 |
| CGST41 | Gastric Cancer | Preoperative, Treatment naïve | N | Y | 100 | 80930 | 6975053100 | 3224065662 | 46% | 38300 | 4016 |
| CGST45 | Gastric Cancer | Preoperative, Treatment naïve | N | Y | 100 | 80930 | 6130812200 | 2944524278 | 48% | 35264 | 4745 |
| CGST47 | Gastric Cancer | Preoperative, Treatment naïve | N | Y | 100 | 80930 | 5961400000 | 3083523351 | 52% | 37008 | 3112 |
| CGST48 | Gastric Cancer | Preoperative, Treatment naïve | N | Y | 100 | 80930 | 6418652700 | 1497230327 | 23% | 17782 | 2410 |
| CGST58 | Gastric Cancer | Preoperative, Treatment naïve | N | Y | 100 | 80930 | 5818344500 | 1274708429 | 22% | 15281 | 2924 |
| CGST80 | Gastric Cancer | Preoperative, Treatment naïve | N | Y | 100 | 80930 | 6368064600 | 3298497188 | 52% | 39692 | 5280 |
| CGST81 | Gastric Cancer | Preoperative, Treatment naïve | N | Y | 100 | 80930 | 8655691400 | 1519121452 | 18% | 17988 | 6419 |

TABLE 3

| Patient | Patient Type | Stage at Diagnosis | Alteration Type | Gene | Amino Acid (Protein) | Nucleotide | Mutation Type |
|---|---|---|---|---|---|---|---|
| CGCRC291 | Colorectal Cancer | IV | Tumor-derived | STK11 | 39R>C | chr19_1207027-1207027_C_T | Substitution |
| CGCRC291 | Colorectal Cancer | IV | Tumor-derived | TP53 | 272V>M | chr17 7577124-7577124 C T | Substitution |
| CGCRC291 | Colorectal Cancer | IV | Tumor-derived | TP53 | 167Q>X | chr17_7578431-7578431_G_A | Substitution |
| CGCRC291 | Colorectal Cancer | IV | Tumor-derived | KRAS | 12G>A | chr12_25398284-25398284_C_G | Substitution |
| CGCRC291 | Colorectal Cancer | IV | Tumor-derived | APC | 1260Q>X | chr5_112175069-112175069_C_T | Substitution |
| CGCRC291 | Colorectal Cancer | IV | Tumor-derived | APC | 1450R>X | chr5_112175639-112175639_C_T | Substitution |
| CGCRC291 | Colorectal Cancer | IV | Tumor-derived | PIK3CA | 542E>K | chr3_178936082-178936082_G_A | Substitution |
| CGCRC292 | Colorectal Cancer | IV | Tumor-derived | KRAS | 146A>V | chr12_25378561-25378561_G_A | Substitution |
| CGCRC292 | Colorectal Cancer | IV | Tumor-derived | CTNNB1 | 41T>A | chr3_41266124-41266124_A_G | Substitution |
| CGCRC292 | Colorectal Cancer | IV | Germline | EGFR | 2284−4C>G | chr7_55248982-55248982_C_G | Substitution |
| CGCRC293 | Colorectal Cancer | IV | Tumor-derived | TP53 | 176C>S | chr17_7578404-7578404_A_T | Substitution |
| CGCRC294 | Colorectal Cancer | II | Tumor-derived | APC | 213R>X | chr5_112116592-112116592_C_T | Substitution |
| CGCRC294 | Colorectal Cancer | II | Tumor-derived | APC | 1367Q>X | chr5_112175390-112175390_C_T | Substitution |
| CGCRC295 | Colorectal Cancer | IV | Tumor-derived | PDGFRA | 49+4C>T | chr4_55124988-55124988_C_T | Substitution |
| CGCRC295 | Colorectal Cancer | IV | Hematopoietic | IDH1 | 104G>V | chr2_209113196-209113196_C_A | Substitution |
| CGCRC296 | Colorectal Cancer | II | Germline | EGFR | 922E>K | chr7_55266472-55266472_G_A | Substitution |
| CGCRC297 | Colorectal Cancer | III | Germline | KIT | 18L>F | chr4_55524233-55524233_C_T | Substitution |
| CGCRC298 | Colorectal Cancer | II | Hematopoietic | DNMT3A | 882R>H | chr2_25457242-25457242_C_T | Substitution |
| CGCRC298 | Colorectal Cancer | II | Hematopoietic | DNMT3A | 714S>C | chr2_25463541-25463541_G_C | Substitution |
| CGCRC298 | Colorectal Cancer | II | Tumor-derived | PIK3CA | 414G>V | chr3_178927478-178927478_G_T | Substitution |
| CGCRC299 | Colorectal Cancer | I | Hematopoietic | DNMT3A | 735Y>C | chr2_25463289 25463289_T_C | Substitution |
| CGCRC299 | Colorectal Cancer | I | Hematopoietic | DNMT3A | 710C>S | chr2_25463553-25463553_C_G | Substitution |
| CGCRC300 | Colorectal Cancer | I | Hematopoietic | DNMT3A | 720R>G | chr2_25463524-25463524_G_C | Substitution |
| CGCRC301 | Colorectal Cancer | I | Tumor-derived | ATM | 2397Q>X | chr11_108199847-108199847_C_T | Substitution |
| CGCRC302 | Colorectal Cancer | II | Tumor-derived | TP53 | 141C>Y | chr17_7578508-7578508_C_T | Substitution |
| CGCRC302 | Colorectal Cancer | II | Tumor-derived | BRAF | 600V>E | chr7_140453136-140453136_A_T | Substitution |
| CGCRC303 | Colorectal Cancer | III | Tumor-derived | TP53 | 173V>L | chr17_7578413-7578413_C_A | Substitution |
| CGCRC303 | Colorectal Cancer | III | Hematopoietic | DNMT3A | 755F>3 | chr2_25463229-25463229_A_G | Substitution |
| CGCRC303 | Colorectal Cancer | III | Hematopoietic | DNMT3A | 2173+1G>A | chr2_25463508-25463508_C_T | Substitution |
| CGCRC304 | Colorectal Cancer | II | Tumor-derived | EGFR | 1131T>S | chr7_55273068-55273068_A_T | Substitution |
| CGCRC304 | Colorectal Cancer | II | Tumor-derived | ATM | 3077+1G>A | chr11_108142134-108142134_G_A | Substitution |
| CGCRC304 | Colorectal Cancer | II | Hematopoietic | ATM | 3008R>C | chr11_108236086-108236086_C_T | Substitution |
| CGCRC305 | Colorectal Cancer | II | Tumor-derived | GNA11 | 213R>Q | chr19_3118954-3118954_G_A | Substitution |
| CGCRC305 | Colorectal Cancer | II | Tumor-derived | TP53 | 273R>H | chr17_7577120-7577120_C_T | Substitution |
| CGCRC306 | Colorectal Cancer | II | Tumor-derived | TP53 | 196R>X | chr17_7578263-7578263_G_A | Substitution |
| CGCRC306 | Colorectal Cancer | II | Tumor-derived | CDKN2A | 107R>C | chr9_21971039-21971039_G_A | Substitution |
| CGCRC306 | Colorectal Cancer | II | Tumor-derived | KRAS | 61Q>K | chr12_25380277-25380277_G_T | Substitution |

TABLE 3-continued

APPENDIX C: Targeted cfDNA fragment analyses in cancer patients

| CGCRC306 | Colorectal Cancer | II | Germline | PDGFRA | 200T>S | chr4_55130065-55130065_C_G | Substitution |
|---|---|---|---|---|---|---|---|
| CGCRC306 | Colorectal Cancer | II | Tumor-derived | EGFR | 618H>R | chr7_55233103-55233103_A_G | Substitution |
| CGCRC306 | Colorectal Cancer | II | Tumor-derived | PIK3CA | 545E>A | chr3_178936092-178936092_A_C | Substitution |
| CGCRC3G6 | Colorectal Cancer | II | Germline | ERBB4 | 1155R>X | chr2_212251596-212251596_G_A | Substitution |
| CGCRC307 | Colorectal Cancer | II | Tumor-derived | JAK2 | 805L>V | chr9_5080662-5080662_C_G | Substitution |
| CGCRC307 | Colorectal Cancer | II | Tumor-derived | SMARCB1 | 5C1-2A>G | chr22_24145480-24145480_A_G | Substitution |
| CGCRC307 | Colorectal Cancer | II | Tumor-derived | GNAS | 201R>C | chr20_57484420-57484420_C_T | Substitution |
| CGCRC307 | Colorectal Cancer | II | Tumor-derived | BRAF | 600V>E | chr7_140453136-140453136_A_T | Substitution |
| CGCRC307 | Colorectal Cancer | II | Tumor-derived | FBXW7 | 465R>C | chr4_153249365-153249385_G_A | Substitution |
| CGCRC307 | Colorectal Cancer | II | Tumor-derived | ER8B4 | 17A>V | chr2_213403205-213403205_G_A | Substitution |
| CGCRC308 | Colorectal Cancer | III | Hematopoietic | DNMT3A | 882R>H | chr2_25457242-25457242_C_T | Substitution |
| CGCRC308 | Colorectal Cancer | III | Germline | EGFR | 848P>L | chr7_55259485-55259485_C_T | Substitution |
| CGCRC308 | Colorectal Cancer | III | Tumor-derived | APC | 1480Q>X | chr5_112175729-112175729_C_T | Substitution |
| CGCRC309 | Colorectal Cancer | III | Tumor-derived | AKT1 | 17E>K | chr14_105246551-105246551_C_T | Substitution |
| CGCRC309 | Colorectal Cancer | III | Tumor-derived | BRAF | 600V>E | chr7_140453136-140453136_A_T | Substitution |
| CGCRC310 | Colorectal Cancer | II | Tumor-derived | KRAS | 12G>V | chr12_25398284-25398284_C_A | Substitution |
| CGCRC310 | Colorectal Cancer | II | Tumor-derived | APC | 1513E>X | chr5_112175828-112175828_G_T | Substitution |
| CGCRC310 | Colorectal Cancer | II | Tumor-derived | APC | 1521E>X | chr5_112175852-112175352_G_T | Substitution |
| CGCRC311 | Colorectal Cancer | I | Hematopoietic | DNMT3A | 882R>H | chr2_25457242-25457242_C_T | Substitution |
| CGCRC312 | Colorectal Cancer | III | Tumor-derived | APC | 960S>X | chr5_112174170-112174170_C_G | Substitution |
| CGCRC312 | Colorectal Cancer | III | Tumor-derived | NRAS | 61Q>K | chr1_115256530-115256530_G_T | Substitution |
| CGCRC313 | Colorectal Cancer | III | Tumor-derived | KRAS | 12G>S | chr12_25398285-25398285_C_T | Substitution |
| CGCRC313 | Colorectal Cancer | III | Tumor-derived | APC | 876R>X | chr5_112173917-112173917_C_T | Substitution |
| CGCRC314 | Colorectal Cancer | I | Tumor-derived | KRAS | 12G>D | chr12_25398284-25398284_C_T | Substitution |
| CGCRC314 | Colorectal Cancer | I | Hematopoietic | DNMT3A | 738L>Q | chr2_25463280-25463280_A_T | Substitution |
| CGCRC314 | Colorectal Cancer | I | Tumor-derived | APC | 1379E>X | chr5_112175426-112175426_G_T | Substitution |
| CGCRC315 | Colorectal Cancer | III | Tumor-derived | NRAS | 12G>D | chr1_115258747-115258747_C_T | Substitution |
| CGCRC315 | Colorectal Cancer | III | Tumor-derived | FBXW7 | 505R>3 | chr4_153247289-153247289_G_A | Substitution |
| CGCRC316 | Colorectal Cancer | III | Tumor-derived | TP53 | 245G>S | chr17_7577548-7577548_C_T | Substitution |
| CGCRC316 | Colorectal Cancer | III | Tumor-derived | CDKN2A | 1M>R | chr9_21974825-21974825_A_C | Substitution |
| CGCRC316 | Colorectal Cancer | III | Tumor-derived | CTNNB1 | 37S>C | chr3_41266113-41266113_C_G | Substitution |
| CGCRC316 | Colorectal Cancer | III | Tumor-derived | EGFR | 2702-3C>T | chr7_55266407-55266407_C_T | Substitution |
| CGCRC316 | Colorectal Cancer | III | Hematopoietic | ATM | 3008R>P | chr11_108236087-108236087_G_C | Substitution |
| CGCRC317 | Colorectal Cancer | III | Tumor-derived | TP53 | 220Y>C | chr17_7578190-7578190_T_C | Substitution |
| CGCRC317 | Colorectal Cancer | III | Tumor-derived | ATM | 1026W>R | chr11_108142132-108142132_T_C | Substitution |
| CGCRC317 | Colorectal Cancer | III | Tumor-derived | APC | 216R>X | chr5_112128143-112128143_C_T | Substitution |
| CGCRC318 | Colorectal Cancer | I | Hematopoietic | DNMT3A | 698W>X | chr2_25463589-25463589_C_T | Substitution |
| CGCRC320 | Colorectal Cancer | I | Germline | KIT | 18L>F | chr4_55524233-55524233_C_T | Substitution |
| CGCRC320 | Colorectal Cancer | I | Tumor-derived | ERBB4 | 78R>W | chr2_212989479-212989479_G_A | Substitution |

TABLE 3-continued

APPENDIX C: Targeted cfDNA fragment analyses in cancer patients

| | | | | | | | |
|---|---|---|---|---|---|---|---|
| CGCRC321 | Colorectal Cancer | I | Tumor-derived | CDKN2A | 12S>L | chr9_21974792-21974792_G_A | Substitution |
| CGCRC321 | Colorectal Cancer | I | Hematopoietic | DNMT3A | 882R>H | chr2_25457242-25457242_C_T | Substitution |
| CGCRC321 | Colorectal Cancer | I | Germline | EGFR | 511S>Y | chr7_55229225-55229225_C_A | Substitution |
| CGCRC332 | Colorectal Cancer | IV | Tumor-derived | TP53 | 125T>R | chr17_7579313-7579313_G_C | Substitution |
| CGCRC333 | Colorectal Cancer | IV | Tumor-derived | TP53 | 673−2A>G | chr17_7577610-7577610_T_C | Substitution |
| CGCRC333 | Colorectal Cancer | IV | Tumor-derived | BRAF | 600V>E | chr7_140453136-140453136_A_T | Substitution |
| CGCRC333 | Colorectal Cancer | IV | Tumor-derived | ERBB4 | 691E>A | chr2_212495194-212495194_T_G | Substitution |
| CGCRC334 | Colorectal Cancer | IV | Tumor-derived | TP53 | 245G>S | chr17_7577548-7577548_C_T | Substitution |
| CGCRC334 | Colorectal Cancer | IV | Germline | EGFR | 638T>M | chr7_55238900-55238900_C_T | Substitution |
| CGCRC334 | Colorectal Cancer | IV | Tumor-derived | PIK3CA | 104P>R | chr3_178916924-178916924_C_G | Substitution |
| CGCRC335 | Colorectal Cancer | IV | Tumor-derived | BRAF | 600V>E | chr7_140453136-140453136_A_T | Substitution |
| CGCRC336 | Colorectal Cancer | IV | Tumor-derived | TP53 | 175R>H | chr17_7578406-7578406_C_T | Substitution |
| CGCRC336 | Colorectal Cancer | IV | Tumor-derived | KRAS | 12G>V | chr12_25398284-25398284_C_A | Substitution |
| CGCRC336 | Colorectal Cancer | IV | Turner-derived | APC | 1286E>X | chr5_112175147-112175147_G_T | Substitution |
| CGCRC337 | Colorectal Cancer | IV | Tumor-derived | STK11 | 734+2T>A | chr19_1220718-1220718_T_A | Substitution |
| CGCRC337 | Colorectal Cancer | IV | Germline | APC | 485M>I | chr5_112162851-112162851_G_A | Substitution |
| CGCRC338 | Colorectal Cancer | IV | Tumor-derived | KRAS | 12G>D | chr12_25398284-25398284_C_T | Substitution |
| CGCRC339 | Colorectal Cancer | IV | Tumor-derived | KRAS | 13G>D | chr12_25393281-25398281_C_T | Substitution |
| CGCRC339 | Colorectal Cancer | IV | Tumor-derived | APC | 876R>X | chr5_112173917-112173917_C_T | Substitution |
| CGCRC339 | Colorectal Cancer | IV | Tumor-derived | PIK3CA | 407C>F | chr3_178927457-178927457_G_T | Substitution |
| CGCRC339 | Colorectal Cancer | IV | Tumor-derived | PIK3CA | 1047H>L | chr3_178952085-178952085_A_T | Substitution |
| CGCRC340 | Colorectal Cancer | IV | Tumor-derived | TP53 | 196R>X | chr17_7578263-7578263_G_A | Substitution |
| CGCRC340 | Colorectal Cancer | IV | Tumor-derived | APC | 1306E>X | chr5_112175207-112175207_G_T | Substitution |
| CGPLBR38 | Breast Cancer | I | Tumor-derived | TP53 | 241S>P | chr17_7577560-7577560_A_G | Substitution |
| CGPLBR40 | Breast Cancer | III | Germline | AR | 392P>R | chrX_66766163-66766163_C_G | Substitution |
| CGPLBR44 | Breast Cancer | III | Hematopoietic | DNMT3A | 882R>H | chr2_25457242-25457242_C_T | Substitution |
| CGPLBR44 | Breast Cancer | III | Hematopoietic | DNMT3A | 705I>T | chr2_25463568-25463568_A_G | Substitution |
| CGPLBR44 | Breast Cancer | III | Tumor-derived | PDGFRA | 859V>M | chr4_55153609-55153609_G_A | Substitution |
| CGPLBR48 | Breast Cancer | II | Germline | ALK | 1231R>Q | chr2_29436901-29436901_C_T | Substitution |
| CGPLBR48 | Breast Cancer | II | Tumor-derived | EGFR | 669R>Q | chr7_55240762-55240762_G_A | Substitution |
| CGPLBR55 | Breast Cancer | III | Hematopoietic | DNMT3A | 743P>S | chr2_25463266-25463266_G_A | Substitution |
| CGPLBR55 | Breast Cancer | III | Tumor-derived | GNAS | 201R>H | chr20_57484421-57484421_G_A | Substitution |
| CGPLBR55 | Breast Cancer | III | Tumor-derived | PIK3CA | 345N>K | chr3_178921553-178921553_T_A | Substitution |
| CGPLBR63 | Breast Cancer | II | Germline | FGFR3 | 403K>E | chr4_1806188-1806188_A_G | Substitution |
| CGPLBR67 | Breast Cancer | III | Hematopoietic | DNMT3A | 882R>H | chr2_25457242-25457242_C_T | Substitution |
| CGPLBR67 | Breast Cancer | III | Tumor-derived | PIK3CA | 545E>K | chr3_178936091-178936091_G_A | Substitution |
| CGPLBR67 | Breast Cancer | III | Tumor-derived | ERBB4 | 1000D>A | chr2_212285302-212285302_T_G | Substitution |
| CGPLBR69 | Breast Cancer | II | Hematopoietic | DNMT3A | 774E>V | chr2_25463172-25463172_T_A | Substitution |
| CGPLBR69 | Breast Cancer | II | Germline | CTNNB1 | 30Y>S | chr3_41266092-41266092_A_C | Substitution |

TABLE 3-continued

APPENDIX C: Targeted cfDNA fragment analyses in cancer patients

| | | | | | | | |
|---|---|---|---|---|---|---|---|
| CGPLBR69 | Breast Cancer | II | Germline | IDH1 | 231Y>N | chr2_209108158-209108158_A_T | Substitution |
| CGPLBR70 | Breast Cancer | II | Tumor-derived | ATM | 2832R>H | chr11_108216546-108216546_G_A | Substitution |
| CGRLBR70 | Breast Cancer | II | Germline | APC | 1577E>D | chr5_112176022-112176022_A_C | Substitution |
| CGPLBR71 | Breast Cancer | II | Tumor-derived | TP53 | 273R>H | chr17_7577120-7577120_C_T | Substitution |
| CGPLBR72 | Breast Cancer | II | Germline | APC | 1532D>G | chr5_112175886-112175886_A_G | Substitution |
| CGPLBR73 | Breast Cancer | II | Tumor-derived | ALK | 708S>P | chr2_29474053-29474053_A_G | Substitution |
| CGPLBR73 | Breast Cancer | II | Germline | ERBB4 | 158A>E | chr2_212652833-212652833_G_T | Substitution |
| CGPLBR74 | Breast Cancer | II | Germline | AR | 20+1G>T | chrX_66788865-66788865_G_T | Substitution |
| CGPLBR75 | Breast Cancer | II | Tumor-derived | PIK3CA | 1047H>R | chr3_178952085-178352085_A_G | Substitution |
| CGPLBR76 | Breast Cancer | II | Germline | KDR | 1290S>N | chr4_55946310-55946310_C_T | Substitution |
| CGPLBR76 | Breast Cancer | II | Tumor-derived | PIK3CA | 1047H>R | chr3_178952085-178952085_A_G | Substitution |
| CGPLBR77 | Breast Cancer | III | Tumor-derived | PTEN | 170S>I | chr10_89711891-89711891_G_T | Substitution |
| CGPLBR80 | Breast Cancer | II | Tumor-derived | CDKN2A | 12S>L | chr9_21974792-21974792_G_A | Substitution |
| CGPLBR83 | Breast Cancer | II | Germline | AR | 728N>D | chrX_66937328-66937328_A_G | Substitution |
| GGPLBR83 | Breast Cancer | II | Tumor-derived | ATM | 322E>K | chr11_108117753-108117753_G_A | Substitution |
| CGPLBR83 | Breast Cancer | II | Germline | ERBB4 | 539Y>S | chr2_212543783 212543783_T_G | Substitution |
| CGPLBR86 | Breast Cancer | II | Germline | STK11 | 354F>L | chr19_1223125-1223125_C_G | Substitution |
| CGPLBR86 | Breast Cancer | II | Germline | SMARCB1 | 795+3A>G | chr22_24159126-24159126_A_G | Substitution |
| CGPLBR87 | Breast Cancer | II | Tumor-derived | JAK2 | 215R>X | chr9_5054591-5054591_C_T | Substitution |
| CGPLBR87 | Breast Cancer | II | Hematopoietic | DNMT3A | 882R>H | chr2_25457242-25457242_C_T | Substitution |
| CGPLBR87 | Breast Cancer | II | Tumor-derived | SMAD4 | 496R>C | chr18_48304664-48604664_C_T | Substitution |
| CGPLBR87 | Breast Cancer | II | Germline | AR | 651S>N | chrX_66931310-66931310_G_A | Substitution |
| CGPLBR88 | Breast Cancer | II | Tumor-derived | CDK6 | 51E>K | chr7_92462487-92462487_G_T | Substitution |
| CGPLBR88 | Breast Cancer | II | Germline | APC | 1125V>A | chr5_112174665-112174665_T_C | Substitution |
| CGPLBR92 | Breast Cancer | II | Tumor-derived | TP53 | 257L>P | chr17_7577511-7577511_A_G | Substitution |
| CGPLBR96 | Breast Cancer | II | Tumor-derived | TP53 | 213R>X | chr17.1a: 7578212-7576212_G_A | Substitution |
| CGPLBR96 | Breast Cancer | II | Hematopoietic | DNMT3A | 531D>G | chr2_25467484-25467434_T_G | Substitution |
| CGPLBR96 | Breast Cancer | II | Tumor-derived | AR | 13R>Q | chrX_66765026-66765026_G_A | Substitution |
| CGPLBR97 | Breast Cancer | II | Hematopoietic | DNMT3A | 882R>H | chr2_25457242-25457242_C_T | Substitution |
| CGPLBR97 | Breast Cancer | II | Germline | PDGFRA | 401A>D | chr4_55136880-55136880_C_A | Substitution |
| CGPLBR97 | Breast Cancer | II | Tumor-derived | GNAS | 201R>H | chr20_57484421-57484421_G_A | Substitution |
| CGPLLU144 | Lung Cancer | II | Tumor-derived | TP53 | 241S>F | chr17_7577559-7577559_G_A | Substitution |
| CGPLLU144 | Lung Cancer | II | Tumor-derived | KRAS | 12G>C | chr12_25398285-25398285_C_A | Substitution |
| CGPLLU144 | Lung Cancer | II | Tumor-derived | EGFR | 373P>S | chr7_55224336-55224336_C_T | Substitution |
| CGPLLU144 | Lung Cancer | II | Tumor-derived | ATM | 292P>L | chr11_108115727-108115727_C_T | Substitution |
| CGPLLU144 | Lung Cancer | II | Tumor-derived | PIK3CA | 545E>K | chr3_178936091 178936091_G_A | Substitution |
| CGPLLU144 | Lung Cancer | II | Tumor-derived | ERBB4 | 426R>K | chr2_212568841-212568841_C_T | Substitution |
| CGPLLU146 | Lung Cancer | II | Hematopoietic | JAK2 | 617V>F | chr9_5073770-5073770_G_T | Substitution |
| CGPLLU146 | Lung Cancer | II | Tumor-derived | TP53 | 282R>P | chr17_7577093-7577093_C_G | Substitution |

TABLE 3-continued

APPENDIX C: Targeted cfDNA fragment analyses in cancer patients

| | | | | | | |
|---|---|---|---|---|---|---|
| CGPLLU146 | Lung Cancer | II | Hematopoietic | DNMT3A | 737L>H | chr2_25463283-25463283_A_T | Substitution |
| CGPLLU146 | Lung Cancer | II | Tumor-derived | RB1 | 861+2T>C | chr13_48937095-48937095_T_C | Substitution |
| CGPLLU146 | Lung Cancer | II | Tumor-derived | ATM | 581L>F | chr11_108122699-108122699_A_T | Substitution |
| CGPLLU147 | Lung Cancer | III | Tumor-derived | TP53 | 248R>Q | chr17_7577538-7577538_C_T | Substitution |
| CGPLLU147 | Lung Cancer | III | Tumor-derived | TP53 | 201L>X | chr17_7573247-7578247_A_T | Substitution |
| CGPLLU147 | Lung Cancer | III | Tumor-derived | ALK | 1537G>E | chr2_29416343-29416343_C_T | Substitution |
| CGPLLU147 | Lung Cancer | III | Germline | PDGFRA | 200T>S | chr4_55130065-55130065_C_G | Substitution |
| CGPLLU162 | Lung Cancer | II | Tumor-derived | CDKN2A | 12S>L | chr9_21974792-21974792_G_A | Substitution |
| CGPLLU162 | Lung Cancer | II | Tumor-derived | EGFR | 858L>R | chr7_55259515-55259515_T_G | Substitution |
| CGPLLU162 | Lung Cancer | II | Tumor-derived | BRAF | 354R>Q | chr7_140494187-140494187_C_T | Substitution |
| CGPLLU163 | Lung Cancer | II | Tumor-derived | CDKN2A | 12S>L | chr9_21974792-21974792_G_A | Substitution |
| CGPLLU163 | Lung Cancer | II | Hematopoietic | DNMT3A | 528Y>D | chr2_25467494-25467494_A_C | Substitution |
| CGPLLU164 | Lung Cancer | II | Tumor-derived | STK11 | 216S>Y | chr19_1220629-1220629_C_A | Substitution |
| CGPLLU164 | Lung Cancer | II | Germline | STK11 | 354F>L | chr19_1223125-1223125_C_G | Substitution |
| CGPLLU164 | Lung Cancer | II | Tumor-derived | GNA11 | 606−3C>T | chr19_3118919-3118919_C_T | Substitution |
| CGPLLU164 | Lung Cancer | II | Tumor-derived | TP53 | 278P>S | chr17_7577106-7577106_G_A | Substitution |
| CGPLLU164 | Lung Cancer | II | Tumor-derived | TP53 | 161A>S | chr17_7578449-7578449_C_A | Substitution |
| CGPLLU164 | Lung Cancer | II | Tumor-derived | TP53 | 160M>I | chr17_7578450-7578450_C_A | Substitution |
| CGPLLU164 | Lung Cancer | II | Tumor-derived | ERBB4 | 1299P>L | chr2_212248371-212248371_G_A | Substitution |
| CGPLLU164 | Lung Cancer | II | Tumor-derived | ERBB4 | 253N>S | chr2_212587243-212587243_T_C | Substitution |
| CGPLLU165 | Lung Cancer | II | Germline | STK11 | 354F>L | chr19_1223125-1223125_C_G | Substitution |
| CGPLLU165 | Lung Cancer | II | Tumor-derived | GNAS | 201R>H | chr20_57484421-57484421_G_A | Substitution |
| CGPLLU168 | Lung Cancer | I | Tumor-derived | TP53 | 136Q>X | chr17.1a: 7578524-7578524_G_A | Substitution |
| CGPLLU168 | Lung Cancer | I | Hematopoietic | DNMT3A | 736R>S | chr2_25463287-25463287_G_T | Substitution |
| CGPLLU168 | Lung Cancer | I | Tumor-derived | EGFR | 858L>R | chr7.1a: 55259515-55259515_T_G | Substitution |
| CGPLLU174 | Lung Cancer | I | Tumor-derived | STK11 | 597+1G>T | chr19_1220505-1220505_G_T | Substitution |
| CGPLLU174 | Lung Cancer | I | Tumor-derived | JAK2 | 160D>Y | chr9_5050695-5050695_G_T | Substitution |
| CGPLLU174 | Lung Cancer | I | Tumor-derived | KRAS | 12G>C | chr12_25398285-25398285_C_A | Substitution |
| CGPLLU174 | Lung Cancer | I | Hematopoietic | DNMT3A | 891R>W | chr2_25457216-25457216_G_A | Substitution |
| CGPLLU174 | Lung Cancer | I | Hematopoietic | DNMT3A | 715I>M | chr2_25463537-25463537_G_C | Substitution |
| CGPLLU175 | Lung cancer | I | Tumor-derived | TP53 | 179H>R | chr17_7578394-7578394_T_C | Substitution |
| CGPLLU175 | Lung Cancer | I | Hematopoietic | DNMT3A | 2598−1G>A | chr2_25457290-25457290_C_T | Substitution |
| CGPLLU175 | Lung Cancer | I | Hematopoietic | DNMT3A | 755F>L | chr2_25463230-25463230_A_G | Substitution |
| CGPLLU175 | Lung Cancer | I | Germline | ATM | 337R>C | chr11_108117798-108117798_C_T | Substitution |
| CGPLLU175 | Lung Cancer | I | Tumor-derived | ERBB4 | 941Q>X | chr2_212288925-212288925_G_A | Substitution |
| CGPLLU176 | Lung Cancer | I | Hematopoietic | DNMT3A | 750P>S | chr2_25463245-25463245_G_A | Substitution |
| CGPLLU176 | Lung Cancer | I | Hematopoietic | DNMT3A | 735Y>C | chr2_25463239-25463239_T_C | Substitution |
| CGPLLU177 | Lung Cancer | II | Tumor-derived | KRAS | 12G>V | chr12_25398284-25398284_C_A | Substitution |
| CGPLLU177 | Lung Cancer | II | Hematopoietic | DNMT3A | 897V>G | chr2_25457197-25457197_A_C | Substitution |

TABLE 3-continued

APPENDIX C: Targeted cfDNA fragment analyses in cancer patients

| | | | | | | | |
|---|---|---|---|---|---|---|---|
| CGPLLU177 | Lung Cancer | II | Hematopoietic | DNMT3A | 882R>C | chr2_25457243-25457243_G_A | Substitution |
| CGPLLU177 | Lung Cancer | II | Hematopoietic | DNMT3A | 2173+1G>A | chr2_25463508-25463508_C_T | Substitution |
| CGPLLU178 | Lung Cancer | I | Tumor-derived | CDH1 | 251T>M | chr16_68844164-68844164_C_T | Substitution |
| CGPLLU178 | Lung Cancer | I | Tumor-derived | PIK3CA | 861Q>X | chr3_178947145-178947145_C_T | Substitution |
| CGPLLU179 | Lung Cancer | I | Hematopoietic | DNMT3A | 879N>D | chr2_25457252-25457252_T_C | Substitution |
| CGPLLU179 | Lung Cancer | I | Germline | APC | 2611T>I | chr5_112179123-112179123_C_T | Substitution |
| CGPLLU180 | Lung Cancer | I | Tumor-derived | STK11 | 237D>Y | chr19_1220691-1220691_G_T | Substitution |
| CGPLLU180 | Lung Cancer | I | Tumor-derived | TP53 | 293G>V | chr17_7577068-7577060_C_A | Substitution |
| CGPLLU180 | Lung Cancer | I | Tumor-derived | TP53 | 282R>P | chr17_577893-7577093_C_G | Substitution |
| CGPLLU180 | Lung Cancer | I | Tumor-derived | TP53 | 177P>L | chr17.1a: 7578400-7578400_G_A | Substitution |
| CGPLLU180 | Lung Cancer | I | Tumor-derived | RB1 | 565S>X | chr13_48955578-48955578_C_G | Substitution |
| CGPLLU197 | Lung Cancer | I | Hematopoietic | DNMT3A | 882R>C | chr2_25457243-25457243_G_A | Substitution |
| CGPLLU197 | Lung Cancer | I | Hematopoietic | DNMT3A | 879N>D | chr2_25457252-25457252_T_C | Substitution |
| CGPLLU198 | Lung Cancer | I | Tumor-derived | TP53 | 162I>N | chr17_7576445-7576445_A_T | Substitution |
| CGPLLU198 | Lung Cancer | I | Tumor-derived | EGFR | 858L>R | chr7_25259515_55259515_T_G | Substitution |
| CGPLLU202 | Lung Cancer | I | Tumor-derived | EGFR | 790T>M | chr7.1a: 55249071-55249071_C_T | Substitution |
| CGPLLU202 | Lung Cancer | I | Tumor-derived | EGFR | 868E>X | chr7_55259544-55259544_G_T | Substitution |
| CGPLLU204 | Lung Cancer | I | Tumor-derived | KIT | 956R>Q | chr4_55604659-55604659_G_A | Substitution |
| CGPLLU205 | Lung Cancer | II | Hematopoietic | DNMT3A | 736R>C | chr2_25463287-25463287_G_A | Substitution |
| CGPLLU205 | Lung Cancer | II | Hematopoietic | DNMT3A | 696Q>X | chr2_25463596-25463596_G_A | Substitution |
| CGPLLU206 | Lung Cancer | III | Tumor-derived | TP53 | 672+1G>A | chr17_7578176-7578176_C_T | Substitution |
| CGPLLU206 | Luna Cancer | III | Tumor-derived | TP53 | 131N>S | chr17_7573538-7578538_T_C | Substitution |
| CGPLLU207 | Lung Cancer | II | Tumor-derived | TP53 | 376−1G>A | chr17_573555-75785551_C_T | Substitution |
| CGPLLU207 | Lung Cancer | II | Germline | ALK | 419F>L | chr2_29606625-29606625_A_G | Substitution |
| CGPLLU207 | Lung Cancer | II | Tumor-derived | EGFR | 790T>M | chr7.1a: 552493071-55249071_C_T | Substitution |
| CGPLLU208 | Lung Cancer | II | Tumor-derived | TP53 | 250P>L | chr17_7577532-7577532_G_A | Substitution |
| CGPLLU208 | Lung Cancer | II | Germline | EGFR | 224R>H | chr7_55220281-55228281_G_A | Substitution |
| CGPLLU208 | Lung Cancer | II | Tumor-derived | EGFR | 858L>R | chr7_513259515_55259515_T_G | Substitution |
| CGPLLU208 | Lung Cancer | II | Tumor-derived | MYC | 98R>W | chr8_128750755-126750755_C_T | Substitution |
| CGPLLU209 | Lung Cancer | II | Germline | STK11 | 354F>L | chr19_1223125-1223125_C_G | Substitution |
| CGPLLU209 | Lung Cancer | II | Tumor-derived | TP53 | 100Q>X | chr17_7579389-7579389_G_A | Substitution |
| CGPLLU209 | Lung Cancer | II | Tumor-derived | CDKN2A | 88E>X | chr9_21971096-21971_OSS_C_A | Substitution |
| CGPLLU209 | Lung Cancer | II | Tumor-derived | PDGFRA | 921A>T | chr4_55155052_55155052_G_A | Substitution |
| CGPLLU209 | Lung Cancer | II | Germline | EGFR | 567M>V | chr7_55231493-55231493_A_G | Substitution |
| CGPLOV10 | Ovarian Cancer | I | Tumor-derived | TP53 | 342R>X | chr17_7574003-7574003_G_A | Substitution |
| CGPLOV11 | Ovarian Cancer | IV | Tumor-derived | TP53 | 248R>Q | chr17_7577538-7577538_C_T | Substitution |
| CGPLOV11 | Ovarian Cancer | IV | Germline | TP53 | 63A>V | chr17_579499-7579499_G_A | Substitution |
| CGPLOV13 | Ovarian Cancer | IV | Tumor-derived | ALK | 444W>C | chr2_29551298-23551298_C_A | Substitution |
| CGPLOV13 | Ovarian Cancer | IV | Germline | PDGFRA | 401A>D | chr4_55136630-55136830_C_A | Substitution |

TABLE 3-continued

APPENDIX C: Targeted cfDNA fragment analyses in cancer patients

| | | | | | | | |
|---|---|---|---|---|---|---|---|
| CGPLOV13 | Ovarian Cancer | IV | Tumor-derived | KIT | 135R>H | chr4_55564516-555S4516_G_A | Substitution |
| CGPLOV14 | Ovarian Cancer | I | Tumor-derived | HNF1A | 230E>K | chr12_12143484-121431484_G_A | Substitution |
| CGPLOV15 | Ovarian Cancer | III | Tumor-derived | TP53 | 278P>S | chr17_577106-7577106_G_A | Substitution |
| CGPLOV15 | Ovarian Cancer | III | Tumor-derived | EGFR | 433H>D | chr7_55225445_55225445_C_G | Substitution |
| CGPLOV17 | Ovarian Cancer | I | Tumor-derived | TP53 | 248R>Q | chr17_7577539-7577538_C_T | Substitution |
| CGPLOV17 | Ovarian Cancer | I | Germline | PDGFRA | 1071D>N | chr4 55161380-55161380_G_A | Substitution |
| CGPLOV18 | Ovarian Cancer | I | Germline | AFC | 1125V>A | chr5_112174S65-112174365_T_C | Substitution |
| CGPLOV19 | Ovarian Cancer | II | Germline | FGFR3 | 403K>E | chr4_1606163-1806183_A_G | Substitution |
| CGPLOV19 | Ovarian Cancer | II | Tumor-derived | TR53 | 273R>H | chr17_577120-7577120_C_T | Substitution |
| CGPLOV19 | Ovarian Cancer | II | Germline | AR | 176S>R | chrX_66765516-66765516_C_A | Substitution |
| CGPLOV19 | Ovarian Cancer | II | Tumor-derived | APC | 1378Q>X | chr5_112175423-112175423_C_T | Substitution |
| CGPLOV20 | Ovarian Cancer | II | Tumor-derived | TP53 | 195I>T | chr17_7578265-7578265_A_G | Substitution |
| CGPLOV20 | Ovarian Cancer | II | Germline | EGFR | 253K>R | chr7_55221714-55221714_A_G | Substitution |
| CGPLOV21 | Ovarian Cancer | IV | Germline | STK11 | 354F>L | chr19_1223125-1223125_C_G | Substitution |
| CGPLOV21 | Ovarian Cancer | IV | Tumor-derived | TP53 | 275C>Y | chr17_577114-7577114_C_T | Substitution |
| CGPLOV21 | Ovarian Cancer | IV | Tumor-derived | ERBB4 | 602S>T | chr2_212530114_212530114_C_G | Substitution |
| CGPLOV22 | Ovarian Cancer | III | Tumor-derived | TP53 | 193H>P | chr17_7573271-757S271_T_G | Substitution |
| CGPLOV22 | Ovarian Cancer | III | Tumor-derived | CTNNB1 | 41T>A | chr3_41266124-41266124_A_G | Substitution |

| | | | | | Wild-type Fragments | | | |
|---|---|---|---|---|---|---|---|---|
| Patient | Hotspot Alteration | Alteration Detected in Tissue | Mutant Allele Fraction | Distinct Coverage | Minimum cfDNA Fragment Size (bp) | 25th Percentile cfDNA Fragment Size (bp) | Mode cfDNA Fragment Size (bp) | Median cfDNA Fragment Size (bp) |
| CGCRC291 | No | No | 0.14% | 11688 | 100 | 151 | 167 | 169 |
| CGCRC291 | Yes | No | 0.10% | 11779 | 100 | 155 | 171 | 169 |
| CGCRC291 | Yes | Yes | 22.85% | 11026 | 100 | 156 | 166 | 169 |
| CGCRC291 | Yes | Yes | 14.85% | 7632 | 97 | 152 | 169 | 167 |
| CGCRC291 | No | Yes | 11.23% | 7218 | 101 | 155 | 167 | 169 |
| CGCRC291 | Yes | Yes | 11.05% | 10757 | 86 | 154 | 166 | 167 |
| CGCRC291 | Yes | Yes | 18.11% | 5429 | 100 | 151 | 171 | 167 |
| CGCRC292 | Yes | No | 1.41% | 6120 | 101 | 157 | 167 | 169 |
| CGCRC292 | Yes | Yes | 0.13% | 10693 | 100 | 155 | 169 | 168 |
| CGCRC292 | NA | Yes | 31.99% | 7587 | 97 | 158 | 166 | 171 |
| CGCRC293 | No | No | 0.35% | 7672 | 95 | 159 | 168 | 170 |
| CGCRC294 | Yes | Yes | 0.14% | 7339 | 84 | 155 | 166 | 167 |
| CGCRC294 | Yes | Yes | 0.13% | 12054 | 89 | 159 | 167 | 170 |
| CGCRC295 | No | No | 0.45% | 5602 | 101 | 157 | 164 | 170 |
| CGCRC295 | No | Yes | 0.34% | 8330 | 100 | 157 | 166 | 169 |
| CGCRC296 | NA | Yes | 30.48% | 8375 | 89 | 161 | 166 | 172 |
| CGCRC297 | NA | Yes | 41.39% | 3580 | 102 | 159 | 164 | 170 |
| CGCRC298 | Yes | Yes | 0.08% | 13032 | 100 | 159 | 168 | 171 |
| CGCRC298 | No | No | 0.11% | 13475 | 93 | 158 | 169 | 170 |
| CGCRC298 | No | No | 0.55% | 5815 | 100 | 158 | 168 | 169 |
| CGCRC299 | No | Yes | 0.30% | 11995 | 100 | 154 | 164 | 165 |
| CGCRC299 | No | Yes | 0.12% | 15363 | 96 | 151 | 166 | 164 |
| CGCRC300 | No | No | 0.15% | 7487 | 100 | 162 | 179 | 173 |
| CGCRC301 | No | No | 0.21% | 5881 | 100 | 156 | 169 | 169 |
| CGCRC302 | Yes | Yes | 0.05% | 24784 | 84 | 153 | 165 | 164 |
| CGCRC302 | Yes | Yes | 0.12% | 11763 | 95 | 154 | 165 | 165 |
| CGCRC303 | Yes | Yes | 0.08% | 13967 | 95 | 159 | 169 | 171 |
| CGCRC303 | No | No | 0.21% | 10167 | 81 | 160 | 169 | 172 |
| CGCRC303 | No | No | 0.17% | 10845 | 100 | 160 | 169 | 172 |
| CGCRC304 | No | No | 0.22% | 16168 | 90 | 153 | 167 | 164 |
| CGCRC304 | No | No | 0.27% | 10502 | 100 | 152 | 165 | 163 |
| CGCRC304 | No | Yes | 0.43% | 12987 | 101 | 154 | 165 | 165 |
| CGCRC305 | No | Yes | 0.11% | 12507 | 100 | 159 | 169 | 171 |

TABLE 3-continued

APPENDIX C: Targeted cfDNA fragment analyses in cancer patients

| | | | | | | | | |
|---|---|---|---|---|---|---|---|---|
| CGCRC305 | Yes | No | 0.19% | 10301 | 100 | 156 | 168 | 166 |
| CGCRC306 | Yes | No | 0.12% | 8594 | 101 | 157 | 165 | 169 |
| CGCRC306 | No | Yes | 8.02% | 9437 | 90 | 159 | 167 | 171 |
| CGCRC306 | Yes | Yes | 7.30% | 6090 | 100 | 152 | 163 | 166 |
| CGCRC306 | NA | Yes | 34.78% | 4585 | 103 | 158 | 167 | 179 |
| CGCRC306 | No | Yes | 6.32% | 7395 | 81 | 160 | 166 | 171 |
| CGCRC306 | Yes | No | 0.96% | 4885 | 100 | 152 | 170 | 167 |
| CGCRC3G6 | NA | Yes | 38.70% | 3700 | 100 | 159 | 168 | 171 |
| CGCRC307 | No | No | 0.56% | 6860 | 100 | 158 | 170 | 170 |
| CGCRC307 | No | Yes | 0.34% | 10065 | 95 | 157 | 168 | 169 |
| CGCRC307 | Yes | Yes# | 0.24% | 7520 | 102 | 156 | 167 | 168 |
| CGCRC307 | Yes | Yes | 0.38% | 8623 | 76 | 157 | 169 | 168 |
| CGCRC307 | Yes | Yes | 0.31% | 10606 | 100 | 155 | 167 | 168 |
| CGCRC307 | No | No | 0.15% | 13189 | 90 | 158 | 168 | 171 |
| CGCRC308 | Yes | No | 0.06% | 16287 | 90 | 159 | 168 | 169 |
| CGCRC308 | NA | Yes | 27.69% | 7729 | 100 | 160 | 164 | 170 |
| CGCRC308 | No | Yes | 0.11% | 14067 | 92 | 157 | 170 | 169 |
| CGCRC309 | Yes | Yes | 2.70% | 13036 | 85 | 157 | 170 | 169 |
| CGCRC309 | Yes | Yes | 3.00% | 9084 | 101 | 157 | 166 | 168 |
| CGCRC310 | Yes | Yes | 0.13% | 7393 | 100 | 153 | 165 | 164 |
| CGCRC310 | No | Yes | 0.11% | 11689 | 100 | 152 | 166 | 164 |
| CGCRC310 | No | Yes | 0.15% | 10273 | 100 | 153 | 166 | 164 |
| CGCRC311 | Yes | No | 0.86% | 8456 | 94 | 160 | 171 | 172 |
| CGCRC312 | No | Yes | 0.59% | 4719 | 100 | 160 | 165 | 173 |
| CGCRC312 | Yes | Yes | 0.47% | 3391 | 101 | 157 | 172 | 170 |
| CGCRC313 | Yes | Yes | 0.17% | 5013 | 100 | 163 | 166 | 174 |
| CGCRC313 | Yes | Yes | 0.07% | 8150 | 72 | 161 | 171 | 174 |
| CGCRC314 | Yes | Yes | 0.30% | 4684 | 100 | 158 | 165 | 169 |
| CGCRC314 | No | Yes | 2.50% | 6902 | 85 | 159 | 165 | 170 |
| CGCRC314 | Yes | Yes | 0.38% | 7229 | 102 | 158 | 167 | 170 |
| CGCRC315 | Yes | Yes | 0.27% | 8733 | 94 | 155 | 167 | 169 |
| CGCRC315 | Yes | Yes | 0.25% | 9623 | 101 | 158 | 166 | 170 |
| CGCRC316 | Yes | Yes | 6.52% | 12880 | 100 | 150 | 166 | 163 |
| CGCRC316 | No | Yes | 5.74% | 7479 | 93 | 157 | 164 | 168 |
| CGCRC316 | Yes | Yes | 5.47% | 13682 | 100 | 149 | 165 | 162 |
| CGCRC316 | No | No | 0.11% | 16716 | 85 | 153 | 166 | 156 |
| CGCRC316 | No | Yes | 0.13% | 17060 | 100 | 150 | 166 | 153 |
| CGCRC317 | Yes | Yes | 0.36% | 14587 | 84 | 152 | 166 | 154 |
| CGCRC317 | No | Yes | 0.23% | 10483 | 100 | 152 | 164 | 155 |
| CGCRC317 | Yes | No | 0.29% | 3497 | 101 | 149 | 166 | 153 |
| CGCRC318 | No | Yes | 0.25% | 16436 | 98 | 158 | 170 | 170 |
| CGCRC320 | NA | Yes | 34.76% | 6521 | 100 | 163 | 170 | 175 |
| CGCRC320 | No | No | 0.12% | 11633 | 100 | 162 | 174 | 174 |
| CGCRC321 | No | No | 0.20% | 6916 | 88 | 161 | 167 | 174 |
| CGCRC321 | Yes | No | 0.08% | 9559 | 94 | 159 | 171 | 170 |
| CGCRC321 | NA | Yes | 41.86% | 5545 | 100 | 159 | 172 | 172 |
| CGCRC332 | No | Yes | 19.98% | 605 | 104 | 154 | 170 | 176 |
| CGCRC333 | No | Yes | 43.03% | 1265 | 89 | 159 | 165 | 171 |
| CGCRC333 | Yes | Yes | 22.26% | 3338 | 102 | 153 | 165 | 169 |
| CGCRC333 | No | No | 1.00% | 3008 | 102 | 153 | 169 | 169 |
| CGCRC334 | Yes | Yes | 13.44% | 1725 | 105 | 160 | 170 | 175 |
| CGCRC334 | NA | Yes | 35.28% | 1168 | 100 | 159 | 164 | 174 |
| CGCRC334 | No | No | 3.85% | 1798 | 103 | 159 | 166 | 173 |
| CGCRC335 | Yes | Yes | 0.32% | 2411 | 99 | 155 | 167 | 157 |
| CGCRC336 | Yes | Yes | 75.26% | 757 | 104 | 156 | 171 | 170 |
| CGCRC336 | Yes | Yes | 42.87% | 1080 | 102 | 150 | 166 | 167 |
| CGCRC336 | No | Yes | 81.61% | 391 | 102 | 161 | 165 | 171 |
| CGCRC337 | No | No | 0.12%, | 6497 | 72 | 153 | 169 | 177 |
| CGCRC337 | NA | Yes | 46.26% | 1686 | 100 | 147 | 170 | 163 |
| CGCRC338 | Yes | Yes | 27.03% | 1408 | 105 | 153 | 164 | 166 |
| CGCRC339 | Yes | Yes | 1.94% | 1256 | 105 | 158 | 168 | 169 |
| CGCRC339 | Yes | Yes | 2.35% | 1639 | 101 | 158 | 165 | 172 |
| CGCRC339 | No | Yes | 3.14% | 1143 | 100 | 154 | 170 | 167 |
| CGCRC339 | Yes | Yes | 1.71% | 1584 | 108 | 161 | 171 | 173 |
| CGCRC340 | Yes | Yes | 18.26% | 876 | 101 | 159 | 170 | 175 |
| CGCRC340 | Yes | Yes | 22.57% | 796 | 105 | 159 | 164 | 174 |
| CGPLBR38 | No | Yes | 0.53% | 9684 | 95 | 156 | 166 | 168 |
| CGPLBR40 | NA | Yes | 28.99% | 10277 | 78 | 162 | 168 | 173 |
| CGPLBR44 | Yes | Yes | 1.82% | 10715 | 99 | 162 | 171 | 173 |
| CGPLBR44 | No | Yes | 0.41% | 10837 | 100 | 159 | 169 | 171 |
| CGPLBR44 | No | Yes | 0.13% | 12640 | 100 | 159 | 168 | 171 |
| CGPLBR48 | NA | Yes | 34.61% | 5631 | 100 | 164 | 170 | 179 |
| CGPLBR48 | No | No | 0.18% | 12467 | 101 | 167 | 174 | 180 |
| CGPLBR55 | No | No | 0.18% | 10527 | 101 | 158 | 169 | 169 |
| CGPLBR55 | Yes | Yes | 0.68% | 6011 | 101 | 153 | 166 | 167 |
| CGPLBR55 | Yes | Yes | 0.42% | 3973 | 101 | 153 | 166 | 166 |
| CGPLBR63 | NA | Yes | 34.82% | 3405 | 97 | 165 | 170 | 176 |
| CGPLBR67 | Yes | Yes | 0.11% | 10259 | 87 | 157 | 168 | 168 |

TABLE 3-continued

| APPENDIX C: Targeted cfDNA fragment analyses in cancer patients | | | | | | | | |
|---|---|---|---|---|---|---|---|---|
| CGPLBR67 | Yes | Yes | 0.68% | 5163 | 100 | 151 | 167 | 166 |
| CGPLBR67 | No | No | 0.28% | 6250 | 100 | 155 | 166 | 167 |
| CGPLBR69 | No | No | 0.29% | 7558 | 100 | 159 | 166 | 170 |
| CGPLBR69 | NA | Yes | 41.74% | 3938 | 101 | 154 | 169 | 166 |
| CGPLBR69 | NA | Yes | 41.66% | 2387 | 101 | 157 | 166 | 168 |
| CGPLBR70 | No | No | 0.36% | 6916 | 100 | 158 | 171 | 169 |
| CGRLBR70 | NA | Yes | 40.28% | 3580 | 107 | 160 | 169 | 173 |
| CGPLBR71 | Yes | Yes | 0.10% | 7930 | 85 | 156 | 166 | 158 |
| CGPLBR72 | NA | Yes | 44.03% | 2389 | 100 | 157 | 160 | 170 |
| CGPLBR73 | No | No | 0.27% | 11348 | 95 | 161 | 173 | 174 |
| CGPLBR73 | NA | Yes | 35.58% | 3422 | 102 | 157 | 168 | 169 |
| CGPLBR74 | NA | Yes | 36.23% | 3784 | 101 | 163 | 175 | 174 |
| CGPLBR75 | Yes | Yes | 0.14% | 7290 | 103 | 162 | 173 | 172 |
| CGPLBR76 | NA | Yes | 36.57% | 4342 | 104 | 166 | 171 | 179 |
| CGPLBR76 | Yes | Yes | 0.12% | 11785 | 100 | 165 | 168 | 177 |
| CGPLBR77 | No | Yes | 2.29% | 6161 | 100 | 158 | 166 | 169 |
| CGPLBR80 | No | No | 0.54% | 3643 | 96 | 165 | 166 | 185 |
| CGPLBR83 | NA | Yes | 42.66% | 3479 | 105 | 162 | 164 | 174 |
| GGPLBR83 | No | No | 0.28% | 3496 | 103 | 165 | 170 | 177 |
| CGPLBR83 | NA | Yes | 44.91% | 1748 | 100 | 164 | 173 | 175 |
| CGPLBR86 | NA | Yes | 42.32% | 4241 | 98 | 160 | 168 | 175 |
| CGPLBR86 | NA | Yes | 43.38% | 3096 | 88 | 160 | 167 | 174 |
| CGPLBR87 | No | No | 0.35% | 3680 | 101 | 162 | 168 | 175 |
| CGPLBR87 | Yes | No | 0.31% | 6180 | 101 | 163 | 164 | 175 |
| CGPLBR87 | No | No | 0.40% | 7746 | 86 | 160 | 167 | 175 |
| CGPLBR87 | NA | Yes | 42.94% | 2266 | 106 | 160 | 166 | 172 |
| CGPLBR88 | No | No | 0.13% | 17537 | 89 | 185 | 200 | 223 |
| CGPLBR88 | NA | Yes | 31.19% | 5919 | 101 | 162 | 172 | 173 |
| CGPLBR92 | No | Yes | 0.20% | 15530 | 77 | 150 | 164 | 152 |
| CGPLBR96 | Yes | No | 0.10% | 9893 | 100 | 159 | 164 | 171 |
| CGPLBR96 | No | Yes | 5.81% | 8620 | 95 | 162 | 167 | 173 |
| CGPLBR96 | No | No | 0.60% | 8036 | 85 | 162 | 169 | 175 |
| CGPLBR97 | Yes | Yes | 0.11% | 14856 | 93 | 160 | 168 | 170 |
| CGPLBR97 | NA | Yes | 34.12% | 5329 | 100 | 161 | 165 | 171 |
| CGPLBR97 | Yes | Yes | 0.13% | 7010 | 97 | 158 | 169 | 170 |
| CGPLLU144 | Yes | Yes | 1.95% | 11371 | 100 | 156 | 165 | 167 |
| CGPLLU144 | Yes | Yes | 5.10% | 7641 | 100 | 155 | 167 | 166 |
| CGPLLU144 | No | Yes | 0.16% | 9996 | 100 | 158 | 168 | 169 |
| CGPLLU144 | No | No | 0.22% | 4956 | 101 | 159 | 166 | 169 |
| CGPLLU144 | Yes | Yes | 2.94% | 8540 | 100 | 153 | 170 | 166 |
| CGPLLU144 | No | No | 0.18% | 7648 | 101 | 156 | 164 | 166 |
| CGPLLU146 | Yes | No | 0.25% | 5920 | 100 | 155 | 164 | 168 |
| CGPLLU146 | No | Yes | 1.30% | 9356 | 100 | 155 | 166 | 168 |
| CGPLLU146 | No | Yes | 0.84% | 7284 | 101 | 158 | 165 | 170 |
| CGPLLU146 | No | Yes | 0.87% | 4183 | 103 | 160 | 166 | 170 |
| CGPLLU146 | No | No | 0.20% | 6778 | 100 | 157 | 166 | 168 |
| CGPLLU147 | Yes | No | 0.15% | 4807 | 100 | 155 | 166 | 170 |
| CGPLLU147 | No | Yes | 0.55% | 5282 | 100 | 156 | 167 | 171 |
| CGPLLU147 | No | Yes | 0.94% | 7122 | 100 | 158 | 174 | 173 |
| CGPLLU147 | NA | Yes | 43.47% | 2825 | 101 | 160 | 165 | 173 |
| CGPLLU162 | No | No | 0.22% | 9940 | 95 | 161 | 164 | 174 |
| CGPLLU162 | Yes | Yes | 0.22% | 13855 | 87 | 160 | 174 | 173 |
| CGPLLU162 | No | No | 0.14% | 11251 | 100 | 153 | 167 | 166 |
| CGPLLU163 | No | No | 0.21% | 10805 | 85 | 159 | 165 | 173 |
| CGPLLU163 | No | Yes | 0.15% | 20185 | 83 | 158 | 166 | 170 |
| CGPLLU164 | No | Yes | 1.23% | 6795 | 91 | 156 | 161 | 169 |
| CGPLLU164 | NA | Yes | 42.52% | 4561 | 92 | 157 | 164 | 169 |
| CGPLLU164 | No | No | 0.20% | 8097 | 100 | 158 | 170 | 170 |
| CGPLLU164 | Yes | No | 0.10% | 9241 | 100 | 155 | 165 | 157 |
| CGPLLU164 | No | Yes | 1.78% | 10806 | 100 | 157 | 168 | 159 |
| CGPLLU164 | No | Yes | 1.86% | 10919 | 100 | 157 | 168 | 159 |
| CGPLLU164 | No | Yes | 0.96% | 5412 | 103 | 159 | 175 | 171 |
| CGPLLU164 | No | No | 0.22% | 5151 | 101 | 160 | 166 | 169 |
| CGPLLU165 | NA | Yes | 36.62% | 7448 | 95 | 155 | 167 | 167 |
| CGPLLU165 | Yes | Yes | 0.16% | 5822 | 102 | 154 | 166 | 166 |
| CGPLLU168 | Yes | Yes | 0.06% | 15985 | 97 | 152 | 165 | 166 |
| CGPLLU168 | No | No | 0.39% | 11070 | 100 | 156 | 165 | 168 |
| CGPLLU168 | Yes | Yes | 0.07% | 11063 | 83 | 157 | 166 | 169 |
| CGPLLU174 | No | Yes | 0.33% | 5881 | 88 | 162 | 165 | 174 |
| CGPLLU174 | No | Yes | 0.40% | 3696 | 100 | 162 | 167 | 172 |
| CGPLLU174 | Yes | Yes | 0.16% | 4941 | 101 | 162 | 167 | 172 |
| CGPLLU174 | No | Yes | 0.29% | 7527 | 100 | 163 | 168 | 173 |
| CGPLLU174 | No | Yes | 0.26% | 8353 | 101 | 162 | 168 | 173 |
| CGPLLU175 | Yes | Yes | 8.03% | 10214 | 100 | 160 | 166 | 170 |
| CGPLLU175 | No | No | 0.21% | 9739 | 100 | 157 | 168 | 168 |
| CGPLLU175 | No | Yes | 0.15% | 9509 | 100 | 157 | 165 | 168 |
| CGPLLU175 | NA | Yes | 43.84% | 2710 | 101 | 157 | 165 | 167 |
| CGPLLU175 | No | Yes | 3.64% | 6565 | 100 | 158 | 166 | 168 |

TABLE 3-continued

APPENDIX C: Targeted cfDNA fragment analyses in cancer patients

| | | | | | | | | |
|---|---|---|---|---|---|---|---|---|
| CGPLLU176 | No | Yes | 0.92% | 6513 | 101 | 164 | 168 | 175 |
| CGPLLU176 | No | Yes | 0.21% | 5962 | 100 | 164 | 174 | 175 |
| CGPLLU177 | Yes | Yes | 2.49% | 7044 | 102 | 160 | 165 | 170 |
| CGPLLU177 | No | Yes | 1.53% | 9950 | 88 | 160 | 169 | 171 |
| CGPLLU177 | Yes | No | 0.29% | 11233 | 100 | 160 | 168 | 171 |
| CGPLLU177 | No | No | 0.13% | 10966 | 75 | 160 | 169 | 172 |
| CGPLLU178 | No | No | 0.29% | 8378 | 100 | 162 | 176 | 172 |
| CGPLLU178 | No | No | 0.17% | 7235 | 101 | 159 | 167 | 170 |
| CGPLLU179 | No | Yes | 0.38% | 8350 | 103 | 161 | 169 | 171 |
| CGPLLU179 | NA | Yes | 39.91% | 2609 | 103 | 162 | 171 | 173 |
| CGPLLU180 | No | Yes | 2.43% | 6085 | 91 | 158 | 165 | 170 |
| CGPLLU180 | No | Yes | 2.07% | 6680 | 92 | 158 | 164 | 169 |
| CGPLLU180 | No | Yes | 1.94% | 7790 | 92 | 158 | 167 | 168 |
| CGPLLU180 | Yes | No | 0.08% | 9036 | 101 | 160 | 169 | 171 |
| CGPLLU180 | No | Yes | 1.01% | 4679 | 100 | 157 | 169 | 168 |
| CGPLLU197 | Yes | No | 0.16% | 7196 | 102 | 162 | 166 | 172 |
| CGPLLU197 | No | No | 0.38% | 7147 | 100 | 161 | 166 | 172 |
| CGPLLU198 | No | Yes | 0.87% | 9322 | 97 | 157 | 165 | 168 |
| CGPLLU198 | Yes | Yes | 0.52% | 8303 | 100 | 160 | 173 | 172 |
| CGPLLU202 | Yes | Yes | 0.05% | 14197 | 90 | 151 | 165 | 166 |
| CGPLLU202 | No | No | 0.13% | 9279 | 51 | 150 | 168 | 167 |
| CGPLLU204 | No | No | 0.26% | 7185 | 100 | 157 | 165 | 168 |
| CGPLLU205 | No | Yes | 0.70% | 10739 | 96 | 156 | 165 | 166 |
| CGPLLU205 | No | Yes | 3.47% | 12065 | 100 | 154 | 165 | 165 |
| CGPLLU206 | Yes | Yes | 26.13% | 6746 | 94 | 148 | 165 | 164 |
| CGPLLU206 | No | No | 0.21% | 11225 | 100 | 147 | 167 | 164 |
| CGPLLU207 | Yes | Yes | 0.32% | 11224 | 100 | 159 | 165 | 170 |
| CGPLLU207 | NA | Yes | 34.58% | 4960 | 101 | 160 | 166 | 170 |
| CGPLLU207 | Yes | No | 0.09% | 13216 | 85 | 161 | 165 | 172 |
| CGPLLU208 | Yes | Yes | 1.33% | 5211 | 101 | 156 | 166 | 168 |
| CGPLLU208 | NA | Yes | 39.34% | 5253 | 100 | 159 | 164 | 170 |
| CGPLLU208 | Yes | Yes | 0.86% | 10233 | 100 | 160 | 170 | 171 |
| CGPLLU208 | No | No | 0.17% | 11421 | 100 | 158 | 165 | 171 |
| CGPLLU209 | NA | Yes | 26.84% | 11695 | 96 | 153 | 166 | 169 |
| CGPLLU209 | No | Yes | 9.97% | 12771 | 94 | 155 | 163 | 168 |
| CGPLLU209 | Yes | Yes | 9.13% | 16557 | 92 | 157 | 169 | 170 |
| CGPLLU209 | No | Yes | 9.32% | 13057 | 97 | 158 | 167 | 171 |
| CGPLLU209 | NA | Yes | 30.41% | 8521 | 100 | 155 | 167 | 169 |
| CGPLOV10 | Yes | Yes | 3.14% | 4421 | 101 | 161 | 165 | 172 |
| CGPLOV11 | Yes | Yes | 0.87% | 7987 | 100 | 157 | 164 | 169 |
| CGPLOV11 | NA | Yes | 37.77% | 3782 | 97 | 160 | 166 | 171 |
| CGPLOV13 | No | Yes | 0.12% | 12072 | 88 | 157 | 165 | 169 |
| CGPLOV13 | NA | Yes | 37.98% | 4107 | 103 | 159 | 166 | 169 |
| CGPLOV13 | No | Yes | 0.35% | 8427 | 100 | 161 | 165 | 171 |
| CGPLOV14 | No | No | 0.14% | 11418 | 92 | 154 | 167 | 171 |
| CGPLOV15 | Yes | Yes | 3.54% | 7689 | 102 | 157 | 164 | 169 |
| CGPLOV15 | No | No | 0.19% | 7617 | 101 | 159 | 167 | 171 |
| CGPLOV17 | Yes | Yes | 0.32% | 4463 | 96 | 155 | 168 | 163 |
| CGPLOV17 | NA | Yes | 44.10% | 2884 | 110 | 157 | 170 | 170 |
| CGPLOV18 | NA | Yes | 40.81% | 2945 | 101 | 159 | 164 | 169 |
| CGPLOV19 | NA | Yes | 23.80% | 9727 | 95 | 158 | 167 | 172 |
| CGPLOV19 | Yes | Yes | 36.83% | 4387 | 100 | 158 | 165 | 169 |
| CGPLOV19 | NA | Yes | 65.29% | 2775 | 93 | 161 | 171 | 171 |
| CGPLOV19 | Yes | Yes | 46.35% | 3818 | 102 | 156 | 170 | 170 |
| CGPLOV20 | Yes | Yes | 0.21% | 5404 | 94 | 159 | 165 | 170 |
| CGPLOV20 | NA | Yes | 44.05% | 3744 | 102 | 158 | 166 | 169 |
| CGPLOV21 | NA | Yes | 7.68% | 21823 | 81 | 158 | 166 | 169 |
| CGPLOV21 | No | Yes | 2.04% | 18806 | 101 | 159 | 165 | 169 |
| CGPLOV21 | No | No | 14.36% | 10801 | 89 | 160 | 166 | 169 |
| CGPLOV22 | No | Yes | 0.49% | 11952 | 100 | 155 | 165 | 167 |
| CGPLOV22 | Yes | Yes | 0.34% | 12399 | 92 | 150 | 165 | 164 |

| Wild-type Fragments | | | | Mutant Fragments | | | | |
|---|---|---|---|---|---|---|---|---|
| Mean cfDNA Fragment Size (bp) | 75th Percentile cfDNA Fragment Size (bp) | Maximum cfDNA Fragment Size (bp) | Distinct Coverage | Minimum cfDNA Fragment Size (bp) | 25th Percentile cfDNA Fragment Size (bp) | Mode cfDNA Fragment Size (bp) | Median cfDNA Fragment Size (bp) | |
| 179 | 188 | 400 | 19 | 100 | 142 | 233 | 165 | |
| 182 | 185 | 400 | 21 | 132 | 166 | 182 | 176 | |
| 180 | 183 | 400 | 5411 | 92 | 152 | 167 | 169 | |
| 177 | 182 | 400 | 1903 | 100 | 148 | 166 | 166 | |
| 184 | 185 | 400 | 1344 | 108 | 155 | 167 | 170 | |
| 181 | 182 | 400 | 2108 | 100 | 153 | 166 | 168 | |
| 176 | 180 | 400 | 1951 | 101 | 149 | 175 | 167 | |
| 176 | 183 | 399 | 75 | 123 | 162 | 167 | 172 | |

TABLE 3-continued

APPENDIX C: Targeted cfDNA fragment analyses in cancer patients

| | | | | | | | |
|---|---|---|---|---|---|---|---|
| 177 | 182 | 400 | 23 | 101 | 130 | 130 | 139 |
| 183 | 188 | 399 | 6863 | 100 | 160 | 168 | 173 |
| 188 | 186 | 400 | 34 | 77 | 154 | 171 | 170 |
| 175 | 179 | 396 | 9 | 138 | 147 | 176 | 171 |
| 184 | 185 | 400 | 21 | 115 | 145 | 155 | 159 |
| 179 | 185 | 397 | 30 | 137 | 149 | 181 | 162 |
| 179 | 182 | 397 | 44 | 125 | 155 | 155 | 169 |
| 185 | 188 | 400 | 8167 | 101 | 160 | 166 | 171 |
| 187 | 188 | 400 | 3562 | 102 | 158 | 168 | 170 |
| 184 | 187 | 399 | 15 | 93 | 137 | 127 | 174 |
| 183 | 185 | 400 | 26 | 137 | 163 | 166 | 167 |
| 181 | 182 | 397 | 35 | 118 | 147 | 176 | 163 |
| 172 | 175 | 400 | 71 | 133 | 152 | 170 | 165 |
| 169 | 174 | 400 | 55 | 130 | 153 | 165 | 164 |
| 189 | 187 | 399 | 17 | 149 | 155 | 326 | 170 |
| 176 | 183 | 400 | 18 | 156 | 170 | 174 | 174 |
| 169 | 175 | 397 | 51 | 108 | 143 | 268 | 152 |
| 166 | 173 | 397 | 26 | 118 | 147 | 153 | 156 |
| 184 | 186 | 400 | 45 | 116 | 151 | 168 | 163 |
| 185 | 186 | 400 | 25 | 157 | 165 | 191 | 175 |
| 185 | 187 | 400 | 25 | 124 | 168 | 180 | 180 |
| 167 | 175 | 394 | 86 | 121 | 155 | 169 | 166 |
| 167 | 173 | 397 | 45 | 124 | 143 | 197 | 162 |
| 170 | 175 | 398 | 108 | 126 | 147 | 162 | 162 |
| 190 | 189 | 400 | 23 | 131 | 148 | 145 | 166 |
| 182 | 182 | 399 | 42 | 138 | 155 | 155 | 174 |
| 189 | 187 | 399 | 25 | 126 | 153 | 176 | 176 |
| 192 | 193 | 400 | 977 | 101 | 149 | 189 | 170 |
| 173 | 179 | 391 | 525 | 102 | 140 | 168 | 159 |
| 181 | 185 | 399 | 4010 | 100 | 158 | 166 | 170 |
| 178 | 184 | 399 | 625 | 100 | 140 | 167 | 162 |
| 175 | 179 | 398 | 37 | 111 | 143 | 142 | 166 |
| 181 | 186 | 396 | 3184 | 102 | 159 | 168 | 172 |
| 180 | 183 | 399 | 47 | 111 | 148 | 144 | 169 |
| 133 | 184 | 397 | 39 | 111 | 146 | 182 | 162 |
| 185 | 184 | 400 | 24 | 110 | 146 | 309 | 182 |
| 176 | 180 | 400 | 32 | 117 | 146 | 154 | 157 |
| 180 | 184 | 399 | 43 | 111 | 143 | 144 | 177 |
| 185 | 187 | 400 | 29 | 109 | 140 | 204 | 159 |
| 179 | 182 | 399 | 20 | 128 | 152 | 180 | 163 |
| 176 | 184 | 398 | 7515 | 101 | 160 | 170 | 171 |
| 182 | 182 | 399 | 31 | 85 | 146 | 137 | 166 |
| 181 | 182 | 395 | 428 | 100 | 135 | 138 | 149 |
| 175 | 180 | 397 | 352 | 97 | 136 | 132 | 147 |
| 165 | 172 | 397 | 15 | 131 | 137 | 132 | 144 |
| 170 | 173 | 398 | 25 | 107 | 138 | 159 | 161 |
| 171 | 173 | 400 | 27 | 122 | 147 | 161 | 161 |
| 189 | 189 | 400 | 91 | 112 | 165 | 168 | 173 |
| 189 | 189 | 400 | 27 | 124 | 144 | 154 | 154 |
| 178 | 184 | 399 | 24 | 105 | 143 | 132 | 159 |
| 188 | 189 | 399 | 8 | 122 | 143 | 122 | 161 |
| 194 | 192 | 400 | 17 | 144 | 163 | 173 | 173 |
| 180 | 183 | 394 | 15 | 132 | 159 | 186 | 166 |
| 183 | 185 | 399 | 233 | 131 | 162 | 167 | 172 |
| 186 | 186 | 398 | 27 | 136 | 155 | 183 | 163 |
| 192 | 195 | 399 | 23 | 137 | 144 | 175 | 152 |
| 182 | 184 | 399 | 29 | 131 | 157 | 177 | 171 |
| 166 | 172 | 396 | 1616 | 100 | 146 | 164 | 159 |
| 175 | 180 | 400 | 806 | 96 | 158 | 169 | 169 |
| 165 | 172 | 399 | 1410 | 102 | 140 | 149 | 154 |
| 170 | 177 | 397 | 49 | 99 | 153 | 143 | 182 |
| 166 | 173 | 398 | 33 | 140 | 155 | 154 | 170 |
| 180 | 178 | 400 | 73 | 95 | 140 | 140 | 155 |
| 172 | 177 | 400 | 38 | 115 | 160 | 164 | 167 |
| 171 | 174 | 386 | 6 | 124 | 137 | 170 | 156 |
| 180 | 183 | 400 | 70 | 124 | 151 | 151 | 164 |
| 194 | 199 | 399 | 6586 | 96 | 162 | 168 | 175 |
| 184 | 188 | 400 | 41 | 112 | 172 | 176 | 177 |
| 194 | 198 | 399 | 35 | 146 | 168 | 175 | 175 |
| 182 | 184 | 399 | 20 | 166 | 180 | 185 | 191 |
| 183 | 186 | 397 | 5338 | 102 | 159 | 175 | 171 |
| 202 | 203 | 393 | 178 | 101 | 150 | 168 | 171 |
| 195 | 195 | 397 | 1350 | 104 | 153 | 163 | 171 |
| 185 | 189 | 400 | 1257 | 100 | 153 | 168 | 170 |
| 185 | 189 | 396 | 30 | 117 | 163 | 164 | 172 |
| 203 | 210 | 391 | 336 | 105 | 153 | 141 | 171 |
| 188 | 194 | 399 | 741 | 101 | 161 | 169 | 176 |
| 193 | 193 | 396 | 89 | 100 | 145 | 171 | 171 |

TABLE 3-continued

APPENDIX C: Targeted cfDNA fragment analyses in cancer patients

| | | | | | | | |
|---|---|---|---|---|---|---|---|
| 172 | 179 | 396 | 12 | 129 | 143 | 143 | 153 |
| 186 | 188 | 387 | 3559 | 91 | 155 | 164 | 173 |
| 177 | 183 | 392 | 873 | 102 | 149 | 163 | 164 |
| 194 | 200 | 377 | 1909 | 100 | 158 | 167 | 176 |
| 202 | 259 | 400 | 27 | 122 | 157 | 164 | 179 |
| 171 | 178 | 395 | 1818 | 103 | 147 | 169 | 162 |
| 178 | 182 | 374 | 546 | 102 | 151 | 166 | 166 |
| 179 | 184 | 397 | 26 | 132 | 142 | 138 | 171 |
| 195 | 194 | 400 | 53 | 117 | 157 | 166 | 169 |
| 176 | 179 | 397 | 40 | 124 | 150 | 169 | 166 |
| 188 | 191 | 390 | 38 | 107 | 153 | 180 | 174 |
| 205 | 207 | 399 | 217 | 102 | 146 | 144 | 163 |
| 196 | 195 | 397 | 266 | 111 | 147 | 150 | 166 |
| 186 | 184 | 400 | 76 | 123 | 157 | 171 | 169 |
| 179 | 186 | 400 | 9832 | 93 | 161 | 166 | 172 |
| 191 | 190 | 400 | 277 | 104 | 162 | 160 | 176 |
| 191 | 189 | 400 | 65 | 123 | 165 | 166 | 172 |
| 187 | 189 | 400 | 31 | 136 | 163 | 171 | 167 |
| 202 | 202 | 400 | 5286 | 102 | 166 | 168 | 181 |
| 196 | 201 | 400 | 102 | 138 | 166 | 161 | 179 |
| 181 | 182 | 397 | 30 | 138 | 158 | 189 | 185 |
| 181 | 181 | 400 | 64 | 113 | 158 | 163 | 167 |
| 176 | 179 | 398 | 27 | 121 | 163 | 200 | 171 |
| 191 | 192 | 398 | 2943 | 100 | 165 | 176 | 176 |
| 179 | 181 | 399 | 25 | 138 | 153 | 138 | 167 |
| 171 | 177 | 399 | 60 | 110 | 136 | 147 | 147 |
| 172 | 179 | 399 | 26 | 139 | 147 | 180 | 176 |
| 186 | 184 | 398 | 35 | 121 | 149 | 360 | 161 |
| 176 | 178 | 397 | 4000 | 103 | 155 | 166 | 167 |
| 176 | 178 | 385 | 2390 | 99 | 157 | 164 | 168 |
| 182 | 184 | 400 | 28 | 131 | 160 | 168 | 167 |
| 194 | 193 | 400 | 3545 | 100 | 161 | 169 | 173 |
| 179 | 180 | 398 | 15 | 121 | 146 | 166 | 166 |
| 188 | 187 | 400 | 2587 | 103 | 158 | 162 | 169 |
| 189 | 192 | 400 | 86 | 121 | 165 | 183 | 177 |
| 178 | 184 | 399 | 3339 | 101 | 157 | 165 | 169 |
| 179 | 187 | 391 | 3193 | 101 | 163 | 178 | 173 |
| 183 | 186 | 398 | 13 | 111 | 153 | 153 | 161 |
| 197 | 201 | 400 | 4140 | 102 | 166 | 169 | 179 |
| 191 | 194 | 400 | 16 | 130 | 143 | 143 | 157 |
| 183 | 183 | 400 | 209 | 125 | 154 | 175 | 170 |
| 211 | 230 | 400 | 41 | 158 | 176 | 197 | 186 |
| 193 | 193 | 400 | 3445 | 94 | 162 | 175 | 174 |
| 197 | 199 | 400 | 23 | 123 | 182 | 248 | 224 |
| 193 | 195 | 399 | 1787 | 100 | 163 | 163 | 176 |
| 204 | 207 | 400 | 4100 | 100 | 159 | 164 | 173 |
| 196 | 195 | 400 | 3096 | 79 | 159 | 161 | 173 |
| 202 | 203 | 400 | 73 | 142 | 178 | 178 | 184 |
| 205 | 203 | 400 | 23 | 161 | 168 | 168 | 171 |
| 195 | 196 | 400 | 170 | 125 | 158 | 173 | 173 |
| 195 | 192 | 400 | 2086 | 101 | 162 | 169 | 176 |
| 238 | 280 | 400 | 125 | 84 | 192 | 194 | 207 |
| 197 | 194 | 400 | 5715 | 108 | 163 | 154 | 174 |
| 172 | 173 | 398 | 109 | 78 | 148 | 149 | 158 |
| 196 | 191 | 399 | 35 | 119 | 161 | 172 | 171 |
| 189 | 190 | 400 | 826 | 102 | 162 | 166 | 171 |
| 194 | 195 | 400 | 95 | 135 | 160 | 161 | 170 |
| 184 | 184 | 400 | 27 | 128 | 150 | 150 | 169 |
| 179 | 184 | 399 | 4771 | 103 | 161 | 168 | 171 |
| 187 | 185 | 399 | 7 | 147 | 154 | 154 | 167 |
| 179 | 179 | 395 | 330 | 106 | 152 | 165 | 166 |
| 172 | 177 | 399 | 536 | 106 | 151 | 167 | 163 |
| 179 | 183 | 400 | 45 | 138 | 163 | 175 | 172 |
| 182 | 182 | 397 | 16 | 138 | 146 | 146 | 155 |
| 172 | 177 | 397 | 293 | 101 | 152 | 169 | 164 |
| 171 | 177 | 399 | 23 | 130 | 152 | 162 | 162 |
| 180 | 183 | 399 | 54 | 104 | 161 | 154 | 176 |
| 184 | 184 | 400 | 154 | 96 | 149 | 157 | 163 |
| 186 | 187 | 399 | 79 | 102 | 163 | 177 | 174 |
| 183 | 185 | 400 | 44 | 118 | 149 | 163 | 163 |
| 182 | 184 | 400 | 35 | 136 | 164 | 204 | 181 |
| 192 | 191 | 400 | 13 | 138 | 164 | 169 | 169 |
| 199 | 205 | 400 | 50 | 128 | 155 | 161 | 171 |
| 191 | 193 | 400 | 81 | 108 | 150 | 108 | 173 |
| 190 | 191 | 389 | 2597 | 101 | 159 | 165 | 172 |
| 192 | 197 | 400 | 58 | 92 | 173 | 192 | 192 |
| 183 | 189 | 400 | 74 | 90 | 147 | 142 | 167 |
| 175 | 178 | 400 | 37 | 144 | 163 | 185 | 172 |

TABLE 3-continued

APPENDIX C: Targeted cfDNA fragment analyses in cancer patients

| | | | | | | | |
|---|---|---|---|---|---|---|---|
| 194 | 202 | 400 | 61 | 93 | 164 | 181 | 181 |
| 184 | 186 | 400 | 66 | 104 | 158 | 194 | 174 |
| 191 | 190 | 396 | 101 | 126 | 155 | 176 | 176 |
| 188 | 185 | 394 | 4718 | 100 | 156 | 164 | 168 |
| 186 | 186 | 399 | 30 | 134 | 161 | 175 | 175 |
| 180 | 180 | 397 | 34 | 139 | 163 | 155 | 170 |
| 182 | 182 | 400 | 262 | 101 | 150 | 152 | 165 |
| 182 | 182 | 400 | 277 | 101 | 150 | 147 | 166 |
| 180 | 182 | 395 | 65 | 121 | 158 | 161 | 167 |
| 177 | 182 | 400 | 16 | 144 | 172 | 179 | 179 |
| 185 | 184 | 399 | 7186 | 100 | 154 | 167 | 166 |
| 181 | 179 | 394 | 21 | 108 | 164 | 164 | 173 |
| 177 | 180 | 400 | 18 | 111 | 127 | 127 | 158 |
| 179 | 181 | 400 | 72 | 121 | 156 | 173 | 166 |
| 177 | 182 | 400 | 30 | 106 | 160 | 174 | 174 |
| 200 | 199 | 399 | 36 | 131 | 147 | 143 | 177 |
| 184 | 185 | 392 | 20 | 144 | 173 | 266 | 178 |
| 182 | 184 | 395 | 16 | 147 | 156 | 156 | 164 |
| 186 | 187 | 399 | 34 | 159 | 168 | 168 | 176 |
| 186 | 186 | 396 | 5 | 116 | 182 | 182 | 185 |
| 185 | 183 | 399 | 1073 | 100 | 142 | 164 | 152 |
| 179 | 180 | 400 | 46 | 109 | 151 | 143 | 175 |
| 181 | 181 | 400 | 30 | 146 | 154 | 146 | 168 |
| 176 | 179 | 392 | 2742 | 102 | 154 | 164 | 166 |
| 174 | 180 | 399 | 298 | 103 | 140 | 148 | 150 |
| 197 | 194 | 399 | 67 | 115 | 164 | 250 | 173 |
| 195 | 194 | 399 | 19 | 156 | 165 | 165 | 185 |
| 178 | 182 | 395 | 189 | 105 | 138 | 141 | 150 |
| 183 | 185 | 398 | 227 | 123 | 160 | 168 | 169 |
| 185 | 184 | 397 | 53 | 78 | 161 | 175 | 175 |
| 190 | 188 | 395 | 50 | 130 | 161 | 168 | 168 |
| 186 | 187 | 396 | 28 | 139 | 150 | 173 | 170 |
| 179 | 184 | 400 | 24 | 130 | 153 | 176 | 170 |
| 185 | 185 | 394 | 48 | 111 | 154 | 170 | 168 |
| 189 | 187 | 398 | 2337 | 100 | 163 | 166 | 172 |
| 198 | 200 | 396 | 172 | 83 | 152 | 160 | 166 |
| 190 | 188 | 400 | 215 | 123 | 151 | 159 | 163 |
| 184 | 184 | 400 | 207 | 121 | 151 | 157 | 161 |
| 191 | 189 | 397 | 17 | 143 | 170 | 217 | 214 |
| 181 | 182 | 398 | 52 | 122 | 152 | 167 | 164 |
| 191 | 189 | 399 | 17 | 109 | 161 | 173 | 171 |
| 191 | 189 | 399 | 40 | 136 | 164 | 166 | 171 |
| 180 | 181 | 399 | 127 | 88 | 149 | 131 | 162 |
| 181 | 186 | 400 | 68 | 141 | 166 | 175 | 176 |
| 169 | 179 | 398 | 10 | 81 | 167 | 167 | 167 |
| 170 | 181 | 398 | 33 | 107 | 162 | 167 | 167 |
| 175 | 181 | 391 | 23 | 112 | 156 | 190 | 164 |
| 175 | 177 | 400 | 109 | 130 | 153 | 169 | 166 |
| 172 | 176 | 400 | 684 | 105 | 153 | 167 | 166 |
| 179 | 178 | 398 | 2946 | 100 | 138 | 157 | 155 |
| 175 | 178 | 399 | 30 | 121 | 165 | 165 | 176 |
| 187 | 186 | 400 | 63 | 140 | 155 | 154 | 167 |
| 181 | 184 | 400 | 4754 | 101 | 160 | 170 | 170 |
| 182 | 187 | 400 | 31 | 131 | 162 | 162 | 174 |
| 181 | 183 | 400 | 150 | 110 | 144 | 166 | 162 |
| 179 | 184 | 400 | 5290 | 95 | 159 | 167 | 169 |
| 181 | 186 | 400 | 140 | 101 | 155 | 175 | 167 |
| 187 | 190 | 397 | 20 | 92 | 141 | 241 | 168 |
| 190 | 192 | 400 | 8065 | 85 | 156 | 164 | 169 |
| 174 | 182 | 400 | 2586 | 101 | 147 | 165 | 165 |
| 185 | 188 | 400 | 2808 | 100 | 150 | 158 | 167 |
| 182 | 187 | 400 | 2227 | 100 | 154 | 162 | 171 |
| 176 | 183 | 396 | 8425 | 100 | 155 | 165 | 169 |
| 186 | 188 | 399 | 142 | 112 | 146 | 140 | 159 |
| 186 | 185 | 399 | 104 | 132 | 158 | 159 | 167 |
| 183 | 185 | 392 | 3462 | 101 | 160 | 173 | 172 |
| 182 | 183 | 399 | 25 | 94 | 140 | 140 | 158 |
| 177 | 181 | 399 | 3789 | 101 | 159 | 168 | 169 |
| 181 | 184 | 400 | 57 | 131 | 152 | 170 | 170 |
| 183 | 191 | 400 | 36 | 118 | 154 | 201 | 182 |
| 187 | 185 | 399 | 362 | 110 | 152 | 143 | 180 |
| 182 | 188 | 400 | 20 | 158 | 153 | 311 | 174 |
| 186 | 187 | 397 | 23 | 126 | 151 | 184 | 168 |
| 188 | 189 | 400 | 2980 | 100 | 158 | 169 | 170 |
| 183 | 183 | 391 | 2793 | 91 | 158 | 167 | 170 |
| 185 | 189 | 395 | 7357 | 100 | 158 | 175 | 171 |
| 184 | 184 | 398 | 5186 | 101 | 157 | 165 | 170 |
| 182 | 187 | 400 | 15595 | 64 | 159 | 167 | 170 |

TABLE 3-continued

APPENDIX C: Targeted cfDNA fragment analyses in cancer patients

| 186 | 185 | 400 | 6749 | 101 | 158 | 167 | 170 |
| 193 | 190 | 400 | 23 | 127 | 148 | 148 | 194 |
| 182 | 185 | 394 | 3901 | 101 | 160 | 167 | 171 |
| 179 | 180 | 400 | 4633 | 100 | 158 | 169 | 170 |
| 175 | 179 | 400 | 734 | 101 | 151 | 155 | 165 |
| 175 | 180 | 394 | 4022 | 101 | 159 | 167 | 168 |
| 184 | 182 | 400 | 117 | 116 | 156 | 156 | 172 |
| 172 | 176 | 395 | 65 | 109 | 145 | 177 | 167 |

| Wild-type Fragments Mean cfDNA Fragment Size (bp) | Mutant Fragments | | | Difference between Median Mutant and Wild-type cfDNA Fragment Sizes (bp) | Difference between Mean Mutant and Wild-Type cfDNA Fragment Sizes (bp) | Adjusted P Value of Difference between Mutant and Wild-type cfDNA Fragment Sizes |
|---|---|---|---|---|---|---|
| | Mean cfDNA Fragment Size (bp) | 75th Percentile cfDNA Fragment Size (bp) | Maximum cfDNA Fragment Size (bp) | | | |
| 179 | 180 | 230 | 305 | −4.0 | 1.54 | 0.475 |
| 182 | 191 | 198 | 309 | 7.0 | 8.33 | 0.250 |
| 180 | 186 | 191 | 399 | 0.0 | 5.89 | 0.000 |
| 177 | 177 | 183 | 383 | −1.0 | −0.25 | 0.874 |
| 184 | 189 | 131 | 398 | 1.0 | 5.37 | 0.009 |
| 181 | 165 | 187 | 386 | 1.0 | 3.30 | 0.025 |
| 176 | 179 | 182 | 397 | 0.0 | 2.65 | 0.148 |
| 176 | 182 | 190 | 370 | 3.0 | 5.31 | 0.368 |
| 177 | 164 | 155 | 345 | −29.5 | −12.73 | 0.000 |
| 183 | 186 | 189 | 400 | 2.0 | 3.13 | 0.002 |
| 188 | 177 | 192 | 335 | −0.5 | −11.46 | 0.571 |
| 175 | 177 | 176 | 290 | 4.0 | 1.22 | 0.475 |
| 184 | 176 | 175 | 368 | −11.0 | −7.99 | 0.052 |
| 179 | 182 | 181 | 369 | −8.0 | 3.49 | 0.061 |
| 179 | 185 | 194 | 338 | 0.0 | 5.78 | 0.023 |
| 185 | 184 | 187 | 400 | −1.0 | −1.27 | 0.212 |
| 187 | 185 | 185 | 399 | 0.0 | −2.62 | 0.114 |
| 184 | 173 | 193 | 261 | 3.0 | −11.00 | 0.507 |
| 183 | 179 | 180 | 364 | −3.0 | −4.34 | 0.430 |
| 181 | 172 | 176 | 336 | −6.0 | −9.35 | 0.166 |
| 172 | 169 | 173 | 301 | 0.0 | 3.57 | 0.668 |
| 169 | 166 | 168 | 325 | 0.0 | −2.15 | 0.630 |
| 189 | 221 | 301 | 387 | −3.0 | 32.43 | 0.453 |
| 176 | 210 | 219 | 372 | 5.0 | 33.84 | 0.368 |
| 169 | 164 | 178 | 268 | −12.0 | −5.12 | 0.000 |
| 166 | 174 | 158 | 327 | −9.5 | 8.37 | 0.036 |
| 184 | 175 | 177 | 346 | −8.0 | −8.84 | 0.057 |
| 185 | 207 | 199 | 350 | 3.0 | 22.93 | 0.465 |
| 185 | 189 | 191 | 338 | 8.0 | 4.06 | 0.154 |
| 167 | 168 | 175 | 309 | 2.0 | 0.46 | 0.445 |
| 167 | 166 | 168 | 377 | −1.0 | −0.91 | 0.482 |
| 170 | 164 | 174 | 302 | −3.0 | 6.74 | 0.064 |
| 190 | 189 | 205 | 333 | −5.0 | −0.80 | 0.297 |
| 182 | 177 | 187 | 343 | 5.5 | −4.51 | 0.171 |
| 189 | 188 | 229 | 305 | 7.0 | −0.19 | 0.234 |
| 192 | 182 | 192 | 380 | −1.0 | −9.76 | 0.000 |
| 173 | 168 | 176 | 382 | −7.0 | −5.57 | 0.052 |
| 181 | 181 | 185 | 398 | 0.0 | 0.37 | 0.773 |
| 178 | 172 | 181 | 380 | −9.0 | −6.68 | 0.009 |
| 175 | 172 | 186 | 321 | −1.0 | 2.38 | 0.572 |
| 181 | 182 | 187 | 400 | 0.5 | 0.95 | 0.564 |
| 180 | 176 | 183 | 353 | −1.0 | −4.83 | 0.598 |
| 133 | 182 | 185 | 337 | −7.0 | −0.44 | 0.064 |
| 185 | 208 | 284 | 355 | 14.0 | 22.31 | 0.031 |
| 176 | 167 | 166 | 298 | −11.0 | −8.94 | 0.013 |
| 180 | 187 | 212 | 319 | 9.0 | 7.22 | 0.062 |
| 185 | 188 | 204 | 387 | −12.0 | 3.32 | 0.031 |
| 179 | 166 | 180 | 219 | −6.5 | −13.04 | 0.155 |
| 176 | 177 | 185 | 400 | 1.0 | 1.08 | 0.166 |
| 182 | 167 | 176 | 316 | −3.0 | −14.62 | 0.469 |
| 181 | 158 | 166 | 340 | −20.0 | −23.47 | 0.000 |
| 175 | 149 | 159 | 326 | 21.0 | 26.04 | 0.000 |
| 165 | 163 | 171 | 323 | −20.0 | −1.73 | 0.000 |
| 170 | 175 | 190 | 299 | −3.0 | 4.33 | 0.384 |
| 171 | 173 | 171 | 342 | −3.0 | 2.54 | 0.354 |
| 189 | 196 | 192 | 379 | 1.0 | 6.83 | 0.571 |
| 189 | 167 | 172 | 320 | −19.0 | 22.39 | 0.000 |
| 178 | 183 | 190 | 367 | −11.0 | 4.97 | 0.054 |

TABLE 3-continued

APPENDIX C: Targeted cfDNA fragment analyses in cancer patients

| | | | | | | |
|---|---|---|---|---|---|---|
| 188 | 168 | 195 | 241 | −13.0 | −19.21 | 0.100 |
| 194 | 213 | 261 | 372 | 1.0 | 19.22 | 0.587 |
| 180 | 174 | 185 | 265 | −3.0 | −5.62 | 0.461 |
| 183 | 190 | 187 | 394 | 2.0 | 7.27 | 0.137 |
| 186 | 170 | 178 | 262 | −7.0 | −16.03 | 0.131 |
| 192 | 190 | 212 | 327 | −17.0 | −1.76 | 0.018 |
| 182 | 183 | 179 | 319 | 1.0 | 0.74 | 0.564 |
| 166 | 163 | 170 | 354 | −3.5 | −3.57 | 0.000 |
| 175 | 179 | 184 | 366 | 1.0 | 3.80 | 0.054 |
| 165 | 164 | 170 | 398 | −8.0 | −0.35 | 0.816 |
| 170 | 206 | 284 | 333 | 16.0 | 36.25 | 0.000 |
| 166 | 180 | 180 | 296 | 7.0 | 14.38 | 0.104 |
| 180 | 173 | 178 | 324 | −9.0 | −6.66 | 0.000 |
| 172 | 182 | 179 | 329 | 1.5 | 10.09 | 0.479 |
| 171 | 153 | 168 | 178 | −7.5 | 18.98 | 0.411 |
| 180 | 182 | 183 | 385 | −6.0 | 1.71 | 0.064 |
| 194 | 193 | 196 | 399 | 0.0 | −1.79 | 0.166 |
| 184 | 195 | 195 | 373 | 3.0 | 11.02 | 0.397 |
| 194 | 181 | 186 | 312 | 1.0 | −13.40 | 0.587 |
| 182 | 205 | 219 | 357 | 21.0 | 23.48 | 0.013 |
| 183 | 183 | 185 | 394 | −1.0 | 0.03 | 0.984 |
| 202 | 198 | 240 | 357 | −5.0 | −4.34 | 0.571 |
| 195 | 201 | 258 | 400 | 0.0 | 5.94 | 0.066 |
| 185 | 189 | 202 | 392 | 1.0 | 4.37 | 0.064 |
| 185 | 175 | 179 | 372 | 3.0 | −10.29 | 0.463 |
| 203 | 200 | 240 | 399 | 4.0 | 3.10 | 0.571 |
| 188 | 190 | 194 | 400 | 2.0 | 1.96 | 0.571 |
| 193 | 197 | 229 | 393 | −2.0 | 3.42 | 0.479 |
| 172 | 163 | 166 | 275 | −14.0 | −8.99 | 0.084 |
| 186 | 195 | 211 | 398 | 3.0 | 8.92 | 0.001 |
| 177 | 177 | 181 | 400 | −3.0 | −0.39 | 0.880 |
| 194 | 202 | 242 | 398 | 5.0 | 7.98 | 0.061 |
| 202 | 199 | 231 | 350 | 2.0 | −3.82 | 0.685 |
| 171 | 173 | 180 | 396 | 1.0 | 1.92 | 0.372 |
| 178 | 180 | 182 | 381 | 0.0 | 2.87 | 0.416 |
| 179 | 183 | 188 | 351 | 1.5 | 3.29 | 0.572 |
| 195 | 192 | 198 | 336 | −3.0 | −2.86 | 0.451 |
| 176 | 181 | 176 | 309 | −1.0 | 4.53 | 0.539 |
| 188 | 185 | 210 | 326 | 0.5 | −2.59 | 0.576 |
| 205 | 188 | 212 | 360 | −12.0 | −17.11 | 0.004 |
| 196 | 188 | 204 | 379 | −8.0 | −7.53 | 0.208 |
| 186 | 182 | 182 | 346 | 1.0 | −3.64 | 0.479 |
| 179 | 180 | 186 | 399 | −1.0 | 1.04 | 0.155 |
| 191 | 201 | 200 | 384 | 3.0 | 9.95 | 0.061 |
| 191 | 198 | 192 | 371 | 1.0 | 7.08 | 0.560 |
| 187 | 201 | 199 | 387 | −4.0 | 14.14 | 0.341 |
| 202 | 201 | 203 | 400 | 2.0 | −0.88 | 0.587 |
| 196 | 199 | 209 | 372 | −1.5 | 2.90 | 0.679 |
| 181 | 191 | 191 | 311 | 16.0 | 9.25 | 0.000 |
| 181 | 179 | 176 | 318 | 0.0 | −2.85 | 0.679 |
| 176 | 187 | 190 | 392 | 5.0 | 10.89 | 0.314 |
| 191 | 187 | 192 | 398 | 0.0 | −3.83 | 0.015 |
| 179 | 181 | 184 | 340 | −1.0 | 2.00 | 0.571 |
| 171 | 161 | 159 | 327 | −19.0 | −9.77 | 0.000 |
| 172 | 176 | 184 | 344 | 9.0 | 3.52 | 0.015 |
| 186 | 197 | 195 | 360 | −9.0 | 10.77 | 0.314 |
| 176 | 176 | 178 | 397 | 0.5 | 0.65 | 0.610 |
| 176 | 178 | 180 | 400 | 0.0 | 1.78 | 0.314 |
| 182 | 177 | 179 | 338 | −2.0 | −5.83 | 0.463 |
| 194 | 194 | 192 | 399 | 0.0 | 0.40 | 0.825 |
| 179 | 172 | 204 | 221 | −2.0 | −7.32 | 0.564 |
| 188 | 189 | 186 | 399 | −1.0 | 1.12 | 0.598 |
| 189 | 189 | 193 | 373 | 3.0 | −0.01 | 0.293 |
| 178 | 177 | 184 | 400 | 0.0 | −1.73 | 0.598 |
| 179 | 180 | 186 | 389 | 1.0 | 0.22 | 0.839 |
| 183 | 171 | 179 | 323 | −11.0 | −12.36 | 0.061 |
| 197 | 197 | 200 | 400 | 0.0 | −0.32 | 0.839 |
| 191 | 173 | 173 | 325 | −20.0 | −18.40 | 0.000 |
| 183 | 196 | 233 | 357 | 1.0 | 12.55 | 0.025 |
| 211 | 215 | 220 | 374 | 1.0 | 3.72 | 0.603 |
| 193 | 194 | 194 | 399 | 0.0 | 0.65 | 0.714 |
| 197 | 232 | 260 | 359 | 47.0 | 34.97 | 0.000 |
| 193 | 192 | 194 | 400 | 1.0 | −0.85 | 0.718 |
| 204 | 200 | 202 | 400 | −2.0 | −3.65 | 0.062 |
| 196 | 194 | 191 | 397 | −1.0 | −2.45 | 0.251 |
| 202 | 237 | 338 | 377 | 9.0 | 35.30 | 0.114 |
| 205 | 189 | 186 | 380 | −4.0 | −16.38 | 0.435 |
| 195 | 188 | 190 | 400 | −2.0 | −6.17 | 0.293 |

TABLE 3-continued

APPENDIX C: Targeted cfDNA fragment analyses in cancer patients

| | | | | | | |
|---|---|---|---|---|---|---|
| 195 | 203 | 203 | 400 | 4.5 | 8.80 | 0.000 |
| 238 | 243 | 324 | 400 | −16.0 | 5.51 | 0.574 |
| 197 | 200 | 196 | 400 | 1.0 | 2.87 | 0.065 |
| 172 | 166 | 173 | 302 | −4.0 | −5.94 | 0.190 |
| 196 | 191 | 180 | 390 | 0.0 | −4.34 | 0.627 |
| 189 | 187 | 187 | 395 | −2.0 | −1.94 | 0.475 |
| 194 | 182 | 184 | 400 | −5.0 | −11.54 | 0.155 |
| 184 | 174 | 185 | 319 | −1.0 | −9.68 | 0.571 |
| 179 | 179 | 183 | 400 | 0.0 | 0.15 | 0.880 |
| 187 | 164 | 174 | 177 | −3.0 | −22.90 | 0.155 |
| 179 | 178 | 178 | 361 | −1.0 | −1.35 | 0.685 |
| 172 | 172 | 175 | 363 | −3.0 | −0.34 | 0.880 |
| 179 | 185 | 191 | 380 | 3.0 | 6.52 | 0.368 |
| 182 | 162 | 170 | 224 | −14.0 | −19.82 | 0.007 |
| 172 | 170 | 174 | 392 | 2.0 | 1.37 | 0.646 |
| 171 | 163 | 177 | 232 | −4.0 | −7.62 | 0.252 |
| 180 | 195 | 206 | 383 | 7.5 | 14.58 | 0.064 |
| 184 | 176 | 185 | 347 | −5.5 | −7.87 | 0.154 |
| 186 | 200 | 203 | 372 | 4.0 | 14.61 | 0.270 |
| 183 | 185 | 188 | 338 | −7.0 | 1.98 | 0.039 |
| 182 | 194 | 203 | 369 | 13.0 | 11.80 | 0.039 |
| 192 | 198 | 173 | 333 | −1.0 | 6.05 | 0.610 |
| 199 | 216 | 301 | 360 | 0.0 | 17.02 | 0.623 |
| 191 | 198 | 224 | 385 | 0.0 | 6.48 | 0.624 |
| 190 | 185 | 187 | 397 | −1.0 | −5.17 | 0.005 |
| 192 | 202 | 200 | 397 | 18.0 | 9.79 | 0.007 |
| 183 | 176 | 182 | 391 | −6.5 | −6.78 | 0.061 |
| 175 | 192 | 186 | 375 | 6.0 | 17.15 | 0.005 |
| 194 | 197 | 211 | 370 | 8.0 | 3.34 | 0.169 |
| 184 | 189 | 194 | 379 | 3.5 | 4.60 | 0.270 |
| 191 | 194 | 213 | 331 | 7.0 | 2.50 | 0.718 |
| 188 | 190 | 187 | 393 | −1.0 | 2.54 | 0.113 |
| 186 | 190 | 208 | 339 | 5.0 | 4.07 | 0.302 |
| 180 | 178 | 175 | 349 | 3.0 | −1.65 | 0.407 |
| 182 | 181 | 186 | 393 | −4.0 | −0.65 | 0.876 |
| 182 | 182 | 185 | 393 | −3.0 | 0.36 | 0.926 |
| 180 | 186 | 188 | 338 | −4.0 | 6.15 | 0.234 |
| 177 | 187 | 180 | 376 | 10.0 | 9.98 | 0.130 |
| 185 | 183 | 181 | 396 | −1.0 | −1.73 | 0.154 |
| 181 | 196 | 200 | 357 | 7.0 | 14.95 | 0.213 |
| 177 | 189 | 186 | 352 | −8.0 | 12.47 | 0.179 |
| 179 | 183 | 179 | 396 | −2.0 | 4.31 | 0.427 |
| 177 | 180 | 186 | 282 | 5.0 | 3.09 | 0.252 |
| 200 | 196 | 227 | 298 | 2.5 | −4.24 | 0.479 |
| 184 | 199 | 215 | 269 | 6.0 | 15.13 | 0.252 |
| 182 | 177 | 169 | 302 | 8.0 | 4.82 | 0.119 |
| 186 | 206 | 196 | 365 | 3.0 | 20.55 | 0.415 |
| 186 | 201 | 192 | 329 | 12.0 | 14.52 | 0.263 |
| 185 | 157 | 164 | 346 | −18.0 | −27.67 | 0.000 |
| 179 | 174 | 183 | 325 | 7.0 | −5.22 | 0.054 |
| 181 | 186 | 181 | 367 | −0.5 | 5.19 | 0.568 |
| 176 | 176 | 178 | 387 | −1.0 | −0.24 | 0.874 |
| 174 | 152 | 162 | 288 | −18.0 | −22.25 | 0.000 |
| 197 | 187 | 201 | 366 | 2.0 | 9.89 | 0.425 |
| 195 | 197 | 199 | 361 | 10.0 | 2.20 | 0.154 |
| 178 | 164 | 175 | 348 | −20.0 | −14.58 | 0.000 |
| 183 | 185 | 184 | 396 | −2.0 | 1.68 | 0.706 |
| 185 | 189 | 188 | 392 | 4.0 | 3.80 | 0.241 |
| 190 | 184 | 175 | 377 | −4.5 | −5.86 | 0.234 |
| 186 | 170 | 173 | 354 | 2.5 | −15.88 | 0.416 |
| 179 | 193 | 199 | 359 | 0.0 | 13.13 | 0.598 |
| 185 | 173 | 183 | 295 | −3.0 | −11.80 | 0.270 |
| 189 | 187 | 185 | 394 | −1.0 | −1.27 | 0.564 |
| 198 | 193 | 226 | 396 | −4.0 | −4.93 | 0.490 |
| 190 | 188 | 196 | 365 | −6.0 | −1.72 | 0.735 |
| 184 | 181 | 179 | 365 | −7.0 | −3.01 | 0.571 |
| 191 | 198 | 217 | 294 | 43.0 | 7.08 | 0.000 |
| 181 | 179 | 173 | 372 | −4.5 | −2.07 | 0.137 |
| 191 | 181 | 174 | 293 | −1.0 | −9.24 | 0.576 |
| 191 | 185 | 185 | 335 | −1.0 | −5.86 | 0.571 |
| 180 | 168 | 178 | 311 | −6.0 | −11.80 | 0.005 |
| 181 | 198 | 207 | 387 | 4.0 | 17.11 | 0.184 |
| 169 | 159 | 176 | 182 | 1.0 | −10.20 | 0.589 |
| 170 | 174 | 185 | 322 | 0.0 | 4.57 | 0.636 |
| 175 | 175 | 190 | 349 | −4.0 | −0.92 | 0.308 |
| 175 | 175 | 178 | 382 | 0.0 | −0.09 | 0.987 |
| 172 | 172 | 175 | 385 | 1.0 | 0.00 | 0.999 |
| 179 | 172 | 174 | 398 | −9.0 | −7.28 | 0.000 |

TABLE 3-continued

APPENDIX C: Targeted cfDNA fragment analyses in cancer patients

| | | | | | | |
|---|---|---|---|---|---|---|
| 175 | 198 | 219 | 325 | 12.0 | 22.37 | 0.007 |
| 187 | 201 | 215 | 372 | −3.0 | 13.70 | 0.286 |
| 181 | 179 | 181 | 393 | 0.0 | −1.72 | 0.154 |
| 182 | 180 | 185 | 352 | 2.0 | 2.26 | 0.494 |
| 181 | 176 | 173 | 385 | −6.0 | −5.86 | 0.314 |
| 179 | 179 | 184 | 400 | −1.0 | 0.11 | 0.909 |
| 181 | 179 | 180 | 352 | −4.5 | −2.77 | 0.589 |
| 187 | 178 | 209 | 283 | −3.0 | −9.82 | 0.479 |
| 190 | 190 | 190 | 399 | 0.0 | −0.08 | 0.942 |
| 174 | 169 | 179 | 386 | −3.5 | −4.59 | 0.000 |
| 185 | 189 | 200 | 399 | −3.0 | 4.17 | 0.007 |
| 182 | 183 | 190 | 398 | 0.0 | 1.00 | 0.564 |
| 176 | 176 | 184 | 400 | 0.0 | 0.54 | 0.568 |
| 186 | 180 | 193 | 352 | −13.0 | −5.41 | 0.463 |
| 186 | 189 | 180 | 331 | −2.0 | 3.05 | 0.657 |
| 183 | 184 | 187 | 396 | 1.0 | 0.82 | 0.576 |
| 182 | 159 | 163 | 341 | −11.0 | −23.47 | 0.027 |
| 177 | 176 | 181 | 395 | 0.0 | −0.66 | 0.576 |
| 181 | 179 | 184 | 327 | −1.0 | −2.41 | 0.568 |
| 183 | 187 | 201 | 328 | 11.0 | 3.60 | 0.114 |
| 187 | 207 | 268 | 389 | 11.0 | 20.70 | 0.000 |
| 182 | 198 | 209 | 311 | 3.0 | 15.25 | 0.475 |
| 185 | 185 | 185 | 328 | −1.0 | −1.49 | 0.571 |
| 188 | 187 | 189 | 398 | 0.0 | −0.84 | 0.637 |
| 183 | 181 | 182 | 389 | 1.0 | −2.30 | 0.171 |
| 185 | 182 | 187 | 399 | −1.0 | −2.37 | 0.008 |
| 184 | 185 | 186 | 400 | 1.0 | 1.72 | 0.240 |
| 182 | 181 | 185 | 397 | −1.0 | −1.39 | 0.245 |
| 186 | 185 | 187 | 400 | 0.0 | −0.52 | 0.702 |
| 193 | 222 | 292 | 378 | 24.0 | 29.58 | 0.027 |
| 182 | 182 | 185 | 398 | 2.0 | 0.32 | 0.821 |
| 179 | 185 | 187 | 400 | 1.0 | 6.16 | 0.000 |
| 175 | 176 | 178 | 366 | −4.0 | 0.48 | 0.823 |
| 175 | 172 | 178 | 399 | −1.0 | 2.84 | 0.000 |
| 184 | 199 | 184 | 399 | 5.0 | 15.08 | 0.084 |
| 172 | 181 | 181 | 306 | 3.0 | 9.11 | 0.293 |

TABLE 4

APPENDIX - D: Summary of whole genome cfDNA analyses

| Patient | Timepoint | Analysis type | Patient Type | Read Length | Total Bases Sequenced | High Quality Bases Analyzed | Coverage |
|---|---|---|---|---|---|---|---|
| CGCRC291 | Preoperative treatment naïve | WGS | Colorectal Cancer | 100 | 7232125000 | 4695396600 | 1.86 |
| CGCRC292 | Preoperative treatment naïve | WGS | Colorectal Cancer | 100 | 6794092800 | 4471065400 | 1.77 |
| CGCRC293 | Preoperative treatment naïve | WGS | Colorectal Cancer | 100 | 8373899600 | 5686176000 | 2.26 |
| CGCRC294 | Preoperative treatment naïve | WGS | Colorectal Cancer | 100 | 8081312000 | 5347045800 | 2.12 |
| CGCRC296 | Preoperative treatment naïve | WGS | Colorectal Cancer | 100 | 10072029200 | 6770998200 | 2.69 |
| CGCRC299 | Preoperative treatment naïve | WGS | Colorectal Cancer | 100 | 10971591600 | 7632723200 | 3.03 |
| CGCRC300 | Preoperative treatment naïve | WGS | Colorectal Cancer | 100 | 9894332600 | 6699951000 | 2.66 |
| CGCRC301 | Preoperative treatment naïve | WGS | Colorectal Cancer | 100 | 7857346200 | 5021002000 | 1.99 |
| CGCRC302 | Preoperative treatment naïve | WGS | Colorectal Cancer | 100 | 11671913000 | 8335275800 | 3.31 |
| CGCRC304 | Preoperative treatment naïve | WGS | Colorectal Cancer | 100 | 19011739200 | 12957614200 | 5.14 |
| CGCRC305 | Preoperative treatment naïve | WGS | Colorectal Cancer | 100 | 7177341400 | 4809957200 | 1.91 |
| CGCRC306 | Preoperative treatment naïve | WGS | Colorectal Cancer | 100 | 8302233200 | 5608043600 | 2.23 |
| CGCRC307 | Preoperative treatment naïve | WGS | Colorectal Cancer | 100 | 8034729400 | 5342620000 | 2.12 |
| CGCRC308 | Preoperative treatment naïve | WGS | Colorectal Cancer | 100 | 8670084800 | 5934037200 | 2.35 |
| CGCRC311 | Preoperative treatment naïve | WGS | Colorectal Cancer | 100 | 6947634400 | 4704601800 | 1.87 |

TABLE 4-continued

APPENDIX - D: Summary of whole genome cfDNA analyses

| Patient | Timepoint | Analysis type | Patient Type | Read Length | Total Bases Sequenced | High Quality Bases Analyzed | Coverage |
|---|---|---|---|---|---|---|---|
| CGCRC315 | Preoperative treatment naïve | WGS | Colorectal Cancer | 100 | 5205544000 | 3419565400 | 1.36 |
| CGCRC316 | Preoperative treatment naïve | WGS | Colorectal Cancer | 100 | 6405388600 | 4447534800 | 1.76 |
| CGCRC317 | Preoperative treatment naïve | WGS | Colorectal Cancer | 100 | 6060390400 | 4104616600 | 1.63 |
| CGCRC318 | Preoperative treatment naïve | WGS | Colorectal Cancer | 100 | 6848768600 | 4439404800 | 1.76 |
| CGCRC319 | Preoperative treatment naïve | WGS | Colorectal Cancer | 100 | 10545294400 | 7355181600 | 2.92 |
| CGCRC320 | Preoperative treatment naïve | WGS | Colorectal Cancer | 100 | 5961999200 | 3945054000 | 1.57 |
| CGCRC321 | Preoperative treatment naïve | WGS | Colorectal Cancer | 100 | 8248095400 | 5614355000 | 2.23 |
| CGCRC333 | Preoperative treatment naïve | WGS | Colorectal Cancer | 100 | 10540267600 | 6915490600 | 2.74 |
| CGCRC336 | Preoperative treatment naïve | WGS | Colorectal Cancer | 100 | 10675581800 | 7087691800 | 2.81 |
| CGCRC338 | Preoperative treatment naïve | WGS | Colorectal Cancer | 100 | 13788172600 | 3970308600 | 3.56 |
| CGCRC341 | Preoperative treatment naïve | WGS | Colorectal Cancer | 100 | 10753467600 | 7311539200 | 2.90 |
| CGCRC342 | Preoperative treatment naïve | WGS | Colorectal Cancer | 100 | 11836966000 | 7552793200 | 3.00 |
| CGH14 | Human adult elutriated lymphocytes | WGS | Healthy | 100 | 36525427600 | 24950300200 | 9.90 |
| CGH15 | Human adult elutriated lymphocytes | WGS | Healthy | 100 | 29930855000 | 23754049400 | 9.43 |
| CGLU316 | Pre-treatment, Day −53 | WGS | Lung Cancer | 100 | 10354123200 | 6896471400 | 2.74 |
| CGLU316 | Pre-treatment, Day −4 | WGS | Lung Cancer | 100 | 7870039200 | 5254938800 | 2.09 |
| CGLU316 | Post-treatment, Day 18 | WGS | Lung Cancer | 100 | 8155322000 | 5416262400 | 2.15 |
| CGLU316 | Post-treatment, Day 87 | WGS | Lung Cancer | 100 | 9442310400 | 6087893400 | 2.42 |
| CGLU344 | Pre-treatment, Day −21 | WGS | Lung Cancer | 100 | 8728318600 | 5769097200 | 2.29 |
| CGLU344 | Pre-treatment, Day 0 | WGS | Lung Cancer | 100 | 11710249400 | 7826902600 | 3.11 |
| CGLU344 | Post-treatment, Day 0.1875 | WGS | Lung Cancer | 100 | 11569683000 | 7654701600 | 3.04 |
| CGLU344 | Post-treatment, Day 59 | WGS | Lung Cancer | 100 | 11042459200 | 6320138800 | 2.51 |
| CGLU369 | Pre-treatment, Day −2 | WGS | Lung Cancer | 100 | 8630932800 | 5779595800 | 2.29 |
| CGLU369 | Post-treatment, Day 12 | WGS | Lung Cancer | 100 | 9227709600 | 6136755200 | 2.44 |
| CGLU369 | Post-treatment, Day 68 | WGS | Lung Cancer | 100 | 7995282600 | 5239077200 | 2.08 |
| CGLU369 | Post-treatment, Day 110 | WGS | Lung Cancer | 100 | 8750541000 | 5626139000 | 2.23 |
| CGLU373 | Pre-treatment, Day −2 | WGS | Lung Cancer | 100 | 11746059600 | 7547485800 | 3.00 |
| CGLU373 | Post-treatment, Day 0.125 | WGS | Lung Cancer | 100 | 13801136800 | 9255579400 | 3.67 |
| CGLU373 | Post-treatment, Day 7 | WGS | Lung Cancer | 100 | 11537896800 | 7654111200 | 3.04 |
| CGLU373 | Post-treatment, Day 47 | WGS | Lung Cancer | 100 | 8046326400 | 5397702400 | 2.14 |
| CGPLBR100 | Preoperative treatment naïve | WGS | Breast Cancer | 100 | 8440532400 | 5729474800 | 2.27 |
| CGPLBR101 | Preoperative treatment naïve | WGS | Breast Cancer | 100 | 9786253600 | 6673495200 | 2.65 |
| CGPLBR102 | Preoperative treatment naïve | WGS | Breast Cancer | 100 | 8664980400 | 5669781600 | 2.25 |
| CGPLBR103 | Preoperative treatment naïve | WGS | Breast Cancer | 100 | 9846936200 | 6662883400 | 2.64 |
| CGPLBR104 | Preoperative treatment naïve | WGS | Breast Cancer | 100 | 9443375400 | 6497061000 | 2.58 |
| CGPLBR12 | Preoperative treatment naïve | WGS | Breast Cancer | 100 | 7017577800 | 4823327400 | 1.91 |
| CGPLBR18 | Preoperative treatment naïve | WGS | Breast Cancer | 100 | 10309652800 | 7130386000 | 2.83 |

TABLE 4-continued

APPENDIX - D: Summary of whole genome cfDNA analyses

| Patient | Timepoint | Analysis type | Patient Type | Read Length | Total Bases Sequenced | High Quality Bases Analyzed | Coverage |
|---|---|---|---|---|---|---|---|
| CGPLBR23 | Preoperative treatment naïve | WGS | Breast Cancer | 100 | 9034484800 | 6219625800 | 2.47 |
| CGPLBR24 | Preoperative treatment naïve | WGS | Breast Cancer | 100 | 9891454200 | 6601857400 | 2.62 |
| CGPLBR28 | Preoperative treatment naïve | WGS | Breast Cancer | 100 | 7997607200 | 5400803200 | 2.14 |
| CGPLBR30 | Preoperative treatment naïve | WGS | Breast Cancer | 100 | 8502597200 | 5885822400 | 2.34 |
| CGPLBR31 | Preoperative treatment naïve | WGS | Breast Cancer | 100 | 12660085600 | 8551995600 | 3.39 |
| CGPLBR32 | Preoperative treatment naïve | WGS | Breast Cancer | 100 | 8773498600 | 5839034600 | 2.32 |
| CGPLBR33 | Preoperative treatment naïve | WGS | Breast Cancer | 100 | 10931742800 | 6967030600 | 2.76 |
| CGPLBR34 | Preoperative treatment naïve | WGS | Breast Cancer | 100 | 10861398600 | 7453225800 | 2.96 |
| CGPLBR35 | Preoperative treatment naïve | WGS | Breast Cancer | 100 | 9180193600 | 6158440200 | 2.44 |
| CGPLBR36 | Preoperative treatment naïve | WGS | Breast Cancer | 100 | 9159948400 | 6091817800 | 2.42 |
| CGPLBR37 | Preoperative treatment naïve | WGS | Breast Cancer | 100 | 10307505800 | 6929530600 | 2.75 |
| CGPLBR38 | Preoperative treatment naïve | WGS | Breast Cancer | 100 | 9983824000 | 6841725400 | 2.71 |
| CGPLBR40 | Preoperative treatment naïve | WGS | Breast Cancer | 100 | 10148823800 | 7024345400 | 2.79 |
| CGPLBR41 | Preoperative treatment naïve | WGS | Breast Cancer | 100 | 11168192000 | 7562945800 | 3.00 |
| CGPLBR45 | Preoperative treatment naïve | WGS | Breast Cancer | 100 | 8793780600 | 6011109400 | 2.39 |
| CGPLBR46 | Preoperative treatment naïve | WGS | Breast Cancer | 100 | 7228607600 | 4706130000 | 1.87 |
| CGPLBR47 | Preoperative treatment naïve | WGS | Breast Cancer | 100 | 7906911400 | 5341655000 | 2.12 |
| CGPLBR48 | Preoperative treatment naïve | WGS | Breast Cancer | 100 | 6992032000 | 4428636200 | 1.76 |
| CGPLBR49 | Preoperative treatment naïve | WGS | Breast Cancer | 100 | 7311195000 | 4559460200 | 1.81 |
| CGPLBR50 | Preoperative treatment naïve | WGS | Breast Cancer | 100 | 11107960600 | 7582776600 | 3.01 |
| CGPLBR51 | Preoperative treatment naïve | WGS | Breast Cancer | 100 | 8393547400 | 5102069000 | 2.02 |
| CGPLBR52 | Preoperative treatment naïve | WGS | Breast Cancer | 100 | 9491894800 | 6141729000 | 2.44 |
| CGPLBR55 | Preoperative treatment naïve | WGS | Breast Cancer | 100 | 9380109800 | 6518855200 | 2.59 |
| CGPLBR56 | Preoperative treatment naïve | WGS | Breast Cancer | 100 | 12191816800 | 8293011200 | 3.29 |
| CGPLBR57 | Preoperative treatment naïve | WGS | Breast Cancer | 100 | 9847584400 | 6713638000 | 2.66 |
| CGPLBR59 | Preoperative treatment naïve | WGS | Breast Cancer | 100 | 7476477000 | 5059878200 | 2.01 |
| CGPLBR60 | Preoperative treatment naïve | WGS | Breast Cancer | 100 | 6531354600 | 4331253800 | 1.72 |
| CGPLBR61 | Preoperative treatment naïve | WGS | Breast Cancer | 100 | 9311029200 | 6430920800 | 2.55 |
| CGPLBR63 | Preoperative treatment naïve | WGS | Breast Cancer | 100 | 8971949000 | 6044009600 | 2.40 |
| CGPLBR65 | Preoperative treatment naïve | WGS | Breast Cancer | 100 | 7197301400 | 4835015200 | 1.92 |
| CGPLBR68 | Preoperative treatment naïve | WGS | Breast Cancer | 100 | 10003774000 | 6974918800 | 2.77 |
| CGPLBR69 | Preoperative treatment naïve | WGS | Breast Cancer | 100 | 10080881800 | 6903459200 | 2.74 |
| CGPLBR70 | Preoperative treatment naïve | WGS | Breast Cancer | 100 | 8824002800 | 6002533800 | 2.38 |
| CGPLBR71 | Preoperative treatment naïve | WGS | Breast Cancer | 100 | 10164136800 | 6994668600 | 2.78 |
| CGPLBR72 | Preoperative treatment naïve | WGS | Breast Cancer | 100 | 18416841400 | 12328783000 | 4.89 |
| CGPLBR73 | Preoperative treatment naïve | WGS | Breast Cancer | 100 | 10281460200 | 7078613200 | 2.81 |
| CGPLBR76 | Preoperative treatment naïve | WGS | Breast Cancer | 100 | 10105270400 | 6800705000 | 2.70 |

TABLE 4-continued

APPENDIX - D: Summary of whole genome cfDNA analyses

| Patient | Timepoint | Analysis type | Patient Type | Read Length | Total Bases Sequenced | High Quality Bases Analyzed | Coverage |
|---|---|---|---|---|---|---|---|
| CGPLBR81 | Preoperative treatment naïve | WGS | Breast Cancer | 100 | 5087126000 | 3273367200 | 1.30 |
| CGPLBR82 | Preoperative treatment naïve | WGS | Breast Cancer | 100 | 10576496600 | 7186662600 | 2.85 |
| CGPLBR83 | Preoperative treatment naïve | WGS | Breast Cancer | 100 | 8977124400 | 5947525000 | 2.36 |
| CGPLBR84 | Preoperative treatment naïve | WGS | Breast Cancer | 100 | 6272538600 | 4066870600 | 1.61 |
| CGPLBR87 | Preoperative treatment naïve | WGS | Breast Cancer | 100 | 8460954800 | 5375710200 | 2.13 |
| CGPLBR88 | Preoperative treatment naïve | WGS | Breast Cancer | 100 | 8665810400 | 5499898200 | 2.18 |
| CGPLBR90 | Preoperative treatment naïve | WGS | Breast Cancer | 100 | 6663469200 | 4392442400 | 1.74 |
| CGPLBR91 | Preoperative treatment naïve | WGS | Breast Cancer | 100 | 10933002400 | 7647842000 | 3.03 |
| CGPLBR92 | Preoperative treatment naïve | WGS | Breast Cancer | 100 | 10392674000 | 6493598000 | 2.58 |
| CGPLBR93 | Preoperative treatment naïve | WGS | Breast Cancer | 100 | 5659836000 | 3931106800 | 1.56 |
| CGPLH189 | Preoperative treatment naïve | WGS | Healthy | 100 | 11400610400 | 7655568800 | 3.04 |
| CGPLH190 | Preoperative treatment naïve | WGS | Healthy | 100 | 11444671600 | 7581175200 | 3.01 |
| CGPLH192 | Preoperative treatment naïve | WGS | Healthy | 100 | 12199010800 | 8126804800 | 3.22 |
| CGPLH193 | Preoperative treatment naïve | WGS | Healthy | 100 | 10201897600 | 6635285400 | 2.63 |
| CGPLH194 | Preoperative treatment naïve | WGS | Healthy | 100 | 11005087400 | 7081652600 | 2.81 |
| CGPLH196 | Preoperative treatment naïve | WGS | Healthy | 100 | 12891462800 | 8646881800 | 3.43 |
| CGPLH197 | Preoperative treatment naïve | WGS | Healthy | 100 | 11961841600 | 8052855200 | 3.20 |
| CGPLH198 | Preoperative treatment naïve | WGS | Healthy | 100 | 13605489000 | 8885716000 | 3.53 |
| CGPLH199 | Preoperative treatment naïve | WGS | Healthy | 100 | 1818090200 | 5615316000 | 2.23 |
| CGPLH200 | Preoperative treatment naïve | WGS | Healthy | 100 | 14400027600 | 9310342000 | 3.69 |
| CGPLH201 | Preoperative treatment naïve | WGS | Healthy | 100 | 6208766800 | 4171848400 | 1.66 |
| CGPLH202 | Preoperative treatment naïve | WGS | Healthy | 100 | 11282922800 | 7363530600 | 2.92 |
| CGPLH203 | Preoperative treatment naïve | WGS | Healthy | 100 | 13540689600 | 9068747600 | 3.60 |
| CGPLH205 | Preoperative treatment naïve | WGS | Healthy | 100 | 10343537800 | 6696988600 | 2.66 |
| CGPLH208 | Preoperative treatment naïve | WGS | Healthy | 100 | 12796300000 | 8272073400 | 3.28 |
| CGPLH209 | Preoperative treatment naïve | WGS | Healthy | 100 | 13123035400 | 8531813600 | 3.39 |
| CGPLH210 | Preoperative treatment naïve | WGS | Healthy | 100 | 10184218800 | 6832204600 | 2.71 |
| CGPLH211 | Preoperative treatment naïve | WGS | Healthy | 100 | 14655260200 | 8887067600 | 3.53 |
| CGPLH300 | Preoperative treatment naïve | WGS | Healthy | 100 | 7062083400 | 4553351200 | 1.81 |
| CGPLH307 | Preoperative treatment naïve | WGS | Healthy | 100 | 7239128200 | 4547697200 | 1.80 |
| CGPLH308 | Preoperative treatment naïve | WGS | Healthy | 100 | 8512551400 | 5526653600 | 2.19 |
| CGPLH309 | Preoperative treatment naïve | WGS | Healthy | 100 | 11664474200 | 7431836600 | 2.95 |
| CGPLH310 | Preoperative treatment naïve | WGS | Healthy | 100 | 11045691000 | 7451506200 | 2.96 |
| CGPLH311 | Preoperative treatment naïve | WGS | Healthy | 100 | 10406803200 | 6786479600 | 2.69 |
| CGPLH314 | Preoperative treatment naïve | WGS | Healthy | 100 | 10371343800 | 6925866600 | 2.75 |
| CGPLH315 | Preoperative treatment naïve | WGS | Healthy | 100 | 9508538400 | 6208744600 | 2.46 |
| CGPLH316 | Preoperative treatment naïve | WGS | Healthy | 100 | 10131063600 | 6891181000 | 2.73 |

TABLE 4-continued

APPENDIX - D: Summary of whole genome cfDNA analyses

| Patient | Timepoint | Analysis type | Patient Type | Read Length | Total Bases Sequenced | High Quality Bases Analyzed | Coverage |
|---|---|---|---|---|---|---|---|
| CGPLH317 | Preoperative treatment naïve | WGS | Healthy | 100 | 8364314400 | 5302232600 | 2.10 |
| CGPLH319 | Preoperative treatment naïve | WGS | Healthy | 100 | 8780528200 | 5585897000 | 2.22 |
| CGPLH320 | Preoperative treatment naïve | WGS | Healthy | 100 | 8956232600 | 5784619200 | 2.30 |
| CGPLH322 | Preoperative treatment naïve | WGS | Healthy | 100 | 9563837800 | 6445517800 | 2.56 |
| CGPLH324 | Preoperative treatment naïve | WGS | Healthy | 100 | 6765038600 | 4469201600 | 1.77 |
| CGPLH325 | Preoperative treatment naïve | WGS | Healthy | 100 | 8008213400 | 5099262800 | 2.02 |
| CGPLH326 | Preoperative treatment naïve | WGS | Healthy | 100 | 9554226200 | 6112544800 | 2.43 |
| CGPLH327 | Preoperative treatment naïve | WGS | Healthy | 100 | 8239168800 | 5351280200 | 2.12 |
| CGPLH328 | Preoperative treatment naïve | WGS | Healthy | 100 | 7197086800 | 4516894800 | 1.79 |
| CGPLH329 | Preoperative treatment naïve | WGS | Healthy | 100 | 8921554800 | 5493709800 | 2.18 |
| CGPLH330 | Preoperative treatment naïve | WGS | Healthy | 100 | 10693603400 | 7077793600 | 2.81 |
| CGPLH331 | Preoperative treatment naïve | WGS | Healthy | 100 | 8982792000 | 5538096200 | 2.20 |
| CGPLH333 | Preoperative treatment naïve | WGS | Healthy | 100 | 7856985400 | 5178829600 | 2.06 |
| CGPLH335 | Preoperative treatment naïve | WGS | Healthy | 100 | 9370663400 | 6035739400 | 2.40 |
| CGPLH336 | Preoperative treatment naïve | WGS | Healthy | 100 | 8002498200 | 5340331400 | 2.12 |
| CGPLH337 | Preoperative treatment naïve | WGS | Healthy | 100 | 7399022000 | 4954467600 | 1.97 |
| CGPLH338 | Preoperative treatment naïve | WGS | Healthy | 100 | 8917121600 | 6170927200 | 2.45 |
| CGPLH339 | Preoperative treatment naïve | WGS | Healthy | 100 | 8591130800 | 5866411400 | 2.33 |
| CGPLH340 | Preoperative treatment naïve | WGS | Healthy | 100 | 8046351000 | 5368062000 | 2.13 |
| CGPLH341 | Preoperative treatment naïve | WGS | Healthy | 100 | 7914788600 | 5200304800 | 2.06 |
| CGPLH342 | Preoperative treatment naïve | WGS | Healthy | 100 | 8633473000 | 5701972400 | 2.26 |
| CGPLH343 | Preoperative treatment naïve | WGS | Healthy | 100 | 6694769800 | 4410670800 | 1.75 |
| CGPLH344 | Preoperative treatment naïve | WGS | Healthy | 100 | 7628192400 | 4961476600 | 1.97 |
| CGPLH345 | Preoperative treatment naïve | WGS | Healthy | 100 | 7121569400 | 4747223000 | 1.88 |
| CGPLH346 | Preoperative treatment naïve | WGS | Healthy | 100 | 7707924600 | 4873321600 | 1.93 |
| CGPLH35 | Preoperative treatment naïve | WGS | Healthy | 100 | 47305985200 | 4774186200 | 12.63 |
| CGPLH350 | Preoperative treatment naïve | WGS | Healthy | 100 | 9745839800 | 6054055200 | 2.40 |
| CGPLH351 | Preoperative treatment naïve | WGS | Healthy | 100 | 13317435800 | 6714465000 | 3.46 |
| CGPLH352 | Preoperative treatment naïve | WGS | Healthy | 100 | 7659351600 | 4752309400 | 1.89 |
| CGPLH353 | Preoperative treatment naïve | WGS | Healthy | 100 | 8435782400 | 5275098200 | 2.09 |
| CGPLH354 | Preoperative treatment naïve | WGS | Healthy | 100 | 8018644000 | 4857577600 | 1.93 |
| CGPLH355 | Preoperative treatment naïve | WGS | Healthy | 100 | 8624675800 | 5709726400 | 2.27 |
| CGPLH356 | Preoperative treatment naïve | WGS | Healthy | 100 | 8817952800 | 5729595200 | 2.27 |
| CGPLH357 | Preoperative treatment naïve | WGS | Healthy | 100 | 11931696200 | 7690004400 | 3.05 |
| CGPLH358 | Preoperative treatment naïve | WGS | Healthy | 100 | 12802561200 | 8451274800 | 3.35 |
| CGPLH36 | Preoperative treatment naïve | WGS | Healthy | 100 | 40173545600 | 3974810400 | 10.52 |
| CGPLH360 | Preoperative treatment naïve | WGS | Healthy | 100 | 7280078400 | 4918566200 | 1.95 |

TABLE 4-continued

APPENDIX - D: Summary of whole genome cfDNA analyses

| Patient | Timepoint | Analysis type | Patient Type | Read Length | Total Bases Sequenced | High Quality Bases Analyzed | Coverage |
|---|---|---|---|---|---|---|---|
| CGPLH361 | Preoperative treatment naïve | WGS | Healthy | 100 | 7493498400 | 4966813800 | 1.97 |
| CGPLH362 | Preoperative treatment naïve | WGS | Healthy | 100 | 11345644200 | 7532133600 | 2.99 |
| CGPLH363 | Preoperative treatment naïve | WGS | Healthy | 100 | 6117382800 | 3965952400 | 1.57 |
| CGPLH364 | Preoperative treatment naïve | WGS | Healthy | 100 | 10823498400 | 7195657000 | 2.86 |
| CGPLH365 | Preoperative treatment naïve | WGS | Healthy | 100 | 5938367400 | 3954556200 | 1.57 |
| CGPLH366 | Preoperative treatment naïve | WGS | Healthy | 100 | 7063168600 | 4731853000 | 1.88 |
| CGPLH367 | Preoperative treatment naïve | WGS | Healthy | 100 | 7119631800 | 4627888200 | 1.84 |
| CGPLH368 | Preoperative treatment naïve | WGS | Healthy | 100 | 7726718400 | 4975233400 | 1.97 |
| CGPLH369 | Preoperative treatment naïve | WGS | Healthy | 100 | 10967584200 | 7130956800 | 2.83 |
| CGPLH37 | Preoperative treatment naïve | WGS | Healthy | 100 | 45970545400 | 4591328800 | 12.15 |
| CGPLH370 | Preoperative treatment naïve | WGS | Healthy | 100 | 9237170600 | 6106373800 | 2.42 |
| CGPLH371 | Preoperative treatment naïve | WGS | Healthy | 100 | 8077798800 | 5237070600 | 2.08 |
| CGPLH380 | Preoperative treatment naïve | WGS | Healthy | 100 | 14049589200 | 8614241200 | 3.42 |
| CGPLH381 | Preoperative treatment naïve | WGS | Healthy | 100 | 16743792000 | 10767882800 | 4.27 |
| CGPLH382 | Preoperative treatment naïve | WGS | Healthy | 100 | 18474025200 | 12276437200 | 4.87 |
| CGPLH383 | Preoperative treatment naïve | WGS | Healthy | 100 | 13215954000 | 8430420600 | 3.35 |
| CGPLH384 | Preoperative treatment naïve | WGS | Healthy | 100 | 8481814000 | 5463636200 | 2.17 |
| CGPLH385 | Preoperative treatment naïve | WGS | Healthy | 100 | 9596118800 | 6445445600 | 2.56 |
| CGPLH386 | Preoperative treatment naïve | WGS | Healthy | 100 | 7399540400 | 4915484800 | 1.95 |
| CGPLH387 | Preoperative treatment naïve | WGS | Healthy | 100 | 6860332600 | 4339724400 | 1.72 |
| CGPLH388 | Preoperative treatment naïve | WGS | Healthy | 100 | 8679705600 | 5463945400 | 2.17 |
| CGPLH389 | Preoperative treatment naïve | WGS | Healthy | 100 | 7266863600 | 4702386000 | 1.87 |
| CGPLH390 | Preoperative treatment naïve | WGS | Healthy | 100 | 7509035600 | 4913901800 | 1.95 |
| CGPLH391 | Preoperative treatment naïve | WGS | Healthy | 100 | 7252286000 | 4702404800 | 1.87 |
| CGPLH392 | Preoperative treatment naïve | WGS | Healthy | 100 | 7302618200 | 4722407000 | 1.87 |
| CGPLH393 | Preoperative treatment naïve | WGS | Healthy | 100 | 8879138000 | 5947871800 | 2.36 |
| CGPLH394 | Preoperative treatment naïve | WGS | Healthy | 100 | 8737031000 | 5599777400 | 2.22 |
| CGPLH395 | Preoperative treatment naïve | WGS | Healthy | 100 | 7783904800 | 4907146000 | 1.95 |
| CGPLH396 | Preoperative treatment naïve | WGS | Healthy | 100 | 7585567200 | 5076638200 | 2.01 |
| CGPLH398 | Preoperative treatment naïve | WGS | Healthy | 100 | 13001418200 | 8607025000 | 3.42 |
| CGPLH399 | Preoperative treatment naïve | WGS | Healthy | 100 | 9867699200 | 5526646000 | 2.19 |
| CGPLH400 | Preoperative treatment naïve | WGS | Healthy | 100 | 10573939000 | 6290438200 | 2.50 |
| CGPLH401 | Preoperative treatment naïve | WGS | Healthy | 100 | 9415150000 | 6139638000 | 2.44 |
| CGPLH402 | Preoperative treatment naïve | WGS | Healthy | 100 | 5541458000 | 2972027800 | 1.18 |
| CGPLH403 | Preoperative treatment naïve | WGS | Healthy | 100 | 6470913200 | 3549772600 | 1.41 |
| CGPLH404 | Preoperative treatment naïve | WGS | Healthy | 100 | 7369651800 | 4120205000 | 1.64 |
| CGPLH405 | Preoperative treatment naïve | WGS | Healthy | 100 | 7360239000 | 4293522600 | 1.70 |

TABLE 4-continued

APPENDIX - D: Summary of whole genome cfDNA analyses

| Patient | Timepoint | Analysis type | Patient Type | Read Length | Total Bases Sequenced | High Quality Bases Analyzed | Coverage |
|---|---|---|---|---|---|---|---|
| CGPLH406 | Preoperative treatment naïve | WGS | Healthy | 100 | 6028125400 | 3426007400 | 1.36 |
| CGPLH407 | Preoperative treatment naïve | WGS | Healthy | 100 | 7073375200 | 4079286800 | 1.62 |
| CGPLH408 | Preoperative treatment naïve | WGS | Healthy | 100 | 8006103200 | 5121285600 | 2.03 |
| CGPLH409 | Preoperative treatment naïve | WGS | Healthy | 100 | 7343124600 | 4432335600 | 1.76 |
| CGPLH410 | Preoperative treatment naïve | WGS | Healthy | 100 | 7551842000 | 4818779600 | 1.91 |
| CGPLH411 | Preoperative treatment naïve | WGS | Healthy | 100 | 6119676400 | 3636478400 | 1.44 |
| CGPLH412 | Preoperative treatment naïve | WGS | Healthy | 100 | 7960821200 | 4935752200 | 1.96 |
| CGPLH413 | Preoperative treatment naïve | WGS | Healthy | 100 | 7623405400 | 4827888400 | 1.92 |
| CGPLH414 | Preoperative treatment naïve | WGS | Healthy | 100 | 7381312400 | 4743337200 | 1.88 |
| CGPLH415 | Preoperative treatment naïve | WGS | Healthy | 100 | 7240754200 | 4162208800 | 1.65 |
| CGPLH416 | Preoperative treatment naïve | WGS | Healthy | 100 | 7745658600 | 4670226000 | 1.85 |
| CGPLH417 | Preoperative treatment naïve | WGS | Healthy | 100 | 7627498600 | 4403085600 | 1.75 |
| CGPLH418 | Preoperative treatment naïve | WGS | Healthy | 100 | 9090285000 | 5094814000 | 2.02 |
| CGPLH419 | Preoperative treatment naïve | WGS | Healthy | 100 | 7914120200 | 5078389800 | 2.02 |
| CGPLH42 | Preoperative treatment naïve | WGS | Healthy | 100 | 39492040600 | 3901039400 | 10.32 |
| CGPLH420 | Preoperative treatment naïve | WGS | Healthy | 100 | 7014307800 | 4711393600 | 1.87 |
| CGPLH422 | Preoperative treatment naïve | WGS | Healthy | 100 | 9103972800 | 6053559800 | 2.40 |
| CGPLH423 | Preoperative treatment naïve | WGS | Healthy | 100 | 10154714200 | 6128800200 | 2.43 |
| CGPLH424 | Preoperative treatment naïve | WGS | Healthy | 100 | 11002394000 | 6573756000 | 2.61 |
| CGPLH425 | Preoperative treatment naïve | WGS | Healthy | 100 | 14681352600 | 9272557000 | 3.68 |
| CGPLH426 | Preoperative treatment naïve | WGS | Healthy | 100 | 8336731000 | 5177430800 | 2.05 |
| CGPLH427 | Preoperative treatment naïve | WGS | Healthy | 100 | 8242924400 | 5632991800 | 2.24 |
| CGPLH428 | Preoperative treatment naïve | WGS | Healthy | 100 | 8512550400 | 5604756600 | 2.22 |
| CGPLH429 | Preoperative treatment naïve | WGS | Healthy | 100 | 8369802800 | 5477121400 | 2.17 |
| CGPLH43 | Preoperative treatment naïve | WGS | Healthy | 100 | 38513193400 | 3815698400 | 10.10 |
| CGPLH430 | Preoperative treatment naïve | WGS | Healthy | 100 | 10357365400 | 6841611000 | 2.71 |
| CGPLH431 | Preoperative treatment naïve | WGS | Healthy | 100 | 7599875800 | 5006909000 | 1.99 |
| CGPLH432 | Preoperative treatment naïve | WGS | Healthy | 100 | 7932532400 | 4932304200 | 1.96 |
| CGPLH434 | Preoperative treatment naïve | WGS | Healthy | 100 | 10417028600 | 6965998800 | 2.76 |
| CGPLH435 | Preoperative treatment naïve | WGS | Healthy | 100 | 8747793800 | 5677115200 | 2.25 |
| CGPLH436 | Preoperative treatment naïve | WGS | Healthy | 100 | 7990589400 | 5228737800 | 2.07 |
| CGPLH437 | Preoperative treatment naïve | WGS | Healthy | 100 | 10156991200 | 6935537200 | 2.75 |
| CGPLH438 | Preoperative treatment naïve | WGS | Healthy | 100 | 9473604000 | 6445455600 | 2.56 |
| CGPLH439 | Preoperative treatment naïve | WGS | Healthy | 100 | 8303723400 | 5439877200 | 2.16 |
| CGPLH440 | Preoperative treatment naïve | WGS | Healthy | 100 | 9055233800 | 6018631400 | 2.39 |
| CGPLH441 | Preoperative treatment naïve | WGS | Healthy | 100 | 10290682000 | 6896415200 | 2.74 |
| CGPLH442 | Preoperative treatment naïve | WGS | Healthy | 100 | 9876551600 | 6591249800 | 2.62 |

TABLE 4-continued

APPENDIX - D: Summary of whole genome cfDNA analyses

| Patient | Timepoint | Analysis type | Patient Type | Read Length | Total Bases Sequenced | High Quality Bases Analyzed | Coverage |
|---|---|---|---|---|---|---|---|
| CGPLH443 | Preoperative treatment naive | WGS | Healthy | 100 | 9837225800 | 6360740800 | 2.52 |
| CGPLH444 | Preoperative treatment naive | WGS | Healthy | 100 | 9199271400 | 5755941600 | 2.28 |
| CGPLH445 | Preoperative treatment naive | WGS | Healthy | 100 | 8089236400 | 5218259800 | 2.07 |
| CGPLH446 | Preoperative treatment naive | WGS | Healthy | 100 | 7890664200 | 5181606000 | 2.06 |
| CGPLH447 | Preoperative treatment naive | WGS | Healthy | 100 | 7775775000 | 5120239800 | 2.03 |
| CGPLH448 | Preoperative treatment naive | WGS | Healthy | 100 | 8686964800 | 5605079200 | 2.22 |
| CGPLH449 | Preoperative treatment naive | WGS | Healthy | 100 | 8604545400 | 5527726600 | 2.19 |
| CGPLH45 | Preoperative treatment naive | WGS | Healthy | 100 | 39029653000 | 3771601200 | 9.98 |
| CGPLH450 | Preoperative treatment naive | WGS | Healthy | 100 | 8428254800 | 5439950000 | 2.16 |
| CGPLH451 | Preoperative treatment naive | WGS | Healthy | 100 | 8128977600 | 5186265600 | 2.06 |
| CGPLH452 | Preoperative treatment naive | WGS | Healthy | 100 | 6474313400 | 4216316400 | 1.67 |
| CGPLH453 | Preoperative treatment naive | WGS | Healthy | 100 | 9831832800 | 6224917600 | 2.47 |
| CGPLH455 | Preoperative treatment naive | WGS | Healthy | 100 | 7373753000 | 4593473600 | 1.82 |
| CGPLH456 | Preoperative treatment naive | WGS | Healthy | 100 | 8455416200 | 5457148200 | 2.17 |
| CGPLH457 | Preoperative treatment naive | WGS | Healthy | 100 | 8647618000 | 5534503800 | 2.20 |
| CGPLH458 | Preoperative treatment naive | WGS | Healthy | 100 | 6633156400 | 4415186000 | 1.75 |
| CGPLH459 | Preoperative treatment naive | WGS | Healthy | 100 | 8361048200 | 5497193800 | 2.18 |
| CGPLH46 | Preoperative treatment naive | WGS | Healthy | 100 | 35361484600 | 3516232800 | 9.30 |
| CGPLH460 | Preoperative treatment naive | WGS | Healthy | 100 | 6788835400 | 4472282800 | 1.77 |
| CGPLH463 | Preoperative treatment naive | WGS | Healthy | 100 | 8534880800 | 5481759200 | 2.18 |
| CGPLH464 | Preoperative treatment naive | WGS | Healthy | 100 | 6692520000 | 4184463400 | 1.66 |
| CGPLH465 | Preoperative treatment naive | WGS | Healthy | 100 | 7772884600 | 4878430800 | 1.94 |
| CGPLH466 | Preoperative treatment naive | WGS | Healthy | 100 | 9056275000 | 5830877400 | 2.31 |
| CGPLH467 | Preoperative treatment naive | WGS | Healthy | 100 | 9331419200 | 4585861000 | 1.82 |
| CGPLH468 | Preoperative treatment naive | WGS | Healthy | 100 | 9334067400 | 6314830400 | 2.51 |
| CGPLH469 | Preoperative treatment naive | WGS | Healthy | 100 | 7376691000 | 4545246600 | 1.80 |
| CGPLH47 | Preoperative treatment naive | WGS | Healthy | 100 | 38485647600 | 3534883600 | 9.35 |
| CGPLH470 | Preoperative treatment naive | WGS | Healthy | 100 | 7899727600 | 5221650600 | 2.07 |
| CGPLH471 | Preoperative treatment naive | WGS | Healthy | 100 | 9200430600 | 6102371000 | 2.42 |
| CGPLH472 | Preoperative treatment naive | WGS | Healthy | 100 | 8143742400 | 5399946600 | 2.14 |
| CGPLH473 | Preoperative treatment naive | WGS | Healthy | 100 | 8123924600 | 5419825400 | 2.15 |
| CGPLH474 | Preoperative treatment naive | WGS | Healthy | 100 | 8853071400 | 6084059400 | 2.41 |
| CGPLH475 | Preoperative treatment naive | WGS | Healthy | 100 | 8115374000 | 5291718000 | 2.10 |
| CGPLH476 | Preoperative treatment naive | WGS | Healthy | 100 | 8163162600 | 5096869600 | 2.02 |
| CGPLH477 | Preoperative treatment naive | WGS | Healthy | 100 | 8350093200 | 5465468600 | 2.17 |
| CGPLH478 | Preoperative treatment naive | WGS | Healthy | 100 | 8259642200 | 5406516200 | 2.15 |
| CGPLH479 | Preoperative treatment naive | WGS | Healthy | 100 | 8027598600 | 5417376800 | 2.15 |

TABLE 4-continued

APPENDIX - D: Summary of whole genome cfDNA analyses

| Patient | Timepoint | Analysis type | Patient Type | Read Length | Total Bases Sequenced | High Quality Bases Analyzed | Coverage |
|---|---|---|---|---|---|---|---|
| CGPLH48 | Preoperative treatment naïve | WGS | Healthy | 100 | 42232410000 | 4165893400 | 11.02 |
| CGPLH480 | Preoperative treatment naïve | WGS | Healthy | 100 | 7832983200 | 5020127000 | 1.99 |
| CGPLH481 | Preoperative treatment naïve | WGS | Healthy | 100 | 7578518800 | 4883280800 | 1.94 |
| CGPLH482 | Preoperative treatment naïve | WGS | Healthy | 100 | 8279364800 | 5652263600 | 2.24 |
| CGPLH483 | Preoperative treatment naïve | WGS | Healthy | 100 | 8660338800 | 5823859200 | 2.31 |
| CGPLH484 | Preoperative treatment naïve | WGS | Healthy | 100 | 8445420000 | 5794328000 | 2.30 |
| CGPLH485 | Preoperative treatment naïve | WGS | Healthy | 100 | 8371255400 | 5490207800 | 2.18 |
| CGPLH486 | Preoperative treatment naïve | WGS | Healthy | 100 | 8216712200 | 5506871000 | 2.19 |
| CGPLP487 | Preoperative treatment naïve | WGS | Healthy | 100 | 7936294200 | 5309250200 | 2.11 |
| CGPLH488 | Preoperative treatment naïve | WGS | Healthy | 100 | 8355603600 | 5453160000 | 2.16 |
| CGPLH49 | Preoperative treatment naïve | WGS | Healthy | 100 | 33912191800 | 3310056000 | 8.76 |
| CGPLH490 | Preoperative treatment naïve | WGS | Healthy | 100 | 7768712400 | 5175567800 | 2.05 |
| CGPLH491 | Preoperative treatment naïve | WGS | Healthy | 100 | 9070904000 | 6011275000 | 2.39 |
| CGPLH492 | Preoperative treatment naïve | WGS | Healthy | 100 | 7208727200 | 4753213800 | 1.89 |
| CGPLH493 | Preoperative treatment naïve | WGS | Healthy | 100 | 10542882600 | 7225870800 | 2.87 |
| CGPLH494 | Preoperative treatment naïve | WGS | Healthy | 100 | 10908197600 | 7046645000 | 2.80 |
| CGPLH495 | Preoperative treatment naïve | WGS | Healthy | 100 | 8945040400 | 5891697800 | 2.34 |
| CGPLH496 | Preoperative treatment naïve | WGS | Healthy | 100 | 10859723400 | 7549608000 | 3.00 |
| CGPLH497 | Preoperative treatment naïve | WGS | Healthy | 100 | 9630507400 | 6473162800 | 2.57 |
| CGPLH498 | Preoperative treatment naïve | WGS | Healthy | 100 | 10060232600 | 6744622800 | 2.68 |
| CGPLH499 | Preoperative treatment naïve | WGS | Healthy | 100 | 10221293600 | 6951282800 | 2.76 |
| CGPLH50 | Preoperative treatment naïve | WGS | Healthy | 100 | 41243860600 | 4073272800 | 10.78 |
| CGPLH500 | Preoperative treatment naïve | WGS | Healthy | 100 | 9703168200 | 6239893800 | 2.48 |
| CGPLH501 | Preoperative treatment naïve | WGS | Healthy | 100 | 9104779800 | 6161602800 | 2.45 |
| CGPLH502 | Preoperative treatment naïve | WGS | Healthy | 100 | 8514467400 | 5290881400 | 2.10 |
| CGPLH503 | Preoperative treatment naïve | WGS | Healthy | 100 | 9019992200 | 6100383400 | 2.42 |
| CGPLH504 | Preoperative treatment naïve | WGS | Healthy | 100 | 9320330200 | 6199750200 | 2.46 |
| CGPLH505 | Preoperative treatment naïve | WGS | Healthy | 100 | 7499497400 | 4914559000 | 1.95 |
| CGPLH506 | Preoperative treatment naïve | WGS | Healthy | 100 | 10526142000 | 6963312600 | 2.76 |
| CGPLH507 | Preoperative treatment naïve | WGS | Healthy | 100 | 9091018400 | 6146678600 | 2.44 |
| CGPLH508 | Preoperative treatment naïve | WGS | Healthy | 100 | 10989315600 | 7360201400 | 2.92 |
| CGPLH509 | Preoperative treatment naïve | WGS | Healthy | 100 | 9729084600 | 6702691600 | 2.66 |
| CGPLH51 | Preoperative treatment naïve | WGS | Healthy | 100 | 35967451400 | 3492833200 | 9.24 |
| CGPLH510 | Preoperative treatment naïve | WGS | Healthy | 100 | 11162691600 | 7626795400 | 3.03 |
| CGPLH511 | Preoperative treatment naïve | WGS | Healthy | 100 | 11888619600 | 8110427600 | 3.22 |
| CGPLH512 | Preoperative treatment naïve | WGS | Healthy | 100 | 10726438400 | 7110078000 | 2.82 |
| CGPLH513 | Preoperative treatment naïve | WGS | Healthy | 100 | 10701564200 | 7155271400 | 2.84 |

TABLE 4-continued

APPENDIX - D: Summary of whole genome cfDNA analyses

| Patient | Timepoint | Analysis type | Patient Type | Read Length | Total Bases Sequenced | High Quality Bases Analyzed | Coverage |
|---|---|---|---|---|---|---|---|
| CGPLH514 | Preoperative treatment naïve | WGS | Healthy | 100 | 8822067000 | 5958773800 | 2.36 |
| CGPLH515 | Preoperative treatment naïve | WGS | Healthy | 100 | 7792074800 | 5317464600 | 2.11 |
| CGPLH516 | Preoperative treatment naïve | WGS | Healthy | 100 | 8642620000 | 5846439400 | 2.32 |
| CGPLH517 | Preoperative treatment naïve | WGS | Healthy | 100 | 11915929600 | 8013937000 | 3.18 |
| CGPLH518 | Preoperative treatment naïve | WGS | Healthy | 100 | 12804517400 | 8606661600 | 3.42 |
| CGPLH519 | Preoperative treatment naïve | WGS | Healthy | 100 | 11513222200 | 7922798400 | 3.14 |
| CGPLH52 | Preoperative treatment naïve | WGS | Healthy | 100 | 49247304200 | 4849631400 | 12.83 |
| CGPLH520 | Preoperative treatment naïve | WGS | Healthy | 100 | 8942102400 | 6030683400 | 2.39 |
| CGPLH54 | Preoperative treatment naïve | WGS | Healthy | 100 | 45399346400 | 4466164600 | 11.82 |
| CGPLH55 | Preoperative treatment naïve | WGS | Healthy | 100 | 42547725000 | 4283337600 | 11.33 |
| CGPLH56 | Preoperative treatment naïve | WGS | Healthy | 100 | 33460308000 | 3226338000 | 8.53 |
| CGPLH57 | Preoperative treatment naïve | WGS | Healthy | 100 | 36504735200 | 3509125000 | 9.28 |
| CGPLH59 | Preoperative treatment naïve | WGS | Healthy | 100 | 39642810600 | 3820011000 | 10.11 |
| CGPLH625 | Preoperative treatment naïve | WGS | Healthy | 100 | 6408225000 | 4115487600 | 1.63 |
| CGPLH626 | Preoperative treatment naïve | WGS | Healthy | 100 | 9915193600 | 6391657000 | 2.54 |
| CGPLH63 | Preoperative treatment naïve | WGS | Healthy | 100 | 37447047600 | 3506737000 | 9.28 |
| CGPLH639 | Preoperative treatment naïve | WGS | Healthy | 100 | 8158965800 | 5216049600 | 2.07 |
| CGPLH64 | Preoperative treatment naïve | WGS | Healthy | 100 | 34275506800 | 3264508000 | 8.63 |
| CGPLH640 | Preoperative treatment naïve | WGS | Healthy | 100 | 8058876800 | 5333551800 | 2.12 |
| CGPLH642 | Preoperative treatment naïve | WGS | Healthy | 100 | 7545555600 | 4909732800 | 1.95 |
| CGPLH643 | Preoperative treatment naïve | WGS | Healthy | 100 | 7865776800 | 5254772000 | 2.09 |
| CGPLH644 | Preoperative treatment naïve | WGS | Healthy | 100 | 6890139000 | 4599387400 | 1.83 |
| CGPLH646 | Preoperative treatment naïve | WGS | Healthy | 100 | 7757219400 | 5077408200 | 2.01 |
| CGPLH75 | Preoperative treatment naïve | WGS | Healthy | 100 | 23882926000 | 2250344400 | 5.95 |
| CGPLH76 | Preoperative treatment naïve | WGS | Healthy | 100 | 30631483600 | 3086042200 | 8.16 |
| CGPLH77 | Preoperative treatment naïve | WGS | Healthy | 100 | 31651741400 | 3041290200 | 8.04 |
| CGPLH78 | Preoperative treatment naïve | WGS | Healthy | 100 | 31165831200 | 3130079800 | 8.28 |
| CGPLH79 | Preoperative treatment naïve | WGS | Healthy | 100 | 31935043000 | 3128408200 | 8.27 |
| CGPLH80 | Preoperative treatment naïve | WGS | Healthy | 100 | 32965093000 | 3311371800 | 8.76 |
| CGPLH81 | Preoperative treatment naïve | WGS | Healthy | 100 | 27035311200 | 2455084400 | 6.49 |
| CGPLH82 | Preoperative treatment naïve | WGS | Healthy | 100 | 28447051200 | 2893358200 | 7.65 |
| CGPLH83 | Preoperative treatment naïve | WGS | Healthy | 100 | 26702240200 | 2459494000 | 6.50 |
| CGPLH84 | Preoperative treatment naïve | WGS | Healthy | 100 | 25176861400 | 2524467400 | 6.68 |
| CGPLLU13 | Pre-treatment, Day −2 | WGS | Lung Cancer | 100 | 9126585600 | 5915061800 | 2.35 |
| CGPLLU13 | Post-treatment, Day 5 | WGS | Lung Cancer | 100 | 7739120200 | 5071745800 | 2.01 |
| CGPLLU13 | Post-treatment, Day 28 | WGS | Lung Cancer | 100 | 9081585400 | 5764371600 | 2.29 |
| CGPLLU13 | Post-treatment, Day 91 | WGS | Lung Cancer | 100 | 9576557000 | 6160760200 | 2.44 |

TABLE 4-continued

APPENDIX - D: Summary of whole genome cfDNA analyses

| Patient | Timepoint | Analysis type | Patient Type | Read Length | Total Bases Sequenced | High Quality Bases Analyzed | Coverage |
|---|---|---|---|---|---|---|---|
| CGPLLU14 | Pre-treatment, Day −38 | WGS | Lung Cancer | 100 | 13659198400 | 9033455800 | 3.58 |
| CGPLLU14 | Pre-treatment, Day −16 | WGS | Lung Cancer | 100 | 7178855800 | 4856648600 | 1.93 |
| CGPLLU14 | Pre-treatment, Day −3 | WGS | Lung Cancer | 100 | 7653473000 | 4816193600 | 1.91 |
| CGPLLU14 | Pre-treatment, Day 0 | WGS | Lung Cancer | 100 | 7851997400 | 5193256600 | 2.06 |
| CGPLLU14 | Post-treatment, Day 0.33 | WGS | Lung Cancer | 100 | 7193040800 | 4869701600 | 1.93 |
| CGPLLU14 | Post-treatment, Day 7 | WGS | Lung Cancer | 100 | 7102050000 | 4741432600 | 1.88 |
| CGPLLU144 | Preoperative treatment naïve | WGS | Lung Cancer | 100 | 4934013600 | 3415936400 | 1.36 |
| CGPLLU147 | Preoperative treatment naïve | WGS | Lung Cancer | 100 | 24409561000 | 2118672800 | 5.61 |
| CGPLLU161 | Preoperative treatment naïve | WGS | Lung Cancer | 100 | 8998813400 | 6016145000 | 2.39 |
| CGPLLU162 | Preoperative treatment naïve | WGS | Lung Cancer | 100 | 9709792400 | 6407866400 | 2.54 |
| CGPLLU163 | Preoperative treatment naïve | WGS | Lung Cancer | 100 | 9150620200 | 6063569800 | 2.41 |
| CGPLLU165 | Preoperative treatment naïve | WGS | Lung Cancer | 100 | 28374436400 | 2651138600 | 7.01 |
| CGPLLU168 | Preoperative treatment naïve | WGS | Lung Cancer | 100 | 5692739400 | 3695191000 | 1.47 |
| CGPLLU169 | Preoperative treatment naïve | WGS | Lung Cancer | 100 | 9093975600 | 5805320800 | 2.30 |
| CGPLLU175 | Preoperative treatment naïve | WGS | Lung Cancer | 100 | 33794816800 | 3418750400 | 9.04 |
| CGPLLU176 | Preoperative treatment naïve | WGS | Lung Cancer | 100 | 8778553800 | 5794950200 | 2.30 |
| CGPLLU177 | Preoperative treatment naïve | WGS | Lung Cancer | 100 | 3734614800 | 2578696200 | 1.02 |
| CGPLLU180 | Preoperative treatment naïve | WGS | Lung Cancer | 100 | 28305936600 | 2756034200 | 7.29 |
| CGPLLU198 | Preoperative treatment naïve | WGS | Lung Cancer | 100 | 23244959200 | 2218577200 | 5.86 |
| CGPLLU202 | Preoperative treatment naïve | WGS | Lung Cancer | 100 | 21110128200 | 1831279400 | 4.84 |
| CGPLLU203 | Preoperative treatment naïve | WGS | Lung Cancer | 100 | 4304235600 | 2896429000 | 1.15 |
| CGPLLU205 | Preoperative treatment naïve | WGS | Lung Cancer | 100 | 10502467000 | 7386984800 | 2.93 |
| CGPLLU206 | Preoperative treatment naïve | WGS | Lung Cancer | 100 | 21888248200 | 2026666000 | 5.36 |
| CGPLLU207 | Preoperative treatment naïve | WGS | Lung Cancer | 100 | 10806230600 | 7363049000 | 2.92 |
| CGPLLU208 | Preoperative treatment naïve | WGS | Lung Cancer | 100 | 7795426800 | 5199545800 | 2.06 |
| CGPLLU209 | Preoperative treatment naïve | WGS | Lung Cancer | 100 | 26174542000 | 2621961800 | 6.93 |
| CGPLLU244 | Pre-treatment, Day −7 | WGS | Lung Cancer | 100 | 9967531400 | 6704365800 | 2.66 |
| CGPLLU244 | Pre-treatment, Day −1 | WGS | Lung Cancer | 100 | 9547119200 | 5785172600 | 2.30 |
| CGPLLU244 | Post-treatment Day 6 | WGS | Lung Cancer | 100 | 9535898600 | 6452174000 | 2.56 |
| CGPLLU244 | Post-treatment, Day 62 | WGS | Lung Cancer | 100 | 8783628600 | 5914149000 | 2.35 |
| CGPLLU245 | Pre-treatment, Day −32 | WGS | Lung Cancer | 100 | 10025823200 | 6313303800 | 2.51 |
| CGPLLU245 | Pre-treatment, Day 0 | WGS | Lung Cancer | 100 | 9462480400 | 6612867800 | 2.62 |
| CGPLLU245 | Post-treatment, Day 7 | WGS | Lung Cancer | 100 | 9143825000 | 6431013200 | 2.55 |
| CGPLLU245 | Post-treatment, Day 21 | WGS | Lung Cancer | 100 | 9072713800 | 6368533000 | 2.53 |
| CGPLLU246 | Pre-treatment, Day −21 | WGS | Lung Cancer | 100 | 9579787000 | 6458003400 | 2.56 |
| CGPLLU246 | Pre-treatment, Day 0 | WGS | Lung Cancer | 100 | 9512703600 | 6440535600 | 2.56 |
| CGPLLU246 | Post-treatment, Day 9 | WGS | Lung Cancer | 100 | 9512646000 | 6300939200 | 2.50 |

TABLE 4-continued

APPENDIX - D: Summary of whole genome cfDNA analyses

| Patient | Timepoint | Analysis type | Patient Type | Read Length | Total Bases Sequenced | High Quality Bases Analyzed | Coverage |
|---|---|---|---|---|---|---|---|
| CGPLLU246 | Post-treatment, Day 42 | WGS | Lung Cancer | 100 | 11136103000 | 7358747400 | 2.92 |
| CGPLLU264 | Pre-treatment, Day −1 | WGS | Lung Cancer | 100 | 9196005000 | 6239803600 | 2.48 |
| CGPLLU264 | Post-treatment, Day 6 | WGS | Lung Cancer | 100 | 8247416600 | 5600454200 | 2.22 |
| CGPLLU264 | Post-treatment, Day 27 | WGS | Lung Cancer | 100 | 8681022200 | 5856109000 | 2.32 |
| CGPLLU264 | Post-treatment, Day 69 | WGS | Lung Cancer | 100 | 8931976400 | 5974246000 | 2.37 |
| CGPLLU265 | Pre-treatment, Day 0 | WGS | Lung Cancer | 100 | 9460534000 | 6111185200 | 2.43 |
| CGPLLU265 | Post-treatment, Day 3 | WGS | Lung Cancer | 100 | 8051601200 | 4984166600 | 1.98 |
| CGPLLU265 | Post-treatment, Day 7 | WGS | Lung Cancer | 100 | 8082224600 | 5110092600 | 2.03 |
| CGPLLU265 | Post-treatment, Day 84 | WGS | Lung Cancer | 100 | 8368637400 | 5369526400 | 2.13 |
| CGPLLU266 | Pre-treatment, Day 0 | WGS | Lung Cancer | 100 | 8583766400 | 5846473600 | 2.32 |
| CGPLL266 | Post-treatment, Day 16 | WGS | Lung Cancer | 100 | 8795793600 | 5984531400 | 2.37 |
| CGPLLU266 | Post-treatment, Day 83 | WGS | Lung Cancer | 100 | 9157947600 | 6227735000 | 2.47 |
| CGPLLU266 | Post-treatment, Day 328 | WGS | Lung Cancer | 100 | 7299455400 | 5049379000 | 2.00 |
| CGPLLU267 | Pre-treatment, Day −1 | WGS | Lung Cancer | 100 | 10658657800 | 6892067000 | 2.73 |
| CGPLLU267 | Post-treatment, Day 34 | WGS | Lung Cancer | 100 | 8492833400 | 5101097800 | 2.02 |
| CGPLLU267 | Post-treatment, Day 90 | WGS | Lung Cancer | 100 | 12030314800 | 7757930400 | 3.08 |
| CGPLLU269 | Pre-treatment, Day 0 | WGS | Lung Cancer | 100 | 9170168000 | 5830454400 | 2.31 |
| CGPLLU269 | Post-treatment, Day 9 | WGS | Lung Cancer | 100 | 8905640400 | 5298461400 | 2.10 |
| CGPLLU269 | Post-treatment, Day 28 | WGS | Lung Cancer | 100 | 8455306600 | 5387927400 | 2.14 |
| CGPLLU271 | Post-treatment, Day 259 | WGS | Lung Cancer | 100 | 8112060400 | 5404979000 | 2.14 |
| CGPLLU271 | Pre-treatment, Day 0 | WGS | Lung Cancer | 100 | 13150818200 | 8570453400 | 3.40 |
| CGPLLU271 | Post-treatment, Day 6 | WGS | Lung Cancer | 100 | 9008880600 | 5854051400 | 2.32 |
| CGPLLU271 | Post-treatment, Day 20 | WGS | Lung Cancer | 100 | 8670913000 | 5461577000 | 2.17 |
| CGPLLU271 | Post-treatment, Day 104 | WGS | Lung Cancer | 100 | 8887441400 | 5609039000 | 2.23 |
| CGPLLU43 | Pre-treatment, Day −1 | WGS | Lung Cancer | 100 | 8407811200 | 5203486400 | 2.06 |
| CGPLLU43 | Post-treatment, Day 6 | WGS | Lung Cancer | 100 | 9264335200 | 5626714400 | 2.23 |
| CGPLLU43 | Post-treatment, Day 27 | WGS | Lung Cancer | 100 | 8902283000 | 5485656200 | 2.18 |
| CGPLLU43 | Post-treatment, Day 83 | WGS | Lung Cancer | 100 | 9201509200 | 5075084200 | 2.33 |
| CGPLLU86 | Pre-treatment, Day 0 | WGS | Lung Cancer | 100 | 9152729200 | 6248173200 | 2.48 |
| CGPLLU86 | Post-treatment, Day 0.5 | WGS | Lung Cancer | 100 | 6703253000 | 4663026800 | 1.85 |
| CGPLLU86 | Post-treatment, Day 7 | WGS | Lung Cancer | 100 | 6590121400 | 4559562400 | 1.81 |
| CGPLLU86 | Post-treatment, Day 17 | WGS | Lung Cancer | 100 | 8653551800 | 5900136000 | 2.34 |
| CGPLLU88 | Pre-treatment, Day 0 | WGS | Lung Cancer | 100 | 8096528000 | 5505475400 | 2.18 |
| CGPLLU88 | Post-treatment, Day 7 | WGS | Lung Cancer | 100 | 8283192200 | 5784217600 | 2.30 |
| CGPLLU88 | Post-treatment, Day 297 | WGS | Lung Cancer | 100 | 9297110800 | 6407258000 | 2.54 |
| CGPLLU89 | Pre-treatment, Day 0 | WGS | Lung Cancer | 100 | 7842145200 | 5356095400 | 2.13 |
| CGPLLU89 | Post-treatment, Day 7 | WGS | Lung Cancer | 100 | 7234220200 | 4930375200 | 1.96 |

TABLE 4-continued

APPENDIX - D: Summary of whole genome cfDNA analyses

| Patient | Timepoint | Analysis type | Patient Type | Read Length | Total Bases Sequenced | High Quality Bases Analyzed | Coverage |
|---|---|---|---|---|---|---|---|
| CGPLLU89 | Post-treatment, Day 22 | WGS | Lung Cancer | 100 | 6242889800 | 4057361000 | 1.61 |
| CGPLOV11 | Preoperative treatment naïve | WGS | Ovarian Cancer | 100 | 8985130400 | 5871959600 | 2.33 |
| CGPLOV12 | Preoperative treatment naïve | WGS | Ovarian Cancer | 100 | 9705820000 | 6430505400 | 2.55 |
| CGPLOV13 | Preoperative treatment naïve | WGS | Ovarian Cancer | 100 | 10307949490 | 7029712000 | 2.79 |
| CGPLOV15 | Preoperative treatment naïve | WGS | Ovarian Cancer | 100 | 8472829400 | 5562142400 | 2.21 |
| CGPLOV16 | Preoperative treatment naïve | WGS | Ovarian Cancer | 100 | 10977781000 | 7538581600 | 2.99 |
| CGPLOV19 | Preoperative treatment naïve | WGS | Ovarian Cancer | 100 | 8800876200 | 5855304000 | 2.32 |
| CGPLOV20 | Preoperative treatment naïve | WGS | Ovarian Cancer | 100 | 8714443600 | 5695165800 | 2.26 |
| CGPLOV21 | Preoperative treatment naïve | WGS | Ovarian Cancer | 100 | 10180394800 | 7120260400 | 2.83 |
| CGPLOV22 | Preoperative treatment naïve | WGS | Ovarian Cancer | 100 | 10107760000 | 6821916800 | 2.71 |
| CGPLOV23 | Preoperative treatment naïve | WGS | Ovarian Cancer | 100 | 10643399800 | 7206330800 | 2.86 |
| CGPLOV24 | Preoperative treatment naïve | WGS | Ovarian Cancer | 100 | 6780929000 | 4623300400 | 1.83 |
| CGPLOV25 | Preoperative treatment naïve | WGS | Ovarian Cancer | 100 | 7817548600 | 5359975200 | 2.13 |
| CGPLOV26 | Preoperative treatment naïve | WGS | Ovarian Cancer | 100 | 11763101400 | 8178024400 | 3.25 |
| CGPLOV28 | Preoperative treatment naïve | WGS | Ovarian Cancer | 100 | 9522546400 | 6259423400 | 2.48 |
| CGPLOV31 | Preoperative treatment naïve | WGS | Ovarian Cancer | 100 | 9104831200 | 6109358400 | 2.42 |
| CGPLOV32 | Preoperative treatment naïve | WGS | Ovarian Cancer | 100 | 9222073600 | 6035150000 | 2.39 |
| CGPLOV37 | Preoperative treatment naïve | WGS | Ovarian Cancer | 100 | 8898328600 | 5971018200 | 2.37 |
| CGPLOV38 | Preoperative treatment naïve | WGS | Ovarian Cancer | 100 | 8756025200 | 5861536600 | 2.33 |
| CGPLOV40 | Preoperative treatment naïve | WGS | Ovarian Cancer | 100 | 9709391600 | 6654707200 | 2.64 |
| CGPLOV41 | Preoperative treatment naïve | WGS | Ovarian Cancer | 100 | 8923625000 | 5973070400 | 2.37 |
| CGPLOV42 | Preoperative treatment naïve | WGS | Ovarian Cancer | 100 | 10719380400 | 7353214200 | 2.92 |
| CGPLOV43 | Preoperative treatment naïve | WGS | Ovarian Cancer | 100 | 10272189000 | 6423288600 | 2.55 |
| CGPLOV44 | Preoperative treatment naïve | WGS | Ovarian Cancer | 100 | 9861862600 | 6769185800 | 2.69 |
| CGPLOV46 | Preoperative treatment naïve | WGS | Ovarian Cancer | 100 | 8788956400 | 5789863400 | 2.30 |
| CGPLOV47 | Preoperative treatment naïve | WGS | Ovarian Cancer | 100 | 9380561800 | 6480763600 | 2.57 |
| CGPLOV48 | Preoperative treatment naïve | WGS | Ovarian Cancer | 100 | 9258552600 | 6380106400 | 2.53 |
| CGPLOV49 | Preoperative treatment naïve | WGS | Ovarian Cancer | 100 | 8787025400 | 6134503600 | 2.43 |
| CGPLOV50 | Preoperative treatment naïve | WGS | Ovarian Cancer | 100 | 10144154400 | 6984721400 | 2.77 |
| CGPLPA112 | Preoperative treatment naïve | WGS | Pancreatic Cancer | 100 | 12740651400 | 9045622000 | 3.59 |
| CGPLPA113 | Preoperative treatment naïve | WGS | Duodenal Cancer | 100 | 8802479000 | 5909030800 | 2.34 |
| CGPLPA114 | Preoperative treatment naïve | WGS | Bile Duct Cancer | 100 | 8792313600 | 6019061000 | 2.39 |
| CGPLPA115 | Preoperative treatment naïve | WGS | Bile Duct Cancer | 100 | 8636551400 | 5958809000 | 2.36 |
| CGPLPA117 | Preoperative treatment naïve | WGS | Bile Duct Cancer | 100 | 9128885200 | 6288833200 | 2.50 |
| CGPLPA118 | Preoperative treatment naïve | WGS | Bile Duct Cancer | 100 | 7931485800 | 5407532800 | 2.15 |
| CGPLPA122 | Preoperative treatment naïve | WGS | Bile Duct Cancer | 100 | 10888985000 | 7530118800 | 2.99 |
| CGPLPA124 | Preoperative treatment naïve | WGS | Bile Duct Cancer | 100 | 8562012400 | 5860171000 | 2.33 |

TABLE 4-continued

APPENDIX - D: Summary of whole genome cfDNA analyses

| Patient | Timepoint | Analysis type | Patient Type | Read Length | Total Bases Sequenced | High Quality Bases Analyzed | Coverage |
|---|---|---|---|---|---|---|---|
| CGPLPA125 | Preoperative treatment naïve | WGS | Bile Duct Cancer | 100 | 9715576600 | 6390321000 | 2.54 |
| CGPLPA126 | Preoperative treatment naïve | WGS | Bile Duct Cancer | 100 | 8056768800 | 5651600800 | 2.24 |
| CGPLPA127 | Preoperative treatment naïve | WGS | Bile Duct Cancer | 100 | 8000301000 | 5382987600 | 2.14 |
| CGPLPA128 | Preoperative treatment naïve | WGS | Bile Duct Cancer | 100 | 6165751600 | 4256521400 | 1.69 |
| CGPLPA129 | Preoperative treatment naïve | WGS | Bile Duct Cancer | 100 | 7143147400 | 4917370400 | 1.95 |
| CGPLPA130 | Preoperative treatment naïve | WGS | Bile Duct Cancer | 100 | 5664035000 | 3603919400 | 1.43 |
| CGPLPA131 | Preoperative treatment naïve | WGS | Bile Duct Cancer | 100 | 8292982000 | 5844942000 | 2.32 |
| CGPLPA134 | Preoperative treatment naïve | WGS | Bile Duct Cancer | 100 | 7088917000 | 5048887600 | 2.00 |
| CGPLPA135 | Preoperative treatment naïve | WGS | Bile Duct Cancer | 100 | 8759665600 | 5800618200 | 2.30 |
| CGPLPA136 | Preoperative treatment naïve | WGS | Bile Duct Cancer | 100 | 7539715800 | 5248227600 | 2.08 |
| CGPLPA137 | Preoperative treatment naïve | WGS | Bile Duct Cancer | 100 | 8391815400 | 5901273800 | 2.34 |
| CGPLPA139 | Preoperative treatment naïve | WGS | Bile Duct Cancer | 100 | 8992280200 | 6328314400 | 2.51 |
| CGPLPA14 | Preoperative treatment naïve | WGS | Pancreatic Cancer | 100 | 8787706200 | 5731317600 | 2.27 |
| CGPLPA140 | Preoperative treatment naïve | WGS | Bile Duct Cancer | 100 | 16365641800 | 11216732000 | 4.45 |
| CGPLPA141 | Preoperative treatment naïve | WGS | Bile Duct Cancer | 100 | 15086298000 | 10114790200 | 4.01 |
| CGPLPA15 | Preoperative treatment naïve | WGS | Pancreatic Cancer | 100 | 8255566800 | 5531677600 | 2.20 |
| CGPLPA155 | Preoperative treatment naïve | WGS | Bile Duct Cancer | 100 | 9457155800 | 6621881800 | 2.63 |
| CGPLPA156 | Preoperative treatment naïve | WGS | Pancreatic Cancer | 100 | 9345385800 | 6728653000 | 2.67 |
| CGPLPA165 | Preoperative treatment naïve | WGS | Bile Duct Cancer | 100 | 8356604600 | 5829895800 | 2.31 |
| CGPLPA168 | Preoperative treatment naïve | WGS | Bile Duct Cancer | 100 | 10355661600 | 7048115500 | 2.80 |
| CGPLPA17 | Preoperative treatment naïve | WGS | Pancreatic Cancer | 100 | 8073547400 | 4687808000 | 1.86 |
| CGPLPA184 | Preoperative treatment naïve | WGS | Bile Duct Cancer | 100 | 9014218400 | 6230922200 | 2.47 |
| CGPLPA187 | Preoperative treatment naïve | WGS | Bile Duct Cancer | 100 | 8883536200 | 6140874400 | 2.44 |
| CGPLPA23 | Preoperative treatment naïve | WGS | Pancreatic Cancer | 100 | 9335452000 | 6246525400 | 2.48 |
| CGPLPA25 | Preoperative treatment naïve | WGS | Pancreatic Cancer | 100 | 10077515400 | 6103322200 | 2.42 |
| CGPLPA26 | Preoperative treatment naïve | WGS | Pancreatic Cancer | 100 | 8354272400 | 5725781000 | 2.27 |
| CGPLPA28 | Preoperative treatment naïve | WGS | Pancreatic Cancer | 100 | 8477461600 | 5688846800 | 2.26 |
| CGPLPA33 | Preoperative treatment naïve | WGS | Pancreatic Cancer | 100 | 7287615600 | 4596723800 | 1.82 |
| CGPLPA34 | Preoperative treatment naïve | WGS | Pancreatic Cancer | 100 | 6122902400 | 4094828000 | 1.62 |
| CGPLPA37 | Preoperative treatment naïve | WGS | Pancreatic Cancer | 100 | 12714888200 | 8527779200 | 3.38 |
| CGPLPA38 | Preoperative treatment naïve | WGS | Pancreatic Cancer | 100 | 8525500600 | 5501341400 | 2.18 |
| CGPLPA39 | Preoperative treatment naïve | WGS | Pancreatic Cancer | 100 | 10602663600 | 6812333000 | 2.70 |
| CGPLPA40 | Preoperative treatment naïve | WGS | Pancreatic Cancer | 100 | 9083670000 | 5394717800 | 2.14 |
| CGPLPA42 | Preoperative treatment naïve | WGS | Pancreatic Cancer | 100 | 5972126600 | 3890395200 | 1.54 |
| CGPLPA46 | Preoperative treatment naïve | WGS | Pancreatic Cancer | 100 | 4720090200 | 2626298800 | 1.04 |
| CGPLPA47 | Preoperative treatment naïve | WGS | Pancreatic Cancer | 100 | 7317385800 | 4543833000 | 1.80 |
| CGPLPA48 | Preoperative treatment naïve | WGS | Pancreatic Cancer | 100 | 7553856200 | 5022695600 | 1.99 |

TABLE 4-continued

APPENDIX - D: Summary of whole genome cfDNA analyses

| Patient | Timepoint | Analysis type | Patient Type | Read Length | Total Bases Sequenced | High Quality Bases Analyzed | Coverage |
|---|---|---|---|---|---|---|---|
| CGPLPA52 | Preoperative treatment naïve | WGS | Pancreatic Cancer | 100 | 5655875000 | 3551861600 | 1.41 |
| CGPLPA53 | Preoperative treatment naïve | WGS | Pancreatic Cancer | 100 | 9504749000 | 6323344800 | 2.51 |
| CGPLPA58 | Preoperative treatment naïve | WGS | Pancreatic Cancer | 100 | 8088090200 | 5118138200 | 2.03 |
| CGPLPA59 | Preoperative treatment naïve | WGS | Pancreatic Cancer | 100 | 14547364600 | 9617778600 | 3.82 |
| CGPLPA67 | Preoperative treatment naïve | WGS | Pancreatic Cancer | 100 | 8222177400 | 5351172600 | 2.12 |
| CGPLPA69 | Preoperative treatment naïve | WGS | Pancreatic Cancer | 100 | 7899181400 | 5006114800 | 1.99 |
| CGPLPA71 | Preoperative treatment naïve | WGS | Pancreatic Cancer | 100 | 7349620400 | 4955417400 | 1.97 |
| CGPLPA74 | Preoperative treatment naïve | WGS | Pancreatic Cancer | 100 | 6666371400 | 4571394200 | 1.81 |
| CGPLPA76 | Preoperative treatment naïve | WGS | Pancreatic Cancer | 100 | 9755658600 | 6412606800 | 2.54 |
| CGPLPA85 | Preoperative treatment naïve | WGS | Pancreatic Cancer | 100 | 10856223000 | 7309498600 | 2.90 |
| CGPLPA86 | Preoperative treatment naïve | WGS | Pancreatic Cancer | 100 | 8744365400 | 5514523200 | 2.19 |
| CGPLPA92 | Preoperative treatment naïve | WGS | Pancreatic Cancer | 100 | 8073791200 | 5390492800 | 2.14 |
| CGPLPA93 | Preoperative treatment naïve | WGS | Pancreatic Cancer | 100 | 10390273000 | 7186589400 | 2.85 |
| CGPLPA94 | Preoperative treatment naïve | WGS | Pancreatic Cancer | 100 | 11060347600 | 7641336400 | 3.03 |
| CGPLPA95 | Preoperative treatment naïve | WGS | Pancreatic Cancer | 100 | 12416627200 | 7206503800 | 2.86 |
| CGST102 | Preoperative treatment naïve | WGS | Gastric cancer | 100 | 6637004600 | 4545072600 | 1.80 |
| CGST11 | Preoperative treatment naïve | WGS | Gastric cancer | 100 | 9718427800 | 6259679600 | 2.48 |
| CGST110 | Preoperative treatment naïve | WGS | Gastric cancer | 100 | 9319661600 | 6359317400 | 2.52 |
| CGST114 | Preoperative treatment naïve | WGS | Gastric cancer | 100 | 6865213000 | 4841171600 | 1.92 |
| CGST13 | Preoperative treatment naïve | WGS | Gastric cancer | 100 | 9284554800 | 6360843800 | 2.52 |
| CGST131 | Preoperative treatment naïve | WGS | Gastric cancer | 100 | 5924382000 | 3860677200 | 1.53 |
| CGST141 | Preoperative treatment naïve | WGS | Gastric cancer | 100 | 8486380800 | 5860491000 | 2.33 |
| CGST16 | Preoperative treatment naïve | WGS | Gastric cancer | 100 | 13820725800 | 9377828000 | 3.72 |
| CGST18 | Preoperative treatment naïve | WGS | Gastric cancer | 100 | 7781288000 | 5278862400 | 2.09 |
| CGST21 | Preoperative treatment naïve | WGS | Gastric cancer | 100 | 7171165400 | 4103970800 | 1.63 |
| CGST26 | Preoperative treatment naïve | WGS | Gastric cancer | 100 | 8983961800 | 6053405600 | 2.40 |
| CGST28 | Preoperative treatment naïve | WGS | Gastric cancer | 100 | 9683035400 | 6745116400 | 2.68 |
| CGST30 | Preoperative treatment naïve | WGS | Gastric cancer | 100 | 8584086600 | 5741416000 | 2.28 |
| CGST32 | Preoperative treatment naïve | WGS | Gastric cancer | 100 | 8568194600 | 5783369200 | 2.29 |
| CGST33 | Preoperative treatment naïve | WGS | Gastric cancer | 100 | 9351699600 | 6448718400 | 2.56 |
| CGST38 | Preoperative treatment naïve | WGS | Gastric cancer | 100 | 8409876400 | 5770989200 | 2.29 |
| CGST39 | Preoperative treatment naïve | WGS | Gastric cancer | 100 | 10573763000 | 7597016000 | 3.01 |
| CGST41 | Preoperative treatment naïve | WGS | Gastric cancer | 100 | 9434854200 | 6609415400 | 2.62 |
| CGST45 | Preoperative treatment naïve | WGS | Gastric cancer | 100 | 8203868600 | 5625223000 | 2.23 |
| CGST47 | Preoperative treatment naïve | WGS | Gastric cancer | 100 | 8938597600 | 6178990600 | 2.45 |
| CGST48 | Preoperative treatment naïve | WGS | Gastric cancer | 100 | 9106628800 | 6517085200 | 2.59 |
| CGST53 | Preoperative treatment naïve | WGS | Gastric cancer | 100 | 9005374200 | 5854996200 | 2.32 |

TABLE 4-continued

APPENDIX - D: Summary of whole genome cfDNA analyses

| Patient | Timepoint | Analysis type | Patient Type | Read Length | Total Bases Sequenced | High Quality Bases Analyzed | Coverage |
|---|---|---|---|---|---|---|---|
| CGST58 | Preoperative treatment naïve | WGS | Gastric cancer | 100 | 10020368600 | 6133458400 | 2.43 |
| CGST67 | Preoperative treatment naïve | WGS | Gastric cancer | 100 | 9198135600 | 5911071000 | 2.35 |
| CGST77 | Preoperative treatment naïve | WGS | Gastric cancer | 100 | 8228789400 | 5119116800 | 2.03 |
| CGST80 | Preoperative treatment naïve | WGS | Gastric cancer | 100 | 10596963400 | 7283152800 | 2.89 |
| CGST81 | Preoperative treatment naïve | WGS | Gastric cancer | 100 | 8494881200 | 5838064000 | 2.32 |

TABLE 5

APPENDIX E: High coverage whole genome cfDNA analyses of healthy individuals and lung cancer patients

| Patient | Patient Type | Analysis Type | Timepoint | Stage at Diagnosis | Median cfDNA Fragment Size (bp) | Correlation of Fragment Ratio Profile to Median Fragment Ratio Profile of Healthy Individuals | Correlation of GC Corrected Fragment Ratio Profile to Median Fragment Ratio Profile of Healthy Individuals | Correction of Fragment Ratio Profile to Median Fragment Ratio Profile of Lymphocytes | Correlation of Fragment Ratio Profile to Lymphocyte Nucleosome Distances |
|---|---|---|---|---|---|---|---|---|---|
| CGPLH75 | Healthy | WGS | Preoperative treatment naïve | NA | 168 | 0.977 | 0.952 | 0.920 | −0.886 |
| CGPLH77 | Healthy | WGS | Preoperative treatment naïve | NA | 166 | 0.970 | 0.960 | 0.904 | −0.912 |
| CGPLH80 | Healthy | WGS | Preoperative treatment naïve | NA | 168 | 0.955 | 0.949 | 0.960 | −0.917 |
| CGPLH81 | Healthy | WGS | Preoperative treatment naïve | NA | 167 | 0.949 | 0.953 | 0.869 | −0.883 |
| CGPLH82 | Healthy | WGS | Preoperative treatment naïve | NA | 166 | 0.969 | 0.949 | 0.954 | −0.917 |
| CGPLH83 | Healthy | WGS | Preoperative treatment naïve | NA | 167 | 0.949 | 0.939 | 0.919 | −0.904 |
| CGPLH84 | Healthy | WGS | Preoperative treatment naïve | NA | 168 | 0.967 | 0.948 | 0.951 | −0.913 |
| CGPLH52 | Healthy | WGS | Preoperative treatment naïve | NA | 167 | 0.946 | 0.968 | 0.952 | −0.924 |
| CGPLH35 | Healthy | WGS | Preoperative treatment naïve | NA | 166 | 0.981 | 0.973 | 0.945 | −0.921 |
| CGPLH37 | Healthy | WGS | Preoperative treatment naïve | NA | 168 | 0.968 | 0.970 | 0.951 | −0.922 |
| CGPLH54 | Healthy | WGS | Preoperative treatment naïve | NA | 167 | 0.968 | 0.976 | 0.948 | −0.925 |
| CGPLH55 | Healthy | WGS | Preoperative treatment naïve | NA | 166 | 0.947 | 0.964 | 0.948 | −0.917 |
| CGPLH48 | Healthy | WGS | Preoperative treatment naïve | NA | 168 | 0.959 | 0.965 | 0.960 | −0.923 |
| CGPLH50 | Healthy | WGS | Preoperative treatment naïve | NA | 167 | 0.960 | 0.968 | 0.952 | −0.921 |
| CGPLH36 | Healthy | WGS | Preoperative treatment naïve | NA | 168 | 0.955 | 0.954 | 0.955 | −0.919 |
| CGPLH42 | Healthy | WGS | Preoperative treatment naïve | NA | 167 | 0.973 | 0.963 | 0.948 | −0.918 |
| CGPLH43 | Healthy | WGS | Preoperative treatment naïve | NA | 166 | 0.952 | 0.958 | 0.953 | −0.928 |
| CGPLH69 | Healthy | WGS | Preoperative treatment naïve | NA | 168 | 0.970 | 0.965 | 0.951 | −0.925 |
| CGPLH45 | Healthy | WGS | Preoperative treatment naïve | NA | 168 | 0.965 | 0.950 | 0.949 | −0.911 |
| CGPLH47 | Healthy | WGS | Preoperative treatment naïve | NA | 167 | 0.952 | 0.944 | 0.954 | −0.921 |
| CGPLH46 | Healthy | WGS | Preoperative treatment naïve | NA | 168 | 0.966 | 0.965 | 0.953 | −0.923 |
| CGPLH63 | Healthy | WGS | Preoperative treatment naïve | NA | 168 | 0.977 | 0.968 | 0.939 | −0.920 |
| CGPLH51 | Healthy | WGS | Preoperative treatment naïve | NA | 168 | 0.935 | 0.955 | 0.957 | −0.914 |
| CGPLH57 | Healthy | WGS | Preoperative treatment naïve | NA | 169 | 0.965 | 0.954 | 0.955 | −0.917 |

TABLE 5-continued

APPENDIX E: High coverage whole genome cfDNA analyses of healthy individuals and lung cancer patients

| Patient | Patient Type | Analysis Type | Timepoint | Stage at Diagnosis | Median cfDNA Fragment Size (bp) | Correlation of Fragment Ratio Profile to Median Fragment Ratio Profile of Healthy Individuals | Correlation of GC Corrected Fragment Ratio Profile to Median Fragment Ratio Profile of Healthy Individuals | Correction of Fragment Ratio Profile to Median Fragment Ratio Profile of Lymphocytes | Correlation of Fragment Ratio Profile to Lymphocyte Nucleosome Distances |
|---|---|---|---|---|---|---|---|---|---|
| CGPLH49 | Healthy | WGS | Preoperative treatment naïve | NA | 168 | 0.958 | 0.951 | 0.950 | −0.924 |
| CGPLH56 | Healthy | WGS | Preoperative treatment naïve | NA | 166 | 0.940 | 0.957 | 0.959 | −0.911 |
| CGPLH64 | Healthy | WGS | Preoperative treatment naïve | NA | 169 | 0.960 | 0.940 | 0.949 | −0.918 |
| CGPLH78 | Healthy | WGS | Preoperative treatment naïve | NA | 166 | 0.956 | 0.936 | 0.958 | −0.911 |
| CGPLH79 | Healthy | WGS | Preoperative treatment naïve | NA | 168 | 0.960 | 0.957 | 0.953 | −0.917 |
| CGPLH76 | Healthy | WGS | Preoperative treatment naïve | NA | 167 | 0.969 | 0.965 | 0.953 | −0.917 |
| CGPLLU175 | Lung Cancer | WGS | Preoperative treatment naïve | I | 165 | 0.316 | 0.284 | 0.244 | −0.262 |
| CGPLLU180 | Lung Cancer | WGS | Preoperative treatment naïve | I | 166 | 0.907 | 0.846 | 0.826 | −0.819 |
| CGPLLU198 | Lung Cancer | WGS | Preoperative treatment naïve | I | 166 | 0.972 | 0.946 | 0.928 | −0.911 |
| CGPLLU202 | Lung Cancer | WGS | Preoperative treatment naïve | I | 163 | 0.821 | 0.605 | 0.905 | −0.843 |
| CGPLLU165 | Lung Cancer | WGS | Preoperative treatment naïve | II | 163 | 0.924 | 0.961 | 0.815 | −0.851 |
| CGPLLU209 | Lung Cancer | WGS | Preoperative treatment naïve | II | 163 | 0.578 | 0.526 | 0.513 | −0.534 |
| CGPLLU147 | Lung Cancer | WGS | Preoperative treatment naïve | III | 166 | 0.953 | 0.919 | 0.939 | −0.912 |
| CGPLLU206 | Lung Cancer | WGS | Preoperative treatment naïve | III | 158 | 0.488 | 0.343 | 0.460 | −0.481 |

TABLE 6

APPENDIX F: Monitoring response to therapy using whole genome analyses of cfDNA fragmentation profiles and targeted mutations analyses

| Patient | Patient Type | Analysis Type | Timepoint | Stage | Progression-free Survival (months) | Correlation or Fragment Ratio Profile to Median Fragment Ratio Profile of Healthy Individuals | Correlation of Fragment Ratio Profile to Lymphocyte Nucleosome Distances | Targeted Mutation | Maximum Mutant Allele Fraction |
|---|---|---|---|---|---|---|---|---|---|
| CGPLLU14 | Lung Cancer | Targeted Mutation Analysis and WGS | Pre-treatment, Day −38 | IV | 15.4 | 0.941 | −0.841 | EGFR 861L>Q | 0.89% |
| CGPLLU14 | Lung Cancer | Targeted Mutation Analysis and WGS | Pre-treatment, Day −16 | IV | 15.4 | 0.933 | −0.833 | EGFR 861L>Q | 0.18% |
| CGPLLU14 | Lung Cancer | Targeted Mutation Analysis and WGS | Pre-treatment, Day 3 | IV | 15.4 | 0.908 | −0.814 | EGFR 719G>S | 0.49% |
| CGPLLU14 | Lung Cancer | Targeted Mutation Analysis and WGS | Pre-treatment, Day 0 | IV | 15.4 | 0.883 | −0.752 | EGFR 861L>Q | 1.39% |
| CGPLLU14 | Lung Cancer | Targeted Mutation Analysis and WGS | Post-treatment, Day 0.33 | IV | 15.4 | 0.820 | −0.692 | EGFR 719G>S | 1.05% |
| CGPLLU14 | Lung Cancer | Targeted Mutation Analysis and WGS | Post-treatment, Day 7 | IV | 15.4 | 0.927 | −0.887 | EGFR 861L>Q | 0.00% |
| CGPLLU88 | Lung Cancer | Targeted Mutation Analysis and WGS | Pre-treatment, Day 0 | IV | 18.0 | 0.657 | −0.584 | EGFR 745KELREA>T | 9.06% |
| CGPLLU88 | Lung Cancer | Targeted Mutation Analysis and WGS | Post-treatment, Day 7 | IV | 18.0 | 0.939 | −0.799 | EGFR 790T>M | 0.15% |
| CGPLLU88 | Lung Cancer | Targeted Mutation Analysis and WGS | Post-treatment, Day 297 | IV | 18.0 | 0.946 | −0.869 | EGFR 745KELREA>T | 0.93% |
| CGPLLU244 | Lung Cancer | Targeted Mutation Analysis and WGS | Pre-treatment, Day −7 | IV | 1.2 | 0.850 | −0.706 | EGFR 858L>R | 4.98% |
| CGPLLU244 | Lung Cancer | Targeted Mutation Analysis and WGS | Pre-treatment, Day −1 | IV | 1.2 | 0.867 | −0.764 | EGFR 62L>R | 3.41% |
| CGPLLU244 | Lung Cancer | Targeted Mutation Analysis and WGS | Post-treatment, Day 6 | IV | 1.2 | 0.703 | −0.639 | EGFR 858L>R | 5.57% |

TABLE 6-continued

APPENDIX F: Monitoring response to therapy using whole genome analyses of cfDNA fragmentation profiles and targeted mutations analyses

| Patient | Patient Type | Analysis Type | Timepoint | Stage | Progression-free Survival (months) | Correlation or Fragment Ratio Profile to Median Fragment Ratio Profile of Healthy Individuals | Correlation of Fragment Ratio Profile to Lymphocyte Nucleosome Distances | Targeted Mutation | Maximum Mutant Allele Fraction |
|---|---|---|---|---|---|---|---|---|---|
| GGPLLU244 | Lung Cancer | Targeted Mutation Analysis and WGS | Post-treatment, Day 82 | IV | 1.2 | 0.659 | −0.660 | EGFR 858L>R | 11.80% |
| CGPLLU245 | Lung Cancer | Targeted Mutation Analysis and WGS | Pre-treatment, Day −32 | IV | 1.7 | 0.871 | −0.724 | EGFR 745KELREA>K | 10.60% |
| CGPLLU245 | Lung Cancer | Targeted Mutation Analysis and WGS | Pre-treatment, Day 0 | IV | 1.7 | 0.736 | −0.608 | EGFR 745KELREA>K | 14.10% |
| CGPLLU245 | Lung Cancer | Targeted Mutation Analysis and WGS | Post-treatment, Day 7 | IV | 1.7 | 0.731 | −0.559 | EGFR 745KELREA>K | 6.56% |
| CGPLLU245 | Lung Cancer | Targeted Mutation Analysis and WGS | Post-treatment, Day 21 | IV | 1.7 | 0.613 | −0.426 | EGFR 745KELREA>K | 10.69% |
| CGPLLU246 | Lung Cancer | Targeted Mutation Analysis and WGS | Pre-treatment, Day −21 | IV | 1.3 | 0.897 | −0.757 | EGFR 790T>M | 0.49% |
| CGPLLU246 | Lung Cancer | Targeted Mutation Analysis and WGS | Pre-treatment, Day 0 | IV | 1.3 | 0.469 | 0.376 | EGFR 858L>R | 6.17% |
| CGPLLU246 | Lung Cancer | Targeted Mutation Analysis and WGS | Post-treatment, Day 9 | IV | 1.3 | 0.874 | −0.746 | EGFR 858L>R | 1.72% |
| CGPLLU246 | Lung Cancer | Targeted Mutation Analysis and WGS | Post-treatment, Day 42 | IV | 1.3 | 0.775 | −0.665 | EGFR 858L>R | 5.29% |
| CGPLLU86 | Lung Cancer | Targeted Mutation Analysis and WGS | Pre-treatment, Day 0 | IV | 12.4 | 0.817 | −0.630 | EGFR 746ELREATS>D | 0.00% |
| CGPLLU86 | Lung Cancer | Targeted Mutation Analysis and WGS | Post-treatment, Day 0.5 | IV | 12.4 | 0.916 | −0.811 | EGER 746ELREATS>D | 0.19% |
| CGPLLU86 | Lung Cancer | Targeted Mutation Analysis and WGS | Post-treatment, Day 7 | IV | 12.4 | 0.859 | −0.694 | EGFR 746ELREATS>D | 0.00% |
| CGPLLU86 | Lung Cancer | Targeted Mutation Analysis and WGS | Post-treatment, Day 17 | IV | 12.4 | 0.932 | −0.848 | EGFR 746ELREATS>D | 0.00% |
| CGPLLU89 | Lung Cancer | Targeted Mutation Analysis and WGS | Pre-treatment, Day 0 | IV | 6.7 | 0.864 | −0.729 | EGFR 747LREATS>— | 0.42% |
| CGPLLU89 | Lung Cancer | Targeted Mutation Analysis and WGS | Post-treatment, Day 7 | IV | 6.7 | 0.908 | −0.803 | EGFR 747LREATS>— | 0.20% |
| CGPLLU89 | Lung Cancer | Targeted Mutation Analysis and WGS | Post-treatment, Day 22 | IV | 6.7 | 0.853 | −0.881 | EGFR 747LREATS>— | 0.00% |
| CGLU316 | Lung Cancer | Targeted Mutation Analysis and WGS | Pre-treatment, Day −53 | IV | 1.4 | 0.331 | −0.351 | EGFR L861Q | 15.72% |
| CGLU316 | Lung Cancer | Targeted Mutation Analysis and WGS | Pre-treatment, Day −4 | IV | 1.4 | 0.225 | −0.253 | EGFR L861Q | 45.67% |
| CGLU316 | Lung Cancer | Targeted Mutation Analysis and WGS | Post-treatment, Day 18 | IV | 1.4 | 0.336 | −0.364 | EGFR G719A | 33.38% |
| CGLU316 | Lung Cancer | Targeted Mutation Analysis and WGS | Post-treatment, Day 87 | IV | 1.4 | 0.340 | −0.364 | EGFR L861Q | 66.01% |
| CGLU344 | Lung Cancer | Targeted Mutation Analysis and WGS | Pre-treatment, Day −21 | IV | Ongoing | 0.935 | −0.818 | EGFR E746_A750del | 0.00% |
| CGLU344 | Lung Cancer | Targeted Mutation Analysis and WGS | Pre-treatment, Day 0 | IV | Ongoing | 0.919 | −0.774 | EGFR E746_A750del | 0.22% |
| CGLU344 | Lung Cancer | Targeted Mutation Analysis and WGS | Post-treatment, Day 0.1675 | IV | Ongoing | 0.953 | −0.860 | EGFR E746_A750del | 0.40% |
| CGLU344 | Lung Cancer | Targeted Mutation Analysis and WGS | Post-treatment, Day 59 | IV | Ongoing | 0.944 | −0.832 | EGFR E746_A750del | 0.00% |
| CGLU369 | Lung Cancer | Targeted Mutation Analysis and WGS | Pre-treatment, Day −2 | IV | 7.5 | 0.825 | −0.826 | EGFR L858R | 20.61% |
| CGLU369 | Lung Cancer | Targeted Mutation Analysis and WGS | Post-treatment, Day 12 | IV | 7.5 | 0.950 | −0.903 | EGFR L858R | 0.22% |
| CGLU369 | Lung Cancer | Targeted Mutation Analysis and WGS | Post-treatment, Day 68 | IV | 7.5 | 0.945 | −0.889 | EGFR L858R | 0.16% |
| CGLU369 | Lung Cancer | Targeted Mutation Analysis and WGS | Post-treatment, Day 110 | IV | 7.5 | 0.886 | −0.883 | EGFR L858R | 0.10% |
| CGLU373 | Lung Cancer | Targeted Mutation Analysis and WGS | Pre-treatment, Day −2 | IV | Ongoing | 0.922 | −0.804 | EGFR E746_A750del | 0.82% |
| CGLU373 | Lung Cancer | Targeted Mutation Analysis and WGS | Post-treatment, Day 0.125 | IV | Ongoing | 0.959 | −0.853 | EGFR E746_A750del | 0.00% |
| CGLU373 | Lung Cancer | Targeted Mutation Analysis and WGS | Post-treatment, Day 7 | IV | Ongoing | 0.967 | −0.886 | EGFR E746_A750del | 0.15% |
| CGLU373 | Lung Cancer | Targeted Mutation Analysis and WGS | Post-treatment, Day 47 | IV | Ongoing | 0.951 | −0.890 | EGFR E746_A750del | 0.00% |
| CGPLLU13 | Lung Cancer | Targeted Mutation Analysis and WGS | Pre-treatment, Day −2 | IV | 1.5 | 0.425 | −0.400 | EGFR E746_A750del | 7.66% |
| CGPLLU13 | Lung Cancer | Targeted Mutation Analysis and WGS | Post-treatment, Day 5 | IV | 1.5 | 0.272 | −0.257 | EGFR E746_A750del | 13.10% |

TABLE 6-continued

APPENDIX F: Monitoring response to therapy using whole genome analyses of cfDNA fragmentation profiles and targeted mutations analyses

| Patient | Patient Type | Analysis Type | Timepoint | Stage | Progression-free Survival (months) | Correlation or Fragment Ratio Profile to Median Fragment Ratio Profile of Healthy Individuals | Correlation of Fragment Ratio Profile to Lymphocyte Nucleosome Distances | Targeted Mutation | Maximum Mutant Allele Fraction |
|---|---|---|---|---|---|---|---|---|---|
| CGPLLU13 | Lung Cancer | Targeted Mutation Analysis and WGS | Post-treatment, Day 28 | IV | 1.5 | 0.584 | −0.536 | EGFR E746_A750del | 6.09% |
| CGPLLU13 | Lung Cancer | Targeted Mutation Analysis and WGS | Post-treatment, Day 91 | IV | 1.5 | 0.530 | −0.513 | EGFR E746_A750del | 9.28% |
| CGPLLU264 | Lung Cancer | Targeted Mutation Analysis and WGS | Pre-treatment, Day −1 | IV | Ongoing | 0.946 | −0.824 | EGFR D761N | 0.00% |
| CGPLLU264 | Lung Cancer | Targeted Mutation Analysis and WGS | Post-treatment, Day 6 | IV | Ongoing | 0.927 | −0.788 | EGFR D761N | 0.16% |
| CGPLLU264 | Lung Cancer | Targeted Mutation Analysis and WGS | Post-treatment, Day 27 | IV | Ongoing | 0.962 | −0.856 | EGFR D761N | 0.00% |
| CGPLLU264 | Lung Cancer | Targeted Mutation Analysis and WGS | Post-treatment, Day 69 | IV | Ongoing | 0.960 | −0.894 | EGFR D76IN | 0.00% |
| CGPLLU265 | Lung Cancer | Targeted Mutation Analysis and WGS | Pre-treatment, Day 0 | IV | Ongoing | 0.953 | −0.859 | EGFR L858R | 0.21% |
| CGPLLU265 | Lung Cancer | Targeted Mutation Analysis and WGS | Post-treatment, Day 3 | IV | Ongoing | 0.949 | −0.842 | EGFR L858R | 0.21% |
| CGPLLU265 | Lung Cancer | Targeted Mutation Analysis and WGS | Post-treatment, Day 7 | IV | Ongoing | 0.955 | −0.844 | EGFR T790M | 0.21% |
| CGPLLU265 | Lung Cancer | Targeted Mutation Analysis and WGS | Post-treatment, Day 84 | IV | Ongoing | 0.946 | −0.825 | EGFR L858R | 0.00% |
| CGPLLU266 | Lung Cancer | Targeted Mutation Analysis and WGS | Pre-treatment, Day 0 | IV | 9.6 | 0.961 | −0.904 | NA | 0.00% |
| CGPLLU266 | Lung Cancer | Targeted Mutation Analysis and WGS | Post-treatment, Day 16 | IV | 9.6 | 0.959 | −0.886 | NA | 0.00% |
| CGPLLU266 | Lung Cancer | Targeted Mutation Analysis and WGS | Post-treatment, Day 83 | IV | 9.6 | 0.961 | −0.880 | NA | 0.00% |
| CGPLLU266 | Lung Cancer | Targeted Mutation Analysis and WGS | Post-treatment, Day 328 | IV | 9.6 | 0.958 | −0.855 | NA | 0.00% |
| CGPLLU267 | Lung Cancer | Targeted Mutation Analysis and WGS | Pre-treatment, Lay −1 | IV | 3.9 | 0.919 | −0.863 | EGFR L858R | 1.93% |
| CGPLLU267 | Lung Cancer | Targeted Mutation Analysis and WGS | Post-treatment, Day 34 | IV | 3.9 | 0.363 | −0.889 | EGFR L858R | 0.14% |
| CGPLLU267 | Lung Cancer | Targeted Mutation Analysis and WGS | Post-treatment, Day 90 | IV | 3.9 | 0.962 | −0.876 | EGFR L858R | 0.38% |
| CGPLLU269 | Lung Cancer | Targeted Mutation Analysis and WGS | Pre-treatment, Day 0 | IV | Ongoing | 0.951 | −0.864 | EGFR L858R | 0.10% |
| CGPLLU269 | Lung Cancer | Targeted Mutation Analysis and WGS | Post-treatment, Day 9 | IV | Ongoing | 0.941 | −0.894 | EGFR L858R | 0.00% |
| CGPLLU269 | Lung Cancer | Targeted Mutation Analysis and WGS | Post-treatment, Day 28 | IV | Ongoing | 0.957 | −0.876 | EGFR L858R | 0.00% |
| CGPLLU271 | Lung Cancer | Targeted Mutation Analysis and WGS | Pre-treatment, Day 0 | IV | 8.2 | 0.371 | −0.284 | EGFR E746_A750del | 3.36% |
| CGPLLU271 | Lung Cancer | Targeted Mutation Analysis and WGS | Post-treatment, Day 6 | IV | 8.2 | 0.947 | 0.826 | EGFR E746_A750del | 0.17% |
| CGPLLU271 | Lung Cancer | Targeted Mutation Analysis and WGS | Post-treatment, Day 20 | IV | 8.2 | 0.952 | −0.839 | EGFR E746_A750del | 0.00% |
| CGPLLU271 | Lung Cancer | Targeted Mutation Analysis and WGS | Post-treatment, Day 104 | IV | 8.2 | 0.944 | −0.810 | EGFR E746_A750del | 0.00% |
| CGPLLU271 | Lung Cancer | Targeted Mutation Analysis and WGS | Post-treatment, Day 259 | IV | 8.2 | 0.950 | −0.831 | EGFR E746_A750del | 0.44% |
| CGPLLU43 | Lung Cancer | Targeted Mutation Analysis and WGS | Pre-treatment, Day −1 | IV | Ongoing | 0.944 | −0.903 | NA | 0.00% |
| CGPLLU43 | Lung Cancer | Targeted Mutation Analysis and WGS | Post-treatment, Day 6 | IV | Ongoing | 0.956 | −0.899 | NA | 0.00% |
| CGPLLU43 | Lung Cancer | Targeted Mutation Analysis and WGS | Post-treatment, Day 27 | IV | Ongoing | 0.959 | −0.901 | NA | 0.00% |
| CGPLLU43 | Lung Cancer | Targeted Mutation Analysis and WGS | Post-treatment, Day 83 | IV | Ongoing | 0.965 | −0.896 | NA | 0.00% |

TABLE 7

APPENDIX G: Whole genome cfDNA analyses in healthy individuals and cancer patients

| Patient | Patient Type | Analysis Type | Timepoint | Stage at Diagnosis | Median cfDNA Fragment Size (bp) | Correlation of Fragment Ratio Profile to Median Fragment Ratio Profile of Healthy Individuals |
|---|---|---|---|---|---|---|
| CGCRC291 | Colorectal Cancer | Targeted Mutation Analysis and WGS | Preoperative treatment naïve | V | 163 | 0.1972 |
| CGCRC292 | Colorectal Cancer | Targeted Mutation Analysis and WGS | Preoperative treatment naïve | V | 168 | 0.7804 |
| CGCRC293 | Colorectal Cancer | Targeted Mutation Analysis and WGS | Preoperative treatment naïve | V | 166 | 0.9335 |
| CGCRC294 | Colorectal Cancer | Targeted Mutation Analysis and WGS | Preoperative treatment naïve | II | 166 | 0.6531 |
| CGCRC295 | Colorectal Cancer | Targeted Mutation Analysis and WGS | Preoperative treatment naïve | II | 166 | 0.8161 |
| CGCRC299 | Colorectal Cancer | Targeted Mutation Analysis and WGS | Preoperative treatment naïve | I | 162 | 0.7325 |
| CGCRC300 | Colorectal Cancer | Targeted Mutation Analysis and WGS | Preoperative treatment naïve | I | 167 | 0.9382 |
| CGCRC301 | Colorectal Cancer | Targeted Mutation Analysis and WGS | Preoperative treatment naïve | I | 165 | 0.8252 |
| CGCRC302 | Colorectal Cancer | Targeted Mutation Analysis and WGS | Preoperative treatment naïve | II | 163 | 0.7499 |
| CGCRC304 | Colorectal Cancer | Targeted Mutation Analysis and WGS | Preoperative treatment naïve | II | 162 | 0.4642 |
| CGCRC305 | Colorectal Cancer | Targeted Mutation Analysis and WGS | Preoperative treatment naïve | II | 165 | 0.8909 |
| CGCRG306 | Colorectal Cancer | Targeted Mutation Analysis and WGS | Preoperative treatment naïve | II | 165 | 0.8523 |
| CGCRC307 | Colorectal Cancer | Targeted Mutation Analysis and WGS | Preoperative treatment naïve | II | 165 | 0.9140 |
| CGCRC306 | Colorectal Cancer | Targeted Mutation Analysis and WGS | Preoperative treatment naïve | III | 165 | 0.8734 |
| CGCRC311 | Colorectal Cancer | Targeted Mutation Analysis and WGS | Preoperative treatment naïve | I | 166 | 0.8535 |
| CGCRC315 | Colorectal Cancer | Targeted Mutation Analysis and WGS | Preoperative treatment naïve | III | 167 | 0.8083 |
| CGCRC316 | Colorectal Cancer | Targeted Mutation Analysis and WGS | Preoperative treatment naïve | III | 161 | 0.1546 |
| CGCRC317 | Colorectal Cancer | Targeted Mutation Analysis and WGS | Preoperative treatment naïve | III | 163 | 0.6242 |
| CGCRC318 | Colorectal Cancer | Targeted Mutation Analysis and WGS | Preoperative treatment naïve | I | 166 | 0.8824 |
| CGCRC319 | Colorectal Cancer | Targeted Mutation Analysis and WGS | Preoperative treatment naïve | III | 160 | 0.5979 |
| CGCRC320 | Colorectal Cancer | Targeted Mutation Analysis and WGS | Preoperative treatment naïve | I | 167 | 0.7949 |
| CGCRC321 | Colorectal Cancer | Targeted Mutation Analysis and WGS | Preoperative treatment naïve | I | 164 | 0.7604 |
| CGCRC333 | Colorectal Cancer | Targeted Mutation Analysis and WGS | Preoperative treatment naïve | V | 163 | 0.4263 |
| CGCRC335 | Colorectal Cancer | Targeted Mutation Analysis and WGS | Preoperative treatment naïve | V | 162 | 0.6466 |
| CGCRC338 | Colorectal Cancer | Targeted Mutation Analysis and WGS | Preoperative treatment naïve | V | 162 | 0.7740 |
| CGCRC341 | Colorectal Cancer | Targeted Mutation Analysis and WGS | Preoperative treatment naïve | V | 164 | 0.8995 |
| CGCRC342 | Colorectal Cancer | Targeted Mutation Analysis and WGS | Preoperative treatment naïve | V | 158 | 0.2524 |
| CGPLBR100 | Breast Cancer | Targeted Mutation Analysis and WGS | Preoperative treatment naïve | III | 166 | 0.9440 |
| CGPLBR101 | Breast Cancer | Targeted Mutation Analysis and WGS | Preoperative treatment naïve | II | 169 | 0.8664 |
| CGPLBR102 | Breast Cancer | Targeted Mutation Analysis and WGS | Preoperative treatment naïve | II | 169 | 0.9617 |
| CGPLBR103 | Breast Cancer | Targeted Mutation Analysis and WGS | Preoperative treatment naïve | II | 168 | 0.9498 |
| CGPLBR104 | Breast Cancer | Targeted Mutation Analysis and WGS | Preoperative treatment naïve | II | 167 | 0.8490 |
| CGPLBR12 | Breast Cancer | WGS | Preoperative treatment naïve | III | 164 | 0.8350 |
| CGPLBR18 | Breast Cancer | WGS | Preoperative treatment naïve | III | 163 | 0.8411 |

TABLE 7-continued

APPENDIX G: Whole genome cfDNA analyses in healthy individuals and cancer patients

| | | | | | | |
|---|---|---|---|---|---|---|
| CGPLBR23 | Breast Cancer | WGS | Preoperative treatment naïve | II | 166 | 0.9714 |
| CGPLBR24 | Breast Cancer | WGS | Preoperative treatment naïve | II | 156 | 0.8402 |
| CGPLBR26 | Breast Cancer | WGS | Preoperative treatment naïve | III | 165 | 0.9584 |
| CGPLBR30 | Breast Cancer | WGS | Preoperative treatment naïve | II | 161 | 0.6951 |
| CGPLBR31 | Breast Cancer | WGS | Preoperative treatment naïve | II | 167 | 0.9719 |
| CGPLBR32 | Breast Cancer | WGS | Preoperative treatment naïve | II | 165 | 0.9590 |
| CGPLBR33 | Breast Cancer | WGS | Preoperative treatment naïve | II | 166 | 0.9706 |
| CGPLBR34 | Breast Cancer | WGS | Preoperative treatment naïve | II | 163 | 0.3735 |
| CGPLBR35 | Breast Cancer | WGS | Preoperative treatment naïve | II | 168 | 0.9655 |
| CGPLBP36 | Breast Cancer | WGS | Preoperative treatment naïve | II | 169 | 0.9394 |
| CGPLBR37 | Breast Cancer | WGS | Preoperative treatment naïve | II | 167 | 0.9591 |
| CGPLBR38 | Breast Cancer | Targeted Mutation Analysis and WGS | Preoperative treatment naïve | I | 165 | 0.9105 |
| CGPLBR40 | Breast Cancer | Targeted Mutation Analysis and WGS | Preoperative treatment naïve | III | 167 | 0.9273 |
| CGPLBR41 | Breast Cancer | Targeted Mutation Analysis and WGS | Preoperative treatment naïve | III | 168 | 0.9626 |
| CGPLBR45 | Breast Cancer | WGS | Preoperative treatment naïve | II | 164 | 0.9615 |
| CGPLBR46 | Breast Cancer | WGS | Preoperative treatment naïve | III | 168 | 0.9322 |
| CGPLBR47 | Breast Cancer | WGS | Preoperative treatment naïve | I | 166 | 0.9461 |
| CGPLBR48 | Breast Cancer | Targeted Mutation Analysis and WGS | Preoperative treatment naïve | II | 169 | 0.7686 |
| CGPLBR49 | Breast Cancer | Targeted Mutation Analysis and WGS | Preoperative treatment naïve | II | 171 | 0.8867 |
| CGPLBR50 | Breast Cancer | WGS | Preoperative treatment naïve | I | 160 | 0.8593 |
| CGPLBR51 | Breast Cancer | WGS | Preoperative treatment naïve | II | 165 | 0.9353 |
| CGPLBR52 | Breast Cancer | WGS | Preoperative treatment naïve | III | 164 | 0.8688 |
| CGPLBR55 | Breast Cancer | Targeted Mutation Analysis and WGS | Preoperative treatment naïve | III | 165 | 0.9634 |
| CGPLBR56 | Breast Cancer | WGS | Preoperative treatment naïve | II | 163 | 0.9459 |
| CGPLBR57 | Breast Cancer | Targeted Mutation Analysis and WGS | Preoperative treatment naïve | III | 166 | 0.9672 |
| CGPLBR59 | Breast Cancer | Targeted Mutation Analysis and WGS | Preoperative treatment naïve | I | 168 | 0.9438 |
| CGPLBR60 | Breast Cancer | WGS | Preoperative treatment naïve | II | 167 | 0.9479 |
| CGPLBR61 | Breast Cancer | Targeted Mutation Analysis and WGS | Preoperative treatment naïve | II | 165 | 0.9611 |
| CGPLBR63 | Breast Cancer | Targeted Mutation Analysis and WGS | Preoperative treatment naïve | II | 168 | 0.9555 |
| CGPLBR65 | Breast Cancer | WGS | Preoperative treatment naïve | II | 167 | 0.9506 |
| CGPLBR68 | Breast Cancer | Targeted Mutation Analysis and WGS | Preoperative treatment naïve | III | 163 | 0.9154 |
| CGPLBR69 | Breast Cancer | Targeted Mutation Analysis and WGS | Preoperative treatment naïve | II | 165 | 0.9460 |
| CGPLBR70 | Breast Cancer | Targeted Mutation Analysis and WGS | Preoperative treatment naïve | II | 168 | 0.9651 |
| CGPLBR71 | Breast Cancer | Targeted Mutation Analysis and WGS | Preoperative treatment naïve | II | 165 | 0.9577 |
| CGPLBR72 | Breast Cancer | Targeted Mutation Analysis and WGS | Preoperative treatment naïve | II | 167 | 0.9786 |
| CGPLBR73 | Breast Cancer | Targeted Mutation Analysis and WGS | Preoperative treatment naïve | II | 167 | 0.9576 |
| CGPLBR76 | Breast Cancer | Targeted Mutation Analysis and WGS | Preoperative treatment naïve | II | 170 | 0.9410 |
| CGPLBR81 | Breast Cancer | WGS | Preoperative treatment naïve | II | 170 | 0.9043 |
| CGPLBR82 | Breast Cancer | Targeted Mutation Analysis and WGS | Preoperative treatment naïve | I | 166 | 0.9254 |

TABLE 7-continued

| APPENDIX G: Whole genome cfDNA analyses in healthy individuals and cancer patients ||||||| 
|---|---|---|---|---|---|---|
| CGPLBR83 | Breast Cancer | Targeted Mutation Analysis and WGS | Preoperative treatment naive | II | 169 | 0.9451 |
| CGPLBR84 | Breast Cancer | WGS | Preoperative treatment naive | III | 169 | 0.9315 |
| CGPLBR87 | Breast Cancer | Targeted Mutation Analysis and WGS | Preoperative treatment naive | II | 166 | 0.9154 |
| CGPLBR88 | Breast Cancer | Targeted Mutation Analysis and WGS | Preoperative treatment naive | II | 169 | 0.9370 |
| CGPLBR90 | Breast Cancer | WGS | Preoperative treatment naive | II | 169 | 0.9002 |
| CGPLBR91 | Breast Cancer | Targeted Mutation Analysis and WGS | Preoperative treatment naive | III | 164 | 0.7955 |
| CGPLBR92 | Breast Cancer | Targeted Mutation Analysis and WGS | Preoperative treatment naive | II | 162 | 0.6774 |
| CGPLBR93 | Breast Cancer | Targeted Mutation Analysis and WGS | Preoperative treatment naive | II | 164 | 0.8773 |
| CGPLH189 | Healthy | WGS | Preoperative treatment naive | NA | 168 | 0.9325 |
| CGPLH190 | Healthy | WGS | Preoperative treatment naive | NA | 167 | 0.9433 |
| CGPLH192 | Healthy | WGS | Preoperative treatment naive | NA | 167 | 0.9646 |
| CGPLH193 | Healthy | WGS | Preoperative treatment naive | NA | 167 | 0.5423 |
| CGPLH194 | Healthy | WGS | Preoperative treatment naive | NA | 168 | 0.9567 |
| CGPLH196 | Healthy | WGS | Preoperative treatment naive | NA | 167 | 0.9709 |
| CGPLH197 | Healthy | WGS | Preoperative treatment naive | NA | 166 | 0.9605 |
| CGPLH198 | Healthy | WGS | Preoperative treatment naive | NA | 167 | 0.9238 |
| CGPLH199 | Healthy | WGS | Preoperative treatment naive | NA | 165 | 0.9618 |
| CGPLH200 | Healthy | WGS | Preoperative treatment naive | NA | 167 | 0.9183 |
| CGPLH201 | Healthy | WGS | Preoperative treatment naive | NA | 168 | 0.9548 |
| CGPLH202 | Healthy | WGS | Preoperative treatment naive | NA | 168 | 0.9471 |
| CGPLH203 | Healthy | WGS | Preoperative treatment naive | NA | 167 | 0.9534 |
| CGPLH205 | Healthy | WGS | Preoperative treatment naive | NA | 168 | 0.9075 |
| CGPLH208 | Healthy | WGS | Preoperative treatment naive | NA | 168 | 0.9422 |
| CGPLH209 | Healthy | WGS | Preoperative treatment naive | NA | 169 | 0.9556 |
| CGPLH210 | Healthy | WGS | Preoperative treatment naive | NA | 169 | 0.9447 |
| CGPLH211 | Healthy | WGS | Preoperative treatment naive | NA | 169 | 0.5538 |
| CGPLH300 | Healthy | WGS | Preoperative treatment naive | NA | 168 | 0.9019 |
| CGPLH307 | Healthy | WGS | Preoperative treatment naive | NA | 168 | 0.9576 |
| CGPLH308 | Healthy | WGS | Preoperative treatment naive | NA | 168 | 0.9481 |
| CGPLH309 | Healthy | WGS | Preoperative treatment naive | NA | 168 | 0.9672 |
| CGPLN310 | Healthy | WGS | Preoperative treatment naive | NA | 165 | 0.9547 |
| CGPLH311 | Healthy | WGS | Preoperative treatment naive | NA | 167 | 0.9302 |
| CGPLH314 | Healthy | WGS | Preoperative treatment naive | NA | 167 | 0.9482 |
| CGPLH315 | Healthy | WGS | Preoperative treatment naive | NA | 167 | 0.8659 |
| CGPLH316 | Healthy | WGS | Preoperative treatment naive | NA | 165 | 0.9374 |
| CGPLH317 | Healthy | WGS | Preoperative treatment naive | NA | 169 | 0.9542 |
| CGPLH319 | Healthy | WGS | Preoperative treatment naive | NA | 167 | 0.9578 |
| CGPLR320 | Healthy | WGS | Preoperative treatment naive | NA | 164 | 0.8913 |
| CGPLH322 | Healthy | WGS | Preoperative treatment naive | NA | 167 | 0.8751 |

TABLE 7-continued

APPENDIX G: Whole genome cfDNA analyses in healthy individuals and cancer patients

| | | | | | | |
|---|---|---|---|---|---|---|
| CGPLH324 | Healthy | WGS | Preoperative treatment naïve | NA | 169 | 0.9519 |
| CGPLH325 | Healthy | WGS | Preoperative treatment naïve | NA | 167 | 0.9124 |
| CGPLH326 | Healthy | WGS | Preoperative treatment naïve | NA | 166 | 0.9574 |
| CGPLH327 | Healthy | WGS | Preoperative treatment naïve | NA | 168 | 0.9533 |
| CGPLH328 | Healthy | WGS | Preoperative treatment naïve | NA | 166 | 0.9643 |
| CGPLH329 | Healthy | WGS | Preoperative treatment naïve | NA | 167 | 0.9609 |
| CGPLH330 | Healthy | WGS | Preoperative treatment naïve | NA | 167 | 0.9118 |
| CGPLH331 | Healthy | WGS | Preoperative treatment naïve | NA | 166 | 0.9679 |
| CGPLH333 | Healthy | WGS | Preoperative treatment naïve | NA | 169 | 0.9474 |
| CGPLH335 | Healthy | WGS | Preoperative treatment naïve | NA | 167 | 0.8909 |
| CGPLH336 | Healthy | WGS | Preoperative treatment naïve | NA | 169 | 0.9248 |
| CGPLH337 | Healthy | WGS | Preoperative treatment naïve | NA | 167 | 0.9533 |
| CGPLH338 | Healthy | WGS | Preoperative treatment naïve | NA | 165 | 0.9388 |
| CGPLH339 | Healthy | WGS | Preoperative treatment naïve | NA | 167 | 0.9396 |
| CGPLH340 | Healthy | WGS | Preoperative treatment naïve | NA | 167 | 0.9488 |
| CGPLH341 | Healthy | WGS | Preoperative treatment naïve | NA | 166 | 0.9533 |
| CGPLH342 | Healthy | WGS | Preoperative treatment naïve | NA | 166 | 0.7858 |
| CGPLH343 | Healthy | WGS | Preoperative treatment naïve | NA | 167 | 0.9421 |
| CGPLH344 | Healthy | WGS | Preoperative treatment naïve | NA | 169 | 0.9192 |
| CGPLH345 | Healthy | WGS | Preoperative treatment naïve | NA | 169 | 0.9345 |
| CGPLH346 | Healthy | WGS | Preoperative treatment naïve | NA | 169 | 0.9475 |
| CGPLH350 | Healthy | WGS | Preoperative treatment naïve | NA | 171 | 0.9570 |
| CGPLH351 | Healthy | WGS | Preoperative treatment naïve | NA | 166 | 0.8176 |
| CGPLH352 | Healthy | WGS | Preoperative treatment naïve | NA | 168 | 0.9521 |
| CGPLH353 | Healthy | WGS | Preoperative treatment naïve | NA | 167 | 0.9435 |
| CGPLH354 | Healthy | WGS | Preoperative treatment naïve | NA | 168 | 0.9481 |
| CGPLH355 | Healthy | WGS | Preoperative treatment naïve | NA | 167 | 0.9613 |
| CGPLH356 | Healthy | WGS | Preoperative treatment naïve | NA | 165 | 0.9474 |
| CGPLH357 | Healthy | WGS | Preoperative treatment naïve | NA | 167 | 0.9255 |
| CGPLH358 | Healthy | WGS | Preoperative treatment naïve | NA | 167 | 0.7777 |
| CGPLH360 | Healthy | WGS | Preoperative treatment naïve | NA | 166 | 0.8500 |
| CGPLH361 | Healthy | WGS | Preoperative treatment naïve | NA | 167 | 0.9261 |
| CGPLH362 | Healthy | WGS | Preoperative treatment naïve | NA | 167 | 0.9236 |
| CGPLH363 | Healthy | WGS | Preoperative treatment naïve | NA | 167 | 0.9488 |
| CGPLH364 | Healthy | WGS | Preoperative treatment naïve | NA | 168 | 0.9311 |
| CGPLH365 | Healthy | WGS | Preoperative treatment naïve | NA | 165 | 0.9371 |
| CGPLH366 | Healthy | WGS | Preoperative treatment naïve | NA | 167 | 0.9536 |
| CGPLH367 | Healthy | WGS | Preoperative treatment naïve | NA | 166 | 0.8748 |
| CGPLH368 | Healthy | WGS | Preoperative treatment naïve | NA | 169 | 0.9490 |

TABLE 7-continued

APPENDIX G: Whole genome cfDNA analyses in healthy individuals and cancer patients

| | | | | | | |
|---|---|---|---|---|---|---|
| CGPLH369 | Healthy | WGS | Preoperative treatment naive | NA | 167 | 0.9428 |
| CGPLH370 | Healthy | WGS | Preoperative treatment naive | NA | 167 | 0.9642 |
| CGPLH371 | Healthy | WGS | Preoperative treatment naive | NA | 168 | 0.9621 |
| CGPLH380 | Healthy | WGS | Preoperative treatment naive | NA | 170 | 0.9662 |
| CGPLH381 | Healthy | WGS | Preoperative treatment naive | NA | 169 | 0.9541 |
| CGPLH382 | Healthy | WGS | Preoperative treatment naive | NA | 167 | 0.9380 |
| CGPLH383 | Healthy | WGS | Preoperative treatment naive | NA | 168 | 0.9700 |
| CGPLH384 | Healthy | WGS | Preoperative treatment naive | NA | 169 | 0.8061 |
| CGPLH385 | Healthy | WGS | Preoperative treatment naive | NA | 167 | 0.8666 |
| CGPLH386 | Healthy | WGS | Preoperative treatment naive | NA | 167 | 0.6920 |
| CGPLH387 | Healthy | WGS | Preoperative treatment naive | NA | 169 | 0.9583 |
| CGPLH388 | Healthy | WGS | Preoperative treatment naive | NA | 167 | 0.9348 |
| CGPLH389 | Healthy | WGS | Preoperative treatment naive | NA | 168 | 0.9409 |
| CGPLH390 | Healthy | WGS | Preoperative treatment naive | NA | 167 | 0.9216 |
| CGPLH391 | Healthy | WGS | Preoperative treatment naive | NA | 166 | 0.9334 |
| CGPLH392 | Healthy | WGS | Preoperative treatment naive | NA | 167 | 0.9165 |
| CGPLH393 | Healthy | WGS | Preoperative treatment naive | NA | 169 | 0.9256 |
| CGPLH394 | Healthy | WGS | Preoperative treatment naive | NA | 167 | 0.9257 |
| CGPLH395 | Healthy | WGS | Preoperative treatment naive | NA | 166 | 0.8611 |
| CGPLH396 | Healthy | WGS | Preoperative treatment naive | NA | 167 | 0.7884 |
| CGPLH398 | Healthy | WGS | Preoperative treatment naive | NA | 167 | 0.9463 |
| CGPLH399 | Healthy | WGS | Preoperative treatment naive | NA | 169 | 0.8780 |
| CGPLH400 | Healthy | WGS | Preoperative treatment naive | NA | 168 | 0.6662 |
| CGPLH401 | Healthy | WGS | Preoperative treatment naive | NA | 167 | 0.9428 |
| CGPLH402 | Healthy | WGS | Preoperative treatment naive | NA | 167 | 0.9353 |
| CGPLH403 | Healthy | WGS | Preoperative treatment naive | NA | 168 | 0.9329 |
| CGPLH404 | Healthy | WGS | Preoperative treatment naive | NA | 169 | 0.9402 |
| CGPLH405 | Healthy | WGS | Preoperative treatment naive | NA | 166 | 0.9579 |
| CGPLH406 | Healthy | WGS | Preoperative treatment naive | NA | 167 | 0.8188 |
| CGPLH407 | Healthy | WGS | Preoperative treatment naive | NA | 169 | 0.9527 |
| CGPLH408 | Healthy | WGS | Preoperative treatment naive | NA | 167 | 0.9584 |
| CGPLH409 | Healthy | WGS | Preoperative treatment naive | NA | 198 | 0.9220 |
| CGPLH410 | Healthy | WGS | Preoperative treatment naive | NA | 168 | 0.9102 |
| CGPLH411 | Healthy | WGS | Preoperative treatment naive | NA | 167 | 0.9392 |
| CGPLH412 | Healthy | WGS | Preoperative treatment naive | NA | 167 | 0.9561 |
| CGPLH413 | Healthy | WGS | Preoperative treatment naive | NA | 167 | 0.9461 |
| CGPLH414 | Healthy | WGS | Preoperative treatment naive | NA | 168 | 0.9258 |
| CGPLH415 | Healthy | WGS | Preoperative treatment naive | NA | 169 | 0.9217 |
| CGPLH416 | Healthy | WGS | Preoperative treatment naive | NA | 167 | 0.9672 |

TABLE 7-continued

APPENDIX G: Whole genome cfDNA analyses in healthy individuals and cancer patients

| | | | | | | |
|---|---|---|---|---|---|---|
| CGPLH417 | Healthy | WGS | Preoperative treatment naive | NA | 168 | 0.9578 |
| CGPLH418 | Healthy | WGS | Preoperative treatment naive | NA | 169 | 0.9376 |
| CGPLH419 | Healthy | WGS | Preoperative treatment naive | NA | 167 | 0.9228 |
| CGPLH420 | Healthy | WGS | Preoperative treatment naive | NA | 169 | 0.9164 |
| CGPLH422 | Healthy | WGS | Preoperative treatment naive | NA | 166 | 0.9069 |
| CGPLH423 | Healthy | WGS | Preoperative treatment naive | NA | 169 | 0.9606 |
| CGPLH424 | Healthy | WGS | Preoperative treatment naive | NA | 167 | 0.9553 |
| CGPLH425 | Healthy | WGS | Preoperative treatment naive | NA | 168 | 0.9722 |
| CGPLH426 | Healthy | WGS | Preoperative treatment naive | NA | 168 | 0.9560 |
| CGPLH427 | Healthy | WGS | Preoperative treatment naive | NA | 167 | 0.9594 |
| CGPLH428 | Healthy | WGS | Preoperative treatment naive | NA | 167 | 0.9591 |
| CGPLH429 | Healthy | WGS | Preoperative treatment naive | NA | 168 | 0.9358 |
| CGPLH430 | Healthy | WGS | Preoperative treatment naive | NA | 167 | 0.9639 |
| CGPLH431 | Healthy | WGS | Preoperative treatment naive | NA | 167 | 0.9570 |
| CGPLH432 | Healthy | WGS | Preoperative treatment naive | NA | 168 | 0.9485 |
| CGPLH434 | Healthy | WGS | Preoperative treatment naive | NA | 168 | 0.9571 |
| CGPLH435 | Healthy | WGS | Preoperative treatment naive | NA | 170 | 0.9133 |
| CGPLH436 | Healthy | WGS | Preoperative treatment naive | NA | 168 | 0.9360 |
| CGPLH437 | Healthy | WGS | Preoperative treatment naive | NA | 170 | 0.9445 |
| CGPLH438 | Healthy | WGS | Preoperative treatment naive | NA | 170 | 0.9537 |
| CGPLM439 | Healthy | WGS | Preoperative treatment naive | NA | 171 | 0.9547 |
| CGPLH440 | Healthy | WGS | Preoperative treatment naive | NA | 169 | 0.9562 |
| CGPLH441 | Healthy | WGS | Preoperative treatment naive | NA | 167 | 0.9660 |
| CGPLH442 | Healthy | WGS | Preoperative treatment naive | NA | 167 | 0.9569 |
| CGPLH443 | Healthy | WGS | Preoperative treatment naive | NA | 170 | 0.9431 |
| CGPLH444 | Healthy | WGS | Preoperative treatment naive | NA | 171 | 0.9429 |
| CGPLH445 | Healthy | WGS | Preoperative treatment naive | NA | 171 | 0.9446 |
| CGPLH446 | Healthy | WGS | Preoperative treatment naive | NA | 167 | 0.9502 |
| CGPLH447 | Healthy | WGS | Preoperative treatment naive | NA | 169 | 0.9421 |
| CGPLH448 | Healthy | WGS | Preoperative treatment naive | NA | 167 | 0.9553 |
| CGPLH449 | Healthy | WGS | Preoperative treatment naive | NA | 167 | 0.9550 |
| CGPLH450 | Healthy | WGS | Preoperative treatment naive | NA | 167 | 0.9572 |
| CGPLH451 | Healthy | WGS | Preoperative treatment naive | NA | 169 | 0.9548 |
| CGPLH452 | Healthy | WGS | Preoperative treatment naive | NA | 167 | 0.9498 |
| CGPLH453 | Healthy | WGS | Preoperative treatment naive | NA | 166 | 0.9572 |
| CGPLH455 | Healthy | WGS | Preoperative treatment naive | NA | 166 | 0.9526 |
| CGPLH450 | Healthy | WGS | Preoperative treatment naive | NA | 166 | 0.9507 |
| CGPLH457 | Healthy | WGS | Preoperative treatment naive | NA | 167 | 0.9429 |
| CGPLH458 | Healthy | WGS | Preoperative treatment naive | NA | 167 | 0.9511 |

TABLE 7-continued

APPENDIX G: Whole genome cfDNA analyses in healthy individuals and cancer patients

| | | | | | | |
|---|---|---|---|---|---|---|
| CGPLH459 | Healthy | WGS | Preoperative treatment naive | NA | 168 | 0.9609 |
| CGPLH460 | Healthy | WGS | Preoperative treatment naive | NA | 168 | 0.9331 |
| CGPLH463 | Healthy | WGS | Preoperative treatment naive | NA | 167 | 0.9506 |
| CGPLH464 | Healthy | WGS | Preoperative treatment naive | NA | 170 | 0.9133 |
| CGPLH465 | Healthy | WGS | Preoperative treatment naive | NA | 167 | 0.9251 |
| CGPLH466 | Healthy | WGS | Preoperative treatment naive | NA | 167 | 0.9679 |
| CGPLH467 | Healthy | WGS | Preoperative treatment naive | NA | 168 | 0.9273 |
| CGPLH468 | Healthy | WGS | Preoperative treatment naive | NA | 167 | 0.8553 |
| CGPLH469 | Healthy | WGS | Preoperative treatment naive | NA | 169 | 0.8225 |
| CGPLH470 | Healthy | WGS | Preoperative treatment naive | NA | 168 | 0.9073 |
| CGPLH471 | Healthy | WGS | Preoperative treatment naive | NA | 167 | 0.9354 |
| CGPLH472 | Healthy | WGS | Preoperative treatment naive | NA | 166 | 0.8509 |
| CGPLH473 | Healthy | WGS | Preoperative treatment naive | NA | 167 | 0.9206 |
| CGPLH474 | Healthy | WGS | Preoperative treatment naive | NA | 168 | 0.8474 |
| CGPLH475 | Healthy | WGS | Preoperative treatment naive | NA | 167 | 0.9155 |
| CGPLH476 | Healthy | WGS | Preoperative treatment naive | NA | 169 | 0.8807 |
| CGPLH477 | Healthy | WGS | Preoperative treatment naive | NA | 169 | 0.9129 |
| CGPLH478 | Healthy | WGS | Preoperative treatment naive | NA | 167 | 0.9588 |
| CGPLN479 | Healthy | WGS | Preoperative treatment naive | NA | 167 | 0.9503 |
| CGPLH480 | Healthy | WGS | Preoperative treatment naive | NA | 169 | 0.9522 |
| CGPLH481 | Healthy | WGS | Preoperative treatment naive | NA | 168 | 0.9568 |
| CGPLH482 | Healthy | WGS | Preoperative treatment naive | NA | 168 | 0.9379 |
| CGPLH483 | Healthy | WGS | Preoperative treatment naive | NA | 168 | 0.9518 |
| CGPLH484 | Healthy | WGS | Preoperative treatment naive | NA | 166 | 0.9630 |
| CGPLH485 | Healthy | WGS | Preoperative treatment naive | NA | 166 | 0.9547 |
| CGPLH486 | Healthy | WGS | Preoperative treatment naive | NA | 169 | 0.9199 |
| CGPLH487 | Healthy | WGS | Preoperative treatment naive | NA | 169 | 0.9575 |
| CGPLH488 | Healthy | WGS | Preoperative treatment naive | NA | 167 | 0.9618 |
| CGPLH490 | Healthy | WGS | Preoperative treatment naive | NA | 167 | 0.8950 |
| CGPLH491 | Healthy | WGS | Preoperative treatment naive | NA | 168 | 0.9631 |
| CGPLH492 | Healthy | WGS | Preoperative treatment naive | NA | 170 | 0.9335 |
| CGPLH493 | Healthy | WGS | Preoperative treatment naive | NA | 168 | 0.8718 |
| CGPLH494 | Healthy | WGS | Preoperative treatment naive | NA | 169 | 0.9623 |
| CGPLH495 | Healthy | WGS | Preoperative treatment naive | NA | 166 | 0.8777 |
| CGPLH496 | Healthy | WGS | Preoperative treatment naive | NA | 166 | 0.8788 |
| CGPLH497 | Healthy | WGS | Preoperative treatment naive | NA | 167 | 0.9576 |
| CGPLH498 | Healthy | WGS | Preoperative treatment naive | NA | 167 | 0.9526 |
| CGPLH499 | Healthy | WGS | Preoperative treatment naive | NA | 167 | 0.9733 |
| CGPLH500 | Healthy | WGS | Preoperative treatment naive | NA | 168 | 0.9542 |

TABLE 7-continued

APPENDIX G: Whole genome cfDNA analyses in healthy individuals and cancer patients

| | | | | | | |
|---|---|---|---|---|---|---|
| CGPLH501 | Healthy | WGS | Preoperative treatment naive | NA | 169 | 0.9526 |
| CGPLH502 | Healthy | WGS | Preoperative treatment naive | NA | 167 | 0.9512 |
| CGPLH503 | Healthy | WGS | Preoperative treatment naive | NA | 169 | 0.8947 |
| CGPLH504 | Healthy | WGS | Preoperative treatment naive | NA | 167 | 0.9561 |
| CGPLH505 | Healthy | WGS | Preoperative treatment naive | NA | 166 | 0.9554 |
| CGPLH506 | Healthy | WGS | Preoperative treatment naive | NA | 167 | 0.9733 |
| CGPLH507 | Healthy | WGS | Preoperative treatment naive | NA | 168 | 0.9222 |
| CGPLH508 | Healthy | WGS | Preoperative treatment naive | NA | 167 | 0.9674 |
| CGPLH509 | Healthy | WGS | Preoperative treatment naive | NA | 167 | 0.9475 |
| CGPLH510 | Healthy | WGS | Preoperative treatment naive | NA | 167 | 0.9459 |
| CGPLH511 | Healthy | WGS | Preoperative treatment naive | NA | 166 | 0.9714 |
| CGPLH512 | Healthy | WGS | Preoperative treatment naive | NA | 168 | 0.9442 |
| CGPLH513 | Healthy | WGS | Preoperative treatment naive | NA | 166 | 0.9705 |
| CGPLH514 | Healthy | WGS | Preoperative treatment naive | NA | 167 | 0.9690 |
| CGPLH515 | Healthy | WGS | Preoperative treatment naive | NA | 167 | 0.9568 |
| CGPLH516 | Healthy | WGS | Preoperative treatment naive | NA | 166 | 0.9508 |
| CGPLH517 | Healthy | WGS | Preoperative treatment naive | NA | 168 | 0.9635 |
| CGPLH518 | Healthy | WGS | Preoperative treatment naive | NA | 168 | 0.9647 |
| CGPLH519 | Healthy | WGS | Preoperative treatment naive | NA | 166 | 0.9366 |
| CGPLH520 | Healthy | WGS | Preoperative treatment naive | NA | 166 | 0.3649 |
| CGPLH625 | Healthy | WGS | Preoperative treatment naive | NA | 166 | 0.8766 |
| CGPLH626 | Healthy | WGS | Preoperative treatment naive | NA | 170 | 0.9011 |
| CGPLH639 | Healthy | WGS | Preoperative treatment naive | NA | 165 | 0.9482 |
| CGPLH640 | Healthy | WGS | Preoperative treatment naive | NA | 166 | 0.9131 |
| CGPLH642 | Healthy | WGS | Preoperative treatment naive | NA | 167 | 0.9641 |
| CGPLH643 | Healthy | WGS | Preoperative treatment naive | NA | 169 | 0.9450 |
| CGPLH644 | Healthy | WGS | Preoperative treatment naive | NA | 170 | 0.9398 |
| CGPLH646 | Healthy | WGS | Preoperative treatment naive | NA | 172 | 0.9296 |
| CGPLLU144 | Lung Cancer | Targeted Mutation Analysis and WGS | Preoperative treatment naive | II | 164 | 0.8702 |
| CGPLLU161 | Lung Cancer | Targeted Mutation Analysis and WGS | Preoperative treatment naive | II | 165 | 0.9128 |
| CGPLLU162 | Lung Cancer | Targeted Mutation Analysis and WGS | Preoperative treatment naive | II | 165 | 0.7753 |
| CGPLLU163 | Lung Cancer | Targeted Mutation Analysis and WGS | Preoperative treatment naive | II | 166 | 0.4770 |
| CGPLLU168 | Lung Cancer | Targeted Mutation Analysis and WGS | Preoperative treatment naive | I | 163 | 0.9164 |
| CGPLLU169 | Lung Cancer | Targeted Mutation Analysis and WGS | Preoperative treatment naive | I | 163 | 0.9326 |
| CGPLLU176 | Lung Cancer | Targeted Mutation Analysis and WGS | Preoperative treatment naive | I | 168 | 0.9572 |
| CGPLLU177 | Lung Cancer | Targeted Mutation Analysis and WGS | Preoperative treatment naive | II | 166 | 0.8472 |
| CGPLLU203 | Lung Cancer | Targeted Mutation Analysis and WGS | Preoperative treatment naive | II | 164 | 0.9119 |
| CGPLLU205 | Lung Cancer | Targeted Mutation Analysis and WGS | Preoperative treatment naive | II | 163 | 0.9518 |
| CGPLLU207 | Lung Cancer | Targeted Mutation Analysis and WGS | Preoperative treatment naive | II | 166 | 0.9344 |

TABLE 7-continued

APPENDIX G: Whole genome cfDNA analyses in healthy individuals and cancer patients

| | | | | | | |
|---|---|---|---|---|---|---|
| CGPLLU208 | Lung Cancer | Targeted Mutation Analysis and WGS | Preoperative treatment naive | II | 164 | 0.9091 |
| CGPLOV11 | Ovarian Cancer | Targeted Mutation Analysis and WGS | Preoperative treatment naive | V | 166 | 0.8902 |
| CGPLOV12 | Ovarian Cancer | Targeted Mutation Analysis and WGS | Preoperative treatment naive | I | 167 | 0.8779 |
| CGPLOV13 | Ovarian Cancer | Targeted Mutation Analysis and WGS | Preoperative treatment naive | V | 166 | 0.7560 |
| CGPLOV15 | Ovarian Cancer | Targeted Mutation Analysis and WGS | Preoperative treatment naive | III | 155 | 0.8585 |
| CGPLOV18 | Ovarian Cancer | Targeted Mutation Analysis and WGS | Preoperative treatment naive | III | 165 | 0.9052 |
| CGPLOV19 | Ovarian Cancer | Targeted Mutation Analysis and WGS | Preoperative treatment naive | II | 165 | 0.7854 |
| CGPLOV20 | Ovarian Cancer | Targeted Mutation Analysis and WGS | Preoperative treatment naive | II | 165 | 0.8711 |
| CGPLOV21 | Ovarian Cancer | Targeted Mutation Analysis and WGS | Preoperative treatment naive | V | 167 | 0.8942 |
| CGPLOV22 | Ovarian Cancer | Targeted Mutation Analysis and WGS | Preoperative treatment naive | III | 164 | 0.8944 |
| CGPLOV23 | Ovarian Cancer | Targeted Mutation Analysis and WGS | Preoperative treatment naive | I | 169 | 0.8510 |
| CGPLOV24 | Ovarian Cancer | Targeted Mutation Analysis and WGS | Preoperative treatment naive | I | 166 | 0.9449 |
| CGPLOV25 | Ovarian Cancer | Targeted Mutation Analysis and WGS | Preoperative treatment naive | I | 166 | 0.9590 |
| CGPLOV26 | Ovarian Cancer | Targeted Mutation Analysis and WGS | Preoperative treatment naive | I | 161 | 0.8148 |
| CGPLOV28 | Ovarian Cancer | Targeted Mutation Analysis and WGS | Preoperative treatment naive | I | 167 | 0.9635 |
| CGPLOV31 | Ovarian Cancer | Targeted Mutation Analysis and WGS | Preoperative treatment naive | III | 167 | 0.9461 |
| CGPLOV32 | Ovarian Cancer | Targeted Mutation Analysis and WGS | Preoperative treatment naive | I | 168 | 0.9582 |
| CGPLOV37 | Ovarian Cancer | Targeted Mutation Analysis and WGS | Preoperative treatment naive | I | 170 | 0.9397 |
| CGPLOV38 | Ovarian Cancer | Targeted Mutation Analysis and WGS | Preoperative treatment naive | I | 166 | 0.5779 |
| CGPLOV40 | Ovarian Cancer | Targeted Mutation Analysis and WGS | Preoperative treatment naive | V | 170 | 0.6097 |
| CGPLOV41 | Ovarian Cancer | Targeted Mutation Analysis and WGS | Preoperative treatment naive | V | 167 | 0.9403 |
| CGPLOV42 | Ovarian Cancer | Targeted Mutation Analysis and WGS | Preoperative treatment naive | I | 166 | 0.9265 |
| CGPLOV43 | Ovarian Cancer | Targeted Mutation Analysis and WGS | Preoperative treatment naive | I | 167 | 0.9626 |
| CGPLOV44 | Ovarian Cancer | Targeted Mutation Analysis and WGS | Preoperative treatment naive | I | 164 | 0.9536 |
| CGPLOV45 | Ovarian Cancer | Targeted Mutation Analysis and WGS | Preoperative treatment naive | I | 166 | 0.9622 |
| CGPLOV47 | Ovarian Cancer | Targeted Mutation Analysis and WGS | Preoperative treatment naive | I | 165 | 0.9704 |
| CGPLOV48 | Ovarian Cancer | Targeted Mutation Analysis and WGS | Preoperative treatment naive | I | 167 | 0.9675 |
| CGPLOV49 | Ovarian Cancer | Targeted Mutation Analysis and WGS | Preoperative treatment naive | III | 164 | 0.8998 |
| CGPLOV50 | Ovarian Cancer | Targeted Mutation Analysis and WGS | Preoperative treatment naive | III | 165 | 0.9682 |
| CGPLPA112 | Pancreatic Cancer | WGS | Preoperative treatment naive | II | 164 | 0.8914 |
| CGPLPA113 | Duodenal Cancer | WGS | Preoperative treatment naive | I | 170 | 0.8751 |
| CGPLPA114 | Bile Duct Cancer | WGS | Preoperative treatment naive | II | 166 | 0.9098 |
| CGPLPA115 | Bile Duct Cancer | WGS | Preoperative treatment naive | V | 165 | 0.8053 |
| CGPLPA117 | Bile Duct Cancer | WGS | Preoperative treatment naive | II | 165 | 0.9395 |
| CGPLPA118 | Bile Duct Cancer | Targeted Mutation Analysis and WGS | Preoperative treatment naive | I | 157 | 0.9406 |
| CGPLPA122 | Bile Duct Cancer | Targeted Mutation Analysis and WGS | Preoperative treatment naive | II | 164 | 0.8231 |
| CGPLPA124 | Bile Duct Cancer | Targeted Mutation Analysis and WGS | Preoperative treatment naive | II | 166 | 0.9108 |
| CGPLPA125 | Bile Duct Cancer | WGS | Preoperative treatment naive | II | 165 | 0.9675 |
| CGPLPA126 | Bile Duct Cancer | Targeted Mutation Analysis and WGS | Preoperative treatment naive | II | 166 | 0.9155 |

TABLE 7-continued

APPENDIX G: Whole genome cfDNA analyses in healthy individuals and cancer patients

| | | | | | | |
|---|---|---|---|---|---|---|
| CGPLPA127 | Bile Duct Cancer | WGS | Preoperative treatment naive | V | 167 | 0.8916 |
| CGPLPA128 | Bile Duct Cancer | Targeted Mutation Analysis and WGS | Preoperative treatment naive | II | 167 | 0.9262 |
| CGPLPA129 | Bile Duct Cancer | Targeted Mutation Analysis and WGS | Preoperative treatment naive | II | 166 | 0.9220 |
| CGPLPA130 | Bile Duct Cancer | Targeted Mutation Analysis and WGS | Preoperative treatment naive | II | 169 | 0.8586 |
| CGPLPA131 | Bile Duct Cancer | Targeted Mutation Analysis and WGS | Preoperative treatment naive | II | 165 | 0.7707 |
| CGPLPA134 | Bile Duct Cancer | Targeted Mutation Analysis and WGS | Preoperative treatment naive | II | 160 | 0.7502 |
| CGPLPA135 | Bile Duct Cancer | WGS | Preoperative treatment naive | I | 165 | 0.9495 |
| CGPLPA136 | Bile Duct Cancer | Targeted Mutation Analysis and WGS | Preoperative treatment naive | II | 164 | 0.9289 |
| CGPLPA137 | Bile Duct Cancer | WGS | Preoperative treatment naive | II | 166 | 0.9568 |
| CGPLPA139 | Bile Duct Cancer | WGS | Preoperative treatment naive | V | 166 | 0.9511 |
| CGPLPA14 | Pancreatic Cancer | WGS | Preoperative treatment naive | II | 167 | 0.8718 |
| CGPLPA140 | Bile Duct Cancer | Targeted Mutation Analysis and WGS | Preoperative treatment naive | II | 166 | 0.9215 |
| CGPLPA141 | Bile Duct Cancer | WGS | Preoperative treatment naive | II | 165 | 0.3172 |
| CGPLPA15 | Pancreatic Cancer | WGS | Preoperative treatment naive | II | 167 | 0.9111 |
| CGPLPA155 | Bile Duct Cancer | WGS | Preoperative treatment naive | II | 165 | 0.9496 |
| CGPLPA156 | Pancreatic Cancer | WGS | Preoperative treatment naive | II | 167 | 0.9479 |
| CGPLPA165 | Bile Duct Cancer | WGS | Preoperative treatment naive | I | 168 | 0.9596 |
| CGPLPA168 | Bile Duct Cancer | WGS | Preoperative treatment naive | II | 162 | 0.7838 |
| CGPLPA17 | Pancreatic Center | WGS | Preoperative treatment naive | II | 166 | 0.8624 |
| CGPLPA184 | Bile Duct Cancer | WGS | Preoperative treatment naive | II | 165 | 0.9100 |
| CGPLPA187 | Bile Duct Cancer | WGS | Preoperative treatment naive | II | 165 | 0.8577 |
| CGPLPA23 | Pancreatic Cancer | WGS | Preoperative treatment naive | II | 165 | 0.7887 |
| CGPLPA25 | Pancreatic Cancer | WGS | Preoperative treatment naive | II | 166 | 0.9549 |
| CGPLPA26 | Pancreatic Cancer | WGS | Preoperative treatment naive | II | 166 | 0.9598 |
| CGPLPA28 | Pancreatic Cancer | WGS | Preoperative treatment naive | II | 165 | 0.9069 |
| CGPLPA33 | Pancreatic Cancer | WGS | Preoperative treatment naive | II | 166 | 0.8361 |
| CGPLPA34 | Pancreatic Cancer | WGS | Preoperative treatment naive | II | 168 | 0.9846 |
| CGPLPA37 | Pancreatic Cancer | WGS | Preoperative treatment naive | II | 165 | 0.8840 |
| CGPLPA38 | Pancreatic Cancer | WGS | Preoperative treatment naive | II | 167 | 0.8746 |
| CGPLPA39 | Pancreatic Cancer | WGS | Preoperative treatment naive | II | 167 | 0.8562 |
| CGPLPA40 | Pancreatic Cancer | WGS | Preoperative treatment naive | II | 165 | 0.8563 |
| CGPLPA42 | Pancreatic Cancer | WGS | Preoperative treatment naive | II | 167 | 0.9126 |
| CGPLPA46 | Pancreatic Cancer | WGS | Preoperative treatment naive | II | 169 | 0.8274 |
| CGPLPA47 | Pancreatic Cancer | WGS | Preoperative treatment naive | II | 166 | 0.8376 |
| CGPLPA48 | Pancreatic Cancer | WGS | Preoperative treatment naive | I | 167 | 0.9391 |
| CGPLPA52 | Pancreatic Cancer | WGS | Preoperative treatment naive | II | 167 | 0.9452 |
| CGPLPA53 | Pancreatic Cancer | WGS | Preoperative treatment naive | I | 163 | 0.9175 |
| CGPLPA58 | Pancreatic Cancer | WGS | Preoperative treatment naive | II | 165 | 0.9587 |
| CGPLPA59 | Pancreatic Cancer | WGS | Preoperative treatment naive | II | 163 | 0.9230 |

TABLE 7-continued

APPENDIX G: Whole genome cfDNA analyses in healthy individuals and cancer patients

| | | | | | | |
|---|---|---|---|---|---|---|
| CGPLPA67 | Pancreatic Cancer | WGS | Preoperative treatment naive | II | 165 | 0.9574 |
| CGPLPA69 | Pancreatic Cancer | WGS | Preoperative treatment naive | I | 168 | 0.9172 |
| CGPLPA71 | Pancreatic Cancer | WGS | Preoperative treatment naive | II | 167 | 0.9424 |
| CGPLPA74 | Pancreatic Cancer | WGS | Preoperative treatment naive | II | 165 | 0.9688 |
| CGPLPA78 | Pancreatic Cancer | WGS | Preoperative treatment naive | II | 163 | 0.9681 |
| CGPLPA85 | Pancreatic Cancer | WGS | Preoperative treatment naive | II | 165 | 0.9137 |
| CGPLPA86 | Pancreatic Cancer | WGS | Preoperative treatment naive | II | 165 | 0.8875 |
| CGPLPA92 | Pancreatic Cancer | WGS | Preoperative treatment naive | II | 167 | 0.9389 |
| CGPLPA93 | Pancreatic Cancer | WGS | Preoperative treatment naive | II | 166 | 0.8585 |
| CGPLPA94 | Pancreatic Cancer | WGS | Preoperative treatment naive | II | 162 | 0.9365 |
| CGPLPA95 | Pancreatic Cancer | WGS | Preoperative treatment naive | II | 163 | 0.8542 |
| CGST102 | Gastric cancer | Targeted Mutation Analysis and WGS | Preoperative treatment naive | II | 167 | 0.9496 |
| CGST11 | Gastric cancer | WGS | Preoperative treatment naive | IV | 169 | 0.9419 |
| CGST110 | Gastric cancer | Targeted Mutation Analysis and WGS | Preoperative treatment naive | II | 167 | 0.9626 |
| CGST114 | Gastric cancer | Targeted Mutation Analysis and WGS | Preoperative treatment naive | II | 164 | 0.9535 |
| CGST13 | Gastric cancer | Targeted Mutation Analysis and WGS | Preoperative treatment naive | II | 166 | 0.9369 |
| CGST131 | Gastric cancer | WGS | Preoperative treatment naive | II | 171 | 0.9428 |
| CGST141 | Gastric cancer | Targeted Mutation Analysis and WGS | Preoperative treatment naive | II | 168 | 0.9621 |
| CGST16 | Gastric cancer | Targeted Mutation Analysis and WGS | Preoperative treatment naive | II | 166 | 0.7804 |
| CGST18 | Gastric cancer | Targeted Mutation Analysis and WGS | Preoperative treatment naive | II | 169 | 0.9523 |
| CGST21 | Gastric cancer | WGS | Preoperative treatment naive | II | 165 | −0.4778 |
| CGST26 | Gastric cancer | WGS | Preoperative treatment naive | IV | 166 | 0.9554 |
| CG3T28 | Gastric cancer | Targeted Mutation Analysis and WGS | Preoperative treatment naive | X | 169 | 0.9076 |
| CGST30 | Gastric cancer | Targeted Mutation Analysis and WGS | Preoperative treatment naive | II | 169 | 0.9246 |
| CGST32 | Gastric cancer | Targeted Mutation Analysis and WGS | Preoperative treatment naive | II | 169 | 0.9431 |
| CGST33 | Gastric cancer | Targeted Mutation Analysis and WGS | Preoperative treatment naive | I | 168 | 0.7999 |
| CGST38 | Gastric cancer | WGS | Preoperative treatment naive | 0 | 168 | 0.9368 |
| CGST39 | Gastric cancer | Targeted Mutation Analysis and WGS | Preoperative treatment naive | IV | 164 | 0.8742 |
| CGST41 | Gastric cancer | Targeted Mutation Analysis and WGS | Preoperative treatment naive | IV | 168 | 0.8194 |
| CGST45 | Gastric cancer | Targeted Mutation Analysis and WGS | Preoperative treatment naive | II | 168 | 0.9576 |
| CGST47 | Gastric cancer | Targeted Mutation Analysis and WGS | Preoperative treatment naive | I | 168 | 0.9611 |
| CGST48 | Gastric cancer | Targeted Mutation Analysis and WGS | Preoperative treatment naive | IV | 167 | 0.7469 |
| CGST53 | Gastric cancer | WGS | Preoperative treatment naive | 0 | 173 | 0.0019 |
| CGST58 | Gastric cancer | Targeted Mutation Analysis and WGS | Preoperative treatment naive | II | 169 | 0.9470 |
| CGST67 | Gastric cancer | WGS | Preoperative treatment naive | I | 170 | 0.9352 |
| CGST77 | Gastric cancer | WGS | Preoperative treatment naive | IV | 170 | 0.00438 |
| CGST80 | Gastric cancer | Targeted Mutation Analysis and WGS | Preoperative treatment naive | II | 168 | 0.9313 |
| CGST81 | Gastric cancer | Targeted Mutation Analysis and WGS | Preoperative treatment naive | I | 168 | 0.9480 |

TABLE 7-continued

| APPENDIX G: Whole genome cfDNA analyses in healthy individuals and cancer patients | | | | | | |
|---|---|---|---|---|---|---|
| Patient | Correlation of GC Corrected Fragment Ratio Profile to Median Fragment Ratio Profile of Healthy Individuals | Fraction of Reads Mapped to Mitochondrial Genome | DELFI Scene | Detected using DELFI (95% specificity) | Detected using DELFI (98% specificity) | Mutant Alelle Fraction Detected using Targeted sequencing* |
| CGCRC291 | 0.5268 | 0.0484% | 0.9976 | Y | Y | 22.85% |
| CGCRC232 | 0.8835 | 0.0270% | 0.7299 | Y | N | 1.41% |
| CGCRC293 | 0.9206 | 0.0748% | 0.5534 | N | N | 0.35% |
| CGCRC294 | 0.8904 | 0.0188% | 0.8757 | Y | Y | 0.17% |
| CGCRC295 | 0.8895 | 0.0369% | 0.9951 | Y | Y | ND |
| CGCRC299 | 0.9268 | 0.0392% | 0.9648 | Y | Y | ND |
| CGCRC300 | 0.0303 | 0.0235% | 0.4447 | N | N | ND |
| CGCRC301 | 0.9151 | 0.0310% | 0.2190 | N | N | 0.21% |
| CGCRC302 | 0.9243 | 0.0112% | 0.9897 | Y | Y | 0.12% |
| CGCRC304 | 0.9360 | 0.0393% | 0.9358 | Y | Y | 0.27% |
| CGCRC305 | 0.9250 | 0.0120% | 0.3988 | Y | Y | 0.19% |
| CGCRG306 | 0.8186 | 0.0781% | 0.9486 | Y | Y | 8.02% |
| CGCRC307 | 0.9342 | 0.0181% | 0.7042 | Y | N | 0.58% |
| CGCRC306 | 0.9324 | 0.0078% | 0.9082 | Y | Y | 0.11% |
| CGCRC311 | 0.9156 | 0.0173% | 0.1887 | N | N | ND |
| CGCRC315 | 0.8846 | 0.0241% | 0.6422 | Y | N | 0.27% |
| CGCRC316 | 0.5879 | 0.0315% | 0.9971 | Y | Y | 5.52% |
| CGCRC317 | 0.8944 | 0.0184% | 0.9855 | Y | Y | 0.36% |
| CGCRC318 | 0.9140 | 0.0156% | 0.5615 | N | N | ND |
| CGCRC319 | 0.8230 | 0.1259% | 0.9925 | Y | Y | 3.11% |
| CGCRC320 | 0.9101 | 0.0383% | 0.8019 | Y | Y | 0.84% |
| CGCRC321 | 0.9021 | 0.0829% | 0.9759 | Y | Y | 0.20% |
| CGCRC333 | 0.4355 | 0.4284% | 0.9974 | Y | Y | 43.03% |
| CGCRC335 | 0.6856 | 0.1154% | 0.9887 | Y | Y | 81.61% |
| CGCRC338 | 0.7573 | 0.1436% | 0.9976 | Y | Y | 36.00% |
| CGCRC341 | 0.9191 | 0.0197% | 0.9670 | Y | Y | ND |
| CGCRC342 | 0.1345 | 0.1732% | 0.9987 | Y | Y | 30.72% |
| CGPLBR100 | 0.8945 | 0.1234% | 0.8684 | Y | Y | ND |
| CGPLBR101 | 0.9304 | 0.0709% | 0.9385 | Y | Y | ND |
| CGPLBR102 | 0.9345 | 0.4742% | 0.9052 | Y | Y | 0.25% |
| CGPLBR103 | 0.9251 | 0.0775% | 0.5994 | N | N | ND |
| CGPLBR104 | 0.9192 | 0.0532% | 0.9950 | Y | Y | 0.13% |
| CGPLBR12 | 0.7760 | 0.1407% | 0.7598 | Y | Y | — |
| CGPLBR18 | 0.9534 | 0.0267% | 0.3886 | N | N | — |
| CGPLBR23 | 0.9312 | 0.0144% | 0.1235 | N | N | — |
| CGPLBR24 | 0.8766 | 0.0210% | 0.7480 | Y | Y | — |
| CGPLBR26 | 0.9120 | 0.1456% | 0.9630 | Y | Y | — |
| CGPLBR30 | 0.6611 | 0.0952% | 0.9956 | Y | Y | — |
| CGPLBR31 | 0.9556 | 0.0427% | 0.2227 | N | N | — |
| CGPLBR32 | 0.9229 | 0.0306% | 0.9815 | Y | Y | — |
| CGPLBR33 | 0.9432 | 0.0817% | 0.2853 | N | N | — |
| CGPLBR34 | 0.9425 | 0.0115% | 0.1637 | N | N | — |
| CGPLBR35 | 0.9348 | 0.1371% | 0.5057 | N | N | — |
| CGPLBR36 | 0.8884 | 0.0813% | 0.4017 | N | N | — |
| CGPLBR37 | 0.9495 | 0.0516% | 0.0314 | N | N | — |
| CGPLBR38 | 0.0349 | 0.1352% | 0.8983 | Y | Y | 0.53% |
| CGPLBR40 | 0.9244 | 0.0923% | 0.9846 | Y | Y | ND |
| CGPLBR41 | 0.9346 | 0.0544% | 0.9416 | Y | Y | 0.32% |
| CGPLBR45 | 0.9286 | 0.0296% | 0.3860 | N | N | — |
| CGPLBR46 | 0.9005 | 0.0345% | 0.7270 | Y | N | — |
| CGPLBR47 | 0.2028 | 0.0591% | 0.8247 | Y | Y | — |
| CGPLBR48 | 0.8246 | 0.0504% | 0.9973 | Y | Y | 0.18% |
| CGPLBR49 | 0.7887 | 0.0377% | 0.9946 | Y | Y | ND |
| CGPLBR50 | 0.8332 | 0.0137% | 0.6820 | Y | N | — |
| CGPLBR51 | 0.9160 | 0.0863% | 0.6915 | Y | N | — |
| CGPLBR52 | 0.9196 | 0.0165% | 0.6390 | Y | N | — |
| CGPLBR55 | 0.9341 | 0.0356% | 0.9494 | Y | Y | 0.68% |
| CGPLBR56 | 0.9428 | 0.2025% | 0.4700 | N | N | — |
| CGPLBR57 | 0.9416 | 0.0902% | 0.9090 | Y | Y | ND |
| CGPLBR59 | 0.9130 | 0.0761% | 0.5828 | N | N | ND |
| CGPLBR60 | 0.8916 | 0.0626% | 0.8779 | Y | Y | — |
| CGPLBR61 | 0.9422 | 0.0601% | 0.4417 | N | N | 0.44% |
| CGPLBR63 | 0.9132 | 0.0514% | 0.8788 | Y | Y | ND |
| CGPLBR65 | 0.8970 | 0.0264% | 0.9048 | Y | Y | — |
| CGPLBR68 | 0.9532 | 0.0164% | 0.7863 | Y | Y | ND |
| CGPLBR69 | 0.9474 | 0.0279% | 0.0600 | N | N | ND |
| CGPLBR70 | 0.9388 | 0.0171% | 0.6447 | Y | N | 0.36% |
| CGPLBR71 | 0.9368 | 0.0271% | 0.6706 | Y | N | 0.10% |

TABLE 7-continued

APPENDIX G: Whole genome cfDNA analyses in healthy individuals and cancer patients

| | | | | | | |
|---|---|---|---|---|---|---|
| CGPLBR72 | 0.9640 | 0.0263% | 0.6129 | N | N | ND |
| CGPLBR73 | 0.9421 | 0.0142% | 0.0746 | N | N | 0.27% |
| CGPLBR76 | 0.9254 | 0.0775% | 0.9334 | Y | Y | 3.12% |
| CGPLBR81 | 0.8193 | 0.0241% | 0.9899 | Y | Y | — |
| CGPLBR82 | 0.9288 | 0.1640% | 0.9834 | Y | Y | 0.12% |
| CGPLBR83 | 0.9138 | 0.0419% | 0.9810 | Y | Y | 0.28% |
| CGPLBR84 | 0.8359 | 0.0274% | 0.9901 | Y | Y | — |
| CGPLBR87 | 0.8797 | 0.0294% | 0.9988 | Y | Y | 0.45% |
| CGPLBR88 | 0.8547 | 0.0181% | 0.9988 | Y | Y | 0.38% |
| CGPLBR90 | 0.8330 | 0.0417% | 0.9687 | Y | Y | — |
| CGPLBR91 | 0.9408 | 0.0799% | 0.8710 | Y | Y | ND |
| CGPLBR92 | 0.8835 | 0.1042% | 0.9866 | Y | Y | 0.20% |
| CGPLBP93 | 0.9072 | 0.0352% | 0.7253 | Y | N | ND |
| CGPLH189 | 0.8947 | 0.0591% | 0.1748 | N | N | — |
| CGPLH190 | 0.9369 | 0.1193% | 0.5188 | N | N | — |
| CGPLH192 | 0.9487 | 0.0276% | 0.0178 | N | N | — |
| CGPLH193 | 0.9442 | 0.0420% | 0.5794 | N | N | — |
| CGPLH194 | 0.9289 | 0.0407% | 0.1616 | N | N | — |
| CGPLH196 | 0.9512 | 0.0266% | 0.0999 | N | N | — |
| CGPLH197 | 0.9416 | 0.0334% | 0.4699 | N | N | — |
| CGPLH198 | 0.9457 | 0.0302% | 0.6571 | Y | N | — |
| CGPLH199 | 0.9439 | 0.0170% | 0.5564 | N | N | — |
| CGPLH200 | 0.9391 | 0.0362% | 0.3833 | N | N | — |
| CGPLH201 | 0.9180 | 0.0470% | 0.8395 | Y | Y | — |
| CGPLH202 | 0.9436 | 0.0501% | 0.1088 | N | N | — |
| CGPLH203 | 0.9575 | 0.0455% | 0.2485 | N | N | — |
| CGPLH205 | 0.9283 | 0.0409% | 0.4401 | N | N | — |
| CGPLH208 | 0.9409 | 0.0371% | 0.2706 | N | N | — |
| CGPLH209 | 0.9367 | 0.0427% | 0.2213 | N | N | — |
| CGPLH210 | 0.9181 | 0.0279% | 0.3500 | N | N | — |
| CGPLH211 | 0.9410 | 0.0317% | 0.1752 | N | N | — |
| CGPLH300 | 0.9200 | 0.0397% | 0.0226 | N | N | — |
| CGPLH307 | 0.9167 | 0.0388% | 0.1789 | N | N | — |
| CGPLH308 | 0.9352 | 0.0311% | 0.0185 | N | N | — |
| CGPLH309 | 0.9451 | 0.0226% | 0.0441 | N | N | — |
| CGPLN310 | 0.9527 | 0.0145% | 0.7135 | Y | N | — |
| CGPLH311 | 0.9348 | 0.0202% | 0.2589 | N | N | — |
| CGPLH314 | 0.9491 | 0.0212% | 0.1632 | N | N | — |
| CGPLH315 | 0.9427 | 0.0071% | 0.3450 | N | N | — |
| CGPLH316 | 0.9552 | 0.0191% | 0.4697 | N | N | — |
| CGPLH317 | 0.9352 | 0.0232% | 0.1330 | N | N | — |
| CGPLH319 | 0.9189 | 0.0263% | 0.2232 | N | N | — |
| CGPLR320 | 0.9166 | 0.0222% | 0.1095 | N | N | — |
| CGPLH322 | 0.9411 | 0.0248% | 0.0749 | N | N | — |
| CGPLH324 | 0.9133 | 0.0402% | 0.0128 | N | N | — |
| CGPLH325 | 0.9202 | 0.0711% | 0.0102 | N | N | — |
| CGPLH326 | 0.9408 | 0.0213% | 0.0475 | N | N | — |
| CGPLH327 | 0.9071 | 0.1275% | 0.4891 | N | N | — |
| CGPLH328 | 0.9332 | 0.0256% | 0.0234 | N | N | — |
| CGPLH329 | 0.9396 | 0.0269% | 0.0139 | N | N | — |
| CGPLH330 | 0.9403 | 0.0203% | 0.2642 | N | N | — |
| CGPLH331 | 0.9377 | 0.0314% | 0.0304 | N | N | — |
| CGPLH333 | 0.9132 | 0.0350% | 0.1633 | N | N | — |
| CGPLH335 | 0.9333 | 0.0285% | 0.0096 | N | N | — |
| CGPLH336 | 0.9159 | 0.0159% | 0.3872 | N | N | — |
| CGPLH337 | 0.9262 | 0.0367% | 0.2976 | N | N | — |
| CGPLH338 | 0.9303 | 0.0103% | 0.0431 | N | N | — |
| CGPLH339 | 0.9338 | 0.0280% | 0.0379 | N | N | — |
| CGPLH340 | 0.9321 | 0.0210% | 0.0379 | N | N | — |
| CGPLH341 | 0.9187 | 0.0448% | 0.1775 | N | N | — |
| CGPLH342 | 0.8986 | 0.0283% | 0.0904 | N | N | — |
| CGPLH343 | 0.9067 | 0.0632% | 0.0160 | N | N | — |
| CGPLH344 | 0.8998 | 0.0257% | 0.0120 | N | N | — |
| CGPLH345 | 0.9107 | 0.0445% | 0.0031 | N | N | — |
| CGPLH346 | 0.9074 | 0.0208% | 0.0686 | N | N | — |
| CGPLH350 | 0.9288 | 0.0284% | 0.0071 | N | N | — |
| CGPLH351 | 0.9294 | 0.0223% | 0.0207 | N | N | — |
| CGPLH352 | 0.9190 | 0.0613% | 0.0512 | N | N | — |
| CGPLH353 | 0.9130 | 0.0408% | 0.0132 | N | N | — |
| CGPLH354 | 0.9121 | 0.0318% | 0.0082 | N | N | — |
| CGPLH355 | 0.9308 | 0.0400% | 0.6407 | Y | N | — |
| CGPLH356 | 0.9312 | 0.0427% | 0.2437 | N | N | — |
| CGPLH357 | 0.9340 | 0.0217% | 0.0070 | N | N | — |
| CGPLH358 | 0.9372 | 0.0174% | 0.1451 | N | N | — |
| CGPLH360 | 0.8775 | 0.3395% | 0.0048 | N | N | — |
| CGPLH361 | 0.9283 | 0.0266% | 0.1524 | N | N | — |
| CGPLH362 | 0.9503 | 0.0309% | 0.4832 | N | N | — |
| CGPLH363 | 0.9187 | 0.0620% | 0.0199 | N | N | — |

TABLE 7-continued

APPENDIX G: Whole genome cfDNA analyses in healthy individuals and cancer patients

| | | | | | | |
|---|---|---|---|---|---|---|
| CGPLH364 | 0.9480 | 0.0282% | 0.8719 | Y | Y | — |
| CGPLH365 | 0.9051 | 0.1740% | 0.9683 | Y | Y | — |
| CGPLH366 | 0.9170 | 0.0344% | 0.0952 | N | N | — |
| CGPLH367 | 0.9181 | 0.0353% | 0.1235 | N | N | — |
| CGPLH368 | 0.9076 | 0.1073% | 0.1252 | N | N | — |
| CGPLH369 | 0.9541 | 0.0246% | 0.2821 | N | N | — |
| CGPLH370 | 0.9423 | 0.0410% | 0.0989 | N | N | — |
| CGPLH371 | 0.9414 | 0.0734% | 0.2173 | N | N | — |
| CGPLH380 | 0.9424 | 0.0523% | 0.0128 | N | N | — |
| CGPLH381 | 0.9501 | 0.0435% | 0.0152 | N | N | — |
| CGPLH382 | 0.9584 | 0.0340% | 0.0326 | N | N | — |
| CGPLH383 | 0.9407 | 0.0389% | 0.0035 | N | N | — |
| CGPLH384 | 0.9043 | 0.0207% | 0.0258 | N | N | — |
| CGPLH385 | 0.9245 | 0.0165% | 0.0566 | N | N | — |
| CGPLH386 | 0.8859 | 0.0502% | 0.2677 | N | N | — |
| CGPLH387 | 0.9223 | 0.0375% | 0.0081 | N | N | — |
| CGPLH388 | 0.9266 | 0.0527% | 0.0499 | N | N | — |
| CGPLH389 | 0.9035 | 0.0667% | 0.6585 | Y | N | — |
| CGPLH390 | 0.9182 | 0.0229% | 0.0837 | N | N | — |
| CGPLH391 | 0.9162 | 0.0223% | 0.0716 | N | N | — |
| CGPLH392 | 0.9014 | 0.0424% | 0.1305 | N | N | — |
| CGPLH393 | 0.9045 | 0.0407% | 0.0037 | N | N | — |
| CGPLH394 | 0.9292 | 0.6522% | 0.1073 | N | N | — |
| CGPLH395 | 0.9254 | 0.0424% | 0.0171 | N | N | — |
| CGPLH396 | 0.8928 | 0.0393% | 0.0303 | N | N | — |
| CGPLH398 | 0.9578 | 0.0242% | 0.3195 | N | N | — |
| CGPLH399 | 0.9195 | 0.0573% | 0.0685 | N | N | — |
| CGPLH400 | 0.9047 | 0.0300% | 0.2103 | N | N | — |
| CGPLH401 | 0.9339 | 0.0146% | 0.0620 | N | N | — |
| CGPLH402 | 0.8800 | 0.1516% | 0.0395 | N | N | — |
| CGPLH403 | 0.8829 | 0.0515% | 0.0223 | N | N | — |
| CGPLH404 | 0.8948 | 0.0528% | 0.0027 | N | N | — |
| CGPLH405 | 0.9204 | 0.0359% | 0.0188 | N | N | — |
| CGPLH406 | 0.8592 | 0.0667% | 0.0206 | N | N | — |
| CGPLH407 | 0.9099 | 0.0229% | 0.0040 | N | N | — |
| CGPLH408 | 0.9192 | 0.0415% | 0.1257 | N | N | — |
| CGPLH409 | 0.8950 | 0.0302% | 0.0056 | N | N | — |
| CGPLH410 | 0.9006 | 0.0453% | 0.0019 | N | N | — |
| CGPLH411 | 0.8857 | 0.0621% | 0.0188 | N | N | — |
| CGPLH412 | 0.9191 | 0.0140% | 0.0417 | N | N | — |
| CGPLH413 | 0.9145 | 0.0355% | 0.0084 | N | N | — |
| CGPLH414 | 0.9127 | 0.0290% | 0.0284 | N | N | — |
| CGPLH415 | 0.9025 | 0.0296% | 0.0131 | N | N | — |
| CGPLH416 | 0.9388 | 0.0198% | 0.0645 | N | N | — |
| CGPLH417 | 0.9192 | 0.0241% | 0.0836 | N | N | — |
| CGPLH418 | 0.9234 | 0.0306% | 0.0052 | N | N | — |
| CGPLH419 | 0.9295 | 0.0280% | 0.0469 | N | N | — |
| CGPLH420 | 0.9108 | 0.0187% | 0.0420 | N | N | — |
| CGPLH422 | 0.9006 | 0.0209% | 0.0324 | N | N | — |
| CGPLH423 | 0.9289 | 0.0832% | 0.0139 | N | N | — |
| CGPLH424 | 0.9265 | 0.1119% | 0.0864 | N | N | — |
| CGPLH425 | 0.9488 | 0.0722% | 0.0156 | N | N | — |
| CGPLH426 | 0.9080 | 0.0548% | 0.1075 | N | N | — |
| CGPLH427 | 0.9257 | 0.0182% | 0.0470 | N | N | — |
| CGPLH428 | 0.9272 | 0.0346% | 0.0182 | N | N | — |
| CGPLH429 | 0.8757 | 0.0593% | 0.8143 | Y | Y | — |
| CGPLH430 | 0.9307 | 0.0258% | 0.0369 | N | N | — |
| CGPLH431 | 0.9185 | 0.0234% | 0.0174 | N | N | — |
| CGPLH432 | 0.9082 | 0.0433% | 0.0181 | N | N | — |
| CGPLH434 | 0.9442 | 0.0297% | 0.0050 | N | N | — |
| CGPLH435 | 0.9097 | 0.0179% | 0.0441 | N | N | — |
| CGPLH436 | 0.9158 | 0.0290% | 0.0958 | N | N | — |
| CGPLH437 | 0.3245 | 0.0156% | 0.0136 | N | N | — |
| CGPLH438 | 0.9138 | 0.0169% | 0.1041 | N | N | — |
| CGPLM439 | 0.9028 | 0.0225% | 0.0078 | N | N | — |
| CGPLH440 | 0.9295 | 0.0330% | 0.0887 | N | N | — |
| CGPLH441 | 0.9430 | 0.0178% | 0.0085 | N | N | — |
| CGPLH442 | 0.9406 | 0.0169% | 0.0582 | N | N | — |
| CGPLH443 | 0.8801 | 0.0207% | 0.0578 | N | N | — |
| CGPLH444 | 0.9066 | 0.6464% | 0.0097 | N | N | — |
| CGPLH445 | 0.8750 | 0.0267% | 0.1939 | N | N | — |
| CGPLH446 | 0.9257 | 0.0281% | 0.0340 | N | N | — |
| CGPLH447 | 0.8968 | 0.0167% | 0.0017 | N | N | — |
| CGPLH448 | 0.8181 | 0.0401% | 0.0389 | N | N | — |
| CGPLH449 | 0.9254 | 0.0236% | 0.0116 | N | N | — |
| CGPLH450 | 0.9195 | 0.0331% | 0.0597 | N | N | — |
| CGPLH451 | 0.9167 | 0.0262% | 0.0104 | N | N | — |
| CGPLH452 | 0.8948 | 0.0480% | 0.4722 | N | N | — |

TABLE 7-continued

APPENDIX G: Whole genome cfDNA analyses in healthy individuals and cancer patients

| | | | | | | |
|---|---|---|---|---|---|---|
| CGPLH453 | 0.9339 | 0.0186% | 0.3419 | N | N | — |
| CGPLH455 | 0.9322 | 0.0455% | 0.4536 | N | N | — |
| CGPLH456 | 0.9098 | 0.0207% | 0.0365 | N | N | — |
| CGPLH457 | 0.9022 | 0.0298% | 0.0354 | N | N | — |
| CGPLH458 | 0.9275 | 0.0298% | 0.1891 | N | N | — |
| CGPLH459 | 0.9209 | 0.0281% | 0.0371 | N | N | — |
| CGPLH460 | 0.8863 | 0.0227% | 0.1157 | N | N | — |
| CGPLH463 | 0.9372 | 0.0130% | 0.0865 | N | N | — |
| CGPLH464 | 0.8511 | 0.0659% | 0.2040 | N | N | — |
| CGPLH465 | 0.9164 | 0.0325% | 0.0121 | N | N | — |
| CGPLH466 | 0.9408 | 0.0155% | 0.1733 | N | N | — |
| CGPLH467 | 0.9024 | 0.0229% | 0.2303 | N | N | — |
| CGPLH468 | 0.9345 | 0.0247% | 0.5427 | N | N | — |
| CGPLH469 | 0.8799 | 0.0201% | 0.5351 | N | N | — |
| CGPLH470 | 0.2228 | 0.0715% | 0.0327 | N | N | — |
| CGPLH471 | 0.9333 | 0.0153% | 0.0406 | N | N | — |
| CGPLH472 | 0.8915 | 0.0481% | 0.6152 | N | N | — |
| CGPLH473 | 0.9128 | 0.0443% | 0.2995 | N | N | — |
| CGPLH474 | 0.9245 | 0.0316% | 0.5246 | Y | N | — |
| CGPLH475 | 0.9233 | 0.0269% | 0.0736 | N | N | — |
| CGPLH476 | 0.9059 | 0.0236% | 0.0143 | N | N | — |
| CGPLH477 | 0.9376 | 0.0382% | 0.1111 | N | N | — |
| CGPLH478 | 0.9344 | 0.0256% | 0.0828 | N | N | — |
| CGPLN479 | 0.9207 | 0.0221% | 0.0648 | N | N | — |
| CGPLH480 | 0.9046 | 0.0672% | 0.7473 | Y | N | — |
| CGPLH481 | 0.9113 | 0.0311% | 0.0282 | N | N | — |
| CGPLH482 | 0.9336 | 0.0162% | 0.0058 | N | N | — |
| CGPLH483 | 0.9275 | 0.0251% | 0.0495 | N | N | — |
| CGPLH484 | 0.9366 | 0.0261% | 0.0048 | N | N | — |
| CGPLH485 | 0.9128 | 0.0291% | 0.1084 | N | N | — |
| CGPLH486 | 0.9042 | 0.0220% | 0.0820 | N | N | — |
| CGPLH487 | 0.9098 | 0.0594% | 0.2154 | N | N | — |
| CGPLH488 | 0.9298 | 0.0409% | 0.0903 | N | N | — |
| CGPLH490 | 0.8794 | 0.0432% | 0.0424 | N | N | — |
| CGPLH491 | 0.9332 | 0.0144% | 0.0223 | N | N | — |
| CGPLH492 | 0.8799 | 0.0322% | 0.0311 | N | N | — |
| CGPLH493 | 0.9330 | 0.0065% | 0.0280 | N | N | — |
| CGPLH494 | 0.9303 | 0.0232% | 0.0824 | N | N | — |
| CGPLH495 | 0.8908 | 0.0513% | 0.0465 | N | N | — |
| CGPLH496 | 0.9398 | 0.0208% | 0.0572 | N | N | — |
| CGPLH497 | 0.9330 | 0.0335% | 0.0404 | N | N | — |
| CGPLH498 | 0.9315 | 0.0403% | 0.0752 | N | N | — |
| CGPLH499 | 0.9442 | 0.0198% | 0.0149 | N | N | — |
| CGPLH500 | 0.9240 | 0.0433% | 0.0754 | N | N | — |
| CGPLH501 | 0.9308 | 0.0300% | 0.0159 | N | N | — |
| CGPLH502 | 0.9200 | 0.0351% | 0.0841 | N | N | — |
| CGPLH503 | 0.8939 | 0.0398% | 0.0649 | N | N | — |
| CGPLH504 | 0.9324 | 0.0440% | 0.1231 | N | N | — |
| CGPLH505 | 0.9243 | 0.0605% | 0.1889 | N | N | — |
| CGPLH506 | 0.9498 | 0.0284% | 0.0180 | N | N | — |
| CGPLH507 | 0.9192 | 0.0186% | 0.0848 | N | N | — |
| CGPLH508 | 0.9410 | 0.0150% | 0.1077 | N | N | — |
| CGPLH509 | 0.9323 | 0.0163% | 0.0828 | N | N | — |
| CGPLH510 | 0.9548 | 0.0128% | 0.0378 | N | N | — |
| CGPLH511 | 0.9493 | 0.0224% | 0.1779 | N | N | — |
| CGPLH512 | 0.9244 | 0.0094% | 0.0076 | N | N | — |
| CGPLH513 | 0.9595 | 0.0441% | 0.5250 | N | N | — |
| CGPLH514 | 0.9369 | 0.0114% | 0.3131 | N | N | — |
| CGPLH515 | 0.9283 | 0.0352% | 0.4936 | N | N | — |
| CGPLH516 | 0.9298 | 0.0175% | 0.0916 | N | N | — |
| CGPLH517 | 0.9494 | 0.0161% | 0.0059 | N | N | — |
| CGPLH518 | 0.9432 | 0.0274% | 0.0130 | N | N | — |
| CGPLH519 | 0.9351 | 0.0171% | 0.0949 | N | N | — |
| CGPLH520 | 0.9476 | 0.0241% | 0.0944 | N | N | — |
| CGPLH625 | 0.9231 | 0.0697% | 0.4977 | N | N | — |
| CGPLH626 | 0.9269 | 0.0231% | 0.3100 | N | N | — |
| CGPLH639 | 0.9410 | 0.0549% | 0.0773 | N | N | — |
| CGPLH640 | 0.9264 | 0.0232% | 0.0327 | N | N | — |
| CGPLH642 | 0.9376 | 0.0768% | 0.0555 | N | N | — |
| CGPLH643 | 0.9271 | 0.0579% | 0.1325 | N | N | — |
| CGPLH644 | 0.8948 | 0.0621% | 0.3819 | N | N | — |
| CGPLH646 | 0.8691 | 0.0462% | 0.2423 | N | N | — |
| CGPLLU144 | 0.8681 | 0.0423% | 0.9892 | Y | Y | 5.10% |
| CGPLLU161 | 0.9187 | 0.0273% | 0.9955 | Y | Y | 0.20% |
| CGPLLU162 | 0.8836 | 0.1410% | 0.9986 | Y | Y | 0.22% |
| CGPLLU163 | 0.3033 | 0.0724% | 0.9940 | Y | Y | 0.21% |
| CGPLLU168 | 0.8842 | 0.0712% | 0.9861 | Y | Y | 0.07% |
| CGPLLU169 | 0.9189 | 0.0846% | 0.9866 | Y | Y | 0.13% |

TABLE 7-continued

APPENDIX G: Whole genome cfDNA analyses in healthy individuals and cancer patients

| | | | | | | |
|---|---|---|---|---|---|---|
| CGPLLU176 | 0.9081 | 0.0626% | 0.8769 | Y | Y | ND |
| CGPLLU177 | 0.6790 | 0.0564% | 0.9924 | Y | Y | 3.22% |
| CGPLLU203 | 0.8741 | 0.0568% | 0.9178 | Y | Y | 0.11% |
| CGPLLU205 | 0.9476 | 0.0495% | 0.9677 | Y | Y | ND |
| CGPLLU207 | 0.9379 | 0.0421% | 0.9908 | Y | Y | 0.32% |
| CGPLLU208 | 0.8342 | 0.0815% | 0.9273 | Y | Y | 1.33% |
| CGPLOV11 | 0.8872 | 0.0463% | 0.9343 | Y | Y | 0.87% |
| CGPLOV12 | 0.8973 | 0.2767% | 0.9764 | Y | Y | ND |
| CGPLOV13 | 0.9146 | 0.1017% | 0.9690 | Y | Y | 0.35% |
| CGPLOV15 | 0.8552 | 0.0876% | 0.9945 | Y | Y | 3.54% |
| CGPLOV18 | 0.9046 | 0.0400% | 0.9983 | Y | Y | 1.12% |
| CGPLOV19 | 0.7578 | 0.1089% | 0.9989 | Y | Y | 46.35% |
| CGPLOV20 | 0.9154 | 0.0581% | 0.9749 | Y | Y | 0.21% |
| CGPLOV21 | 0.8889 | 0.0677% | 0.9951 | Y | Y | 14.36% |
| CGPLOV22 | 0.9355 | 0.0251% | 0.9775 | Y | V | 0.49% |
| CGPLOV23 | 0.8850 | 0.1520% | 0.9916 | Y | Y | 1.39% |
| CGPLOV24 | 0.8995 | 0.0303% | 0.9856 | Y | Y | ND |
| CGPLOV25 | 0.9228 | 0.0141% | 0.8544 | Y | Y | ND |
| CGPLOV26 | 0.9351 | 0.0646% | 0.9946 | Y | Y | ND |
| CGPLOV28 | 0.9378 | 0.0647% | 0.8160 | Y | Y | ND |
| CGPLOV31 | 0.9293 | 0.1605% | 0.9795 | Y | Y | ND |
| CGPLOV32 | 0.9338 | 0.1351% | 0.8609 | Y | Y | ND |
| CGPLOV37 | 0.8831 | 0.0986% | 0.9849 | Y | Y | 0.29% |
| CGPLOV38 | 0.6502 | 0.0490% | 0.9990 | Y | Y | 4.89% |
| CGPLOV40 | 0.8127 | 0.6145% | 0.9983 | Y | Y | 6.73% |
| CGPLOV41 | 0.8929 | 0.1110% | 0.9484 | Y | Y | 0.60% |
| CGPLOV42 | 0.9086 | 0.0489% | 0.9979 | Y | Y | 1.24% |
| CGPLOV43 | 0.9342 | 0.0432% | 0.6042 | N | N | ND |
| CGPLOV44 | 0.9173 | 0.1946% | 0.9962 | Y | Y | 0.37% |
| CGPLOV45 | 0.9291 | 0.0801% | 0.9128 | Y | Y | ND |
| CGPLOV47 | 0.9461 | 0.0270% | 0.3410 | N | N | 3.20% |
| CGPLOV48 | 0.9429 | 0.0422% | 0.4874 | N | N | 10.70% |
| CGPLOV49 | 0.8083 | 0.1527% | 0.9897 | Y | Y | 2.03% |
| CGPLOV50 | 0.9382 | 0.0807% | 0.9955 | Y | Y | ND |
| CGPLPA112 | 0.0429 | 0.0268% | 0.0856 | N | N | — |
| CGPLPA113 | 0.7674 | 1.0116% | 0.9935 | Y | Y | — |
| CGPLPA114 | 0.9246 | 0.0836% | 0.7598 | Y | Y | — |
| CGPLPA115 | 0.8310 | 0.0763% | 0.9974 | Y | Y | — |
| CGPLPA117 | 0.8767 | 0.1084% | 0.9049 | Y | Y | — |
| CGPLPA118 | 0.9001 | 0.1842% | 0.9859 | Y | Y | 0.14% |
| CGPLPA122 | 0.8058 | 0.2047% | 0.9983 | Y | Y | 37.22% |
| CGPLPA124 | 0.9238 | 0.1542% | 0.8791 | Y | Y | 0.62% |
| CGPLPA125 | 0.9373 | 0.0273% | 0.0228 | N | N | — |
| CGPLPA126 | 0.9139 | 0.4349% | 0.9908 | Y | Y | ND |
| CGPLPA127 | 0.8117 | 0.4371% | 0.9789 | Y | Y | — |
| CGPLPA128 | 0.9003 | 0.1317% | 0.9812 | Y | Y | ND |
| CGPLPA129 | 0.9155 | 0.0612% | 0.9839 | Y | Y | ND |
| CGPLPA130 | 0.8499 | 0.1005% | 0.9895 | Y | Y | ND |
| CGPLPA131 | 0.9195 | 0.0780% | 0.9885 | Y | Y | 3.21% |
| CGPLPA134 | 0.8847 | 0.0260% | 0.9896 | Y | Y | 0.93% |
| CGPLPA135 | 0.9184 | 0.0558% | 0.6594 | Y | N | — |
| CGPLPA136 | 0.9050 | 0.0769% | 0.9596 | Y | Y | 0.10% |
| CGPLPA137 | 0.9320 | 0.0499% | 0.7282 | Y | N | — |
| CGPLPA139 | 0.9374 | 0.0465% | 0.0743 | N | N | — |
| CGPLPA14 | 0.9069 | 0.0515% | 0.9824 | Y | Y | |
| CGPLPA140 | 0.9548 | 0.0330% | 0.9761 | Y | Y | 0.21% |
| CGPLPA141 | 0.9381 | 0.0920% | 0.9988 | Y | Y | — |
| CGPLPA15 | 0.8927 | 0.0160% | 0.8737 | Y | Y | |
| CGPLPA155 | 0.9313 | 0.0260% | 0.8013 | Y | Y | |
| CGPLPA156 | 0.9432 | 0.0290% | 0.0159 | N | N | — |
| CGPLPA165 | 0.9309 | 0.0555% | 0.2158 | N | N | — |
| CGPLPA168 | 0.7757 | 0.3123% | 0.9878 | Y | Y | — |
| CGPLPA17 | 0.6771 | 1.2600% | 0.9956 | Y | Y | — |
| CGPLPA184 | 0.9203 | 0.0897% | 0.9926 | Y | Y | |
| CGPLPA187 | 0.8968 | 0.0658% | 0.9675 | Y | Y | — |
| CGPLPA23 | 0.6938 | 0.5785% | 0.9984 | Y | Y | |
| CGPLPA25 | 0.9239 | 0.0380% | 0.8103 | Y | Y | |
| CGPLPA26 | 0.9356 | 0.0247% | 0.8231 | Y | Y | |
| CGPLPA28 | 0.8938 | 0.0546% | 0.9036 | Y | Y | |
| CGPLPA33 | 0.8553 | 0.0894% | 0.9367 | Y | Y | — |
| CGPLPA34 | 0.8885 | 0.0439% | 0.7977 | Y | Y | — |
| CGPLPA37 | 0.9294 | 0.0410% | 0.9924 | Y | Y | — |
| CGPLPA38 | 0.8941 | 0.0372% | 0.9851 | Y | Y | — |
| CGPLPA39 | 0.7972 | 0.5058% | 0.9951 | Y | Y | — |
| CGPLPA40 | 0.8865 | 0.2268% | 0.9920 | Y | Y | |
| CGPLPA42 | 0.8363 | 0.0283% | 0.3544 | N | N | — |
| CGPLPA46 | 0.7525 | 1.0982% | 0.9952 | Y | Y | — |
| CGPLPA47 | 0.8439 | 0.1596% | 0.9346 | Y | Y | — |

TABLE 7-continued

APPENDIX G: Whole genome cfDNA analyses in healthy individuals and cancer patients

| | | | | | | |
|---|---|---|---|---|---|---|
| CGPLPA48 | 0.9207 | 1.0232% | 0.2251 | N | N | — |
| CGPLPA52 | 0.8863 | 0.0154% | 0.0963 | N | N | — |
| CGPLPA53 | 0.8776 | 0.1824% | 0.8946 | Y | Y | — |
| CGPLPA58 | 0.9224 | 0.0803% | 0.9056 | Y | Y | — |
| CGPLPA59 | 0.9193 | 0.1479% | 0.9759 | Y | Y | — |
| CGPLPA67 | 0.9248 | 0.0329% | 0.6716 | Y | N | — |
| CGPLPA69 | 0.8592 | 0.0459% | 0.1245 | N | N | — |
| CGPLPA71 | 0.8888 | 0.0479% | 0.0524 | N | N | — |
| CGPLPA74 | 0.9372 | 0.0292% | 0.0108 | N | N | — |
| CGPLPA78 | 0.9441 | 0.0345% | 0.0897 | N | N | — |
| CGPLPA85 | 0.9337 | 0.0363% | 0.0508 | N | N | — |
| CGPLPA86 | 0.8042 | 0.7564% | 0.9864 | Y | Y | — |
| CGPLPA92 | 0.9003 | 0.1459% | 0.7061 | Y | N | — |
| CGPLPA93 | 0.8023 | 0.6250% | 0.9978 | Y | Y | — |
| CGPLPA94 | 0.9433 | 0.0160% | 0.9025 | Y | Y | — |
| CGPLPA95 | 0.8571 | 0.0815% | 0.9941 | Y | Y | — |
| CGST102 | 0.9057 | 0.0704% | 0.8581 | Y | Y | 0.43% |
| CGST11 | 0.9161 | 0.0651% | 0.1435 | N | N | — |
| CGST110 | 0.9232 | 0.0817% | 0.8900 | Y | Y | ND |
| CGST114 | 0.9038 | 0.0317% | 0.5593 | N | N | ND |
| CGST13 | 0.9156 | 0.0321% | 0.9754 | Y | Y | ND |
| CGST131 | 0.8886 | 0.2752% | 0.9409 | Y | Y | — |
| CGST141 | 0.9206 | 0.0338% | 0.2008 | N | N | ND |
| CGST16 | 0.8355 | 0.1744% | 0.9974 | Y | Y | 0.93% |
| CGST18 | 0.9111 | 0.0299% | 0.3842 | N | N | 0.14% |
| CGST21 | 0.2687 | 0.2299% | 0.9910 | Y | Y | — |
| CGST26 | 0.9140 | 0.0399% | 0.5009 | N | N | — |
| CG3T28 | 0.7832 | 0.1295% | 0.9955 | Y | Y | 1.62% |
| CGST30 | 0.9121 | 0.0338% | 0.9183 | Y | Y | 0.42% |
| CGST32 | 0.8639 | 0.0247% | 0.9612 | Y | Y | 2.99% |
| CGST33 | 0.7770 | 0.0799% | 0.9805 | Y | Y | 2.32% |
| CGST38 | 0.8758 | 0.0540% | 0.9416 | Y | Y | — |
| CGST39 | 0.9401 | 0.0287% | 0.8480 | Y | Y | ND |
| CGST41 | 0.9284 | 0.0398% | 0.9263 | Y | Y | ND |
| CGST45 | 0.9036 | 0.0220% | 0.9713 | Y | Y | ND |
| CGST47 | 0.9096 | 0.0157% | 0.9687 | Y | Y | 0.45% |
| CGST48 | 0.5445 | 0.0220% | 0.9975 | Y | Y | 4.21% |
| CGST53 | 0.7888 | 0.1140% | 0.9914 | Y | Y | — |
| CGST58 | 0.9094 | 0.0596% | 0.9705 | Y | Y | ND |
| CGST67 | 0.8853 | 0.3245% | 0.9002 | Y | Y | — |
| CGST77 | 0.8295 | 0.1851% | 0.9981 | Y | Y | — |
| CGST80 | 0.8846 | 0.0490% | 0.9513 | Y | Y | 1.04% |
| CGST81 | 0.8851 | 0.0138% | 0.9748 | Y | Y | 0.20% |

*ND indicates not detected. Please see reference 10 for additional information on targeted sequencing analyes. DELFI cancer detection at 95% and 98% specificity is based on scores greater than 0.6200 and 0.7500, respectively.

What is claimed is:

1. A method of determining a cell free DNA (cfDNA) fragmentation profile of a mammal, the method comprising:
   processing cfDNA fragments obtained from a sample obtained from the mammal into sequencing libraries;
   subjecting the sequencing libraries to whole genome sequencing to obtain sequenced fragments, wherein genome coverage is about 9× to 0.1×;
   mapping the sequenced fragments to a genome to obtain genomic intervals of mapped sequences; and,
   analyzing the genomic intervals of mapped sequences to determine cfDNA fragment lengths and determining the cfDNA fragmentation profile using the lengths;
   detecting that the cfDNA fragmentation profile that is more variable than a reference cfDNA fragmentation profile from a healthy subject, wherein increased variability of the fragmentation profile obtained from the mammal compared to the reference profile is indicative of the mammal as having cancer; and
   administering to the mammal identified as having cancer, a therapeutic treatment suitable for treatment of the cancer.

2. The method of claim 1, wherein the mapped sequences comprise tens or hundreds to thousands of genomic intervals.

3. The method of claim 1, wherein the genomic intervals are non-overlapping.

4. The method of claim 1, wherein the genomic intervals each comprise thousands to millions of base pairs.

5. The method of claim 1, wherein a cfDNA fragmentation profile is determined within each genomic intervals.

6. The method of claim 1, wherein the cfDNA fragmentation profile comprises a median fragment size.

7. The method of claim 1, wherein the cfDNA fragmentation profile comprises a fragment size distribution.

8. The method of claim 1, wherein the cfDNA fragmentation profile comprises a ratio of small cfDNA fragments to large cfDNA fragments in said windows of mapped sequences.

9. The method of claim 1, wherein the cfDNA fragmentation profile comprises the sequence coverage of small cfDNA fragments in genomic intervals across the genome.

10. The method of claim 1, wherein the cfDNA fragmentation profile comprises the sequence coverage of large cfDNA fragments in genomic intervals across the genome.

11. The method of claim 1, wherein the cfDNA fragmentation profile comprises the sequence coverage of small and large cfDNA fragments in genomic intervals across the genome.

12. The method of claim 1, wherein the cfDNA fragmentation profile is over the whole genome or a subgenomic interval.

13. The method of claim 1, wherein the cancer is selected from the group consisting of: colorectal cancer, lung cancer, breast cancer, gastric cancer, pancreatic cancer, bile duct cancer, and ovarian cancer.

14. The method of claim 1, wherein cfDNA fragmentation patterns provide over 20,000 reads per genomic interval.

15. The method of claim, 1, wherein genome coverage is from about 2×, 1×, 0.5×, 0.2× or 0.1×.

16. The method of claim 1, wherein the mammal is a human.

* * * * *